United States Patent
Hurtado et al.

(10) Patent No.: US 12,409,230 B2
(45) Date of Patent: Sep. 9, 2025

(54) COMPOSITIONS COMPRISING PLN-TARGETING ANTI-TRANSFERRIN RECEPTOR ANTIBODY-POLYNUCLEOTIDES AND METHODS OF USE THEREOF TO TREAT CARDIOMYOPATHY

(71) Applicant: Avidity Biosciences, Inc., San Diego, CA (US)

(72) Inventors: Cecilia Hurtado, San Diego, CA (US); Georgios Karamanlidis, Thousand Oaks, CA (US); Sami Abdulwahab Abdulkadir, San Diego, CA (US); Subbarao Nallagatla, San Diego, CA (US); Maryam Jordan, Escondido, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/759,724

(22) Filed: Jun. 28, 2024

(65) Prior Publication Data

US 2025/0032622 A1    Jan. 30, 2025

Related U.S. Application Data

(60) Provisional application No. 63/511,450, filed on Jun. 30, 2023.

(51) Int. Cl.
| | |
|---|---|
| *A61K 47/54* | (2017.01) |
| *A61K 47/68* | (2017.01) |
| *A61P 9/00* | (2006.01) |
| *C12N 15/113* | (2010.01) |

(52) U.S. Cl.
CPC ........ *A61K 47/549* (2017.08); *A61K 47/6849* (2017.08); *A61P 9/00* (2018.01); *C12N 15/113* (2013.01); *C12N 2310/14* (2013.01); *C12N 2310/315* (2013.01); *C12N 2310/321* (2013.01); *C12N 2310/3231* (2013.01); *C12N 2310/3513* (2013.01)

(58) Field of Classification Search
CPC .............. A61K 47/549; A61K 47/6849; A61K 47/6807; A61K 2039/505; A61K 31/712; A61K 31/7125; A61K 31/713; A61P 9/00; C12N 15/113; C12N 2310/14; C12N 2310/315; C12N 2310/321; C12N 2310/3231; C12N 2310/3513; C07K 16/2881; C07K 2317/55; C07K 19/00
See application file for complete search history.

(56) References Cited

U.S. PATENT DOCUMENTS

| | | |
|---|---|---|
| 4,694,778 A | 9/1987 | Learn et al. |
| 5,142,047 A | 8/1992 | Summerton et al. |
| 5,185,444 A | 2/1993 | Summerton et al. |
| 5,334,711 A | 8/1994 | Sproat et al. |
| 5,627,053 A | 5/1997 | Usman et al. |
| 5,716,824 A | 2/1998 | Beigelman et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,821,783 B1 | 11/2004 | Comely et al. |
| 6,884,869 B2 | 4/2005 | Senter et al. |
| 7,498,298 B2 | 3/2009 | Doronina et al. |
| 7,850,975 B2 | 12/2010 | Mullis |
| 8,090,542 B2 | 1/2012 | Khvorova et al. |
| 8,288,352 B2 | 10/2012 | Doronina et al. |
| 8,501,930 B2 | 8/2013 | Rozema et al. |
| 8,591,910 B2 | 11/2013 | Mullis |
| 8,604,184 B2 | 12/2013 | Mullis et al. |
| 8,609,105 B2 | 12/2013 | Senter et al. |
| 8,697,688 B2 | 4/2014 | Howard et al. |
| 8,936,910 B2 | 1/2015 | Mitsch et al. |
| 9,089,614 B2 | 7/2015 | Lin et al. |
| 10,550,188 B2 | 2/2020 | Geall et al. |
| 10,612,027 B2 | 4/2020 | Maier et al. |
| 10,881,743 B2 | 1/2021 | Geall et al. |
| 10,913,800 B2 | 2/2021 | Darimont et al. |
| 10,994,020 B2 | 5/2021 | Levin et al. |
| 11,110,180 B2 | 9/2021 | Geall et al. |
| 11,555,190 B2 | 1/2023 | Malecova et al. |
| 2006/0148742 A1 | 7/2006 | Kaye et al. |
| 2008/0113351 A1 | 5/2008 | Naito et al. |
| 2013/0028919 A1 | 1/2013 | Howard et al. |
| 2013/0309256 A1 | 11/2013 | Lyon et al. |
| 2014/0127239 A1 | 5/2014 | Howard |
| 2014/0194610 A1 | 7/2014 | Verdine et al. |

(Continued)

FOREIGN PATENT DOCUMENTS

| | | |
|---|---|---|
| EP | 1579015 A2 | 9/2005 |
| EP | 2126084 B1 | 3/2014 |

(Continued)

OTHER PUBLICATIONS

Yoshida T, et al. (2019) Genes Cells. 24:827-835. (DOI: 10.1111/gtc.12730).*

Shao Y, et al. (2006) Nucleic Acids Research. 34(19):5660-5669. (doi:10.1093/nar/gkl715).*

Abramova, Tatyana V. et al. Novel Oligonucleotide Analogues Based on Morpholino Nucleoside Subunits Antisense Technologies: New Chemical Possibilities. Indian Journal of Chemistry 48B:1721-1726 (2009).

Agarwal, Paresh. et al. A Pictet-Spengler Ligation for Protein Chemical Modification. PNAS USA 110(1):46-51 (2013).

Albarran, Brian. et al. Efficient intracellular delivery of a pro-apoptotic peptide with a pH-responsive carrier. Reactive and Functional Polymers 71(3):261-265 (2011).

(Continued)

*Primary Examiner* — Robert S Landsman
(74) *Attorney, Agent, or Firm* — WILSON SONSINI GOODRICH & ROSATI

(57) ABSTRACT

Disclosed herein are polynucleic acid molecules, pharmaceutical compositions, and methods of use for antibody-PLN targeting oligonucleotide conjugates (AOC).

27 Claims, 21 Drawing Sheets

Specification includes a Sequence Listing.

(56) References Cited

U.S. PATENT DOCUMENTS

| | | |
|---|---|---|
| 2014/0286970 A1 | 9/2014 | Jeffrey et al. |
| 2014/0294851 A1 | 10/2014 | Nguyen |
| 2015/0037360 A1 | 2/2015 | Smith |
| 2015/0105539 A1 | 4/2015 | Miao et al. |
| 2015/0105540 A1 | 4/2015 | Miao et al. |
| 2015/0211006 A1 | 7/2015 | Butler et al. |
| 2019/0240346 A1 | 8/2019 | Sugo et al. |
| 2022/0008550 A1* | 1/2022 | Geall ............ C07K 16/18 |
| 2024/0401061 A1 | 12/2024 | Kubli et al. |

FOREIGN PATENT DOCUMENTS

| | | | |
|---|---|---|---|
| WO | WO-9207065 A1 | 4/1992 | |
| WO | WO-9315187 A1 | 8/1993 | |
| WO | WO-9726270 A2 | 7/1997 | |
| WO | WO-9734631 A1 | 9/1997 | |
| WO | WO-9813526 A1 | 4/1998 | |
| WO | WO-0116312 A2 * | 3/2001 | ........ A61P 1/16 |
| WO | WO-2006096441 A2 | 9/2006 | |
| WO | WO-2009099942 A2 | 8/2009 | |
| WO | WO-2009126933 A2 | 10/2009 | |
| WO | WO-2012177639 A2 | 12/2012 | |
| WO | WO-2013166155 A1 | 11/2013 | |
| WO | WO-2014080251 A1 | 5/2014 | |
| WO | WO-2014140317 A2 | 9/2014 | |
| WO | WO-2014145090 A1 | 9/2014 | |
| WO | WO-2014177042 A1 | 11/2014 | |
| WO | WO-2014197854 A1 | 12/2014 | |
| WO | WO-2015038426 A1 | 3/2015 | |
| WO | WO-2015057699 A2 | 4/2015 | |
| WO | WO-2015069587 A2 | 5/2015 | |
| WO | WO-2015107425 A2 | 7/2015 | |
| WO | WO-2022147249 A1 | 7/2022 | |
| WO | WO-2022173976 A1 | 8/2022 | |
| WO | WO-2023064530 A1 | 4/2023 | |
| WO | WO-2023215481 A1 | 11/2023 | |
| WO | WO-2025007063 A1 | 1/2025 | |

OTHER PUBLICATIONS

Alegre, Maria-Luisa. et al. Effect of a Single Amino Acid Mutation on the Activating and Immunosuppressive Properties of a "Humanized" OKT3 Monoclonal Antibody. Journal of Immunology 148(11):3461-3468 (1992).

Armanious, G.P. et al. GenBank Accession No. NM_002667. Version No. NM_002667.5. Homo sapiens phospholamban (PLN), mRNA: pp. 1-4. Record created Nov. 22, 2018. Retrieved Jul. 8, 2024. Retrieved from: https://www.ncbi.nlm.nih.gov/nuccore/NM_002667.5.

Axup, Jun Y. et al. Synthesis of Site-specific Antibody-drug Conjugates Using Unnatural Amino Acids. PNAS USA 109(40):16101-16106 (2012).

Beigelman, Leonid. et al. Chemical Modification of Hammerhead Ribozymes: Catalytic Activity and Nuclease Resistance. Journal of Biological Chemistry 270(43):25702-25708 (1995).

Bird, Robert E. et al. Single-chain Antigen-binding Proteins. Science 242(4877):423-426 (1988).

Blaney, Paul. et al. Traceless Solid-phase Organic Synthesis. Chemical Reviews 102(7):2607-2624 (2002).

Bolger, Anthony M. et al. Trimmomatic: A Flexible Trimmer For Illumina Sequence Data. Bioinformatics 30(15):2114-2120 (2014).

Burlina, Fabienne. et al. Chemical Engineering of RNase Resistant and Catalytically Active Hammerhead Ribozymes. Bioorganic and Medicinal Chemistry 5(11):1999-2010 (1997).

Casi, Giulio. et al. Site-specific Traceless Coupling of Potent Cytotoxic Drugs to Recombinant Antibodies for Pharmacodelivery. Journal of the American Chemical Society 134(13):5887-5892 (2012).

Chen, Caifu. et al. Real-Time Quantification Of microRNAs By Stem-loop RT-PCR. Nucleic Acids Research 33(20):e179, 1-9 (2005).

Clackson, Tim. et al. Making antibody fragments using phage display libraries. Nature 352(6336):624-628 (1991).

Colberre-Garapin, Florence. et al. A New Dominant Hybrid Selective Marker for Higher Eukaryotic Cells. Journal of Molecular Biology 150(1):1-14 (1981).

Cole, S.P.C. et al. The EBV-Hybridoma Technique and its Application to Human Lung Cancer. Monoclonal Antibodies and Cancer Therapy 27:77-96 (1985).

Crouse, Gray F. et al. Expression and Amplification of Engineered Mouse Dihydrofolate Reductase Minigenes. Molecular Cell Biology 3(2):257-266 (1983).

Dawson, Philip E. et al. Modulation of Reactivity in Native Chemical Ligation through the Use of Thiol Additives. Journal of American Chemical Society 119(19):4325-4329 (1997).

Dawson, Philip E. et al. Synthesis of Proteins by Native Chemical Ligation. 266(5186):776-779 (1994).

Dimasi, Nazzareno. et al. Development of a Trispecific Antibody Designed to Simultaneously and Efficiently Target Three Different Antigens on Tumor Cells. Molecular Pharmaceutics 12(9):3490-3501 (2015).

Dobin, Alexander. et al. STAR: Ultrafast Universal RNA-seq Aligner. Bioinformatics 29(1):15-21 (2013).

Earnshaw, David J. et al. Modified Oligoribonucleotides as Site-Specific Probes of RNA Structure and Function. Biopolymers (Nucleic Acid Sciences) 48(1):39-55 (1998).

Gaffin, Robert D. et al. Long-Term Rescue of a Familial Hypertrophic Cardiomyopathy Caused by a Mutation in the Thin Filament Protein, Tropomyosin, via Modulation of a Calcium Cycling Protein. Journal of Molecular and Cellular Cardiology 51(5):812-820 (2011).

GenBank Accession No. XM_005551677. Version No. XM_005551677.2. Predicted: Macaca fascicularis phospholamban (PLN), mRNA: pp. 1-2. Record created Jan. 25, 2016. Retrieved Jul. 8, 2024. Retrieved from: https://www.ncbi.nlm.nih.gov/nuccore/XM_005551677.2.

GenBank Accession No. XM_015448593. Version No. XM_015448593.1. Ppredicted: Macaca fascicularis centrosomal protein 85kDa-like (CEP85L), transcript variant X2, mRNA: pp. 1-3. Record created Jan. 25, 2016. Retrieved Jul. 9, 2024. Retrieved from: https://www.ncbi.nlm.nih.gov/nuccore/XM_015448593.1?report=genbank.

Goldspiel, Barry R. et al. Human Gene Therapy. Clinical Pharmacy 12(7):488-505 (1993).

Griffey, Richard H. et al. 2'-O-aminopropyl Ribonucleotides: A Zwitterionic Modification that Enhances the Exonuclease Resistance and Biological Activity of Antisense Oligonucleotides. Journal of Medicinal Chemistry 39(26):5100-5109 (1997).

Hackeng, Tilman M. et al. Protein Synthesis by Native Chemical Ligation: Expanded Scope by Using Straightforward Methodology. PNAS USA 96(18):10068-10073 (1999).

Hanes, Jozef, and A Pluckthun. In Vitro Selection and Evolution of Functional Proteins by Using Ribosome Display. PNAS USA 94(10):4937-4942 (1997).

Hejesen, Christian. et al. A Traceless Aryl-triazene Linker for DNA-directed Chemistry. Organic and Biomolecular Chemistry 11(15):2493-2497 (2013).

Huse, William D. et al. Generation Of A Large Combinatorial Library Of The Immunoglobulin Repertoire In Phage Lambda. Science 246(4935):1275-1281 (1989).

Huston, James S. et al. Protein engineering of antibody binding sites: recovery of specific activity in an anti-digoxin single-chain fv analogue produced in Escherichia coli. PNAS USA 85(16):5879-5883 (1988).

Idusogie, Esohe E. et al. Engineered Antibodies with Increased Activity to Recruit Complement. Journal of Immunology 166(4):2571-2575 (2001).

Kaneko, Etsuji. et al. Optimizing Therapeutic Antibody Function: Progress with Fc Domain Engineering. Bio Drugs 25(1):1-11 (2011).

Karpeisky, Alexander et al. Highly Efficient Synthesis of 2-O-amino Nucleosides and their Incorporation in Hammerhead Ribozymes. Tetrahedron Letters 39:1131-1134 (1998).

Klocke, B. et al. GenBank Accession No. NM_001141927. Version No. NM_001141927.1. Mus musculus phospholamban (Pln), transcript variant 1, mRNA: pp. 1-4. Record created Nov. 20, 2008. Retrieved Jul. 8, 2024. Retrieved from: https://www.ncbi.nlm.nih.gov/nuccore/NM_001141927.1.

(56) References Cited

OTHER PUBLICATIONS

Kohler, G, and Milstein, C. Continuous Cultures of Fused Cells Secreting Antibody of Predefined Specificity. Nature 256(5517):495-497 (1975).
Koizumi, Makoto. ENA Oligonucleotides as Therapeutics. Current Opinion in Molecular Therapeutics 8(2):144-149 (2006).
Kozbor, Danuta, and J C Roder. The Production of Monoclonal Antibodies From Human Lymphocytes. Immunology Today 4(3):72-79 (1983).
Kutmeier, G. et al. Assembly of Humanized Antibody Genes from Synthetic Oligonucleotides Using a Single-round PCR. Biotechniques 17(2):242-246 (1994).
Lazar, Greg A. et al. Engineered Antibody Fc Variants with Enhanced Effector Function. PNAS USA 103(11):4005-4010 (2006).
Li, Bo. et al. RSEM: Accurate Transcript Quantification From RNA-seq Data With Or Without A Reference Genome. BMC Bioinformatics 12:323, 1-16 (2011).
Loakes, David. Survey and Summary: The applications of universal DNA base analogues. Nucleic Acids Research 29(12):2437-2447 (2001).
Lowy, Israel et al. Isolation of Transforming DNA: Cloning the Hamster Aprt Gene. Cell 22(3):817-823 (1980).
Lyon, Robert P. et al. Self-Hydrolyzing Maleimides improve the Stability and Pharmacological Properties of Antibody-drug Conjugates. Nature Biotechnology 32(10):1059-1062 (2014).
Martinez, Javier. et al. Single-Stranded Antisense siRNAs Guide Target RNA Cleavage in RNAi. Cell 110(5):563-574 (2002).
McEnaney, Patrick J. et al. Antibody-Recruiting Molecules: An Emerging Paradigm for Engaging Immune Function in Treating Human Disease. ACS Chemical Biology 7(7):1139-1151 (2012).
Moore, Gregory L. et al. Engineered Fc Variant Antibodies with Enhanced Ability to Recruit Complement and Mediate Effector Functions. mAbs 2(2):181-189 (2010).
Morgan, Richard A, and W F Anderson. Human Gene Therapy. Annual Review of Biochemistry 62:191-217 (1993).
Morrison, Sherie L. et al. Chimeric Human Antibody Molecules: Mouse Antigen-binding Domains With Human Constant Region Domains. PNAS USA 81(21):6851-6855 (1984).
Mulligan, Richard C, and P Berg. Selection for Animal Cells that Express the *Escherichia coli* Gene Coding for Xanthine-guanine Phosphoribosyltransferase. PNAS USA 78(4):2072-2076 (1981).
Mulligan, Richard C. The Basic Science of Gene Therapy. Science 260(5110):926-932 (1993).
Naisbitt, D J. et al. Disposition of Amodiaquine and Related Antimalarial Agents in Human Neutrophils: Implications for Drug Design. The Journal of Pharmacology and Experimental Therapeutics 280(2):884-893 (1997).
Natsume, Akito. et al. Engineered Antibodies of IgG1/IgG3 Mixed Isotype with Enhanced Cytotoxic Activities. Cancer Research 68(10):3863-3872 (2008).
Neuberger, Michael S. et al. Recombinant Antibodies Possessing Novel Effector Functions. Nature 312(5995):604-608 (1984).
Obika, Satosh et al. Synthesis of 2'-0,4'-C-methyleneuridine and -cytidine. Novel bicyclic nucleosides having a fixed C3'-endo sugar puckering. Tetrahedron Letters 38(50):8735-8738 (1997).
O'Hare, K. et al. Transformation of Mouse Fibroblasts to Methotrexate Resistance by a Recombinant Plasmid Expressing a Prokaryotic Dihydrofolate Reductase. PNAS USA 78(3):1527-1531 (1981).
Perrault, Jean-Pierre. et al. Mixed Deoxyribo- and Ribo-Oligonucleotides with Catalytic Activity. Nature 344(6266):565-568 (1990).
Pieken, Wolfgang A. et al. Kinetic Characterization of Ribonuclease-Resistant 2'-Modified Hammerhead Ribozymes. Science 253(5017):314-317 (1991).
Prabhakar, Rethinasamy. et al. A Familial Hypertrophic Cardiomyopathy Alpha-tropomyosin Mutation Causes Severe Cardiac Hypertrophy And Death In Mice. Journal of Molecular and Cellular Cardiology 33(10):1815-1828 (2001).

Prabhakar, Rethinasamy. et al. A Mouse Model Of Familial Hypertrophic Cardiomyopathy Caused By A Alpha-Tropomyosin Mutation. Molecular and Cellular Biochemistry 251(1-2):33-42 (2003).
Santerre, Robert F. et al. Expression of Prokaryotic Genes for Hygromycin B and G418 Resistance as Dominant-selection Markers in Mouse L Cells. Gene 30(3):147-156 (1984).
Schwarz, Dianne S. et al. Evidence that siRNAs Function as Guides, not Primers, in the *Drosophila* and Human RNAi Pathways. Molecular Cell 10:537-548 (2002).
Shields, Robert L. et al. High Resolution Mapping of the Binding Site on Human IgG1 for Fc Gamma RI, Fc Gamma RII, Fc Gamma RIII, and FcRn and design of IgG1 variants with improved binding to the Fc gamma R. Journal of Biological Chemistry 276(9):6591-6604 (2001).
Skerra, Arne, and A Pluckthun. Assembly of a Functional Immunoglobulin Fv Fragment in *Escherichia coli*. Science 240(4855):1038-1041 (1988).
Stavenhagen, Jeffrey B. et al. Enhancing the Potency of Therapeutic Monoclonal Antibodies via Fc Optimization. Advances in Enzyme Regulation 48:152-64 (2008).
Stavenhagen, Jeffrey B. et al. Fc Optimization of Therapeutic Antibodies Enhances their Ability to Kill Tumor Cells In vitro and Controls Tumor Expansion In vivo via Low-Affinity Activating Fcgamma Receptors. Cancer Research 67(18):8882-8890 (2007).
Strop, Pavel. et al. Location Matters: Site of Conjugation Modulates Stability and Pharmacokinetics of Antibody Drug Conjugates. Chemistry and Biology 20(2):161-167 (2013).
Szybalska, Elizabeth H, and W Szybalski. Genetics of Human Cell Lines, IV. DNA-Mediated Heritable Transformation of a Biochemical Trait. PNAS USA 48(12):2026-2034 (1962).
Takeda, Shun-Ichi. et al. Construction of Chimaeric Processed Immunoglobulin Genes Containing Mouse Variable and Human Constant Region Sequences. Nature 314(6010):452-454 (1985).
Tolstoshev, Paul. Gene Therapy, Concepts, Current Trials and Future Directions. Annual Review Pharmacology and Toxicology 32:573-596 (1993).
US Food and Drug Administration. Guide for the Care and Use of Laboratory Animals. US National Institutes of Health:1-246 (2011).
Usman, Nassim, and Cedergren, Robert. Exploiting the Chemical Synthesis of RNA. Trends in Biochemical Sciences 17:334-339 (1992).
Verma, Sandeep. et al. Modified Oligonucleotides: Synthesis and Strategy for Users. Annual Review of Biochemistry 67:99-134 (1998).
Ward, E Sally. et al. Binding Activities of a Repertoire of Single Immunoglobulin Variable Domains Secreted from *Escherichia coli*. Nature 341(6242):544-546 (1989).
Wigler, Michael. et al. Transfer of Purified Herpes Virus Thymidine Kinase Gene to Cultured Mouse Cells. Cell 11(1):223-232 (1977).
Wigler, Michael. et al. Transformation of Mammalian Cells With an Amplifiable Dominant-acting Gene. PNAS USA 77(6):3567-3570 (1980).
Wu, Bin. et al. Building Complex Glycopeptides: Development of a Cysteine-free Native Chemical Ligation Protocol. Angewandte Chemie 45(25):4116-4125 (2006).
Wu, George Y, and C H Wu et al. Delivery systems for Gene Therapy. Biotherapy 3(1):87-95 (1991).
Wu, Peng. et al. Site-specific Chemical Modification of Recombinant Proteins Produced in Mammalian Cells by Using the Genetically Encoded Aldehyde Tag. PNAS USA 106(9):3000-3005 (2009).
Zhang, Andrew X. et al. A Remote Arene-Binding Site on Prostate Specific Membrane Antigen Revealed by Antibody-Recruiting Small Molecules. Journal of the American Chemical Society 132(36):12711-12716 (2010).
Biermans, Sam. Recombinant Adeno-Associated Virus as a Therapeutic Therapy for PLN R14del Patients. PLN Heart foundation Thesis. Retrieved from Retrieved from the internet: URL: https://plnheart.org/wp-content/uploads/Research-project_SamBiermans.pdf (pp. 1-57) (2021).
Karakikes, Ioannis et al. Correction of human phospholamban R14del mutation associated with cardiomyopathy using targeted nucleases and combination therapy. Nature Communications 6:6955, 1-10 (2015).

(56) References Cited

OTHER PUBLICATIONS

PCT/US2024/036259 International Search Report and Written Opinion dated Dec. 3, 2024.
Summerton, James E., Morpholino, siRNA, and S-DNA Compared: Impact of Structure and Mechanism of Action on Off-Target Effects and Sequence Specificity. Current Topics in Medicinal Chemistry 7:651-660 (2007).

* cited by examiner

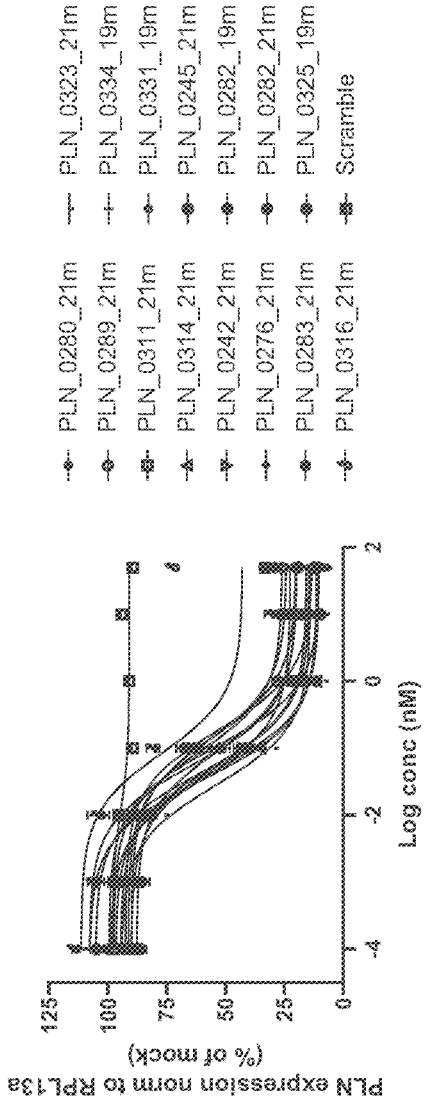
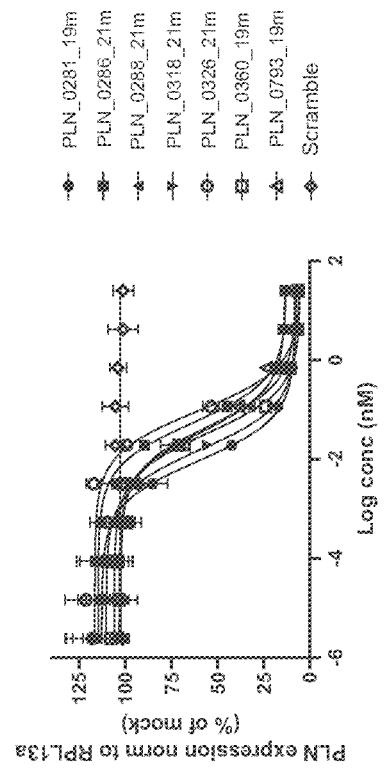
FIG. 4A
FIG. 4B

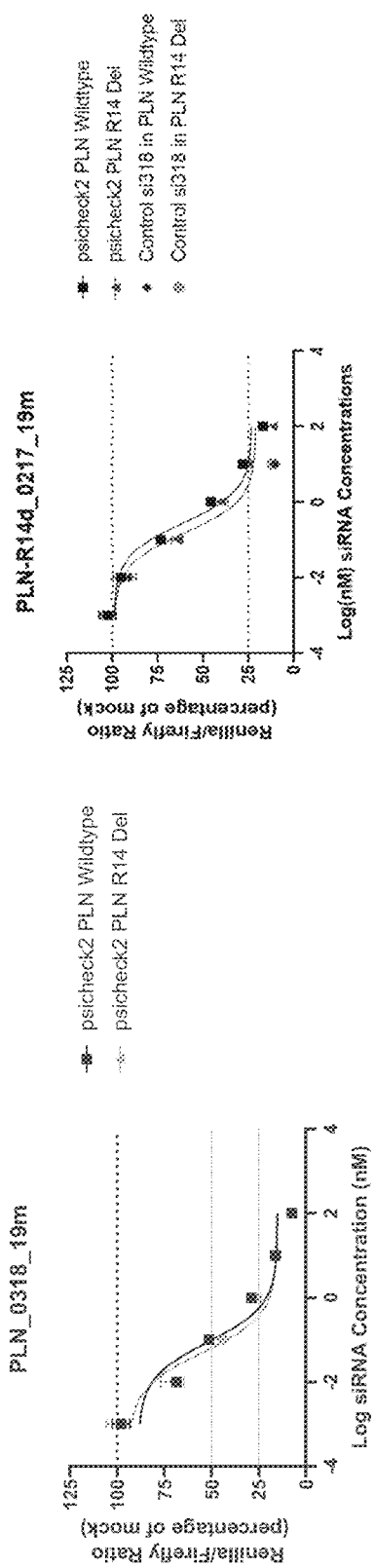
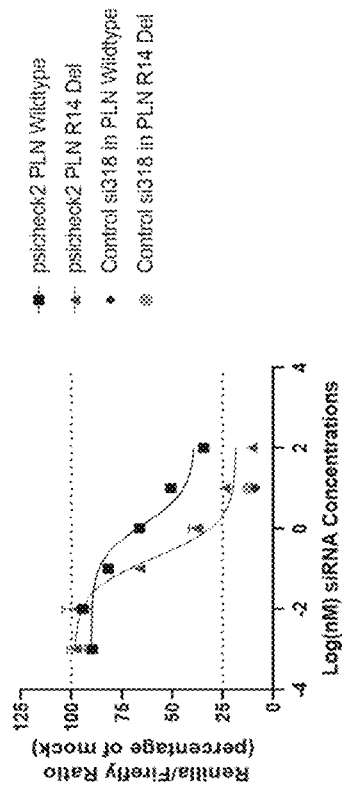
FIG. 9A
FIG. 9B
FIG. 9C

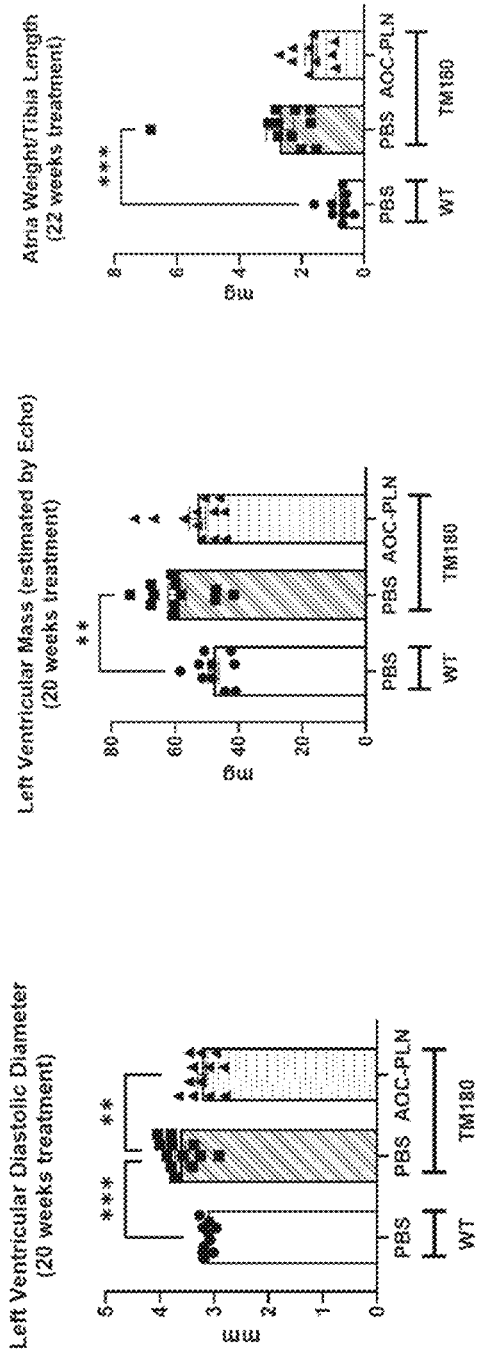
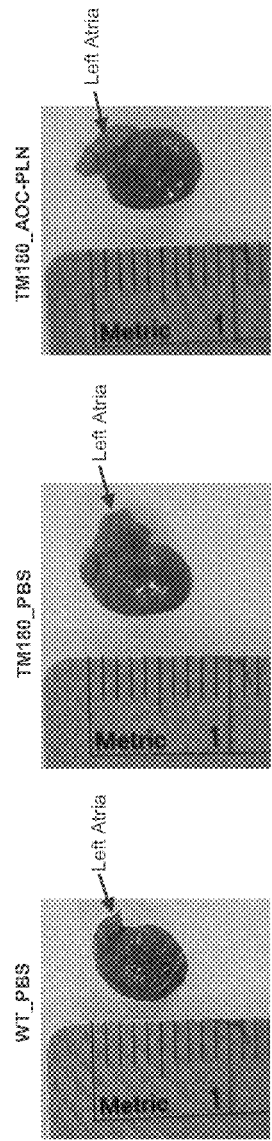
FIG. 18B
FIG. 18C
FIG. 18D
FIG. 18E

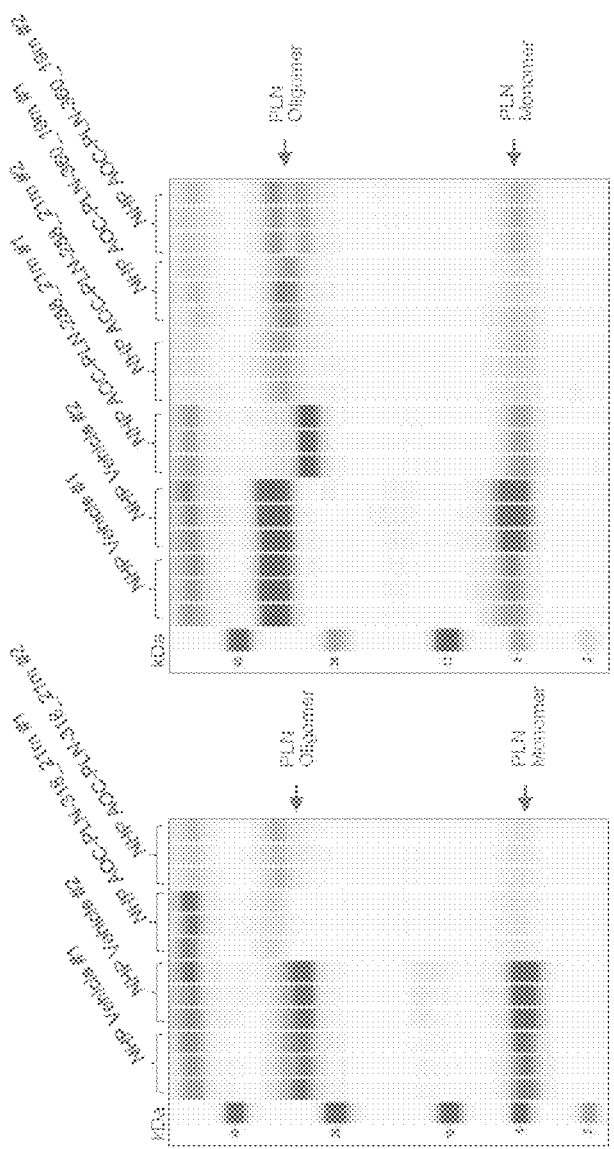
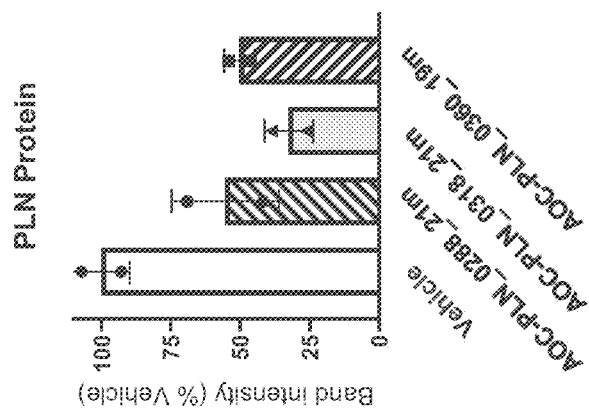
FIG. 20A
FIG. 20B

COMPOSITIONS COMPRISING PLN-TARGETING ANTI-TRANSFERRIN RECEPTOR ANTIBODY-POLYNUCLEOTIDES AND METHODS OF USE THEREOF TO TREAT CARDIOMYOPATHY

CROSS-REFERENCE

This application claims the benefit of U.S. Provisional Application No. 63/511,450 filed Jun. 30, 2023, which is incorporated herein by reference in its entirety.

REFERENCE TO A SEQUENCE LISTING XML

This application contains a Sequence Listing which has been submitted electronically in XML format. The Sequence Listing XML is incorporated herein by reference. Said XML file, created on Oct. 8, 2024, is named 45532-774_201_SL.xml and is 449,101 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effects over multiple cell divisions. As such, RNAi represents a viable method useful for drug target validation, gene function analysis, pathway analysis, and disease therapeutics.

Cycling of calcium is the underlying basis of cardiac function and is commonly dysregulated in several forms of cardiac diseases. Altered calcium homeostasis results in arrhythmias and heart failure, which are lead causes of sudden death and cardiac transplantation.

Phospholamban (PLN) functions as a natural reversible inhibitor of calcium cycling in cardiomyocytes, via inhibition of the Sarcoendoplasmic Reticulum Calcium ATPase (SERCA) pump. PLN binding to SERCA reduces SERCA affinity for calcium, which results in depressed cardiac contraction and slower rate of relaxation. As such, exacerbated activity of PLN is associated with cardiac diseases, which are caused by low SERCA expression levels or by super-inhibitory effect of PLN on SERCA associated with PLN mutations. The reduction of PLN expression levels in the heart could therefore be used as a therapeutic approach to restore calcium homeostasis and improve cardiac function.

A number of PLN mutations have been described to result in cardiomyopathies. PLN Arg14del (R14del) causes arrhythmogenic and dilated cardiomyopathy and is of high prevalence in the population of Dutch descent. R14del is the most prevalent disease variant of the PLN gene. Disease onset commonly occurs in middle age and is characterized by severe ventricular arrhythmias and/or ventricular dilation that progresses rapidly to heart failure. Traditional antiarrhythmic and heart failure medications proved ineffective in the R14del patient population, requiring most carriers to receive an implantable cardioverter-defibrillator to mitigate the risk of sudden cardiac death. As heart failure progresses, patients often need to be placed under cardiac mechanical support and eventually require cardiac transplantation.

Current understanding of the PLN R14del disease suggests that the mutant protein acts as a toxic peptide that affects calcium signaling, proteostasis, and cardiac metabolism. Antibody oligonucleotide conjugates offer promising therapeutic potential by reducing the expression of the mutant PLN. Antibody oligonucleotide conjugates can target regions outside the mutated area, thereby reducing both wild-type and mutant alleles, or they can be specifically designed to target the mutated region with the aim of preferentially knocking down the mutant transcript. All carriers of this mutation identified to date are heterozygous, having one wild-type and one R14del PLN allele.

Other PLN mutations include Arg9Cys (R9C) and Arg25Cys (R25C) and these mutations are gain of function mutations associated with expression of toxic PLN protein. In addition, cardiomyopathy associated with PLN includes dilated cardiomyopathy associated with TTN, LMNA, RI3M20, SCN5A, MYH7, TNNT2, and TPM1 mutations.

Furthermore, cardiomyopathy associated with PLN includes hypertrophic cardiomyopathy associated with MYH7, MYBPC3, TNNT2, TNNC, and TPM1 mutations. Hypertrophic cardiomyopathy affects 1 in 500 individuals. Approximately 50% of the cases are monogenic disorders due to mutations of sarcomere proteins that cause increased myofilament calcium sensitivity. Mutant hearts show characteristic diastolic dysfunction and develop hypertrophy. Thickening of the interventricular septum can result in outflow tract obstruction, leading to disease symptoms.

Current treatments that include standard heart failure and antiarrhythmic treatment, pacemaker, defibrillator implantation and surgical ablation, may alleviate the symptoms but cannot be effective treatment to the cardiac diseases caused by genetic abnormalities of PLN gene. However, there are no specific treatments available that target PLN. There is a need to develop therapeutics for treating cardiomyopathy associated with PLN.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

In the present disclosure, methods and compositions of antibody-oligonucleotide conjugates (AOC) targeting PLN mRNA are provided to inhibit the expression of PLN. In addition, the present disclosure provides methods and compositions to treat cardiomyopathy associated with PLN with antibody-oligonucleotide conjugates to deliver the oligonucleotide (e.g., inhibitory oligonucleotide) that target PLN mRNA and inhibit or decrease the expression of PLN in the cell or tissue. In addition, the present disclosure provides methods and compositions to treat cardiomyopathy associated with a genetic PLN variant with antibody-oligonucleotide conjugates to deliver the oligonucleotide (e.g., inhibitory oligonucleotide) that targets PLN mRNA comprising the genetic PLN variant, and inhibit the expression of PLN in cardiac cell or cardiac tissue.

Disclosed herein, in certain aspects, are polynucleic acid molecules and pharmaceutical compositions for modulating a gene associated with cardiomyopathy, especially PLN. In some aspects, also described herein are methods of treating cardiomyopathy associated with a genetic PLN variant with a polynucleic acid molecule or a polynucleic acid molecule conjugate as disclosed herein. In some aspects, also described herein are methods of treating dilated cardiomyopathy associated with a genetic PLN variant with a polynucleic acid molecule or a polynucleic acid molecule conjugate as disclosed herein.

Disclosed herein, in certain aspects, is a polynucleotide conjugate comprising an anti-transferrin receptor antibody or antigen-binding fragment thereof conjugated to a polynucleotide that hybridizes to a target sequence of PLN mRNA and mediates RNA interference against PLN mRNA in a muscle cell. In some instances, the polynucleotide conjugate mediates RNA interference against PLN mRNA preferentially in a muscle cell. In some instances, the polynucleotide conjugate mediates RNA interference against PLN mRNA preferentially in a cardiac muscle cell. In some instances, the target sequence of the PLN mRNA is a genetic PLN variant. In some instances, the genetic PLN variant comprises a genetic mutation selected from Arg14del (R14del), Arg9Cys (R9C), and Arg25Cys (R25C). In some instances, the polynucleotide hybridizes to at least 8 contiguous bases of the target sequence of the PLN mRNA. In some instances, the polynucleotide is from about 8 to about 50 nucleotides in length or from about 10 to about 30 nucleotides in length. In some instances, the polynucleotide is a single-stranded antisense polynucleotide or a double-stranded polynucleotide. In some aspects, the single-stranded antisense polynucleotide is an antisense oligonucleotide (ASO). In some instances, the ASO comprises a nucleic acid sequence having at least 80%, 85%, 90%, 95%, or 100% homology with a sequence selected from SEQ ID NOs: 265-276. In some instances, the ASO comprises a nucleic acid sequence having at least 14, 15, 16, 17, or 18 consecutive nucleotides from a sequence selected from SEQ ID NOs: 265-276, with no more than 1, 2, or 3 mismatches. In some instances, the ASO comprises a nucleic acid sequence selected from SEQ ID NOs: 265-276. In some aspects, the double-stranded polynucleotide is a small interfering RNA (siRNA) comprising a guide strand and a passenger strand. In some instances, the passenger strand comprises a nucleic acid sequence having at least 80%, 85%, 90%, 95%, or 100% homology with a sequence selected from SEQ ID NOs: 133-264, 314-327, 344-359. In some instances, the guide strand of comprises a nucleic acid sequence having at least 80%, 85%, 90%, 95%, or 100% homology with a sequence selected from SEQ ID NOs: 1-132, 300-313, 328-343. In some instances, the passenger strand comprises a nucleic acid sequence having at least 16, 17, 18, 19, 20, or 21 consecutive nucleotides from a sequence selected from SEQ ID NOs: 133-264, 314-327, 344-359, with no more than 1, 2, or 3 mismatches. In some instances, the guide strand comprises a nucleic acid sequence having at least 16, 17, 18, 19, 20, or 21 consecutive nucleotides from a sequence selected from SEQ ID NOs: 1-132, 300-313, 328-343, with no more than 1, 2, or 3 mismatches. In some instances, the guide strand comprises a nucleic acid sequence of SEQ ID NOs: 37, 49, 74, and the passenger strand comprises a nucleic acid sequence of SEQ ID NOs: 169, 181, 206. In some aspects, the polynucleotide hybridizes to a target sequence of the PLN mRNA and mediates RNA interference against the PLN mRNA via RNase H activity in the muscle cell.

In some aspects, the polynucleotide comprises at least one 2' modified nucleotide, at least one modified internucleotide linkage, or at least one inverted abasic moiety. In some aspects, the at least one 2' modified nucleotide comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide; comprises locked nucleic acid (LNA) or ethylene nucleic acid (ENA); or comprises a combination thereof. In some aspects, the at least one modified internucleotide linkage comprises a phosphorothioate linkage or a phosphorodithioate linkage. In some aspects, the polynucleotide comprises a 5'-terminal vinylphosphonate modified nucleotide. In some instances, the anti-transferrin receptor antibody or antigen binding fragment thereof comprises a non-human antibody or antigen binding fragment thereof, a human antibody or antigen binding fragment thereof, a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), or a camelid antibody or antigen binding fragment thereof. In some instances, the polynucleotide conjugate has a polynucleotide to antibody ratio of from about 1 to about 4. In some instances, the polynucleotide conjugate comprises a linker connecting the anti-transferrin receptor antibody or antigen-binding fragment thereof to the polynucleotide. In some instances, mediation of RNA interference against the PLN mRNA in the muscle cell modulates cardiomyopathy in a subject. In some instances, the cardiomyopathy is associated with PLN. In some instances, the cardiomyopathy associated with PLN is associated with a PLN genetic variant. In some instances, the PLN genetic variant has a genetic mutation selected from Arg14del (R14del), Arg9Cys (R9C), and Arg25Cys (R25C). In some aspects, the cardiomyopathy associated with PLN is a dilated cardiomyopathy. In some instances, the dilated cardiomyopathy is a genetic dilated cardiomyopathy associated with TTN, LMNA, RI3M20, SCN5A, MYH7, TNNT2, and TPMI mutations. In some aspects, the cardiomyopathy associated with PLN is hypertrophic cardiomyopathy. In some instances, the hypertrophic cardiomyopathy is associated with MYH7, MYBPC3, TNNT2, TNNC, and TPM1 mutations.

Also disclosed herein, in certain aspects, is a polynucleotide molecule for modulating PLN mRNA expression, comprising a nucleic acid sequence at least 80%, 85%, 90%, 95%, or 100% homology with a sequence selected from SEQ ID NOs: 265-276.

Also disclosed herein, in certain aspects, is a polynucleotide molecule for modulating PLN mRNA expression, comprising a nucleic acid sequence at least sequence having at least 16, 17, 18, 19, 20, or 21 consecutive nucleotides from a sequence selected from SEQ ID NOs: 265-276 with no more than 1, 2, or 3 mismatches.

Also disclosed herein, in certain aspects, is a polynucleotide molecule for modulating PLN mRNA expression, comprising a guide strand and a passenger strand, wherein the guide strand comprises a nucleic acid sequence at least 80%, 85%, 90%, 95%, or 100% homology with a sequence selected from SEQ ID NOs: 1-132, 300-313, 328-343. In some instances, the passenger strand comprises a nucleic acid sequence at least 80%, 85%, 90%, 95%, or 100% homology with a sequence selected from SEQ ID NOs: 133-264, 314-327, 344-359. In some instances, the passenger strand comprises a nucleic acid sequence comprises a nucleic acid sequence at least sequence having at least 16, 17, 18, 19, 20, or 21 consecutive nucleotides from a sequence selected from SEQ ID NOs: 133-264, 314-327, 344-359 with no more than 1, 2, or 3 mismatches.

Also disclosed herein, in certain aspects, is a pharmaceutical composition comprising the polynucleotide conjugate as disclosed herein or the polynucleotide molecule as disclosed herein, and a pharmaceutically acceptable excipient. In some instances, the pharmaceutical composition is formulated for parenteral, oral, intranasal, buccal, rectal, transdermal, intravenous, subcutaneous, or intrathecal administration.

Also disclosed herein, in certain aspects, is a method of treating cardiomyopathy in a subject in need thereof comprising administering to said subject a polynucleotide conjugate as disclosed herein or a polynucleotide molecule of as disclosed herein or a pharmaceutical composition of as disclosed herein, thereby treating cardiomyopathy in said subject. In some instances, the cardiomyopathy is associated with PLN. In some aspects, the cardiomyopathy associated with PLN is a genetic cardiomyopathy associated with a genetic PLN variant. In some instances, the PLN genetic variant comprises a genetic mutation selected from Arg14del (R14del), Arg9Cys (R9C), and Arg25Cys (R25C). In some aspects, the cardiomyopathy associated with PLN is a dilated cardiomyopathy. In some instances, the dilated cardiomyopathy is a genetic dilated cardiomyopathy associated with TTN, LMNA, RI3M20, SCN5A, MYH7, TNNT2, and TPMI mutations. In some aspects, the cardiomyopathy associated with PLN is hypertrophic cardiomyopathy. In some instances, the hypertrophic cardiomyopathy is associated with MYH7, MYBPC3, TNNT2, TNNC, and TPM1 mutations. In some instances, the polynucleotide conjugate is administered parenterally, orally, intranasally, buccally, rectally, transdermally, intravenously, subcutaneously, or intrathecally.

Also disclosed herein, in certain aspects, is a method of modulating PLN expression or activity in a muscle cell comprising contacting the muscle cell with a polynucleotide conjugate as disclosed herein or a polynucleotide molecule as disclosed herein or a pharmaceutical composition as disclosed herein, thereby modulating PLN expression or activity in the muscle cell.

Also disclosed herein, in certain aspects, is a method of modulating PLN expression or activity in a subject in need thereof comprising administering to said subject a polynucleotide conjugate as disclosed herein or a polynucleotide molecule as disclosed herein or a pharmaceutical composition as disclosed herein, thereby modulating PLN expression or activity in the subject.

Also disclosed herein, in certain aspects, is a kit comprising the polynucleic acid molecule conjugate or the pharmaceutical composition as described herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

FIG. 4A is a representative plot showing the dose response curve of PLN mRNA expression levels in Human iPS-cardiomyocytes$^2$ (iCM$^2$) cells transfected with increasing concentrations of 15 PLN siRNAs (as referred to by their compound names represented in Table 10) at 3 days post siRNA transfection.

FIG. 4B is a representative plot showing the dose response curve of PLN mRNA expression levels in Human iPS-cardiomyocytes$^2$ (iCM$^2$) cells transfected with increasing concentrations of seven different PLN siRNAs (corresponding to siRNAs represented in Table 11) at 3 days post siRNA transfection.

FIG. 8A is a representative bar graph showing in vivo PLN siRNA concentrations in heart tissue obtained from mice at 28 days after a single IV injection of 3 mg/kg CD71_PLN AOCs. FIG. 8B is a representative bar graph showing in vivo PLN mRNA expression levels in heart tissue obtained from mice at 28 days after a single IV injection of 3 mg/kg of the AOC-PLN_0288_21m AOC.

FIGS. 9A-9C are representative plots showing *renilla* intensity in HEK cells expressing the recombinant genetic PLN variant R14del (R14d) (triangles) or the recombinant wild-type PLN (squares) transfected with increasing concentrations of PLN siRNA.

FIG. 9A is a representative plot showing *renilla* intensity levels in HEK cells expressing the recombinant PLN variant R14del (R14d) (triangles) or the recombinant wild-type PLN (squares) transfected with increasing concentrations of PLN_0318_19m siRNA.

FIG. 9B is a representative plot showing *renilla* intensity levels in HEK cells expressing the recombinant PLN variant R14del (R14d) (triangles) or the recombinant wild-type PLN (squares) transfected with increasing concentrations of PLN-R14d_0217_19m siRNA.

FIG. 9C is a representative plot showing *renilla* intensity levels in HEK cells the recombinant PLN variant R14del (R14d) (triangles) or the recombinant wild-type PLN (squares) transfected with increasing concentrations of PLN-R14d_0219_19m siRNA.

FIG. 10A is a representative plot showing *renilla* intensity levels using a R14del (circles) and wild-type PLN (squares) luciferase reporter assay in HEK cells transfected with siRNAs targeting the R14del allele (19-mer allele-selective of siRNA library) at a concentration of 100 nM at 48 hours after transfection.

FIG. 10B is a representative plot showing *renilla* intensity levels using a R14del luciferase reporter assay in HEK cells transfected with siRNAs targeting the R14del allele (21-mer allele-selective of siRNA library targeting the R14del allele) at a concentration of 100 nM at 48 hours after transfection. Square data points represent the wild-type PLN allele reporter, and circle data points represent the PLN R14del reporter (N=3, mean±SD).

FIGS. 18A-18E show that AOC-PLN improved cardiac functions and remodeling in the Tpm1 E180G cardiomyopathy mouse model.

FIG. 18A show representative bar graphs of percent cardiac ejection fraction in hearts of Tpm1 E180G cardiomyopathy mice that have been administered AOC-PLN for 6, 12, or 20 weeks, respectively.

FIG. 18B is a representative bar graph showing the size of the left ventricular diameter in hearts of Tpm1 E180G cardiomyopathy mice that have been administered AOC-PLN.

FIG. 18C is a representative bar graph showing the mass of the left ventricle in hearts of Tpm1 E180G cardiomyopathy mice that have been administered AOC-PLN.

FIG. 18D is a representative bar graph showing the atria size in hearts of Tpm1 E180G cardiomyopathy mice that have been administered AOC-PLN.

FIG. 18E illustrates pictures of left atria of hearts of Tpm1 E180G cardiomyopathy mice that have been administered AOC-PLN.

FIG. 19A shows a representative bar graph of PLN mRNA transcript levels in hearts obtained from cynomolgus monkeys that have been administered a single injection of AOC-PLN_0288_21m, AOC-PLN_0318_21m, or AOC-PLN_0360_19m at a dose of 3 mg/kg.

FIG. 19B is a representative bar graph showing relative PLN mRNA expression levels in the hearts obtained from cynomolgus monkeys that have been administered a single injection of AOC-PLN_0288_21m, AOC-PLN_0318_21m, or AOC-PLN_0360_19m at a dose of 3 mg/kg.

FIG. 19C shows representative bar graphs of PLN siRNA tissue concentrations in the hearts of cynomolgus monkeys that have been administered a single injection of AOC-PLN_0288_21m, AOC-PLN_0318_21m, or AOC-PLN_0360_19m at a dose of 3 mg/kg.

FIGS. 20A-20B show PLN protein expression levels in hearts obtained from cynomolgus monkeys that have been administered a single injection of AOC-PLNs (a-TfR1 antibody conjugated with PLN targeting siRNAs): AOC-PLN_0288_21m, AOC-PLN_0318_21m, or AOC-PLN_0360_19m at a dose of 3 mg/kg. FIG. 20A shows the chromatogram image of PLN proteins detected using a PLN specific antibody by Jess protein electrophoresis of hearts of cynomolgus monkeys that have been administered a single injection of AOC-PLN_0288_21m, AOC-PLN_0318_21m, or AOC-PLN_0360_19m at a dose of 3 mg/kg. FIG. 20B is a representative bar graph showing quantification of relative PLN protein levels determined by Jess protein electrophoresis in hearts of cynomolgus monkeys that have been administered a single injection of AOC-PLN_0288_21m, AOC-PLN_0318_21m, or AOC-PLN_0360_19m at a dose of 3 mg/kg.

DETAILED DESCRIPTION OF THE DISCLOSURE

Figure 1:
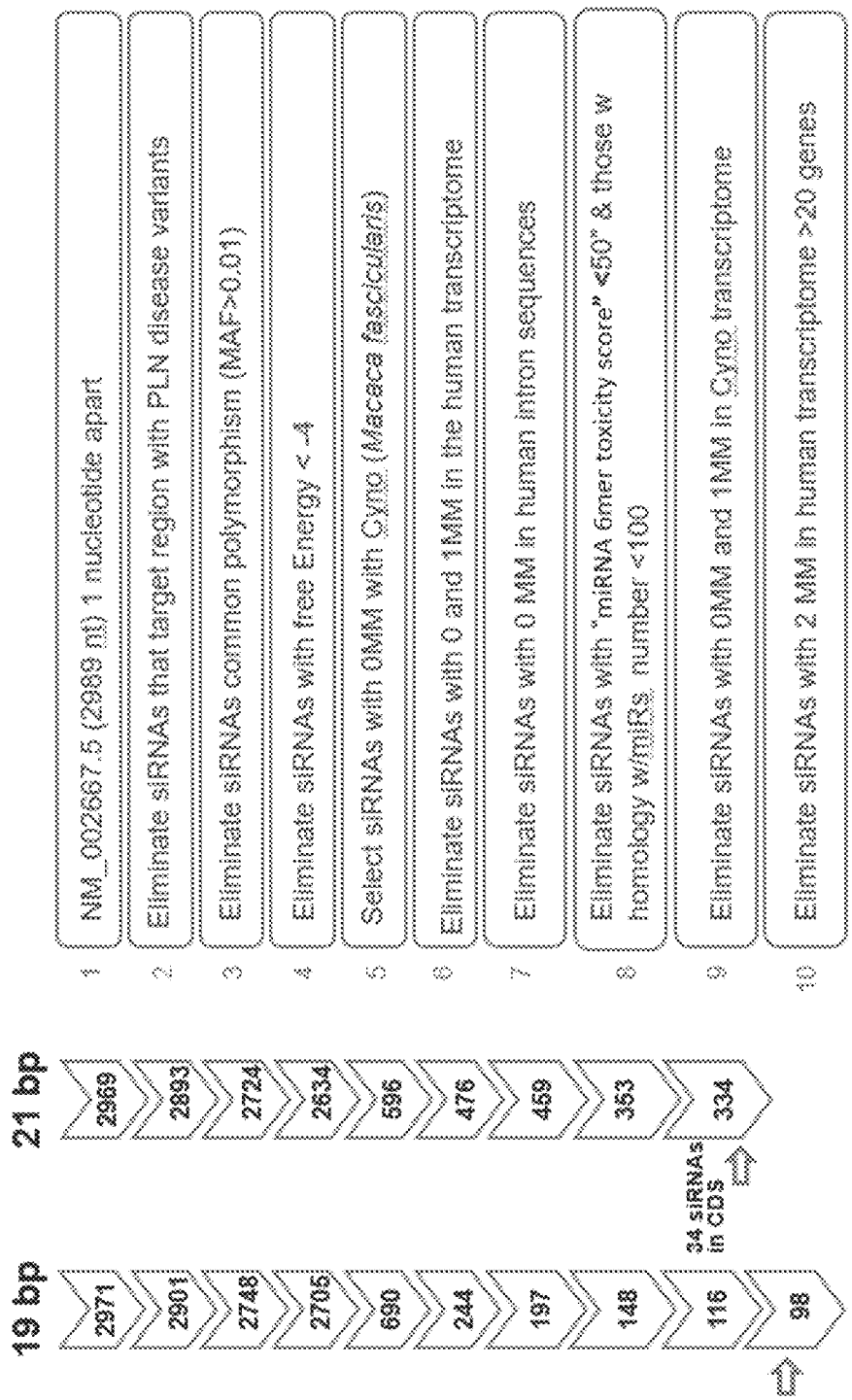
FIG. 1 shows a flowchart diagram of in silico selection of PLN siRNA.

This present disclosure provides methods and compositions for antibody-oligonucleotide conjugate (AOC) targeting PLN mRNA which can inhibit the expression of PLN. Also provided herein includes methods and compositions of antibody-oligonucleotide conjugates that are able to deliver the oligonucleotide targeting the expression of PLN mRNA to the cardiac tissue, preferentially to the cardiac muscle cells.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

The present disclosure provides, in certain aspects, oligonucleotide molecules or antibody-oligonucleotides conjugates (AOC) targeting PLN mRNA, which are capable of inhibiting or modulating the expression of PLN. In some aspects, the present disclosure provides methods of modulating PLN mRNA expression using the oligonucleotide molecules or antibody-oligonucleotides conjugates (AOC) targeting PLN mRNA. In some aspects, described herein include polynucleic acid molecules (interchangeably used with the terms "polynucleotide" or "oligonucleotide") and polynucleic acid molecule conjugates for the treatment of cardiomyopathy. In some instances, the polynucleic acid molecule conjugates described herein have or show enhanced intracellular uptake, stability, and/or efficacy. In some cases, the polynucleic acid molecule conjugates comprise an antibody or antigen binding fragment thereof conjugated to a polynucleic acid molecule. In some cases, the polynucleic acid molecules that hybridize to target sequences of PLN mRNA, preferably human PLN mRNA. In some cases, the polynucleic acid molecules that hybridize to target sequences comprising a mutation in the PLN mRNA.

In some aspects, described herein includes methods of treating cardiomyopathy with PLN in a subject in need thereof, comprising administering to the subject a polynucleic acid molecule or a polynucleic acid molecule conjugate described herein.

In some aspects, described herein includes methods of treating cardiomyopathy associated with a genetic PLN variant comprising administering to a subject a polynucleic acid molecule or a polynucleic acid molecule conjugate described herein.

In some aspects, described herein includes methods of treating cardiomyopathy associated with the PLN variant including one or more mutations e.g., Arg14del (R14del), Arg9Cys (R9C) or Arg25Cys (R25C) by administering to a subject in need thereof a polynucleic acid molecule or a polynucleic acid molecule conjugate described herein.

In some aspects, described herein includes methods of treating dilated cardiomyopathy associated with TTN, LMNA, RI3M20, SCN5A, MYH7, TNNT2, and TPM1 mutations by administering to a subject in need thereof a polynucleotide acid molecule or a polynucleic acid molecule conjugate described herein.

In some aspects, described herein includes methods of treating hypertrophic cardiomyopathy associated with MYH7, MYBPC3, TNNT2, TNNC, and TPM1 mutations by administering to a subject in need thereof a polynucleotide acid molecule or a polynucleic acid molecule conjugate described herein.

Polynucleic Acid Molecules

In certain aspects, a polynucleic acid molecule hybridizes to a target sequence of PLN gene (e.g., PLN mRNA). In some instances, a polynucleic acid molecule described herein hybridizes to a target sequence of human PLN gene (e.g., human PLN mRNA) and reduces the expression of PLN mRNA in cardiac muscle cells.

In certain aspects, a polynucleic acid molecule hybridizes to a target sequence of the PLN mRNA variant. In some instances, a polynucleic acid molecule described herein hybridizes to a target sequence of a genetic PLN variant having a mutation that includes Arg14del (R14del), Arg9Cys (R9C) or Arg25Cys (R25C) and reduces the expression of PLN mRNA in cardiac muscle cells. In some instances, a polynucleic acid molecule described herein hybridizes to a target sequence of PLN mRNA and reduces the expression of PLN mRNA in subject with dilated cardiomyopathy associated with TTN, LMNA, RI3M20, SCN5A, MYH7, TNNT2, and TPMI mutations. In some instances, a polynucleic acid molecule described herein hybridizes to a target sequence of PLN mRNA and reduces the expression of PLN mRNA in subject with hypertrophic cardiomyopathy associated with MYH7, MYBPC3, TNNT2, TNNC, and TPM1 mutations In some instances, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 1-132. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 1-132. In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 133-264. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 133-264. In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 300-313. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 300-313. In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 314-327. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 314-327. In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 328-343. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 328-343. In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 344-359. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 344-359.

In some embodiments, the polynucleic acid molecule comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 265-276. In some instances, the polynucleic acid molecule comprises a nucleic acid sequence comprising at least 14, 15, 16, 17, 18, 19, 20, or 21 consecutive nucleotide sequences with no more than 1, 2, or 3 mismatches from SEQ ID NOs: 265-276.

In some embodiments, the polynucleic acid molecule comprises a single-stranded polynucleotide (e.g., an antisense oligonucleotide (ASO)). In some instances, the single-stranded polynucleotide (e.g., an antisense oligonucleotide) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 265-276. In some instances, the single-stranded polynucleotide (e.g., an antisense oligonucleotide) comprises a nucleic acid sequence comprising at least 14, 15, 16, 17, 18, 19, 20, or 21 consecutive nucleotide sequences with no more than 1, 2, or 3 mismatches from SEQ ID NOs: 265-276. In some instances, single-stranded polynucleotide (e.g., an antisense oligonucleotide (ASO)) comprises a nucleic acid sequence as presented in Tables 12A-12B.

In some instances, the ASO is a gapmer or a mixmer. In some instances, the ASO comprises a central region of consecutive DNA nucleotides flanked by a 5'-wing region and 3'-wing region, and the flanked 5' and/or 3' wing region comprises one or more modified nucleotides (e.g., locked nucleic acid (LNA) or 2'-methoxyethyl (2'-MOE) RNA). In some instances, the locked nucleic acid comprises at least one or more of a beta-D-oxy LNA, an alpha-L-oxy-LNA, a beta-D-amino-LNA, an alpha-L-amino-LNA, a beta-D-thio-LNA, an alpha-L-thio-LNA, a 5'-methyl-LNA, a beta-D-ENA, or an alpha-L-ENA. In some instances, the ASO comprises 3-10-3 configurations (3 nucleotides for 5'-flanked region, 10 nucleotides of central region, and 3 nucleotides for 3'-flanked region), 5-10-5 configuration (5 nucleotides for 5'-flanked region, 10 nucleotides of central region, and 5 nucleotides for 3'-flanked region), or X-Y-Z configuration where X can be 1-10 nucleotides, Y can be 8-20 nucleotides, Z can be 1-10 nucleotides.

In some embodiments, the polynucleic acid molecule is a double-stranded polynucleotides, comprising a first polynucleotide and a second polynucleotide. In some instances, the first polynucleotide comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 1-132, 300-313, and 328-343. In some instances, the first nucleotide comprises a nucleic acid sequence comprising at least 14, 15, 16, 17, 18, 19, 20, or 21 consecutive nucleotide sequences with no more than 1, 2, or 3 mismatches from SEQ ID NOs: 1-132, 300-313, and 328-343. In some cases, the second polynucleotide comprises a nucleic acid sequence having at least 50%, 55%, 60%, 65%, 70%, 75%, 80%, 85%, 90%, 95%, 96%, 97%, 98%, 99%, or 100% sequence identity to a nucleic acid sequence selected from SEQ ID NOs: 133-264, 314-327, and 344-359. In some instances, the second nucleotide comprises a nucleic acid sequence comprising at least 14, 15, 16, 17, 18, 19, 20, or 21 consecutive nucleotide sequences with no more than 1, 2, or 3 mismatches from SEQ ID NOs: 133-264, 314-327, and 344-359.

In some aspects, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the oligonucleotides are phosphorodiamidate morpholino oligomers (PMOs), which are short single-stranded oligonucleotide analogs that are built upon a backbone of morpholine rings connected by phosphorodiamidate linkages. In some instances, the RNA comprises siRNA. In some instances, the polynucleic acid molecule comprises siRNA.

In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 133-264, 314-327, and 344-359. In some instances, the sense strand (e.g., the passenger strand) comprises a nucleic acid sequence comprising at least 14, 15, 16, 17, 18, 19, 20, or 21 consecutive nucleotide sequences with no more than 1, 2, or 3 mismatches from SEQ ID NOs: 133-264. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-132, 300-313, and 328-343. In some instances, the antisense strand (e.g., the guide strand) comprises a nucleic acid sequence comprising at least 14, 15, 16, 17, 18, 19, 20, or 21 consecutive nucleotide sequences with no more than 1, 2, or 3 mismatches from SEQ ID NOs: 1-132, 300-313, and 328-343. In some instances, the siRNA comprises a sense strand and an antisense strand as presented in Table 10, Table 15A, and Table 15B.

In some aspects, the polynucleic acid molecule is from about 8 to about 50 nucleotides in length. In some embodiments, the polynucleic acid molecule is from about 10 to about 50 nucleotides in length. In some instances, the polynucleic acid molecule is from about 10 to about 30, from about 15 to about 30, from about 18 to about 25, from about 18 to about 24, from about 19 to about 23, or from about 20 to about 22 nucleotides in length.

In some aspects, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is about 8 nucleotides in length. In some instances, the polynucleic acid molecule is between about 8 and about 50 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 20 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some aspects, the polynucleic acid molecule comprises a first polynucleotide and a second polynucleotide. In some instances, the first polynucleotide is a sense strand (passenger strand) and the second polynucleotide is an antisense strand (guide strand) of a double stranded inhibitory RNA (dsRNA) or an siRNA. In some embodiments, each of the first and/or second polynucleotide is from about 8 to about 50 nucleotides in length. In some embodiments, each of the first and/or second polynucleotide is from about 10 to about 50 nucleotides in length. In some instances, the first polynucleotide is from about 10 to about 30, from about 15 to about 30, from about 18 to about 25, from about 18 to about 24, from about 19 to about 23, or from about 20 to about 22 nucleotides in length. In some instances, each of the first and/or second polynucleotide is about 50, 45, 40, 35, 30, 25, 24, 23, 22, 21, 20, 19, 18, 17 nucleotides in length.

In some aspects, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides. In some embodiments, the polynucleic acid molecule comprises a sense strand and an antisense strand, and the antisense strand includes two non-base pairing nucleotides as an overhang at the 3'-end while the sense strand has no overhang. Optionally, in such embodiments, the non-base pairing nucleotides have a sequence of TT, dTdT, or UU. In some embodiments, the polynucleic acid molecule comprises a sense strand and an antisense strand, and the sense strand has one or more nucleotides at the 5'-end that are complementary to the antisense sequence.

In some aspects, the sequence of the polynucleic acid molecule is at least 40%, 50%, 55%, 60%, 65%, 70%, 75%, 80%, 85%, 90%, 95%, 98%, 99%, or 99.5% complementary to a target sequence of PLN mRNA. In some embodiments, the target sequence of PLN mRNA is a nucleic acid sequence of about 10-50 nucleotides in length, about 15-50 nucleotides in length, 15-40 nucleotides in length, 15-30 nucleotides in length, or 15-25 nucleotides in length sequences in PLN mRNA, in which the first nucleotide of the target sequence starts at any nucleotide in PLN mRNA transcript in the coding region, or in the 5' or 3'-untranslated region (UTR).

In some aspects, the sequence of the polynucleic acid molecule is at least 50% complementary to a target sequence described herein. In some aspects, the sequence of the polynucleic acid molecule is at least 60% complementary to a target sequence described herein. In some aspects, the sequence of the polynucleic acid molecule is at least 70% complementary to a target sequence described herein. In some aspects, the sequence of the polynucleic acid molecule is at least 80% complementary to a target sequence described herein. In some aspects, the sequence of the polynucleic acid molecule is at least 90% complementary to a target sequence described herein. In some aspects, the sequence of the polynucleic acid molecule is at least 95% complementary to a target sequence described herein. In some aspects, the sequence of the polynucleic acid molecule is at least 99% complementary to a target sequence described herein. In some instances, the sequence of the polynucleic acid molecule is 100% complementary to a target sequence described herein.

In some aspects, the sequence of the polynucleic acid molecule has 5 or less mismatches to a target PLN mRNA sequence described herein. In some aspects, the sequence of the polynucleic acid molecule has 4 or less mismatches to a target PLN mRNA sequence described herein. In some instances, the sequence of the polynucleic acid molecule has 3 or less mismatches to a target PLN mRNA sequence described herein. In some cases, the sequence of the polynucleic acid molecule has 2 or less mismatches to a target PLN mRNA sequence described herein. In some cases, the sequence of the polynucleic acid molecule has 1 or less mismatches to a target PLN mRNA sequence described herein.

In some aspects, a group of polynucleic acid molecules among all the polynucleic acid molecules potentially binds to the target PLN mRNA sequence are selected to generate a polynucleic acid molecule library. In certain embodiments, such selection process is conducted in silico via one or more steps of eliminating less desirable polynucleic acid molecules from candidates using one or more selection criteria (e.g., similarity to miRNA sequences, expected off-target effects, etc.).

In some aspects, the specificity of the polynucleic acid molecule that hybridizes to a target sequence described herein is a 95%, 98%, 99%, 99.5% or 100% sequence complementarity of the polynucleic acid molecule to a target PLN mRNA sequence. In some instances, the hybridization is a high stringent hybridization condition.

In some aspects, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some aspects, the polynucleic acid molecule comprises natural or synthetic or artificial nucleotide analogues or bases. In some cases, the polynucleic acid molecule comprises combinations of DNA, RNA and/or synthetic or artificial nucleotide analogues. In some instances, the synthetic or artificial nucleotide analogues or bases comprise modifications at one or more of ribose moiety, phosphate moiety, base moiety, or a combination thereof.

In some aspects, nucleotide analogues or artificial nucleotide comprise a nucleotide with a modification at a 2' hydroxyl group of the ribose moiety. In some instances, the modification includes an H, OR, R, halo, SH, SR, $NH_2$, NHR, $NR_2$, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

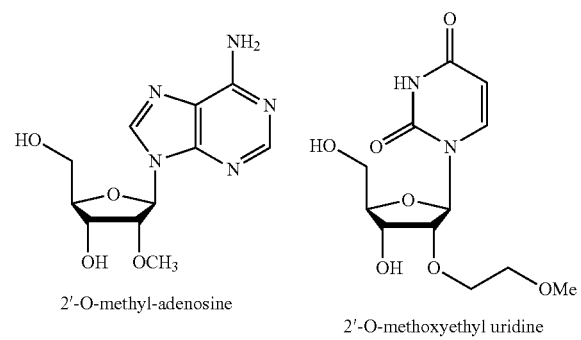

2'-O-methyl-adenosine

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

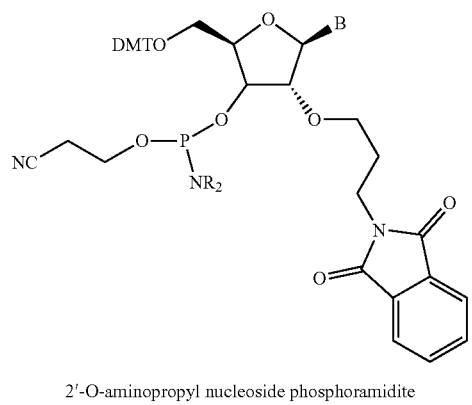

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

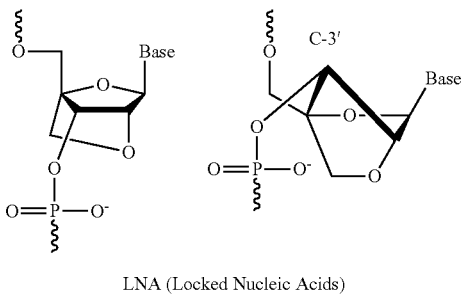

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

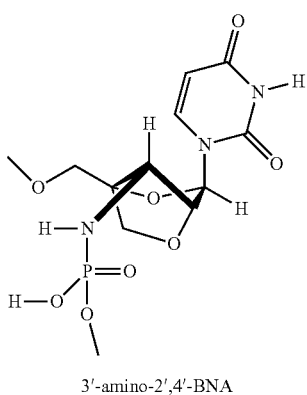

3'-amino-2',4'-BNA

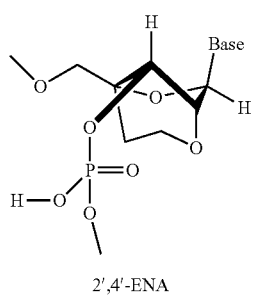

2',4'-ENA

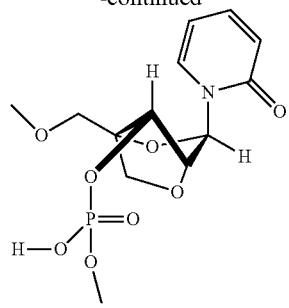

2',4'-BNA-2-pyridone

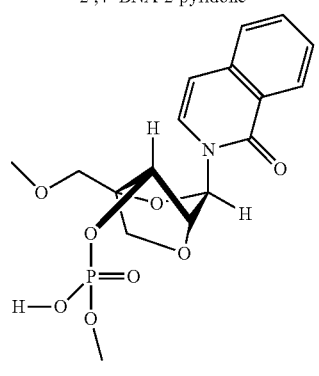

2',4'-BNA-1-isoquinolone

In some aspects, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some aspects, nucleotide analogues comprise modified bases such as, but not limited to, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some aspects, nucleotide analogues further comprise morpholinos, peptide nucleic acids (PNAs), methylphosphonate nucleotides, thiolphosphonate nucleotides, 2'-fluoro N3-P5'-phosphoramidites, 1',5'-anhydrohexitol nucleic acids (HNAs), or a combination thereof. Morpholinos or phosphorodiamidate morpholino oligomers (PMOs) comprise synthetic molecules whose structure mimics natural a nucleic acid structure, but deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

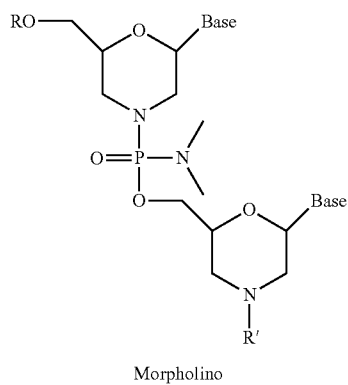

Morpholino

In some aspects, peptide nucleic acid (PNA) does not contain sugar ring or phosphate linkage, and the bases are attached and appropriately spaced by oligoglycine-like molecules, therefore, eliminating a backbone charge.

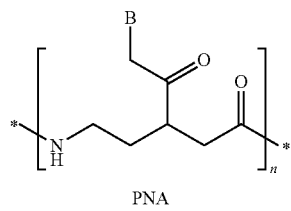

PNA

In some aspects, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5' linkage or 2'-5' linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

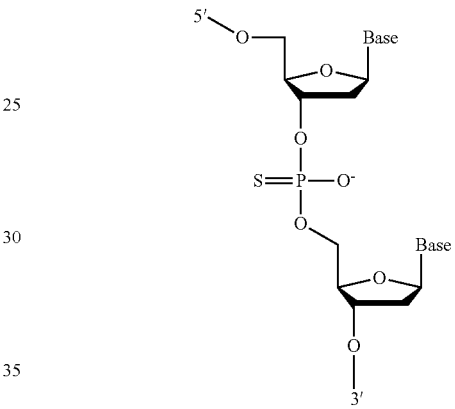

In some instances, the modification is a methyl or thiol modification such as methylphosphonate or thiolphosphonate modification. Exemplary thiolphosphonate nucleotide (left) and methylphosphonate nucleotide (right) are illustrated below.

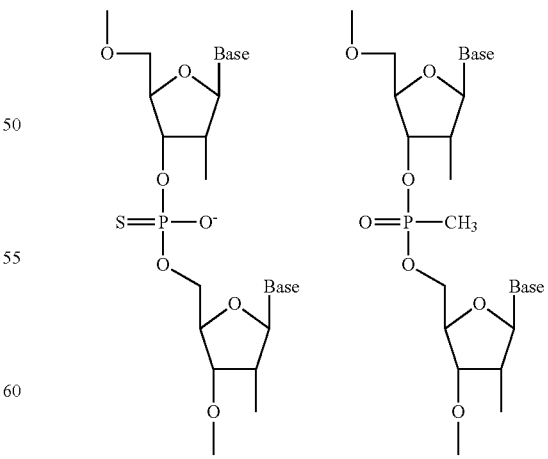

In some instances, a modified nucleotide includes, but is not limited to, 2'-fluoro N3-P5'-phosphoramidites illustrated as:

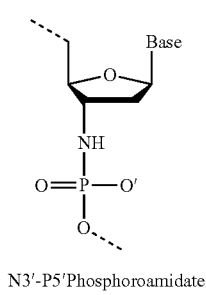

N3'-P5'Phosphoroamidate

In some instances, a modified nucleotide includes, but is not limited to a 5'-vinylphosphonate modified non-natural nucleotide selected from:

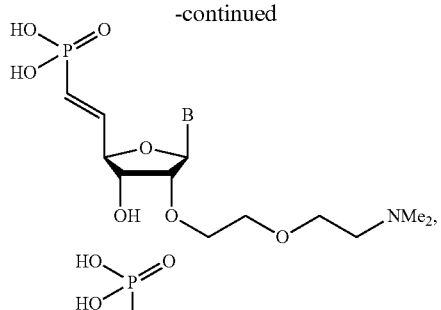

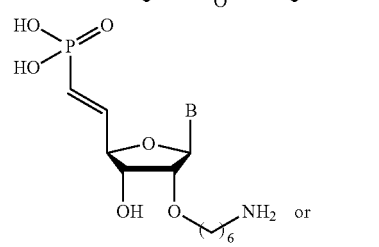

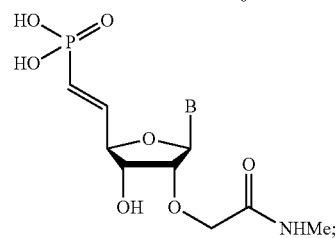

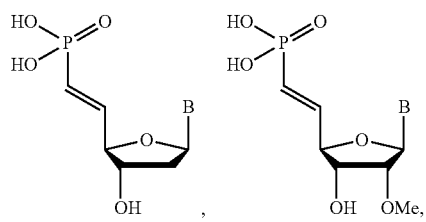

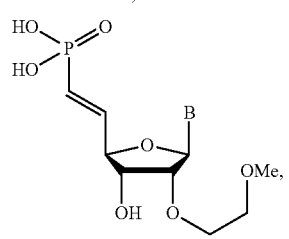

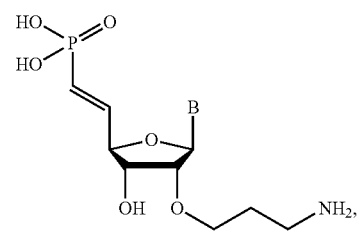

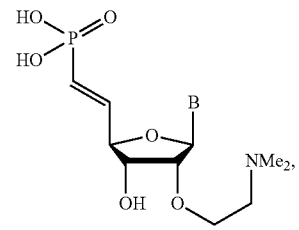

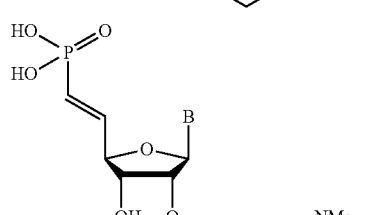

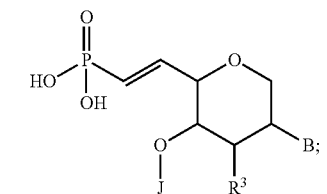

wherein B is a heterocyclic base moiety.

In some instances, a modified nucleotide includes, but is not limited to one 5'-vinylphosphonate modified non-natural nucleotide selected from:

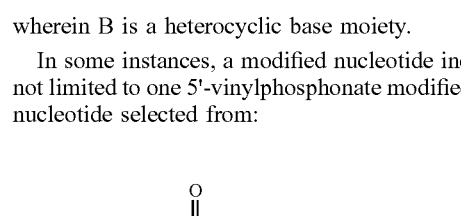

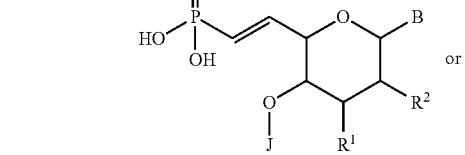

wherein B is a heterocyclic base moiety;
R$^1$, R$^2$, and R$^3$ are independently selected from hydrogen, halogen, alkyl or alkoxy; and
J is an internucleotide linking group linking to the adjacent nucleotide of the polynucleotide.

In some instances, a modified nucleotide includes, but is not limited to one 5'-vinylphosphonate modified non-natural nucleotide selected from:

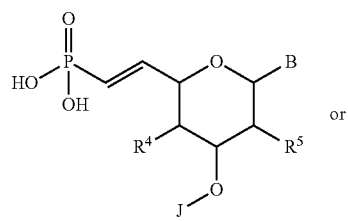

or

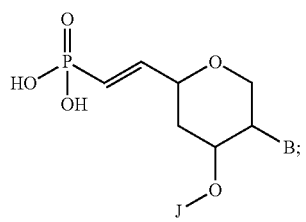

wherein B is a heterocyclic base moiety;

R⁴, and R⁵ are independently selected from hydrogen, halogen, alkyl or alkoxy; and J is an internucleotide linking group linking to the adjacent nucleotide of the polynucleotide.

In some instances, a modified nucleotide includes, but is not limited to one 5'-vinylphosphonate modified non-natural nucleotide selected from:

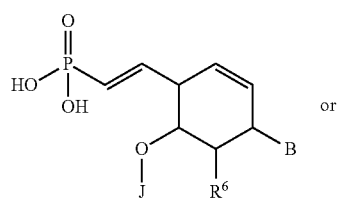

or

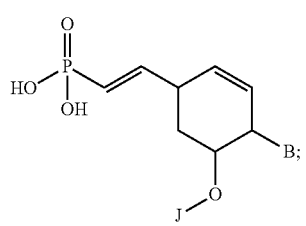

wherein B is a heterocyclic base moiety;

R⁶ is selected from hydrogen, halogen, alkyl or alkoxy; and

J is an internucleotide linking group linking to the adjacent nucleotide of the polynucleotide.

In some instances, a modified nucleotide includes, but is not limited to one 5'-vinylphosphonate modified non-natural nucleotide selected from locked nucleic acid (LNA) or ethylene nucleic acid (ENA).

In some instances, a modified nucleotide includes, but is not limited to one 5'-vinylphosphonate modified non-natural nucleotide selected from:

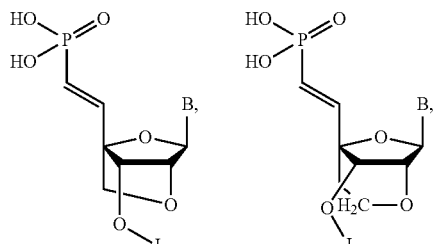

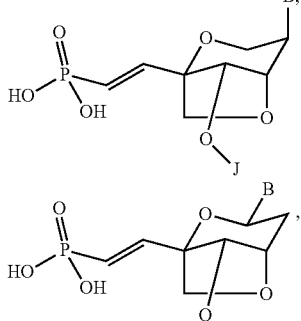

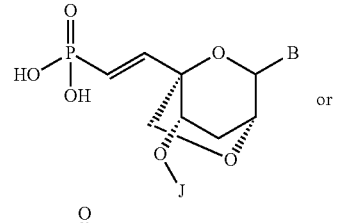

or

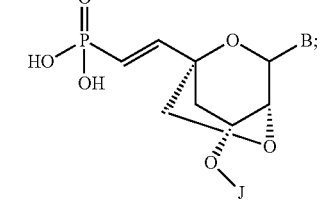

wherein B is a heterocyclic base moiety; and

J is an internucleotide linking group linking to the adjacent nucleotide of the polynucleotide.

In some instances, a modified nucleotide includes, but is not limited to one 5'-vinylphosphonate modified non-natural nucleotide selected from:

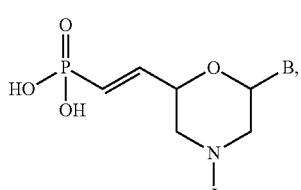

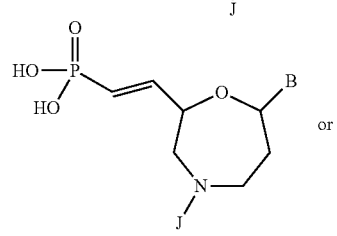

or

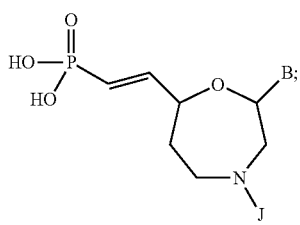

wherein B is a heterocyclic base moiety; and

J is an internucleotide linking group linking to the adjacent nucleotide of the polynucleotide.

In some instances, a modified nucleotide includes, but is not limited to one 5'-vinylphosphonate modified non-natural nucleotide selected from:

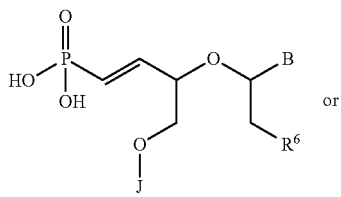

or

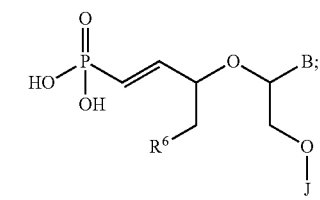

wherein B is a heterocyclic base moiety;

R6 is selected from hydrogen, halogen, alkyl or alkoxy; and

J is an internucleotide linking group linking to the adjacent nucleotide of the polynucleotide.

In some instances, a modified nucleotide includes, but is not limited to one 5'-vinylphosphonate modified non-natural nucleotide is:

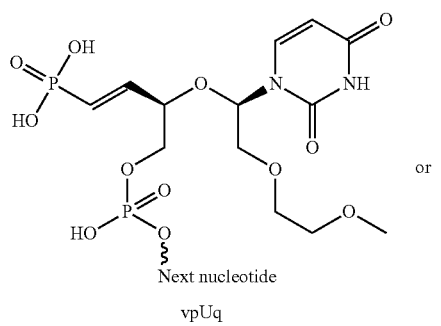

vpUq or

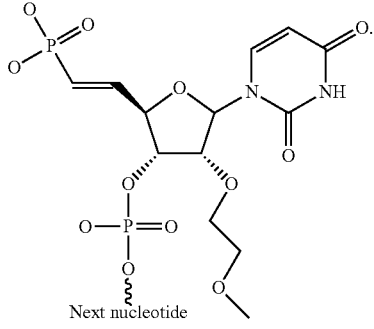

(vpUm)

In some instances, a modified nucleotide includes, but is not limited to, hexitol nucleic acid (or 1',5'-anhydrohexitol nucleic acids (HNA)) illustrated as:

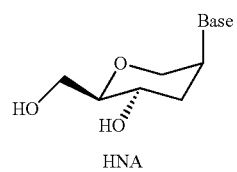

HNA

In some aspects, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some aspects, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—

N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100%, from about 10% to about 90%, from about 20% to about 100%, from about 10% to about 90%, from about 30% to about 100%, from about 30% to about 90%, from about 40% to about 100%, from about 40% to about 90%, from about 50% to about 100%, from about 50% to about 90%, from about 60% to about 100%, from about 60% to about 90% modification, from about 70% to about 100%, from about 70% to about 90%, from about 80% to about 100%, and from about 90% to about 100% modification.

In some cases, the polynucleic acid molecule comprises at least one of: from about 10% to about 80% modification, from about 20% to about 80%, from about 20% to about 70%, from about 30% to about 80%, from about 30% to about 70%, from about 40% to about 80%, from about 40% to about 70%, from about 50% to about 80%, from about 50% to about 70%, from about 60% to about 80%, from about 60% to about 70%, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogue described herein. In some embodiments, the polynucleic acid molecule comprises about 1, 2, 3, 4, 5, 6, 7, 8, 9, 10, 11, 12, 13, 14, 15, 16, 17, 18, 19, 20, 21, 22, 23, 24, or 25 modifications in which the modification comprises an artificial nucleotide analogue described herein.

In some aspects, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some aspects, a polynucleic acid molecule comprises a sense strand and antisense strand, and at least one of sense strand and antisense strands has a plurality of (e.g., two or more, three or more, four or more, five or more, six or more, seven or more, or eight or more, etc.) 2'-O-methyl or 2'-deoxy-2'-fluoro modified nucleotides. In some embodiments, where at least two out of the plurality of 2'-O-methyl or 2'-deoxy-2'-fluoro modified nucleotides are consecutive nucleotides. In some embodiments, where at least two consecutive 2'-O-methyl or 2'-deoxy-2'-fluoro modified nucleotides are located at the 5'-end of the sense strand and/or the antisense strand. In some embodiments, where at least two consecutive 2'-O-methyl or 2'-deoxy-2'-fluoro modified nucleotides are located at the 3'-end of the sense strand and/or the antisense strand. In some embodiments, the sense strand of polynucleic acid molecule includes at least four, at least five, at least six consecutive 2'-O-methyl modified nucleotides at its 5' end and/or 3' end, or both. Optionally, in such embodiments, the sense strand of polynucleic acid molecule includes at least one, at least two, at least three, at least four 2'-deoxy-2'-fluoro modified nucleotides at the 3' end of the at least four, at least five, at least six consecutive 2'-O-methyl modified nucleotides at the polynucleotides' 5' end, or at the 5' end of the at least four, at least five, at least six consecutive 2'-O-methyl modified nucleotides at polynucleotides' 3' end. Also optionally, such at least two, at least three, or at least four 2'-deoxy-2'-fluoro modified nucleotides are consecutive nucleotides.

In some aspects, a polynucleic acid molecule comprises a sense strand and antisense strand, and at least one of sense strand and antisense strands has 2'-O-methyl modified nucleotide located at the 5'-end of the sense strand and/or the antisense strand. In some embodiments, at least one of sense strand and antisense strands has 2'-O-methyl modified nucleotide located at the 3'-end of the sense strand and/or the antisense strand. In some embodiments, the 2'-O-methyl modified nucleotide located at the 5'-end of the sense strand and/or the antisense strand is a purine nucleotide. In some embodiments, the 2'-O-methyl modified nucleotide located at the 5'-end of the sense strand and/or the antisense strand is a pyridine nucleotide.

In some aspects, a polynucleic acid molecule comprises a sense strand and antisense strand, and the antisense strand has two or more consecutive 2'-deoxy-2'-fluoro modified nucleotides at 5'-end. In some embodiments, a polynucleic acid molecule comprises a sense strand and antisense strand, and the antisense strand has two or more consecutive 2'-O-methyl modified nucleotides at 3'-end. In some embodiments, a polynucleic acid molecule comprises a sense strand and antisense strand, and the antisense strand has at least 2, 3, 4, 5, 6, or 7 consecutive 2'-O-methyl modified nucleotides.

In some aspects, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some aspects, a polynucleic acid molecule comprises a sense strand and an antisense strand, wherein the antisense strand comprises a glyceryl modification at the 3' end of the antisense strand.

In some aspects, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/ or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some aspects, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides at the 3'-end, the 5'-end, or both of the 3'- and 5'-ends of the sense strand and/or antisense strand, and optionally a terminal cap molecule at the 3'-end, the 5'-end, or both of the 3'- and 5'-ends of the sense strand. In some embodiments, the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some aspects, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/ or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/ or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some aspects, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule. In some embodiments, a polynucleic acid molecule comprises a sense strand and an antisense strand, and the antisense strand comprises a phosphate backbone modification at the 3' end of the antisense strand. Alternatively, and/or additionally, a polynucleic acid molecule comprises a sense strand and an antisense strand, and the sense strand comprises a phosphate backbone modification at the 5' end of the antisense strand. In some instances, the phosphate backbone modification is a phosphorothioate. In some embodiments, the sense or antisense strand has three consecutive nucleosides that are coupled via two phosphorothioate backbone.

In another aspects, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some aspects, a polynucleic acid molecule is a single-stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, the 5' conjugates described herein inhibit 5'-3' exonucleolytic cleavage. In some instances, the 3' conjugates described herein inhibit 3'-5' exonucleolytic cleavage.

In some aspects, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some cases, the increased affinity is illustrated with a lower Kd, a higher melt temperature (Tm), or a combination thereof.

In some aspects, a polynucleic acid molecule comprises a sense strand and antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification). In some aspects, a polynucleic acid molecule comprises a sense strand and antisense strand, and the antisense strand comprises a nucleic acid of 5'-UfsNfsnnnNfnnnnnnnnNfnNfnnnsusu-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification) and the antisense strand comprises a nucleic acid of 5'-UfsNfsnnnNfnnnnnnnnNfnNfnnnsusu-3' (lower case (n)=2'-O-Me (methyl), Nf=2'-F (fluoro); s=phosphorothioate backbone modification).

In some aspects, a polynucleic acid molecule comprises a sense strand and antisense strand, and the sense strand comprises a nucleic acid of 5'-nsnsnnnnNfNfNfnnnnnnnnnsnsn-3' (lower case (n)=2'-O-Me (methyl), Nf=2'-F (fluoro); s=phosphorothioate backbone modification), and the antisense strand comprises a nucleic acid of 5'-nsNfsnnnNfnnnnnnnnNfnNfnnnnnsnsn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nnnnnnnnNfNfNfnnnnnnnnnn-3' (lower case (n)=2'-O-Me (methyl), Nf=2'-F (fluoro); and the antisense strand comprises a nucleic acid of 5'-nNfnnnNfnnnnnnnnNfnNfnnnnnnn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnNfNfNfnnnnnnnnnsnsn-3' (lower case (n)=2'-O-Me (methyl), Nf=2'-F (fluoro); s=phosphorothioate backbone modification), and the antisense strand comprises a nucleic acid of 5'-nsNfsnnnNfnnnnnnnnNfnNfnnnnnsnsn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nnnnnnnnNfNfNfnnnnnnnnnn-3' (lower case (n)=2'-O-Me (methyl), Nf=2'-F (fluoro); and the antisense strand comprises a nucleic acid of 5'-VpUqNfnnnNfnnnnnnnnNfnNfnnnnnnn-3' (lower case (n)=2'-O-Me (methyl), Nf=2'-F (fluoro); s=phosphorothioate backbone modification). In some aspects, a polynucleic acid molecule comprises a sense strand and antisense strand, and the sense strand comprises a nucleic acid of 5'-nsnsnnnnNfNfNfnnnnnnnnnsnsn-3' (lower case (n)=2'-O-Me (methyl), Nf=2'-F (fluoro); s=phosphorothioate backbone modification), and the antisense strand comprises a nucleic acid of 5'-VpUqsNfsnnnNfnnnnnnnnNfnNfnnnnnsnsn-3' (lower case (n)=2'-O-Me (methyl), Nf=2'-F (fluoro); s=phosphorothioate backbone modification). In some instances, modified guide strand comprises U at the 5' end (e.g., VpUq or U). In some instances, such U replaces the 5' end nucleotides of the base sequence. In some instances, modified guide stranded includes an overhang sequence of "UU" or "dTdT" or "TT". In some instances, the modified passenger strand comprises A at the 5' end.

In some aspects, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instances, a polynucleic acid molecule composition comprises less than 30%, 25%, 20%, 15%, 10%, 5%, 4%, 3%, 2%, 10%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No: WO2015/107425.

In some aspects, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In some aspects, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is partially or fully complementary to nucleotide sequence in a target nucleic acid molecule or a portion thereof and the sense region having nucleotide sequence partially or fully corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region having a nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having a nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single-stranded polynucleotide further comprises a terminal phosphate group, such as a 5'-phosphate (see for example Martinez et al., 2002, *Cell*, 110, 563-574 and Schwarz et al., 2002, *Molecular Cell*, 10, 537-568), or 5',3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complementary nucleotides to base pair with the antisense region and form a duplex with the loop portion. For example, an asymmetric hairpin polynucleic acid molecule comprises an antisense region having a length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex polynucleic acid molecule comprises an antisense region having a length sufficient to mediate RNAi in a cell or in vitro system (e.g., about 19 to about 22 nucleotides) and a sense region having about 3 to about 18 nucleotides that are complementary to the antisense region.

In some cases, a universal base refers to a nucleotide base analog that forms base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

Polynucleic Acid Molecule Synthesis

In some aspects, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication NO. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-O,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some aspects, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Eamshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some aspects, a polynucleic acid molecule (B) is further conjugated to a polypeptide (A) for delivery to a site of interest. In some instances, at least one polypeptide A is conjugated to at least one B. In some instances, the at least one polypeptide A is conjugated to the at least one B to form an A-B conjugate. In some embodiments, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some cases, a polynucleic acid molecule is conjugated to a polypeptide (A) and optionally a polymeric moiety (C). In some embodiments, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C—B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Binding Moiety

In some embodiments, the binding moiety A is a polypeptide. In some instances, the polypeptide is an antibody or its fragment thereof. In some cases, the fragment is a binding fragment. In some instances, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, a binding fragment having a light chain domain and a heavy chain domain, a binding fragment having two light chain domains and two heavy chain domains, a binding fragment having two or more light chain domains and heavy chain domains, monovalent Fab, Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or biding fragment thereof, or a chemically modified derivative thereof.

In some embodiments, the binding moiety A is a bispecific antibody or antigen binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab$_2$, F(ab)'$_3$ fragments, bis-scFv, (scFv)$_2$, diabody, minibody, triabody, tetrabody or a bispecific T-cell engager (BiTE). In some embodiments, the bi-specific T-cell engager is a fusion protein that contains two single-chain variable fragments (scFvs) in which the two scFvs target epitopes of two different antigens.

In some embodiments, the binding moiety A is a bispecific mini-antibody. In some instances, A is a bispecific Fab$_2$. In some instances, A is a bispecific F(ab)'$_3$ fragment. In some cases, A is a bispecific bis-scFv. In some cases, A is a bispecific (scFv)$_2$. In some embodiments, A is a bispecific diabody. In some embodiments, A is a bispecific minibody. In some embodiments, A is a bispecific triabody. In other embodiments, A is a bispecific tetrabody. In other embodiments, A is a bi-specific T-cell engager (BiTE).

In some embodiments, the binding moiety A is a trispecific antibody. In some instances, the trispecific antibody comprises F(ab)'$_3$ fragments or a triabody. In some instances, A is a trispecific F(ab)'$_3$ fragment. In some cases, A is a triabody. In some embodiments, A is a trispecific antibody as described in Dimas, et al., "Development of a trispecific antibody designed to simultaneously and efficiently target three different antigens on tumor cells," *Mol. Pharmaceutics,* 12(9): 3490-3501 (2015).

In some embodiments, the binding moiety A is an antibody or antigen binding fragment thereof that recognizes a cell surface protein. In some instances, the binding moiety A is an antibody or antigen binding fragment thereof that recognizes a cell surface protein on a muscle cell. In some cases, the binding moiety A is an antibody or antigen binding fragment thereof that recognizes a cell surface protein on a skeletal muscle cell.

In some embodiments, exemplary antibodies include, but are not limited to, an anti-myosin antibody, an anti-transferrin receptor antibody, and an antibody that recognizes Muscle-Specific kinase (MuSK). In some instances, the antibody is an anti-transferrin receptor (anti-CD71) antibody.

In some embodiments, where the antibody is an anti-transferrin receptor (anti-CD71) antibody, the anti-transferrin antibody specifically binds to a transferrin receptor (TfR), preferably, specifically binds to transferrin receptor 1 (TfR1), or more preferably, specifically binds to human transferrin receptor 1 (TfR1) (or human CD71).

In some instances, the anti-transferrin receptor antibody comprises a variable heavy chain (VH) region and a variable light chain (VL) region, wherein the VH region comprises HCDR1 sequence comprising SEQ ID NO: 360; HCDR2 sequence EINPIX$_1$GRSNYAX$_2$KFQG (SEQ ID NO: 361), wherein X$_1$ is selected from N or Q and X$_2$ is selected from Q or E; and HCDR3 sequence comprising SEQ ID NO: 365.

In some embodiments, the VH region of the anti-transferrin receptor antibody comprises HCDR1, HCDR2, and HCDR3 sequences selected from Table 1.

TABLE 1

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYWMH | 360 | EINPINGRSNYAQKFQG | 362 | GTRAMHY | 365 |
| 13E4_VH2* | YTFTNYWMH | 360 | EINPINGRSNYAEKFQG | 363 | GTRAMHY | 365 |
| 13E4_VH3 | YTFTNYWMH | 360 | EINPIQGRSNYAEKFQG | 364 | GTRAMHY | 365 |

*13E4_VH2 shares the same HCDR1, HCDR2, and HCDR3 sequences with anti-transferrin receptor antibody 13E4_VH4

In some embodiments, the VH region comprises HCDR1 sequence comprising SEQ ID NO: 360; HCDR2 sequence comprising SEQ ID NO: 362, 363, or 364; and HCDR3 sequence comprising SEQ ID NO: 365. In some instances, the VH region comprises HCDR1 sequence comprising SEQ ID NO: 360, HCDR2 sequence comprising SEQ ID NO: 362, and HCDR3 sequence comprising SEQ ID NO: 365. In some instances, the VH region comprises HCDR1 sequence comprising SEQ ID NO: 360, HCDR2 sequence comprising SEQ ID NO: 363, and HCDR3 sequence comprising SEQ ID NO: 365. In some instances, the VH region comprises HCDR1 sequence comprising SEQ ID NO: 360, HCDR2 sequence comprising SEQ ID NO: 364, and HCDR3 sequence comprising SEQ ID NO: 365.

In some embodiments, the VL region of the anti-transferrin receptor antibody comprises LCDR1 sequence RTSENIYX$_3$NLA (SEQ ID NO: 366), LCDR2 sequence AX$_4$TNLAX$_5$ (SEQ ID NO: 369), and LCDR3 sequence QHFWGTPLTX$_6$ (SEQ ID NO: 373), wherein X$_3$ is selected from N or S, X$_4$ is selected from A or G, X$_5$ is selected from D or E, and X$_6$ is present or absence, and if present, is F.

In some embodiments, the VL region of the anti-transferrin receptor antibody comprises LCDR1, LCDR2, and LCDR3 sequences selected from Table 2.

TABLE 2

| Name | LCDR1 | SEQ ID NO: | LCDR2 | SEQ ID NO: | LCDR3 | SEQ ID NO: |
|---|---|---|---|---|---|---|
| 13E4_VL1* | RTSENIYNNLA | 367 | AATNLAD | 370 | QHFWGTPLT | 374 |
| 13E4_VL3 | RTSENIYNNLA | 367 | AATNLAE | 371 | QHFWGTPLTF | 375 |
| 13E4_VL4 | RTSENIYSNLA | 368 | AGTNLAD | 372 | QHFWGTPLTF | 375 |

*13E4_VL1 shares the same LCDR1, LCDR2, and LCDR3 sequences with anti-transferrin receptor antibody 13E4_VL2

In some instances, the VL region comprises LCDR1 sequence RTSENIYX$_3$NLA (SEQ ID NO: 366), LCDR2 sequence comprising SEQ ID NO: 370, 371, or 372, and LCDR3 sequence comprising SEQ ID NO: 374 or 375, wherein X$_3$ is selected from N or S.

In some instances, the VL region comprises LCDR1 sequence comprising SEQ ID NO: 367 or 368, LCDR2 sequence AX$_4$TNLAX$_5$ (SEQ ID NO: 369), and LCDR3 sequence comprising SEQ ID NO: 374 or 375, wherein X$_4$ is selected from A or G, and X$_5$ is selected from D or E.

In some instances, the VL region comprises LCDR1 sequence comprising SEQ ID NO: 367 or 368, LCDR2 sequence SEQ ID NO: 370, 371, or 372, and LCDR3 sequence QHFWGTPLTX$_6$ (SEQ ID NO: 373), wherein X$_6$ is present or absence, and if present, is F.

In some instances, the VL region comprises LCDR1 sequence comprising SEQ ID NO: 367, LCDR2 sequence AX$_4$TNLAX$_5$ (SEQ ID NO: 369), and LCDR3 sequence QHFWGTPLTX$_6$ (SEQ ID NO: 373), wherein X$_4$ is selected from A or G, X$_5$ is selected from D or E and X$_6$ is present or absence, and if present, is F.

In some instances, the VL region comprises LCDR1 sequence comprising SEQ ID NO: 367, LCDR2 sequence comprising SEQ ID NO: 370, and LCDR3 sequence comprising SEQ ID NO: 374.

In some instances, the VL region comprises LCDR1 sequence comprising SEQ ID NO: 367, LCDR2 sequence comprising SEQ ID NO: 371, and LCDR3 sequence comprising SEQ ID NO: 375.

In some instances, the VL region comprises LCDR1 sequence comprising SEQ ID NO: 368, LCDR2 sequence comprising SEQ ID NO: 372, and LCDR3 sequence comprising SEQ ID NO: 375.

In some embodiments, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence RTSENIYX$_3$NLA (SEQ ID NO: 366), LCDR2 sequence AX$_4$TNLAX$_5$ (SEQ ID NO: 369), and LCDR3 sequence QHFWGTPLTX$_6$ (SEQ ID NO: 373), wherein X$_3$ is selected from N or S, X$_4$ is selected from A or G, X$_5$ is selected from D or E, and X$_6$ is present or absence, and if present, is F.

In some instances, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence RTSENIYX$_3$NLA (SEQ ID NO: 366), LCDR2 sequence comprising SEQ ID NO: 370, 371, or 372, and LCDR3 sequence comprising SEQ ID NO: 374 or 375, wherein X$_3$ is selected from N or S.

In some instances, the anti-transferrin receptor antibody comprises a VH region and a VL region, wherein the VH region comprises HCDR1 sequence comprising SEQ ID NO: 360; HCDR2 sequence EINPIX$_1$GRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 367 or 368, LCDR2 sequence AX$_4$TNLAX$_5$ (SEQ ID NO: 369), and LCDR3 sequence comprising SEQ ID NO: 374 or 375, wherein X$_4$ is selected from A or G, and X$_5$ is selected from D or E.

In some instances, the anti-transferrin receptor antibody comprises a VH region and a VL region, wherein the VH region comprises HCDR1 sequence comprising SEQ ID NO: 360; HCDR2 sequence EINPIX$_1$GRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 367 or 368, LCDR2 sequence SEQ ID NO: 370, 371, or 372, and LCDR3 sequence QHFWGTPLTX$_6$ (SEQ ID NO: 373), wherein X$_6$ is present or absence, and if present, is F.

In some instances, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 367, LCDR2 sequence AX$_4$TNLAX$_5$ (SEQ ID NO: 369), and LCDR3 sequence QHFWGTPLTX$_6$ (SEQ ID NO: 373), wherein X$_4$ is selected from A or G, X$_5$ is selected from D or E and X$_6$ is present or absence, and if present, is F.

In some instances, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 367, LCDR2 sequence comprising SEQ ID NO: 370, and LCDR3 sequence comprising SEQ ID NO: 374.

In some instances, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 367, LCDR2 sequence comprising SEQ ID NO: 371, and LCDR3 sequence comprising SEQ ID NO: 375.

In some instances, the anti-transferrin receptor antibody comprises a VH region and a VL region, wherein the VH region comprises HCDR1 sequence comprising SEQ ID NO: 360; HCDR2 sequence EINPIXiGRSNYAX$_2$KFQG (SEQ ID NO: 361), wherein X$_1$ is selected from N or Q and X$_2$ is selected from Q or E; and HCDR3 sequence comprising SEQ ID NO: 365; and the VL region comprises LCDR1 sequence comprising SEQ ID NO: 368, LCDR2 sequence comprising SEQ ID NO: 372, and LCDR3 sequence comprising SEQ ID NO: 375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence RTSENIYX$_3$NLA (SEQ ID NO: 366), LCDR2 sequence comprising SEQ ID NO: 370, 371, or 372, and LCDR3 sequence comprising SEQ ID NO: 374 or 375, wherein X$_3$ is selected from N or S.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence comprising SEQ ID NO: 367 or 368, LCDR2 sequence AX$_4$TNLAX$_5$ (SEQ ID NO: 369), and LCDR3 sequence comprising SEQ ID NO: 374 or 375, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 360, HCDR2 sequence comprising SEQ ID NO: 2, and HCDR3 sequence comprising SEQ ID NO: 365; and the VL region comprises LCDR1 sequence comprising SEQ ID NO: 367 or 368, LCDR2 sequence SEQ ID NO: 370, 371, or 372, and LCDR3 sequence QHFWGTPLTX$_6$ (SEQ ID NO: 373), wherein X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence comprising SEQ ID NO: 367, LCDR2 sequence AX$_4$TNLAX$_5$ (SEQ ID NO: 369), and LCDR3 sequence QHFWGTPLTX$_6$ (SEQ ID NO: 373), wherein X$_4$ is selected from A or G, X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence comprising SEQ ID NO: 367, LCDR2 sequence comprising SEQ ID NO: 370, and LCDR3 sequence comprising SEQ ID NO: 374.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence comprising SEQ ID NO: 367, LCDR2 sequence comprising SEQ ID NO: 9, and LCDR3 sequence comprising SEQ ID NO: 375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 362, and HCDR3 sequence comprising SEQ ID NO: 365; and the VL region comprises LCDR1 sequence comprising SEQ ID NO: 368, LCDR2 sequence comprising SEQ ID NO: 372, and LCDR3 sequence comprising SEQ ID NO: 375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence RTSENIYX$_3$NLA (SEQ ID NO: 366), LCDR2 sequence comprising SEQ ID NO: 370, 371, or 372, and LCDR3 sequence comprising SEQ ID NO: 374 or 375, wherein X$_3$ is selected from N or S.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 367 or 368, LCDR2 sequence AX$_4$TNLAX$_5$ (SEQ ID NO: 369), and LCDR3 sequence comprising SEQ ID NO: 374 or 375, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 367 or 368, LCDR2 sequence SEQ ID NO: 370, 371, or 372, and LCDR3 sequence QHFWGTPLTX$_6$ (SEQ ID NO: 373), wherein X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 367, LCDR2 sequence AX$_4$TNLAX$_5$ (SEQ ID NO: 369), and LCDR3 sequence QHFWGTPLTX$_6$ (SEQ ID NO: 373), wherein X$_4$ is selected from A or G, X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 367, LCDR2 sequence comprising SEQ ID NO: 370, and LCDR3 sequence comprising SEQ ID NO: 374.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 367, LCDR2 sequence comprising SEQ ID NO: 371, and LCDR3 sequence comprising SEQ ID NO:375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 363, and HCDR3 sequence comprising SEQ ID NO: 365; and the VL region comprises LCDR1 sequence comprising SEQ ID NO: 368, LCDR2 sequence comprising SEQ ID NO: 372, and LCDR3 sequence comprising SEQ ID NO: 375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence RTSENIYX$_3$NLA (SEQ ID NO: 366), LCDR2 sequence comprising SEQ ID NO: 370, 371, or 29, and LCDR3 sequence comprising SEQ ID NO: 374 or 375, wherein X$_3$ is selected from N or S.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence comprising SEQ ID NO: 367 or 368, LCDR2 sequence AX$_4$TNLAX$_5$ (SEQ ID NO: 369), and LCDR3 sequence comprising SEQ ID NO: 374 or 375, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence comprising SEQ ID NO: 367 or 368, LCDR2 sequence SEQ ID NO: 370, 371, or 372, and LCDR3 sequence QHFWGTPLTX$_6$ (SEQ ID NO: 373), wherein X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365 and the VL region comprises LCDR1 sequence comprising SEQ ID NO: 367, LCDR2 sequence AX$_4$TNLAX$_5$ (SEQ ID NO: 369), and LCDR3 sequence QHFWGTPLTX$_6$ (SEQ ID NO: 373), wherein X$_4$ is selected from A or G, X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence comprising SEQ ID NO: 367, LCDR2 sequence comprising SEQ ID NO: 370, and LCDR3 sequence comprising SEQ ID NO: 374.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence comprising SEQ ID NO: 367, LCDR2 sequence comprising SEQ ID NO: 371, and LCDR3 sequence comprising SEQ ID NO: 375.

In some instances, the anti-transferrin receptor antibody comprises a VH region and a VL region, in which the VH region comprises HCDR1 sequence comprising SEQ ID NO: 360, HCDR2 sequence comprising SEQ ID NO: 364, and HCDR3 sequence comprising SEQ ID NO: 365; and the VL region comprises LCDR1 sequence comprising SEQ ID NO: 368, LCDR2 sequence comprising SEQ ID NO: 372, and LCDR3 sequence comprising SEQ ID NO: 375.

In some embodiments, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 376-380 and the sequence of the VL region comprises about 80%, 85%, 90%, 95%, 96% 97%, 98%, 99%, or 10000 sequence identity to SEQ ID NOs: 381-385.

In some embodiments, the VH region comprises a sequence selected from SEQ ID NOs: 376-380 (Table 3) and the VL region comprises a sequence selected from SEQ ID NOs: 381-385 (Table 4). The underlined regions in Table 3 and Table 4 denote the respective CDR1, CDR2, or CDR3 sequence.

TABLE 3

| NAME | VH SEQUENCE | SEQ ID NO: |
|---|---|---|
| 13E4_VH1 | QVQLVQSGAEVKKPGASVKVSCKASGYTFTNYWMHWVRQAPGQGLEW MGEINPINGRSNYAQKFQGRVTLTVDTSISTAYMELSRLRSDDTAVYYCA RGTRAMHYWGQGTLVTVSS | 376 |
| 13E4_VH2 | QVQLVQSGAEVKKPGASVKVSCKASGYTFTNYWMHWVRQAPGQGLEW IGEINPINGRSNYAEKFQGRVTLTVDTSSSTAYMELSRLRSDDTAVYYCAR GTRAMHYWGQGTLVTVSS | 377 |
| 13E4_VH3 | QVQLVQSGAEVKKPGASVKVSCKASGYTFTNYWMHWVRQAPGQGLEW MGEINPIQGRSNYAEKFQGRVTLTVDTSSSTAYMELSSLRSEDTATYYCA RGTRAMHYWGQGTLVTVSS | 378 |
| 13E4_VH4 | QVQLVQSGAEVKKPGASVKVSCKASGYTFTNYWMHWVRQAPGQGLEW MGEINPINGRSNYAEKFQGRVTLTVDTSSSTAYMELSSLRSEDTATYYCA RGTRAMHYWGQGTLVTVSS | 379 |
| 13E4_VH | QVQLQQPGAELVKPGASVKLSCKASGYTFTNYWMHWVKQRPGQGLEWI GEINPINGRSNYGERFKTKATLTVDKSSSTAYMQLSSLTSEDSAVYYCAR GTRAMHYWGQGTSVTVSS | 380 |

TABLE 4

| NAME | VL SEQUENCE | SEQ ID NO: |
|------|-------------|------------|
| 13E4_VL1 | DIQMTQSPSSLSASVGDRVTITCRTSENIYNNLAWYQQKPGKSPKLLIYAATNLADGVPSRFSGSGSGTDYTLTISSLQPEDFATYYCQHFWGTPLTFGGGTKVEIK | 381 |
| 13E4_VL2 | DIQMTQSPSSLSASVGDRVTITCRTSENIYNNLAWYQQKPGKAPKLLIYAATNLADGVPSRFSGSGSGTDYTLTISSLQPEDFATYYCQHFWGTPLTFGGGTKVEIK | 382 |
| 13E4_VL3 | DIQMTQSPSSLSASVGDRVTITCRTSENIYNNLAWYQQKPGKAPKLLIYAATNLAEGVPSRFSGSGSGTDYTLTISSLQPEDFATYYCQHFWGTPLTFGGGTKVEIK | 383 |
| 13E4_VL4 | DIQMTQSPSSLSASVGDRVTITCRTSENIYSNLAWYQQKPGKAPKLLIYAGTNLADGVPSRFSGSGSGTDYTLTISSLQPEDFANYYCQHFWGTPLTFGGGTKVEIK | 384 |
| 13E4_VL | DIQMTQSPASLSVSVGETVTITCRTSENIYNNLAWYQQKQGKSPQLLVYAATNLADGVPSRFSGSGSGTQYSLKINSLQSEDFGNYYCQHFWGTPLTFGAGTKLELK | 385 |

In some embodiments, the anti-transferrin receptor antibody comprises a VH region and a VL region as illustrated in Table 5.

TABLE 5

|  | 13E4_VH1 (SEQ ID NO: 376) | 13E4_VH2 (SEQ ID NO: 377) | 13E4_VH3 (SEQ ID NO: 378) | 13E4_VH4 (SEQ ID NO: 379) |
|---|---|---|---|---|
| 13E4_VL1 (SEQ ID NO: 381) | SEQ ID NO: 376 + SEQ ID NO: 381 | SEQ ID NO: 377 + SEQ ID NO: 381 | SEQ ID NO: 378 + SEQ ID NO: 381 | SEQ ID NO: 379 + SEQ ID NO: 381 |
| 13E4_VL2 (SEQ ID NO: 382) | SEQ ID NO: 376 + SEQ ID NO: 382 | SEQ ID NO: 377 + SEQ ID NO: 382 | SEQ ID NO: 378 + SEQ ID NO: 382 | SEQ ID NO: 379 + SEQ ID NO: 382 |
| 13E4_VL3 (SEQ ID NO: 383) | SEQ ID NO: 376 + SEQ ID NO: 383 | SEQ ID NO: 377 + SEQ ID NO: 383 | SEQ ID NO: 378 + SEQ ID NO: 383 | SEQ ID NO: 379 + SEQ ID NO: 383 |
| 13E4_VL4 (SEQ ID NO: 384) | SEQ ID NO: 376 + SEQ ID NO: 384 | SEQ ID NO: 377 + SEQ ID NO: 384 | SEQ ID NO: 378 + SEQ ID NO: 384 | SEQ ID NO: 379 + SEQ ID NO: 384 |

In some embodiments, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some embodiments, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N297, K322, L328, or P329, or a combination thereof. In some instances, the mutations comprise L234 and L235 in combination with a mutation at residue position K322, L328, or P329. In some cases, the Fc region comprises mutations at L234, L235, and K322. In some cases, the Fc region comprises mutations at L234, L235, and L328. In some cases, the Fc region comprises mutations at L234, L235, and P329. In some cases, the Fc region comprises mutations at D265 and N297. In some cases, the residue position is in reference to IgG1.

In some instances, the Fc region comprises L234A, L235A, D265A, N297G, K322G, L328R, or P329G, or a combination thereof. In some instances, the Fc region comprises L234A and L235A in combination with K322G, L328R, or P329G. In some cases, the Fc region comprises L234A, L235A, and K322G. In some cases, the Fc region comprises L234A, L235A, and L328R. In some cases, the Fc region comprises L234A, L235A, and P329G. In some cases, the Fc region comprises D265A and N297G. In some cases, the residue position is in reference to IgG1.

In some instances, the Fc region comprises a mutation at residue position L235, L236, D265, N297, K322, L328, or P329, or a combination of the mutations. In some instances, the Fc region comprises mutations at L235 and L236. In some instances, the Fc region comprises mutations at L235 and L236 in combination with a mutation at residue position K322, L328, or P329. In some cases, the Fc region comprises mutations at L235, L236, and K322. In some cases, the Fc region comprises mutations at L235, L236, and L328. In some cases, the Fc region comprises mutations at L235, L236, and P329. In some cases, the Fc region comprises mutations at D265 and N297. In some cases, the residue position is in reference to IgG2b.

In some embodiments, the Fc region comprises L235A, L236A, D265A, N297G, K322G, L328R, or P329G, or a combination thereof. In some instances, the Fc region comprises L235A and L236A. In some instances, the Fc region comprises L235A and L236A in combination with K322G, L328R, or P329G. In some cases, the Fc region comprises L235A, L236A, and K322G. In some cases, the Fc region comprises L235A, L236A, and L328R. In some cases, the Fc region comprises L235A, L236A, and P329G. In some cases, the Fc region comprises D265A and N297G. In some cases, the residue position is in reference to IgG2b.

In some embodiments, the Fc region comprises a mutation at residue position L233, L234, D264, N296, K321, L327, or P328, wherein the residues correspond to positions 233, 234, 264, 296, 321, 327, and 328 of SEQ ID NO: 390. In some instances, the Fc region comprises mutations at L233 and L234. In some instances, the Fc region comprises mutations at L233 and L234 in combination with a mutation at residue position K321, L327, or P328. In some cases, the Fc region comprises mutations at L233, L234, and K321. In some cases, the Fc region comprises mutations at L233, L234, and L327. In some cases, the Fc region comprises mutations at L233, L234, and K321. In some cases, the Fc region comprises mutations at L233, L234, and P328. In some instances, the Fc region comprises mutations at D264 and N296. In some cases, equivalent positions to residue L233, L234, D264, N296, K321, L327, or P328 in an IgG1, IgG2, IgG3, or IgG4 framework are contemplated. In some cases, mutations to a residue that corresponds to residue L233, L234, D264, N296, K321, L327, or P328 of SEQ ID NO: 390 in an IgG1, IgG2, or IgG4 framework are also contemplated.

In some embodiments, the Fc region comprises L233A, L234A, D264A, N296G, K321G, L327R, or P328G, wherein the residues correspond to positions 233, 234, 264, 296, 321, 327, and 328 of SEQ ID NO: 390. In some instances, the Fc region comprises L233A and L234A. In some instances, the Fc region comprises L233A and L234A in combination with K321G, L327R, or P328G. In some cases, the Fc region comprises L233A, L234A, and K321G. In some cases, the Fc region comprises L233A, L234A, and L327R. In some cases, the Fc region comprises L233A, L234A, and K321G. In some cases, the Fc region comprises L233A, L234A, and P328G. In some instances, the Fc region comprises D264A and N296G.

In some embodiments, the human IgG constant region is modified to alter antibody-dependent cellular cytotoxicity (ADCC) and/or complement-dependent cytotoxicity (CDC), e.g., with an amino acid modification described in Natsume et al., 2008 *Cancer Res*, 68(10): 3863-72; Idusogie et al., 2001 *J Immunol*, 166(4): 2571-5; Moore et al., 2010 *mAbs*, 2(2): 181-189; Lazar et al., 2006 *PNAS*, 103(11): 4005-4010, Shields et al., 2001 *JBC*, 276(9): 6591-6604; Stavenhagen et al., 2007 *Cancer Res*, 67(18): 8882-8890; Stavenhagen et al., 2008 *Advan. Enzyme Regul.*, 48: 152-164; Alegre et al, 1992 *J Immunol*, 148: 3461-3468; Reviewed in Kaneko and Niwa, 2011 *Biodrugs*, 25(1): 1-11.

In some embodiments, an anti-transferrin receptor antibody described herein is a full-length antibody, comprising a heavy chain (HC) and a light chain (LC). In some cases, the heavy chain (HC) comprises a sequence selected from Table 6. In some cases, the light chain (LC) comprises a sequence selected from Table 7. The underlined region denotes the respective CDRs.

TABLE 6

| NAME | HC SEQUENCE | SEQ ID NO: |
|---|---|---|
| 13E4_VH1 | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPELLGGPSVFLFPPKPKDTLM ISRTPEVTCVVVDVSHEDPEVKFNWYVDGVEVHNAKTKPRE EQYNSTYRVVSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQ QGNVFSCSVMHEALHNHYTQKSLSLSPG | 390 |
| 13E4_VH1_a | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 391 |

TABLE 6-continued

| NAME | HC SEQUENCE | SEQ ID NO: |
|---|---|---|
| 13E4_VH1_b | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCGVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 392 |
| 13E4_VH1_c | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKARPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 393 |
| 13E4_VH1_d | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALGAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 394 |
| 13E4_VH1_e | QVQLVQSGAEVKKPGASVKVSCKASGYTFTNYWMHWVRQA PGQGLEWMGEINPINGRSNYAQKFQGRVTLTVDTSISTAYME LSRLRSDDTAVYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPELLGGPSVFLFPPKPKDTLM ISRTPEVTCVVVAVSHEDPEVKFNWYVDGVEVHNAKTKPRE EQYGSTYRVVSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQ QGNVFSCSVMHEALHNHYTQKSLSLSPG | 395 |
| 13E4_VH2 | QVQLVQSGAEVKKPGASVKVSCKASGYTFTNYWMHWVRQA PGQGLEWIGEINPINGRSNYAEKFQGRVTLTVDTSSSTAYMEL SRLRSDDTAVYYCARGTRAMHYWGQGTLVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPELLGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI SKAKGQPREPQVYTLPPSREEMTKNQVSLTCLVKGFYPSDIA VEWESNGQPENNYKTTPPVLDSDGSFFLYSKLTVDKSRWQQ GNVFSCSVMHEALHNHYTQKSLSLSPG | 396 |
| 13E4_VH2_a | QVQLVQSGAEVKKPGASVKVSCKASGYTFTNYWMHWVRQA PGQGLEWIGEINPINGRSNYAEKFQGRVTLTVDTSSSTAYMEL SRLRSDDTAVYYCARGTRAMHYWGQGTLVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPEAAGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI SKAKGQPREPQVYTLPPSREEMTKNQVSLTCLVKGFYPSDIA VEWESNGQPENNYKTTPPVLDSDGSFFLYSKLTVDKSRWQQ GNVFSCSVMHEALHNHYTQKSLSLSPG | 397 |
| 13E4_VH2_b | QVQLVQSGAEVKKPGASVKVSCKASGYTFTNYWMHWVRQA PGQGLEWIGEINPINGRSNYAEKFQGRVTLTVDTSSSTAYMEL SRLRSDDTAVYYCARGTRAMHYWGQGTLVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK | 398 |

TABLE 6-continued

| NAME | HC SEQUENCE | SEQ ID NO: |
|---|---|---|
| | VDKRVEPKSCDKTHTCPPCPAPEAAGGPSVFLFPPKPKDTLMI<br>SRTPEVTCVVVDVSHEDPEVKFNWYVDGVEVHNAKTKPREE<br>QYNSTYRVVSVLTVLHQDWLNGKEYKCGVSNKALPAPIEKTI<br>SKAKGQPREPQVYTLPPSREEMTKNQVSLTCLVKGFYPSDIA<br>VEWESNGQPENNYKTTPPVLDSDGSFFLYSKLTVDKSRWQQ<br>GNVFSCSVMHEALHNHYTQKSLSLSPG | |
| 13E4_VH2_c | QVQLVQSGAEVKKPGASVKVSCKASG<u>YTFTNYWMH</u>WVRQA<br>PGQGLEWIG<u>EINPINGRSNYAEKFQ</u>GRVTLTVDTSSSTAYMEL<br>SRLRSDDTAVYYCAR<u>GTRAMHY</u>WGQGTLVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKRVEPKSCDKTHTCPPCPAPEAAGGPSVFLFPPKPKDTLMI<br>SRTPEVTCVVVDVSHEDPEVKFNWYVDGVEVHNAKTKPREE<br>QYNSTYRVVSVLTVLHQDWLNGKEYKCKVSNKARPAPIEKTI<br>SKAKGQPREPQVYTLPPSREEMTKNQVSLTCLVKGFYPSDIA<br>VEWESNGQPENNYKTTPPVLDSDGSFFLYSKLTVDKSRWQQ<br>GNVFSCSVMHEALHNHYTQKSLSLSPG | 399 |
| 13E4_VH2_d | QVQLVQSGAEVKKPGASVKVSCKASG<u>YTFTNYWMH</u>WVRQA<br>PGQGLEWIG<u>EINPINGRSNYAEKFQ</u>GRVTLTVDTSSSTAYMEL<br>SRLRSDDTAVYYCAR<u>GTRAMHY</u>WGQGTLVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKRVEPKSCDKTHTCPPCPAPEAAGGPSVFLFPPKPKDTLMI<br>SRTPEVTCVVVDVSHEDPEVKFNWYVDGVEVHNAKTKPREE<br>QYNSTYRVVSVLTVLHQDWLNGKEYKCKVSNKALGAPIEKT<br>ISKAKGQPREPQVYTLPPSREEMTKNQVSLTCLVKGFYPSDIA<br>VEWESNGQPENNYKTTPPVLDSDGSFFLYSKLTVDKSRWQQ<br>GNVFSCSVMHEALHNHYTQKSLSLSPG | 400 |
| 13E4_VH2_e | QVQLVQSGAEVKKPGASVKVSCKASG<u>YTFTNYWMH</u>WVRQA<br>PGQGLEWIG<u>EINPINGRSNYAEKFQ</u>GRVTLTVDTSSSTAYMEL<br>SRLRSDDTAVYYCAR<u>GTRAMHY</u>WGQGTLVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKRVEPKSCDKTHTCPPCPAPELLGGPSVFLFPPKPKDTLMI<br>SRTPEVTCVVVAVSHEDPEVKFNWYVDGVEVHNAKTKPREE<br>QYGSTYRVVSVLTVLHQDWLNGKEYKCKVSNKALPAPIEKTI<br>SKAKGQPREPQVYTLPPSREEMTKNQVSLTCLVKGFYPSDIA<br>VEWESNGQPENNYKTTPPVLDSDGSFFLYSKLTVDKSRWQQ<br>GNVFSCSVMHEALHNHYTQKSLSLSPG | 401 |
| 13E4 VH3 | QVQLVQSGAEVKKPGASVKVSCKASG<u>YTFTNYWMH</u>WVRQA<br>PGQGLEWMG<u>EINPIQGRSNYAEKFQ</u>GRVTLTVDTSSSTAYME<br>LSSLRSEDTATYYCAR<u>GTRAMHY</u>WGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSNT<br>KVDKRVEPKSCDKTHTCPPCPAPELLGGPSVFLFPPKPKDTLM<br>ISRTPEVTCVVVDVSHEDPEVKFNWYVDGVEVHNAKTKPRE<br>EQYNSTYRVVSVLTVLHQDWLNGKEYKCKVSNKALPAPIEK<br>TISKAKGQPREPQVYTLPPSREEMTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPG | 402 |
| 13E4_VH3_a | QVQLVQSGAEVKKPGASVKVSCKASG<u>YTFTNYWMH</u>WVRQA<br>PGQGLEWMG<u>EINPIQGRSNYAEKFQ</u>GRVTLTVDTSSSTAYME<br>LSSLRSEDTATYYCAR<u>GTRAMHY</u>WGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSNT<br>KVDKRVEPKSCDKTHTCPPCPAPEAAGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKALPAPIE<br>KTISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 403 |

TABLE 6-continued

| NAME | HC SEQUENCE | SEQ ID NO: |
|---|---|---|
| 13E4_VH3_b | QVQLVQSGAEVKKPGASVKVSCKASGYTFTNYWMHWVRQA PGQGLEWMGEINPIQGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCGVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 404 |
| 13E4_VH3_c | QVQLVQSGAEVKKPGASVKVSCKASGYTFTNYWMHWVRQA PGQGLEWMGEINPIQGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKARPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 405 |
| 13E4_VH3_d | QVQLVQSGAEVKKPGASVKVSCKASGYTFTNYWMHWVRQA PGQGLEWMGEINPIQGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALGAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 406 |
| 13E4_VH3_e | QVQLVQSGAEVKKPGASVKVSCKASGYTFTNYWMHWVRQA PGQGLEWMGEINPIQGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPELLGGPSVFLFPPKPKDTLM ISRTPEVTCVVVAVSHEDPEVKFNWYVDGVEVHNAKTKPRE EQYGSTYRVVSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQ QGNVFSCSVMHEALHNHYTQKSLSLSPG | 407 |
| 13E4_VH4 | QVQLVQSGAEVKKPGASVKVSCKASGYTFTNYWMHWVRQA PGQGLEWMGEINPINGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPELLGGPSVFLFPPKPKDTLM ISRTPEVTCVVVDVSHEDPEVKFNWYVDGVEVHNAKTKPRE EQYNSTYRVVSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQ QGNVFSCSVMHEALHNHYTQKSLSLSPG | 408 |
| 13E4_VH4_a | QVQLVQSGAEVKKPGASVKVSCKASGYTFTNYWMHWVRQA PGQGLEWMGEINPINGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKRVEPKSCDKTHTCPPCPAPEAAGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPG | 409 |
| 13E4_VH4_b | QVQLVQSGAEVKKPGASVKVSCKASGYTFTNYWMHWVRQA PGQGLEWMGEINPINGRSNYAEKFQGRVTLTVDTSSSTAYME LSSLRSEDTATYYCARGTRAMHYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT | 410 |

TABLE 6-continued

| NAME | HC SEQUENCE | SEQ ID NO: |
|---|---|---|
| | KVDKRVEPKSCDKTHTCPPCPAPEAAGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCGVSNKALPAPIE<br>KTISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | |
| 13E4_VH4_c | QVQLVQSGAEVKKPGASVKVSCKASGYTF<u>TNYWMH</u>WVRQA<br>PGQGLEWMG<u>EINPINGRSNYAEKFQ</u>GRVTLTVDTSSSTAYME<br>LSSLRSEDTATYYCARG<u>TRAMHY</u>WGQGTLVTVSSASTKGPS<br>VFPLAPSSKSTSGGTAALGCLVKDYFPEPVTSWNSGALTSG<br>VHTFPAVLQSSGLYSLSSVVTVPSSSLGTQTYICNVNHKPSNT<br>KVDKRVEPKSCDKTHTCPPCPAPEAAGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKARPAPIE<br>KTISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 411 |
| 13E4_VH4_d | QVQLVQSGAEVKKPGASVKVSCKASGYTF<u>TNYWMH</u>WVRQA<br>PGQGLEWMG<u>EINPINGRSNYAEKFQ</u>GRVTLTVDTSSSTAYME<br>LSSLRSEDTATYYCARG<u>TRAMHY</u>WGQGTLVTVSSASTKGPS<br>VFPLAPSSKSTSGGTAALGCLVKDYFPEPVTSWNSGALTSG<br>VHTFPAVLQSSGLYSLSSVVTVPSSSLGTQTYICNVNHKPSNT<br>KVDKRVEPKSCDKTHTCPPCPAPEAAGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKALGAPIE<br>KTISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPG | 412 |
| 13E4_VH4_e | QVQLVQSGAEVKKPGASVKVSCKASGYTF<u>TNYWMH</u>WVRQA<br>PGQGLEWMG<u>EINPINGRSNYAEKFQ</u>GRVTLTVDTSSSTAYME<br>LSSLRSEDTATYYCARG<u>TRAMHY</u>WGQGTLVTVSSASTKGPS<br>VFPLAPSSKSTSGGTAALGCLVKDYFPEPVTSWNSGALTSG<br>VHTFPAVLQSSGLYSLSSVVTVPSSSLGTQTYICNVNHKPSNT<br>KVDKRVEPKSCDKTHTCPPCPAPELLGGPSVFLFPPKPKDTLM<br>ISRTPEVTCVVVAVSHEDPEVKFNWYVDGVEVHNAKTKPRE<br>EQYGSTYRVVSVLTVLHQDWLNGKEYKCKVSNKALPAPIEK<br>TISKAKGQPREPQVYTLPPSREEMTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPG | 413 |

TABLE 7

| NAME | LC SEQUENCE | SEQ ID NO: |
|---|---|---|
| 13E4_VL1 | DIQMTQSPSSLSASVGDRVTITC<u>RTSENIYNNLA</u>WYQQKPGKS<br>PKLLIY<u>AATNLAD</u>GVPSRFSGSGSGTDYTLTISSLQPEDFATYY<br>C<u>QHFWGTPLT</u>FGGGTKVEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC | 414 |
| 13E4_VL2 | DIQMTQSPSSLSASVGDRVTITC<u>RTSENIYNNLA</u>WYQQKPGKA<br>PKLLIY<u>AATNLAD</u>GVPSRFSGSGSGTDYTLTISSLQPEDFATYY<br>C<u>QHFWGTPLT</u>FGGGTKVEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC | 415 |
| 13E4_VL3 | DIQMTQSPSSLSASVGDRVTITC<u>RTSENIYNNLA</u>WYQQKPGKA<br>PKLLIY<u>AATNLAE</u>GVPSRFSGSGSGTDYTLTISSLQPEDFATYY<br>C<u>QHFWGTPLT</u>FGGGTKVEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC | 416 |
| 13E4_VL4 | DIQMTQSPSSLSASVGDRVTITC<u>RTSENIYSNLA</u>WYQQKPGKA<br>PKLLIY<u>AGTNLAD</u>GVPSRFSGSGSGTDYTLTISSLQPEDFANYY<br>C<u>QHFWGTPLT</u>FGGGTKVEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC | 417 |

In some aspects, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

In some aspects, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue (e.g., lysine residue present in the binding moiety A) in a non-site specific manner. In some cases, the binding moiety A is conjugated to a polynucleic acid molecule (B) via a cysteine residue (e.g., cysteine residue present in the binding moiety A) in a non-site specific manner.

In some aspects, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue (e.g., lysine residue present in the binding moiety A) via a site-specific manner. In some instances, the binding moiety A is conjugated to a polynucleic acid molecule (B) through a cysteine residue (e.g., cysteine residue present in the binding moiety A) via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some aspects, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some aspects, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some aspects, an antibody or antigen binding fragment is further modified using conventional techniques known in the art, for example, by using amino acid deletion, insertion, substitution, addition, and/or by recombination and/or any other modification (e.g., posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or antigen binding fragment is well known to the person skilled in the art.

In some instances, an antigen binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its antigen binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or antigen binding fragment or a reduced off-target effect. For example, the antibody or antigen binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., "A remote arene-binding site on prostate specific membrane antigen revealed by antibody-recruiting small molecules," J Am Chem Soc. 132(36): 12711-12716 (2010); or McEnaney, et al., "Antibody-recruiting molecules: an emerging paradigm for engaging immune function in treating human disease," ACS Chem Biol. 7(7): 1139-1151 (2012).

Production of Antibodies or Antigen Binding Fragment Thereof

In some embodiments, polypeptides described herein (e.g., antibodies and antigen binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or antigen binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its antigen binding is optionally generated by immunizing an animal, such as a rabbit, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its antigen binding fragment described herein. Such host-expression systems represent vehicles by which the coding sequences of the antibody is produced and subsequently purified, but also represent cells that are, when transformed or transfected with the appropriate nucleotide coding sequences, express an antibody or its antigen binding fragment in situ. These include, but are not limited to, microorganisms such as bacteria (e.g., E. coli and B. subtilis) transformed with recombinant bacteriophage DNA, plasmid DNA or cosmid DNA expression vectors containing an antibody or its antigen binding fragment coding sequences; yeast (e.g., Saccharomyces Pichia) transformed with recombinant yeast expression vectors containing an antibody or its antigen binding fragment coding sequences; insect cell systems infected with recombinant virus expression vectors (e.g., baculovirus) containing an antibody or its antigen binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its antigen binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its antigen binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some embodiments, a polynucleic acid molecule B is conjugated to a binding moiety. In some embodiments, a polynucleic acid molecule B is conjugated to a binding moiety in a formula A-X-B (X is a linker conjugating A and B). In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or antigen binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106(9): 3000-3005 (2009); Agarwal, et al., "A Pictet-Spengler ligation for protein chemical modification," *PNAS* 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule in a formula A-$X_1$—B—$X_2$—C($X_1$, $X_2$ as two linkers conjugating A and B, B and C, respectively). In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylene oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylene terephthalate (also known as poly(ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydisperse or monodisperse compound. In some instances, polydisperse material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising, e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some embodiments, the polymer moiety C comprises a cationic mucic acid-based polymer (cMAP). In some instances, cMAP comprises one or more subunit of at least one repeating subunit, and the subunit structure is represented as Formula (V):

Formula V

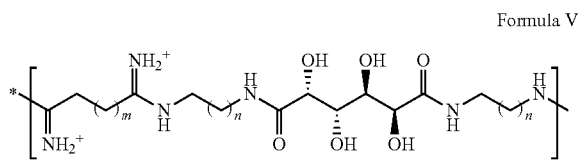

wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety as illustrated supra.

Endosomolytic or Cell Membrane Penetration Moiety

In some embodiments, a molecule of Formula (I): A-$X_1$—B—$X_2$—C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some embodiments, a molecule of Formula (I): A-$X_1$—B—$X_2$—C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a polypeptide comprising CGIFGEIEELIEEGLENLIDWGNA (SEQ ID NO: 418), or GLFEAIEGFIENGWEGMIDGWYGC (SEQ ID NO: 419). In some instances, INF7 or its derivatives comprise a sequence of: GLFEAIEGFIENGWEGMIWDYGSGCG (SEQ ID NO: 420), GLFEAIEGFIENGWEGMIDG WYG-(PEG)$_6$-NH$_2$ (SEQ ID NO: 421), or GLFEAIEGFIEN-GWEGMIWDYG-SGSC-K(GalNAc)$_2$ (SEQ ID NO: 422).

In some cases, melittin is a polypeptide comprising CLI-GAILKVLATGLPTLISWIKNKRKQ (SEQ ID NO: 423), or GIGAVLKVLTTGLPALISWIKRKRQQ (SEQ ID NO: 424). In some instances, melittin comprises a polypeptide sequence as described in U.S. Pat. No. 8,501,930.

In some instances, meucin is an antimicrobial peptide (AMP) derived from the venom gland of the scorpion Mesobuthus eupeus. In some instances, meucin comprises of meucin-13 those sequence comprises IFGAIAGLLKNIF-NH$_2$ (SEQ ID NO: 425) and meucin-18 those sequence comprises FFGHLFKLATKIIPSLFQ (SEQ ID NO: 426).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 418-421. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 418. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 419-422. In some cases, the endosomolytic moiety comprises SEQ ID NO: 418. In some cases, the endosomolytic moiety comprises SEQ ID NO: 419-422. In some cases, the endosomolytic moiety consists of SEQ ID NO: 331. In some cases, the endosomolytic moiety consists of SEQ ID NO: 419-422.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 423 or 424. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 423. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 424. In some cases, the endosomolytic moiety comprises SEQ ID NO: 423. In some cases, the endosomolytic moiety comprises SEQ ID NO: 424. In some cases, the endosomolytic moiety consists of SEQ ID NO: 423. In some cases, the endosomolytic moiety consists of SEQ ID NO: 424.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 425 or 426. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 425. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 426. In some cases, the endosomolytic moiety comprises SEQ ID NO: 425. In some cases, the endosomolytic moiety comprises SEQ ID NO: 426. In some cases, the endosomolytic moiety consists of SEQ ID NO: 425. In some cases, the endosomolytic moiety consists of SEQ ID NO: 426.

In some instances, the endosomolytic moiety comprises a sequence as illustrated in Table 8.

TABLE 8

| Name | Origin | Amino Acid Sequence | SEQ ID NO: | Type |
|---|---|---|---|---|
| Pep-1 | NLS from Simian Virus 40 large antigen and Reverse transcriptase of HIV | KETWWETWWTEWSQPKKKRKV | 427 | Primary amphipathic |
| pVEC | VE-cadherin | LLIILRRRIRKQAHAHSK | 428 | Primary amphipathic |
| VT5 | Synthetic peptide | DPKGDPKGVTVTVTVTVTGKGDPKPD | 429 | β-sheet amphipathic |
| C105Y | 1-antitrypsin | CSIPPEVKFNKPFVYLI | 430 | — |
| Transportan | Galanin and mastoparan | GWTLNSAGYLLGKINLKALAALAKKIL | 431 | Primary amphipathic |
| TP10 | Galanin and mastoparan | AGYLLGKINLKALAALAKKIL | 432 | Primary amphipathic |
| MPG | A hydrophobic domain from the fusion sequence of HIV gp41 and NLS of SV40 T antigen | GALFLGFLGAAGSTMGA | 433 | β-sheet amphipathic |
| gH625 | Glycoprotein gH of HSV type I | HGLASTLTRWAHYNALIRAF | 434 | Secondary amphipathic α-helical |
| CADY | PPTG1 peptide | GLWRALWRLLRSLWRLLWRA | 435 | Secondary amphipathic α-helical |
| GALA | Synthetic peptide | WEAALAEALAEALAEHLAEALAEALEALAA | 436 | Secondary amphipathic α-helical |
| INF | Influenza HA2 fusion peptide | GLFEAIEGFIENGWEGMIDGWYGC | 437 | Secondary amphipathic α-helical/pH-dependent membrane active peptide |
| HA2E5-TAT | Influenza HA2 subunit of influenza virus X31 strain fusion peptide | GLFGAIAGFIENGWEGMIDGWYG | 438 | Secondary amphipathic α-helical/pH-dependent membrane active peptide |
| HA2-penetratin | Influenza HA2 subunit of influenza virus X31 strain fusion peptide | GLFGAIAGFIENGWEGMIDGRQIKIWFQNRRMKWKK-amide | 439 | pH-dependent membrane active peptide |
| HA-K4 | Influenza HA2 subunit of influenza virus X31 strain fusion peptide | GLFGAIAGFIENGWEGMIDG-SSKKKK | 440 | pH-dependent membrane active peptide |
| HA2E4 | Influenza HA2 subunit of influenza virus X31 strain fusion peptide | GLFEAIAGFIENGWEGMIDGGGYC | 441 | pH-dependent membrane active peptide |

TABLE 8-continued

| Name | Origin | Amino Acid Sequence | SEQ ID NO: | Type |
|---|---|---|---|---|
| H5WYG | HA2 analogue | GLFHAIAHFIHGGWHGLIHGWYG | 442 | pH-dependent membrane active peptide |
| GALA-INF3-(PEG)6-NH | INF3 fusion peptide | GLFEAIEGFIENGWEGLAEALAEALEALAA-(PEG)6-NH2 | 443 | pH-dependent membrane active peptide |
| CM18-TAT11 | Cecropin-A-Melittin$_{2-12}$ (CM18) fusion peptide | KWKLFKKIGAVLKVLTTG-YGRKKRRQRRR | 444 | pH-dependent membrane active peptide |

In some cases, the endosomolytic moiety comprises a Bak BH3 polypeptide which induces apoptosis through antagonization of suppressor targets such as Bcl-2 and/or Bcl-x$_L$. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71: 261-265 (2011).

In some instances, the endosomolytic moiety comprises a polypeptide (e.g., a cell-penetrating polypeptide) as described in PCT Publication Nos. WO 2013/166155 or WO 2015/069587.

Endosomolytic Lipids

In some embodiments, the endosomolytic moiety is a lipid (e.g., a fusogenic lipid). In some embodiments, a molecule of Formula (I): A-X$_1$—B—X$_2$—C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I): A-X$_1$—B—X$_2$—C, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline; 4-(4-diethyl-amino-1-butylamino)quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino)quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethyl-hydroxychloroquine); 7-fluoro-4-(4-ethyl-(2-hydroxyethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha,alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Cell Penetrating Polypeptide (CPP)

In some embodiments, cell penetrating polypeptide comprises positively charged short peptides with 5-30 amino acids. In some embodiments, cell penetrating polypeptide comprises arginine or lysine rich amino acid sequences. In some embodiments, cell penetrating polypeptide includes any polypeptide or combination thereof listed in Table 9.

TABLE 9

| Peptide | Sequence | SEQ ID NO: |
|---|---|---|
| Antennapedia Penetratin (43-58) | RQIKIWFQNRRMKWKK | 445 |
| HIV-1 TAT protein (48-60) | GRKKRRQRRRPPQ | 446 |
| pVEC Cadherin (615-632) | LLIILRRRIRKQAHAHSK | 447 |
| Transportan Galanine/Mastoparan | GWTLNSAGYLLGKINLKALAALAKKIL | 448 |
| MPG HIV-gp41/SV40 T-antigen | GALFLGFLGAAGSTMGAWSQPKKKRKV | 449 |

TABLE 9-continued

| Peptide | Sequence | SEQ ID NO: |
|---|---|---|
| Pep-1 HIV-reverse transcriptase/SV40 T-antigen | KETWWETWWTEWSQPKKKRKV | 450 |
| Polyarginines | R(n); 6 < n < 12 | 451 |
| MAP | KLALKLALKALKAALKLA | 452 |
| R6W3 | RRWWRRWRR | 453 |
| NLS | CGYGPKKKRKVGG | 454 |
| 8-lysines | KKKKKKKK | 455 |
| ARF (1-22) | MVRRFLVTLRIRRACGPPRVRV | 456 |
| Azurin-p28 | LSTAADMQGVVTDGMASGLDKDYLKPDD | 457 |

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or C1 alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[D-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoactyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M$_2$C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4- azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such asl-(p-Azidosalicylamido)-4-(iodoacetamido) butane (AsIB), N-[4-(p-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon et al., "Self-hydrolyzing maleimides improve the stability and pharmacological properties of antibody-drug conjugates," Nat. Biotechnol. 32(10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 458), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 459), or Gly-Phe-Leu-Gly (SEQ ID NO: 460). In some instances, the linker comprises a peptide moiety such as: Val-Cit (valine-citrulline), Gly-Gly-Phe-Gly (SEQ ID NO: 458), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 459), or Gly-Phe-Leu-Gly (SEQ ID NO: 460). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO 2015/038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO 2015/

057699; WO 2014/080251; WO 2014/197854; WO 2014/145090; or WO 2014/177042.

In some embodiments, $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases, $X_1$ is a $C_1$-$C_6$ alkyl group, such as for example, a $C_5$, $C_4$, $C_3$, $C_2$, or C1 alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances, $X_1$ includes a homobifunctional linker or a heterobifunctional linker described supra. In some cases, $X_1$ includes a heterobifunctional linker. In some cases, $X_1$ includes sMCC. In other instances, $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances, $X_2$ is a bond. In other cases, $X_2$ is a linker. In additional cases, $X_2$ is a non-polymeric linker. In some embodiments, $X_2$ is a $C_1$-$C_6$ alkyl group. In some instances, $X_2$ is a homobifunctional linker or a heterobifunctional linker described supra. In some instances, $X_2$ is a homobifunctional linker described supra. In some instances, $X_2$ is a heterobifunctional linker described supra. In some instances, $X_2$ comprises a maleimide group, such as maleimidocaproyl (mc) or a self-stabilizing maleimide group described above. In some instances, $X_2$ comprises a peptide moiety, such as Val-Cit. In some instances, $X_2$ comprises a benzoic acid group, such as PABA. In additional instances, $X_2$ comprises a combination of a maleimide group, a peptide moiety, and/or a benzoic acid group. In additional instances, $X_2$ comprises a me group. In additional instances, $X_2$ comprises a mc-val-cit group. In additional instances, $X_2$ comprises a Val-Cit-PABA group. In additional instances, $X_2$ comprises a Mc-Val-Cit-PABA group.

Methods of Use

Muscle atrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one aspect, muscle atrophy refers to a significant loss in muscle strength. By significant loss in muscle strength is meant a reduction of strength in diseased, injured, or unused muscle tissue in a subject relative to the same muscle tissue in a control subject. In some instances, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In some instances, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In some aspects, described herein is a method of treating cardiomyopathy in a subject, which comprises providing polynucleic acid molecule or polynucleic acid molecule conjugate described herein and administering to the subject a therapeutically effective amount of a polynucleic acid molecule described herein. In some instances, the subject is diagnosed or suspected to have cardiomyopathy. In some instances, the subject has suffered, or is suffering from one or more symptoms of cardiomyopathy. In some instances, the polynucleic acid molecule or polynucleic acid molecule conjugate is effective to reduce a quantity of the mRNA transcript of human PLN. In some instances, the polynucleic acid molecule or polynucleic acid molecule conjugate mediates RNA interference against the human PLN mRNA as to modulate or treat cardiomyopathy (and/or its symptoms thereof) associated with PLN in a subject. In some aspects, the polynucleic acid molecule or polynucleic acid molecule conjugate mediates RNA interference against a mutated human PLN mRNA (human PLN mRNA having one or more mutation associated with cardiomyopathy) and modulate or treat cardiomyopathy associated with a genetic PLN variant in a subject. In some aspects, the polynucleic acid moiety mediates RNA interference against a human PLN mRNA having one or more mutation selected from a Arg14del (R14del), Arg9Cys (R9C) or Arg25Cys (R25C) and modulate cardiomyopathy associated with a genetic PLN variant in a subject.

In some aspects, described herein is a method of treating cardiomyopathy in a subject, which comprises providing an siRNA-antibody conjugate (siRNA conjugate) described herein and administering to the subject a therapeutically effective amount of the siRNA-antibody conjugate described herein and reducing the levels of PLN mRNA transcript of human PLN in said subject. In some instances, cardiomyopathy is cardiomyopathy associated with PLN. In some instances, the cardiomyopathy associated with PLN is a cardiomyopathy associated with a genetic PLN variant. In some instances, the genetic PLN variant has a mutation in the human PLN gene that includes Arg14del (R14del), Arg9Cys (R9C) or Arg25Cys (R25C). In some instances, the cardiomyopathy associated with PLN is dilated cardiomyopathy. In some instances, the dilated cardiomyopathy is associated with TTN, LMNA, RI3M20, SCN5A, MYH7, TNNT2, and TPMI mutations.

In some aspects, the therapeutically effective amount of siRNA-antibody conjugate is administered to mediate RNA interference against the human PLN mRNA, thereby reduce the levels of mRNA transcript of human PLN in said subject and treat cardiomyopathy associated with PLN in the subject. In some aspects, the therapeutically effective amount of siRNA-conjugate is administered to mediate RNA interference against a genetic PLN variant that has a mutation in the human PLN gene that includes Arg14del (R14del), Arg9Cys (R9C) or Arg25Cys (R25C), thereby reduces the levels of mRNA transcript of human PLN mRNA and treat a genetic cardiomyopathy associated with a genetic PLN variant in the subject. In some instances, the cardiomyopathy associated with PLN is dilated cardiomyopathy. In some instances, the dilated cardiomyopathy is associated with TTN, LMNA, RI3M20, SCN5A, MYH7, TNNT2, and TPMI mutations.

In some aspects, described herein is a method of treating cardiomyopathy in a subject, which comprises providing an siRNA-antibody conjugate (siRNA conjugate) described herein and administering to the subject a therapeutically effective amount of the siRNA-antibody conjugate described herein and reducing the levels of PLN mRNA transcript of human PLN in said subject. The siRNA-conjugate mediates RNA interference against the human PLN mRNA as to treat cardiomyopathy associated with PLN in the subject. In some aspects, the siRNA-conjugate mediates RNA interference against a genetic PLN variant that has a mutation in the human PLN gene that includes Arg14del (R14del), Arg9Cys (R9C) or Arg25Cys (R25C) to reduce the levels of mRNA transcript of human PLN in said subject thereby treat cardiomyopathy associated with a genetic PLN variant in the subject. In some instances, the cardiomyopathy associated with PLN is dilated cardiomyopathy. In some instances, the dilated cardiomyopathy is associated with TTN, LMNA, RI3M20, SCN5A, MYH7, TNNT2, and TPMI mutations.

In some aspects, described herein is a method of alleviating symptoms in a subject with cardiomyopathy, which comprises providing a PLN siRNA-antibody conjugate (PLN-siRNA conjugate or AOC-PLN) described herein and administering to the subject a therapeutically effective amount of the siRNA-antibody conjugate described herein by reducing the levels of mRNA transcript of human PLN. In some instances, the cardiomyopathy is associated with PLN. In some aspects, described herein is a method of alleviating symptoms in a subject with a cardiomyopathy associated with PLN which comprises providing an siRNA-antibody conjugate described herein and administering to the patient with cardiomyopathy associated with PLN a therapeutically effective amount of the siRNA conjugate describes herein by targeting a genetic PLN variant that has a mutation in the human PLN gene that includes Arg14del (R14del), Arg9Cys (R9C) or Arg25Cys (R25C) and reducing the levels of mRNA transcript of human PLN comprising the genetic variant or reducing the levels of PLN protein having the genetic variant. In some instances, the cardiomyopathy associated with PLN is dilated cardiomyopathy. In some instances, dilated cardiomyopathy is associated with TTN, LMNA, RI3M20, SCN5A, MYH7, TNNT2, and TPMI mutations.

In some instances, the symptoms of cardiomyopathy are related to the thickening of the heart muscle or cardiac muscles (e.g., hypertrophied cardiac muscles, etc.). In some instances, the symptoms of cardiomyopathy include arrhythmia (irregular heart rate or rhythm). In some instances, the symptoms of cardiomyopathy include chest pain, especially during activity. In some instances, the symptoms of cardiac hypertrophy include fatigue. In some instances, the symptoms of cardiomyopathy include fluttering or pounding feeling in the chest. In some instances, the symptoms of cardiomyopathy include heart murmur. In some instances, the symptoms of cardiomyopathy include lightheadedness or dizziness. In some instances, the symptoms of cardiomyopathy include fainting. In some instances, the symptoms of cardiomyopathy include shortness of breath, especially during activity.

In some aspects, described herein is a method of improving cardiac muscle functions in a patient comprising by administering to the cardiomyopathy patient a therapeutically effective amount of the siRNA-antibody conjugate described herein thereby reducing the levels of mRNA transcript of human PLN or reducing the levels of PLN protein. In some instances, cardiomyopathy is cardiomyopathy associated with PLN. In some instance cardiomyopathy is cardiomyopathy associated with genetic PLN variant.

In some aspects, described herein is a method of improving cardiac muscle functions or alleviating cardiomyopathy symptoms as described above in a patient suffering from cardiomyopathy by administering to the cardiomyopathy caused by PLN syndrome patient a therapeutically effective amount of the siRNA conjugate described herein by reducing the levels of mRNA transcript of human PLN or reducing the levels of PLN protein. In some instances, the cardiomyopathy associated with PLN is dilated cardiomyopathy. In some instances, the dilated cardiomyopathy is associated with TTN, LMNA, RI3M20, SCN5A, MYH7, TNNT2, and TPMI mutations.

In some aspects, described herein is a method of treating cardiomyopathy in a subject, which comprises providing an antisense oligonucleotide (ASO)-antibody conjugate (ASO-conjugate) described herein and administering to the subject a therapeutically effective amount of the ASO conjugate described herein thereby reducing the levels of PLN mRNA transcript of human PLN in said subject. In some instances, cardiomyopathy is cardiomyopathy associated with PLN. In some instances, the ASO-conjugate mediates RNA interference against the human PLN mRNA to reduce the levels of mRNA transcript of human PLN in the subject, thereby treat cardiomyopathy associated with a genetic PLN variant in the subject. In some aspects, the ASO-conjugate mediates RNA interference against a genetic PLN variant that has a mutation in the human PLN gene that includes Arg14del (R14del), Arg9Cys (R9C) or Arg25Cys (R25C) to reduce the levels of mRNA transcript of human PLN comprising the genetic PLN variant in the subject, thereby treat cardiomyopathy associated with PLN in the subject. In some instances, the cardiomyopathy associated with PLN is dilated cardiomyopathy. In some instances, the dilated cardiomyopathy is associated with TTN, LMNA, RI3M20, SCN5A, MYH7, TNNT2, and TPMI mutations.

In some aspects, described herein is a method of treating cardiomyopathy in a subject. In some instances, the subject with cardiomyopathy suffers from cardiomyopathy associate with PLN or one or more symptoms of cardiomyopathy associate with PLN. In some instances, the subject with cardiomyopathy suffers from cardiomyopathy associated with a genetic PLN variant. In some instances, the subject with cardiomyopathy associated with a genetic PLN variant suffers from cardiomyopathy associated with genetic PLN variant that has a mutation in the human PLN gene that includes Arg14del (R14del), Arg9Cys (R9C) or Arg25Cys (R25C). In some instances, the subject with cardiomyopathy subject has muscle cells expressing a genetic PLN variant that has a mutation in the human PLN gene that includes Arg14del (R14del), Arg9Cys (R9C) or Arg25Cys (R25C). In some embodiments, the muscle cells are cardiac muscle cells. In some instances, the subject with cardiomyopathy associated with PLN suffers from dilated cardiomyopathy. In some instances, dilated cardiomyopathy is associated with TTN, LMNA, RI3M20, SCN5A, MYH7, TNNT2, and TPMI mutations.

In some aspects, described herein is a method of modulating PLN expression or activity in a muscle cell by contacting the muscle cell with a polynucleotide conjugate (siRNA-antibody conjugate or ASO-antibody conjugate) or a polynucleotide molecule (siRNA or ASO), thereby modulating PLN expression or activity in the muscle cell. In some instances, the polynucleotide conjugate or the polynucleotide molecule reduces the PLN expression or activity at least 20%, 30%, 40%, 50%, 60%, 70%, or 80% compared to untreated muscle cells, or before the treatment. In some instances, the effect of reduced PLN expression or activity is maintained for at least 3 days, 7 days, 14 days, 21 days, 28 days, 60 days, 90 days, 120 days, 5 months, 6 months by maintaining the reduced expression or activity of at least 20%, 30%, 40%, or 50%.

In some aspects, described herein is a method of modulating PLN expression or activity in a subject (e.g., a patient) by administering the subject with a polynucleotide conjugate (siRNA-antibody conjugate or ASO-antibody conjugate) or a polynucleotide molecule (siRNA or ASO), thereby modulating PLN expression or activity in the subject. In some instances, the polynucleotide conjugate or the polynucleotide molecule reduces the PLN expression or activity at least 20%, 30%, 40%, 50%, 60%, 70%, or 80% in the muscle cells (e.g., heart muscle cells, skeletal muscle cells, etc.) in the subject compared to untreated subject, or before the treatment. In some instances, the effect of reduced PLN expression or activity is maintained for at least 3 days, 7 days, 14 days, 21 days, 28 days, 60 days, 90 days, 120 days, 5 months, 6 months by maintaining the reduced expression or activity of at least 20%, 30%, 40%, or 50%.

Pharmaceutical Formulation

In some aspects, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some aspects, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, indium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some aspects, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some aspects, the pharmaceutical formulation includes a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some aspects, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, once in two months, once in three months, once in four months, once in five months, once in six months or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some aspects, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some aspects, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hours, 3 hours, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some aspects, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some aspects, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In certain aspect, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain aspects, the pharmaceutical compositions are presented in a pack or dispenser device which contains one or more unit dosage forms containing a compound provided herein. The pack, for example, contains metal or plastic foil, such as a blister pack. In one aspect, the pack or dispenser device is accompanied by instructions for administration. In one aspect, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

The section headings used herein are for organizational purposes only and are not to be construed as limiting the subject matter described.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

As used herein, the term "polynucleic acid" is interchangeably used with the term "oligonucleotide" or "polynucleotide".

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic effect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while $IC_{50}$ values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carry more oxygen and sustain aerobic activity using fats or carbohydrates for fuel. Type I muscle fibers contract for long periods of time but with little force. Type II muscle fibers are further subdivided into three major subtypes (IIa, Ix, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott Williams & Wilkins, 2000. The production of tomographic images from selected muscle tissues by computed axial tomography and sonographic evaluation are additional methods of measuring muscle mass.

The term antibody oligonucleotide conjugate (AOC) refers to an antibody conjugated to a nucleotide.

The term "siRNA-conjugate" or "siRNA-antibody conjugate" refers to an antibody conjugated to a siRNA.

The term "PLN siRNA-conjugate" or "PLN siRNA-antibody conjugate" refers to an antibody conjugated to a siRNA that is capable of hybridizing to a target sequence of the human PLN mRNA.

The term "AOC-PLN" refers to an antibody conjugated to an oligonucleotide (e.g., siRNA) that is capable of hybridizing to a target sequence of the human PLN mRNA.

The term "CD71-PLN AOC" refers to an anti-TfR1 antibody conjugated to an siRNA or an ASO targeting PLN.

EXAMPLES

These examples are provided for illustrative purposes only and not to limit the scope of the claims provided herein.

Example 1: Bioinformatics siRNA Library Design Against Human PLN Transcript

Figure 2:
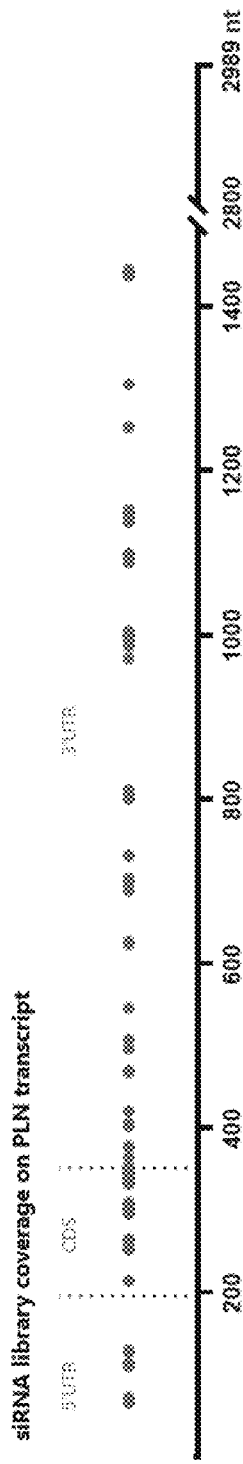
FIG. 2 illustrates the location and quantity of selected PLN siRNA in the PLN mRNA transcript.

FIG. 1 shows a flowchart of in silico selection process of PLN siRNAs. Sequences of all siRNAs that can bind to human PLN mRNA transcript (NM_002667.5) (SEQ ID NO: 295) are collected to generate a starting set of PLN siRNAs. The first eliminating step comprises excluding siRNAs that target regions of transcript with identified disease variants of PLN. Then, the following eliminating steps comprise removing sequences that target areas of transcript with common single nucleotide polymorphism (SNP) and free energy (MEF)<−4. The fourth step comprises selecting for sequences homologous to *Macaca fascicularis* non-human primate (NHP) PLN (XM_005551677.2. The next 2 steps eliminate sequences with 0 and 1 mismatch (MM) with other human transcripts and 0 MM in primary transcript (pre-mRNA). Then, the next step is carrying forward only PLN siRNAs with predicted viability>50. Next, the eliminating step comprises eliminating one or more PLN siRNAs with a match to a seed region of known miRNAs 1-100. Then, the eliminating step continues with eliminating PLN siRNAs with 0 or 1 mismatches (MM) in NHP transcriptome and finally eliminating those with 20 or more predicted off-target hits containing 2 MM. The screen identified a total of 132 siRNA sequences that include 97 siRNA sequences that are 19 bp in length and additional 35 siRNAs that are 21 bp in length. All the PLN siRNA guide and passenger strand sequences are shown in Table 10. Table 10 lists the 132 siRNAs targeting PLN mRNA identified by a bioinformatics approach. All sequences are 100% homologous with non-human primate (NHP) (*Macaca fascicularis*). FIG. 2 shows the location for all selected PLN 132 siRNAs in the PLN mRNA transcript (NM_002667.5) (SEQ ID NO: 295). Thymine (T) and Uracil (U) are interchangeably used in Table 10.

TABLE 10

| Compound | Target Ref NM_002667.5 (SEQ ID NO: 295) Start | End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_047_19m | 47 | 65 | 5'UTR | UUGUGUUGUAUGAAGUCUU | 1 | AAGACUUCAUACAACACAA | 133 |
| PLN_048_19m | 48 | 66 | 5'UTR | AUUGUGUUGUAUGAAGUCU | 2 | AGACUUCAUACAACACAAU | 134 |
| PLN_051_19m | 51 | 69 | 5'UTR | AGUAUUGUGUUGUAUGAAG | 3 | CUUCAUACAACACAAUACU | 135 |
| PLN_054_19m | 54 | 72 | 5'UTR | UAGAGUAUUGUGUUGUAUG | 4 | CAUACAACACAAUACUCUA | 136 |
| PLN_092_19m | 92 | 110 | 5'UTR | UCUUUUAGGUAGCCUUGGC | 5 | GCCAAGGCUACCUAAAAGA | 137 |
| PLN_093_19m | 93 | 111 | 5'UTR | UUCUUUUAGGUAGCCUUGG | 6 | CCAAGGCUACCUAAAAGAA | 138 |
| PLN_094_19m | 94 | 112 | 5'UTR | CUUCUUUUAGGUAGCCUUG | 7 | CAAGGCUACCUAAAAGAAG | 139 |
| PLN_095_19m | 95 | 113 | 5'UTR | UCUUCUUUUAGGUAGCCUU | 8 | AAGGCUACUAAAAGAAGA | 140 |
| PLN_0108_19m | 108 | 126 | 5'UTR | UAUGAGAUAACUGUCUUCU | 9 | AGAAGACAGUUAUCUCAUA | 141 |
| PLN_0110_19m | 110 | 128 | 5'UTR | AAUAUGAGAUAACUGUCUU | 10 | AAGACAGUUAUCUCAUAUU | 142 |
| PLN_0111_19m | 111 | 129 | 5'UTR | AAAUAUGAGAUAACUGUCU | 11 | AGACAGUUAUCUCAUAUUU | 143 |
| PLN_0195_19m | 195 | 213 | CDS | GGUAUGGACUUUCUCCAU | 12 | AUGGAGAAAGUCCAUACC | 144 |
| PLN_0196_19m | 196 | 214 | CDS | AGGUAUUGGACUUUCUCCA | 13 | UGGAGAAAGUCCAAUACCU | 145 |
| PLN_0233_19m | 233 | 251 | CDS | UUCAAUGGUUGAGGCUCUU | 14 | AAGAGCCUCAACCAUUGAA | 146 |
| PLN_0233_21m | 233 | 253 | CDS | AUUUCAAUGGUUGAGGCUCUU | 15 | AAGAGCCUCAACCAUUGAAAU | 147 |
| PLN_0234_19m | 234 | 252 | CDS | UUUCAAUGGUUGAGGCUCU | 16 | AGAGCCUCAACCAUUGAAA | 148 |
| PLN_0234_21m | 234 | 254 | CDS | CAUUUCAAUGGUUGAGGCUCU | 17 | AGAGCCUCAACCAUUGAAAUG | 149 |
| PLN_0236_19m | 236 | 254 | CDS | CAUUUCAAUGGUUGAGGCU | 18 | AGCCUCAACCAUUGAAAUG | 150 |
| PLN_0241_21m | 241 | 261 | CDS | GUUGAGGCAUUUCAAUGGUUG | 19 | CAACCAUUGAAAUGCCUCAAC | 151 |
| PLN_0242_21m | 242 | 262 | CDS | UGUUGAGGCAUUUCAAUGGU | 20 | AACCAUUGAAAUGCCUCAACA | 152 |
| PLN_0243_19m | 243 | 261 | CDS | GUUGAGGCAUUUCAAUGGU | 21 | ACCAUUGAAAUGCCUCAAC | 153 |
| PLN_0243_21m | 243 | 263 | CDS | UUGUUGAGGCAUUUCAAUGGU | 22 | ACCAUUGAAAUGCCUCAACAA | 154 |
| PLN_0244_19m | 244 | 262 | CDS | UGUUGAGGCAUUUCAAUGG | 23 | CCAUUGAAAUGCCUCAACA | 155 |

TABLE 10-continued

| Compound | Target Ref NM_002667.5 (SEQ ID NO: 295) Start | End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_0244_21m | 244 | 264 | CDS | CUUGUUGAGGCAUUUCAAUGG | 24 | CCAUUGAAAUGCCUCAACAAG | 156 |
| PLN_0245_19m | 245 | 263 | CDS | UUGUUGAGGCAUUUCAAUG | 25 | CAUUGAAAUGCCUCAACAA | 157 |
| PLN_0245_21m | 245 | 265 | CDS | GCUGUUGAGGCAUUUCAAUG | 26 | CAUUGAAAUGCCUCAACAAGC | 158 |
| PLN_0276_21m | 276 | 296 | CDS | AUUGAUAAAAUAGAUUCUGUAG | 27 | CUACAGAAUCUAUUUUAUCAAU | 159 |
| PLN_0277_19m | 277 | 295 | CDS | UUGAUAAAAUAGAUUCUGUA | 28 | UACAGAAUCUAUUUUAUCAA | 160 |
| PLN_0277_21m | 277 | 297 | CDS | AAUUGAUAAAAUAGAUUCUGUA | 29 | UACAGAAUCUAUUUUAUCAAUU | 161 |
| PLN_0280_21m | 280 | 300 | CDS | AGAAAUUGAUAAAAUAGAUUCU | 30 | AGAAUCUAUUUUAUCAAUUUCU | 162 |
| PLN_0281_21m | 281 | 301 | CDS | CAGAAAUUGAUAAAAUAGAUUC | 31 | GAAUCUAUUUUAUCAAUUUCUG | 163 |
| PLN_0282_19m | 282 | 300 | CDS | AGAAAUUGAUAAAAUAGAUU | 32 | AAUCUAUUUUAUCAAUUUCU | 164 |
| PLN_0282_21m | 282 | 302 | CDS | ACAGAAAUUGAUAAAAUAGAUU | 33 | AAUCUAUUUUAUCAAUUUCUGU | 165 |
| PLN_0283_21m | 283 | 303 | CDS | GACAGAAAUUGAUAAAAUAGAU | 34 | AUCUAUUUUAUCAAUUUCUGUC | 166 |
| PLN_0284_19m | 284 | 302 | CDS | ACAGAAAUUGAUAAAAUAGA | 35 | UCUAUUUUAUCAAUUUCUGU | 167 |
| PLN_0286_21m | 286 | 306 | CDS | UGAGACAGAAAUUGAUAAAAUA | 36 | UAUUUUAUCAAUUUCUGUCUCA | 168 |
| PLN_0288_21m | 288 | 308 | CDS | GAUGAGACAGAAAUUGAUAAAA | 37 | UUUAUCAAUUUCUGUCUCAUC | 169 |
| PLN_0289_21m | 289 | 309 | CDS | AGAUGAGACAGAAAUUGAUAA | 38 | UUAUCAAUUUCUGUCUCAUCU | 170 |
| PLN_0290_19m | 290 | 308 | CDS | GAUGAGACAGAAAUUGAUA | 39 | UAUCAAUUUCUGUCUCAUC | 171 |
| PLN_0311_21m | 311 | 331 | CDS | CAGAUCAGCAAGAGACAUAUU | 40 | AAUAUGUCUUGCUGAUCUG | 172 |
| PLN_0313_21m | 313 | 331 | CDS | CAGAUCAGCAAGAGACAUA | 41 | UAUGUCUCUUGCUGAUCUG | 173 |
| PLN_0314_21m | 314 | 334 | CDS | AUACAGAUCAGCAAGAGACAU | 42 | AUGUCUCUUGCUGAUCUGUAU | 174 |
| PLN_0315_21m | 315 | 335 | CDS | GAUACAGAUCAGCAAGAGACA | 43 | UGUCUCUUGCUGAUCUGUAUC | 175 |
| PLN_0316_19m | 316 | 334 | CDS | AUACAGAUCAGCAAGAGAC | 44 | GUCUCUUGCUGAUCUGUAU | 176 |
| PLN_0316_21m | 316 | 336 | CDS | UGAUACAGAUCAGCAAGAGAC | 45 | GUCUCUUGCUGAUCUGUAUCA | 177 |
| PLN_0317_19m | 317 | 335 | CDS | GAUACAGAUCAGCAAGAGA | 46 | UCUCUUGCUGAUCUGUAUC | 178 |

TABLE 10-continued

| Compound | Target Ref NM_002667.5 (SEQ ID NO: 295) Start | End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_0317_21m | 317 | 337 | CDS | AUGAUACAGAUCAGCAAGAGA | 47 | UCUCUUGCUGAUCUGUAUCAU | 179 |
| PLN_0318_19m | 318 | 336 | CDS | UGAUACAGAUCAGCAAGAG | 48 | CUCUUGCUGAUCUGUAUCA | 180 |
| PLN_0318_21m | 318 | 338 | CDS | GAUAUACAGAUCAGCAAGAGA | 49 | CUCUUGCUGAUCUGUAUCAUC | 181 |
| PLN_0319_19m | 319 | 337 | CDS | AUGAUACAGAUCAGCAAGA | 50 | UCUUGCUGAUCUGUAUCAU | 182 |
| PLN_0320_21m | 320 | 340 | CDS | ACGAUGAUACAGAUCAGCAAG | 51 | CUUGCUGAUCUGUAUCAUCGU | 183 |
| PLN_0321_21m | 321 | 341 | CDS | CACGAUGAUACAGAUCAGCAA | 52 | UUGCUGAUCUGUAUCAUCGUG | 184 |
| PLN_0322_19m | 322 | 340 | CDS | ACGAUGAUACAGAUCAGCA | 53 | UGCUGAUCUGUAUCAUCGU | 185 |
| PLN_0322_21m | 322 | 342 | CDS | UCACGAUGAUACAGAUCAGCA | 54 | UGCUGAUCUGUAUCAUCGUGA | 186 |
| PLN_0323_19m | 323 | 341 | CDS | CACGAUGAUACAGAUCAGC | 55 | GCUGAUCUGUAUCAUCGUG | 187 |
| PLN_0323_21m | 323 | 343 | CDS | AUCACGAUGAUACAGAUCAGC | 56 | GCUGAUCUGUAUCAUCGUGAU | 188 |
| PLN_0324_21m | 324 | 344 | CDS | CAUCACGAUGAUACAGAUCAG | 57 | CUGAUCUGUAUCAUCGUGAUG | 189 |
| PLN_0325_19m | 325 | 343 | CDS | AUCACGAUGAUACAGAUCA | 58 | UGAUCUGUAUCAUCGUGAU | 190 |
| PLN_0326_21m | 326 | 344 | CDS | AGCAUCACGAUGAUACAGAUC | 59 | GAUCUGUAUCAUCGUGAUG | 191 |
| PLN_0326_21m | 326 | 346 | CDS | AGCAUCACGAUGAUACAGAUC | 60 | GAUCUGUAUCAUCGUGAUGCU | 192 |
| PLN_0327_21m | 327 | 347 | CDS | AAGCAUCACGAUGAUACAGAU | 61 | AUCUGUAUCAUCGUGAUGCUU | 193 |
| PLN_0328_21m | 328 | 348 | CDS | GAAGCAUCACGAUGAUACAGA | 62 | UCUGUAUCAUCGUGAUGCUUC | 194 |
| PLN_0329_19m | 329 | 347 | CDS | AAGCAUCACGAUGAUACAG | 63 | CUGUAUCAUCGUGAUGCUU | 195 |
| PLN_0329_21m | 329 | 349 | CDS | AGAAGCAUCACGAUGAUACAG | 64 | CUGUAUCAUCGUGAUGCUUCU | 196 |
| PLN_0330_19m | 330 | 348 | CDS | GAAGCAUCACGAUGAUACA | 65 | UGUAUCAUCGUGAUGCUUC | 197 |
| PLN_0331_19m | 331 | 349 | CDS | AGAAGCAUCACGAUGAUAC | 66 | GUAUCAUCGUGAUGCUUCU | 198 |
| PLN_0331_21m | 331 | 351 | CDS | AGAGAAGCAUCACGAUGAUAC | 67 | GUAUCAUCGUGAUGCUUCUCU | 199 |
| PLN_0332_21m | 332 | 352 | CDS | CAGAGAAGCAUCACGAUGAUA | 68 | UAUCAUCGUGAUGCUUCUCUG | 200 |
| PLN_0333_19m | 333 | 351 | CDS | AGAGAAGCAUCACGAUGAU | 69 | AUCAUCGUGAUGCUUCUCU | 201 |
| PLN_0333_21m | 333 | 353 | CDS | UCAGAGAAGCAUCACGAUGAU | 70 | AUCAUCGUGAUGCUUCUCUGA | 202 |

TABLE 10-continued

| Compound | Target Ref NM_002667.5 (SEQ ID NO: 295) Start | End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_0334_19m | 334 | 352 | CDS | CAGAGAAGCAUCACGAUGA | 71 | UCAUCGUGAUGCUUCUCUG | 203 |
| PLN_0347_19m | 347 | 365 | CDS-3'UTR | UGUAGCAGAACUUCAGAGA | 72 | UCUCUGAAGUUCUGCUACA | 204 |
| PLN_0358_19m | 358 | 376 | 3'UTR | GAUCUAGAGGUUGUAGCAG | 73 | CUGCUACAACCUCUAGAUC | 205 |
| PLN_0360_19m | 360 | 378 | 3'UTR | CAGAUCUAGAGGUUGUAGC | 74 | GCUACAACCUCUAGAUCUG | 206 |
| PLN_0384_19m | 384 | 402 | 3'UTR | AUUUUAAGCUGAUGUGGCA | 75 | UGCCACAUCAGCUUAAAAU | 207 |
| PLN_0387_19m | 387 | 405 | 3'UTR | CAGAUUUUAAGCUGAUGUG | 76 | CACAUCAGCUUAAAAUCUG | 208 |
| PLN_0402_19m | 402 | 420 | 3'UTR | GUCUGCAUGGGAUGACAGA | 77 | UCUGUCAUCCCAUGCAGAC | 209 |
| PLN_0449_19m | 449 | 467 | 3'UTR | AAACUCUUCUACUCAGGAA | 78 | UUCCUGAGUAGAAGAGUUU | 210 |
| PLN_0450_19m | 450 | 468 | 3'UTR | GAAACUCUUCUACUCAGGA | 79 | UCCUGAGUAGAAGAGUUUC | 211 |
| PLN_0452_19m | 452 | 470 | 3'UTR | AAGAAACUCUUCUACUCAG | 80 | CUGAGUAGAAGAGUUUCUU | 212 |
| PLN_0478_19m | 478 | 496 | 3'UTR | UUAGUCUUAAUCUUGACCU | 81 | AGGUCAAGAUUAAGACUAA | 213 |
| PLN_0479_19m | 479 | 497 | 3'UTR | UUUAGUCUUAAUCUUGACC | 82 | GGUCAAGAUUAAGACUAAA | 214 |
| PLN_0490_19m | 490 | 508 | 3'UTR | UAACAAUAAGUUUUAGUCU | 83 | AGACUAAAACUUAUUGUUA | 215 |
| PLN_0528_19m | 528 | 546 | 3'UTR | UUUCAUGUUUACAAGAUCC | 84 | GGAUCUUGUAAACAUGAAA | 216 |
| PLN_0605_19m | 605 | 623 | 3'UTR | UUGUGAGCCAUGUUGAGGA | 85 | UCCUCAACAUGGCUCACAA | 217 |
| PLN_0609_19m | 609 | 627 | 3'UTR | AAAUUUGUGAGCCAUGUUG | 86 | CAACAUGGCUCACAAAUUU | 218 |
| PLN_0671_19m | 671 | 689 | 3'UTR | GAACUGUUGGCAGUGCAG | 87 | CUGCACUGCCAACAAGUUC | 219 |
| PLN_0679_19m | 679 | 697 | 3'UTR | UAUGAAGUGAACUUGUUGG | 88 | CCAACAAGUUCACUUCAUA | 220 |
| PLN_0681_19m | 681 | 699 | 3'UTR | UAUAUGAAGUGAACUUGUU | 89 | AACAAGUUCACUUCAUAUA | 221 |
| PLN_0685_19m | 685 | 703 | 3'UTR | UUUUAUAUGAAGUGAACUU | 90 | AGUUCACUUCAUAUAAAA | 222 |
| PLN_0712_19m | 712 | 730 | 3'UTR | UUCACCUCAAAAGAGUAAA | 91 | UUUACUCUUUUGAGGUGAA | 223 |
| PLN_0714_19m | 714 | 732 | 3'UTR | UAUUCCACCUCAAAAGAGUA | 92 | UACUCUUUUGAGGUGGAAUA | 224 |
| PLN_0782_19m | 782 | 800 | 3'UTR | UUUGAUACUUGGUGAAGAC | 93 | GUCUUCACCAAGUAUCAAA | 225 |

TABLE 10-continued

| Compound | Target Ref NM_002667.5 (SEQ ID NO: 295) Start | Target Ref NM_002667.5 (SEQ ID NO: 295) End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_0783_19m | 783 | 801 | 3'UTR | CUUUGAUACUUGGUGAAGA | 94 | UCUUCACCAAGUAUCAAAG | 226 |
| PLN_0787_19m | 787 | 805 | 3'UTR | AUUACUUUGAUACUUGGUG | 95 | CACCAAGUAUCAAAGUAAU | 227 |
| PLN_0793_19m | 793 | 811 | 3'UTR | UGUGUAUUACUUUGAUAC | 96 | GUAUCAAAGUAAUAACACA | 228 |
| PLN_0953_19m | 953 | 971 | 3'UTR | UACUUGAUUCUAUCAACU | 97 | AGUUGAUGAGAAUCAAGUA | 229 |
| PLN_0967_19m | 967 | 985 | 3'UTR | GCCUUACUUUUCCAUACUU | 98 | AAGUAUGGAAAAGUAAGGC | 230 |
| PLN_0972_19m | 972 | 990 | 3'UTR | GUAUGGCCUUACUUUUCCA | 99 | UGGAAAAGUAAGGCCAUAC | 231 |
| PLN_0977_19m | 977 | 995 | 3'UTR | UAAGAGUAUGGCCUUACUU | 100 | AAGUAAGGCCAUACUCUUA | 232 |
| PLN_0978_19m | 978 | 996 | 3'UTR | GUAAGAGUAUGGCCUUACU | 101 | AGUAAGGCCAUACUCUUAC | 233 |
| PLN_0979_19m | 979 | 997 | 3'UTR | UGUAAGAGUAUGGCCUUAC | 102 | GUAAGGCCAUACUCUUACA | 234 |
| PLN_0980_19m | 980 | 998 | 3'UTR | AUGUAAGAGUAUGGCCUUA | 103 | UAAGGCCAUACUCUUACAU | 235 |
| PLN_0982_19m | 982 | 1000 | 3'UTR | UUAUGUAAGAGUAUGGCCU | 104 | AGGCCAUACUCUUACAUAA | 236 |
| PLN_0983_19m | 983 | 1001 | 3'UTR | AUUAUGUAAGAGUAUGGCC | 105 | GGCCAUACUCUUACAUAAU | 237 |
| PLN_0984_19m | 984 | 1002 | 3'UTR | UAUUAUGUAAGAGUAUGGC | 106 | GCCAUACUCUUACAUAAUA | 238 |
| PLN_0986_19m | 986 | 1004 | 3'UTR | UUUUAUUAUGUAAGAGUAUG | 107 | CAUACUCUUACAUAAUAAAA | 239 |
| PLN_01070_19m | 1070 | 1088 | 3'UTR | GAUCAUAUGUCUUAGAACA | 108 | UGUUCUAAGACAUAUGAUC | 240 |
| PLN_01072_19m | 1072 | 1090 | 3'UTR | UUGAUCAUAUGUCUUAGAA | 109 | UUCUAAGACAUAUGAUCAA | 241 |
| PLN_01077_19m | 1077 | 1095 | 3'UTR | AUCUGUUGAUCAUAUGUCU | 110 | AGACAUAUGAUCAACAGAU | 242 |
| PLN_01078_19m | 1078 | 1096 | 3'UTR | CAUCUGUUGAUCAUAUGUC | 111 | GACAUAUGAUCAACAGAUG | 243 |
| PLN_01079_19m | 1079 | 1097 | 3'UTR | UCAUCUGUUGAUCAUAUGU | 112 | ACAUAUGAUCAACAGAUGA | 244 |
| PLN_01081_19m | 1081 | 1099 | 3'UTR | UCUCAUCUGUUGAUCAUAU | 113 | AUAUGAUCAACAGAUGAGA | 245 |
| PLN_01119_19m | 1119 | 1137 | 3'UTR | GAUAUGACUAAUCUCACUG | 114 | CAGUGAGAUUAGUCAUAUC | 246 |
| PLN_01120_19m | 1120 | 1138 | 3'UTR | UGAUAUGACUAAUCUCACU | 115 | AGUGAGAUUAGUCAUAUCA | 247 |
| PLN_01121_19m | 1121 | 1139 | 3'UTR | GUGAUAUGACUAAUCUCAC | 116 | GUGAGAUUAGUCAUAUCAC | 248 |
| PLN_01126_19m | 1126 | 1144 | 3'UTR | UAUUAGUGAUAUGACUAAU | 117 | AUUAGUCAUAUCACUAAUA | 249 |

TABLE 10-continued

| Compound | Target Ref NM_002667.5 (SEQ ID NO: 295) Start | End | Region Target | Antisense strand/guide strand sequence (5'-3' end) | SEQ ID NO: | Passenger strand/Sense strand sequence (5'-3' end) | SEQ ID NO: |
|---|---|---|---|---|---|---|---|
| PLN_01129_19m | 1129 | 1147 | 3'UTR | GUAUAUUAGUGAUAUGACU | 118 | AGUCAUAUCACUAAUAUAC | 250 |
| PLN_01130_19m | 1130 | 1148 | 3'UTR | AGUAUAUUAGUGAUAUGAC | 119 | GUCAUAUCACUAAUAUACU | 251 |
| PLN_01132_19m | 1132 | 1150 | 3'UTR | UUAGUAUAUUAGUGAUAUG | 120 | CAUAUCACUAAUAUACUAA | 252 |
| PLN_01134_19m | 1134 | 1152 | 3'UTR | UGUUAGUAUAUUAGUGAUA | 121 | UAUCACUAAUAUACUAACA | 253 |
| PLN_01234_19m | 1234 | 1252 | 3'UTR | AGUCUUAAGGUUUCAUGAU | 122 | AUCAUGAAACCUUAAGACU | 254 |
| PLN_01235_19m | 1235 | 1253 | 3'UTR | AAGUCUUAAGGUUUCAUGA | 123 | UCAUGAAACCUUAAGACUU | 255 |
| PLN_01287_19m | 1287 | 1305 | 3'UTR | GCCUGCAUUGGAUGUUAGG | 124 | CCUAACAUCCAAUGCAGGC | 256 |
| PLN_01419_19m | 1419 | 1437 | 3'UTR | UAGAGAUGGGCCAACAAGUUC | 125 | GAACUUGUUGGCCCAUCUA | 257 |
| PLN_01420_19m | 1420 | 1438 | 3'UTR | AUAGAGAUGGGCCAACAAGU | 126 | AACUUGUUGGCCCAUCUAU | 258 |
| PLN_01421_19m | 1421 | 1439 | 3'UTR | AAUAGAGAUGGGCCAACAAG | 127 | ACUUGUUGGCCCAUCUAUU | 259 |
| PLN_01422_19m | 1422 | 1440 | 3'UTR | UAAUAGAGAUGGGCCAACAA | 128 | CUUGUUGGCCCAUCUAUUA | 260 |
| PLN_01423_19m | 1423 | 1441 | 3'UTR | GUAAUAGAUGGGCCAACAA | 129 | UUGUUGGCCCAUCUAUUAC | 261 |
| PLN_01424_19m | 1424 | 1442 | 3'UTR | UGUAAUAGAUGGGCCAACA | 130 | UGUUGGCCCAUCUAUUACA | 262 |
| PLN_01425_19m | 1425 | 1443 | 3'UTR | AUGUAAUAGAUGGGCCAAC | 131 | GUUGGCCCAUCUAUUACAU | 263 |
| PLN_01426_19m | 1426 | 1444 | 3'UTR | GAUGUAAUAGAUGGGCCAA | 132 | UUGGCCCAUCUAUUACAUC | 264 |

Example 2: siRNA Library Synthesis

Materials and Methods siRNA Sequence and Synthesis

All siRNA single strands were synthesized following standard solid phase synthesis methods on a MerMade12 synthesizer. Standard 2'-O-methyl-base loaded (A/C/G/U) and Universal CPG 1000A0 solid support were used and phosphoramidites (2'-O-methyl, 2'-MOE, 2'-fluoro, 2'-deoxy, LNA) were dissolved in anhydrous acetonitrile to make 0.1M. 3% Trichloroacetic Acid in Dichloromethane, 0.25M 5-ethylthio Tetrazole in acetonitrile were used as deblock reagent and activation reagent respectively. 0.02M Iodine in pyridine/THF/H2O was used as oxidation reagent and 0.05M (dimethylamino-methylidene)amino)-3H-1,2,4-dithiazoline-3-thione (DDTT) in pyridine/acetonitrile was used as sulfurizing reagent. Acetic Anhydride/THF/2,6-Lutidine (Cap A) and 16% N-Methylimidazole in THF (Cap B) were used as capping reagents. Phosphoryl guanidine (PG) sequences were prepared by replacing the oxidation reagent with 0.25M 2-Azido-1,3-dimethylimidazolinium Hexafluorophosphate in acetonitrile/toluene. After synthesis, solid supports were dried and incubated in Ammonium Hydroxide/40% aqueous Methylamine solution (AMA) for 2 hours at room temperature. The CPG was filtered out and washed with Water/Methanol and the combined filtrate was concentrated under vacuum.

Figure 14:
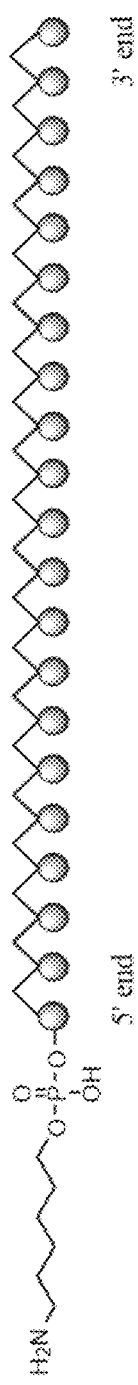
FIG. 14 shows a representative structure of a siRNA passenger strand with a $C_6$—$NH_2$ conjugation handle at the 5' end.
Figure 15:
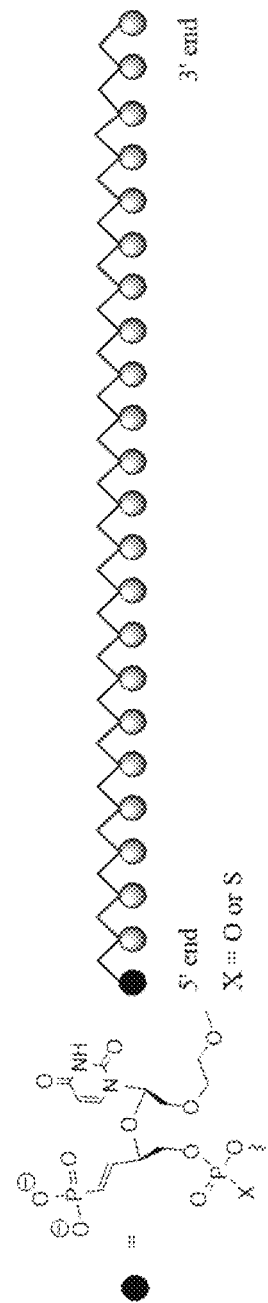
FIG. 15 shows a representative structure of a siRNA guide strand with a 5' (E) vinyl phosphonate.

Purified single strands were duplexed to make double stranded siRNA. siRNA passenger strands were synthesized with or without a C6-NH$_2$ conjugation handle at the 5'end, attached through a phosphodiester linkage. siRNA guide strands were synthesized with or without a 5'-(E)-vinyl phosphonate modified nucleotide. FIG. 14 and FIG. 15 show representative structures of the formats used for in vivo experiments.

concentration was 0.1 nM. All plates contained the following controls: mock transfection (Lipofectamine treatment without siRNA), 2 positive controls from Dharmacon (J-011754-06 and J-011754-07), and one non-targeting siRNA negative control. Cells were maintained in culture for additional 72 hours, at which time, media was removed and 150 µl Trizol (ThermoFisher) was used to harvest the cells for RNA extraction.

RNA was prepared using a ZYMO 96-well RNA kit (Zymo Direct-zol R2056), RT transcribed (High-Capacity cDNA Reverse Transcription Kits, Applied biosystems, ThermoFisher) and relative RNA expression levels quantified by RT-qPCR using commercially available TaqMan probes (PLN: Hs00160179_m1 (FAM) and RPL13A: Hs03043884_g1 (VIC), LifeTechnology). PLN expression data were analyzed using the 2^-ΔΔCT method normalized to RPL13a expression, and are presented as % KD relative to mock-transfected cells.

Results

Figure 3:
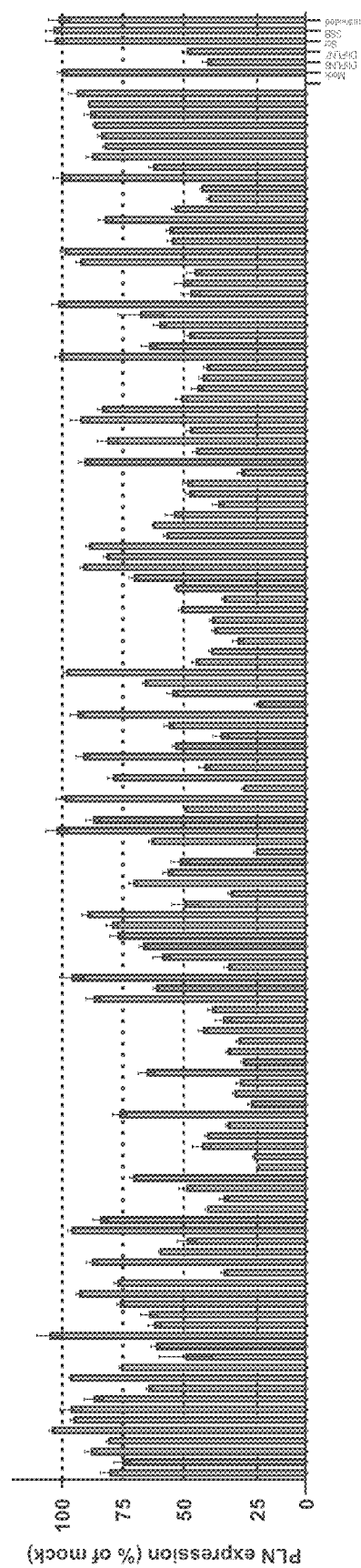
FIG. 3 is a representative bar graph showing PLN mRNA expression levels in iCM$^2$ cells transfected with PLN siRNAs, wherein each of the leftmost 132 bars shown in the bar graph correspond PLN mRNA expression levels in iCM$^2$ cells transfected with PLN siRNAs corresponding to guide strand sequences SEQ ID NOs: 1-132 from left to right, in order of appearance, at a concentration of 0.1 nM at 3 days post transfection. The six rightmost bars of the graph correspond to PLN mRNA expression levels in iCM$^2$ cells transfected with a mock transfection treatment, 2 positive controls, and one non-targeting siRNA negative control (from left to right in order of appearance), each at a concentration of 0.1 nM at 3 days post transfection.

All the 132 Human and NHP cross-reactive PLN siRNAs were tested in a primary in vitro screening in Human iPS-cardiomyocytes[2] (iCM[2], Fujifilm-CDI) at 0.1 nM as shown in FIG. 3. The results indicate that the selected siRNAs have various levels of mRNA knock down. Several PLN siRNAs produced 75% or higher PLN mRNA knock down (KD) at the concentration of 0.1 nM.

Example 3: In Vitro Evaluation of PLN siRNA Potency

Materials and Methods

The synthesis of the siRNA is described in Example 2. The potency and maximum KD activity of 7 siRNA sequences are described in Table 11.

TABLE 11

| SEQ ID NO: | Compound | Target Region | Guide Strand Sequence (5'-3') | IC50 (pM) | mRNA KD% (25 nM) |
|---|---|---|---|---|---|
| 31 | PLN_0281_21m | CDS | CAGAAAUUGAUAAAUAGAUUC | 9 | 92 |
| 36 | PLN_0286_21m | CDS | UGAGACAGAAAUUGAUAAAUA | 54 | 87 |
| 37 | PLN_0288_21m | CDS | GAUGAGACAGAAAUUGAUAAA | 46 | 92 |
| 49 | PLN_0318_21m | CDS | GAUGAUACAGAUCAGCAAGAG | 16 | 93 |
| 59 | PLN_0326_21m | CDS | AGCAUCACGAUGAUACAGAUC | 93 | 95 |
| 74 | PLN_0360_19m | 3'UTR | CAGAUCUAGAGGUUGUAGC | 33 | 95 |
| 96 | PLN_0793_19m | 3'UTR | UGUGUUAUUACUUUGAUAC | 36 | 87 |

Assay

Human iPSC derived cardiomyocytes (Fujifilm C1016) were cultured following Fujifilm protocol, utilizing iCell CM Plating Medium (CMM-100-110-005) and iCell Maintenance Medium (CMM-100-120-005). For transfection, cells were plated at a density of 25,000 cells/well in 96-well plates. Cultures were maintained at 37° C. under 5% CO$_2$ for 72 hrs. At this time, media was exchanged (100 µl) and siRNA transfection mix was added to the wells (20 µl). Transfections were performed with RNAiMax (ThermoFisher) following manufacturer's instruction. Each well contained a final volume of 120 µl (100 µl maintenance media+20 µl optimem) and 0.2 µl lipofectamine. siRNA final Assay Human iPSC derived cardiomyocytes were cultured, processed and analyzed as explained above. Various concentrations of the siRNAs (2.5 fM-50 nM) were used to determine siRNA IC50. Data were analyzed by nonlinear regression using a 3-parameter dose response inhibition function (GraphPad Prism). All knock down results represent the maximal observed KD under these experimental conditions.

Results

The dose response curve of 15 different siRNAs show increasing PLN mRNA knock down (FIG. 4A). The 7 most potent siRNA were further assessed in a dose response curve assay.

The dose response curve of the selected 7 siRNA showed increased PLN mRNA knock down with increasing concentrations (2.5 fM-50 nM) of siRNA with at least 87% knock down at 25 nM (FIG. 4B). The IC50 of these siRNAs ranging from 9 pM for siRNA PLN_0281_21m (SEQ ID NO: 31) to 93 pM for siRNA PLN_0326_19m (SEQ ID NO: 59) are summarized in Table 11. These results show that siRNA having at least 87% knock have different IC50 values ranging from 9 to 93 pM.

Example 4: Analysis of Effects of PLN siRNA on PLN Protein Expression

Materials and Methods

The synthesis of the siRNAs are described in Example 2. The 7 siRNA sequences assessed are described in Table 10, Table 11, Example 1, and Example 3. The method for the knock down assay is described in Example 3.

Assay

For PLN protein knock down (KD) analysis, 300,000 cardiomyocytes were seeded in 12 well format, transfected with siRNAs at 0.1 nM and 1 nM concentrations and collected 5 days post-transfection using 100 ul RIPA buffer with the addition of protease inhibitors. Protein concentration in the lysate was quantified using Pierce BCA assay (ThermoFisher). Protein samples were analyzed by capillary electrophoresis and Jess simple Western, loading 1 ug total protein per capillary. The anti-PLN antibody used was ab85146 (Abcam). Total protein module of Jess was used for normalization and data was processed using the compass software provided by the manufacturer.

Results

Figure 5A:
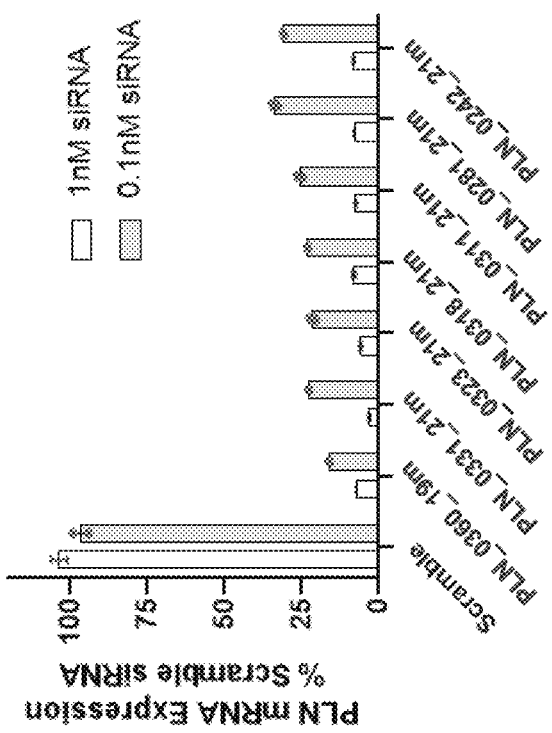
FIG. 5A is a representative bar graph showing PLN mRNA expression levels in iCM$^2$ cells transfected with seven different PLN siRNAs at siRNA concentrations of 0.1 nM and 1 nM at 3 days post PLN siRNA transfection measured by qPCR.
Figure 5B:
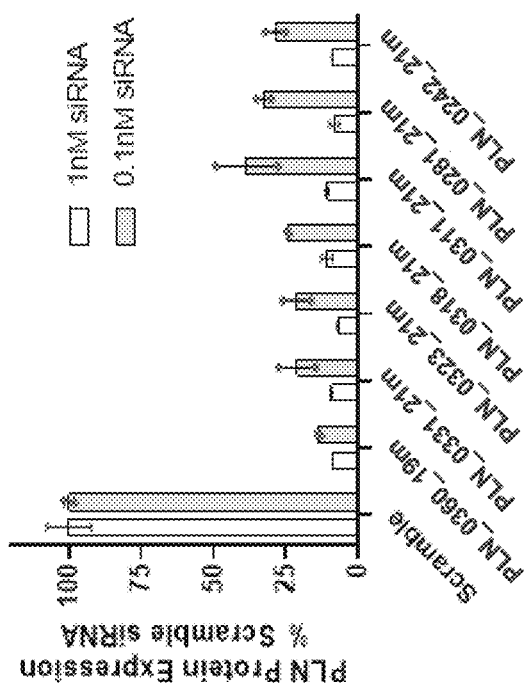
FIG. 5B is a representative bar graph showing relative PLN protein expression levels in iCM$^2$ cells transfected with seven different PLN siRNAs at siRNA concentrations of 0.1 nM and 1 nM at 5 days post PLN siRNA transfection measured by JESS-western blotting.
Figure 5C:
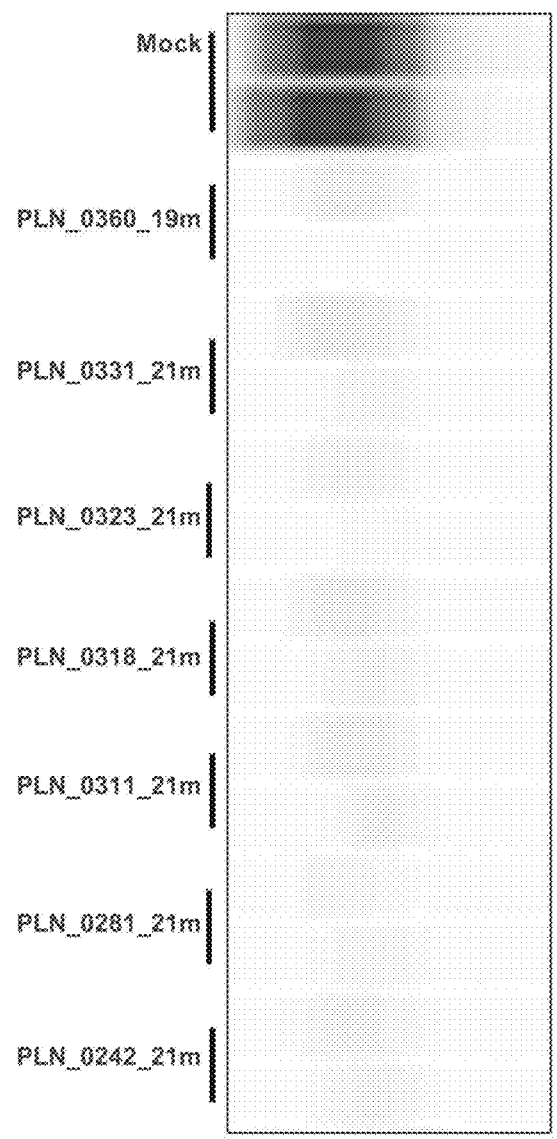
FIG. 5C shows a representative image of PLN protein expression levels in cells treated with seven different PLN siRNAs and analyzed by capillary western blotting using an anti-PLN antibody (Abcam).

The 7 PLN siRNAs induced PLN mRNA knock down (decreased expression) in cells in a dose dependent manner with highest knock down at 1 nM concentration as shown in FIG. 5A. In addition, these selected 7 siRNAs decreased PLN protein expression levels in a dose dependent manner (FIG. 5B). PLN protein expression levels in cells treated with these 7 PLN siRNAs at a concentration of 1 nM were significantly reduced as analyzed by Western Blot (FIG. 5C).

The results indicate that the PLN siRNA induced mRNA knock down correlate with decreased PLN expression levels in cells treated with these 7 PLN siRNAs.

Example 5: In Vitro Evaluation of ASO Activity

Materials and Methods

The synthesis of the ASO are similar to the one described in Example 2. The 6 base ASO sequences are described in Table 12A and the chemically modified ASO sequences are described in Table 12B. The method for the knock down assay is described in Example 3.

TABLE 12A

| Compound | Location | Base ASO Sequence (5'-3') | SEQ ID NO: |
|---|---|---|---|
| ASO 1 | PLN_0281 | CAGAAAUUGAUAAAUAGAUU | 265 |
| ASO 2 | PLN_0318 | AUGAUACAGAUCAGCAAGAG | 266 |
| ASO 3 | PLN_0323 | AUCACGAUGAUACAGAUCAG | 267 |
| ASO 4 | PLN_0358 | CAGAUCUAGAGGUUGUAGCA | 268 |
| ASO 5 | PLN_0360 | GCAGAUCUAGAGGUUGUAGC | 269 |
| ASO 6 | PLN_0780 | UUUGAUACUUGGUGAAGACC | 270 |

TABLE 12B

| Compound | Location | Modified ASO Sequence (5'-3') | SEQ ID NO: |
|---|---|---|---|
| ASO 1 | PLN_0281 | (Cm)s(Am)s(Gm)s(Am)s(Am)sdAsdTsdTsdGsdAsdTsdAsdAsdAsdTs(Am)s(Gm)s(Am)s(Um)s(Um) | 271 |
| ASO 2 | PLN_0318 | (Am)s(Um)s(Gm)s(Am)s(Um)sdAsdCsdAsdGsdAsdTsdCsdAsdGsdCs(Am)s(Am)s(Gm)s(Am)s(Gm) | 272 |
| ASO 3 | PLN_0323 | (Am)s(Um)s(Cm)s(Am)s(Cm)sdGsdAsdTsdGsdAsdTsdAsdCsdAsdGs(Am)s(Um)s(Cm)s(Am)s(Gm) | 273 |
| ASO 4 | PLN_0358 | (Cm)s(Am)s(Gm)s(Am)s(Um)sdCsdTsdAsdGsdAsdGsdGsdTsdTsdGs(Um)s(Am)s(Gm)s(Cm)s(Am) | 274 |
| ASO 5 | PLN_0360 | (Gm)s(Cm)s(Am)s(Gm)s(Am)sdTsdCsdTsdAsdGsdAsdGsdGsdTsdTs(Gm)s(Um)s(Am)s(Gm)s(Cm) | 275 |
| ASO 6 | PLN_0780 | (Um)s(Um)s(Um)s(Gm)s(Am)sdTsdAsdCsdTsdTsdGsdGsdTsdGsdAs(Am)s(Gm)s(Am)s(Cm)s(Cm) | 276 |

(Xm) refers to 2'-OCH₃ modified nucleotide, where X is any base and methylated oxygen at 2' position on ribose; dX refers to 2'-H deoxy modified nucleotide, where X is any base; s refers to a phosphorothioate backbone modification, phosphorothioate linkage between bases; and (5'NH₂C₆) refers to aminohexyl handle/linker. In some instances, (NH₂C₆) is coupled to the 5' end of the ASO.

Human iPSC derived cardiomyocytes seeded at 25,000 cells per well (96 well format) were treated with antisense oligonucleotides targeting human PLN mRNA. The ASOs were transfected at 1 μM concentration using lipofectamine RNAimax for 72 hours. Cells were collected and gene expression was analyzed by qPCR as previously described.

Results

Figure 6:
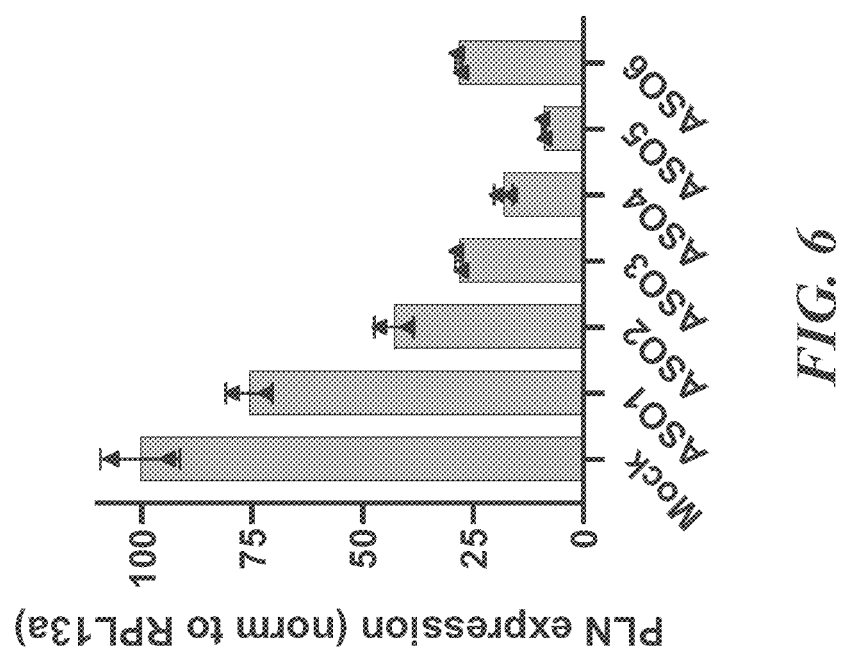
FIG. 6 is a representative bar graph showing PLN mRNA expression levels in iCM$^2$ cells transfected with six different PLN antisense oligonucleotides (ASOs), respectively at a concentration of 1 µM at 3 days post transfection.
Figures 7A, 7B, 7C, 7D:
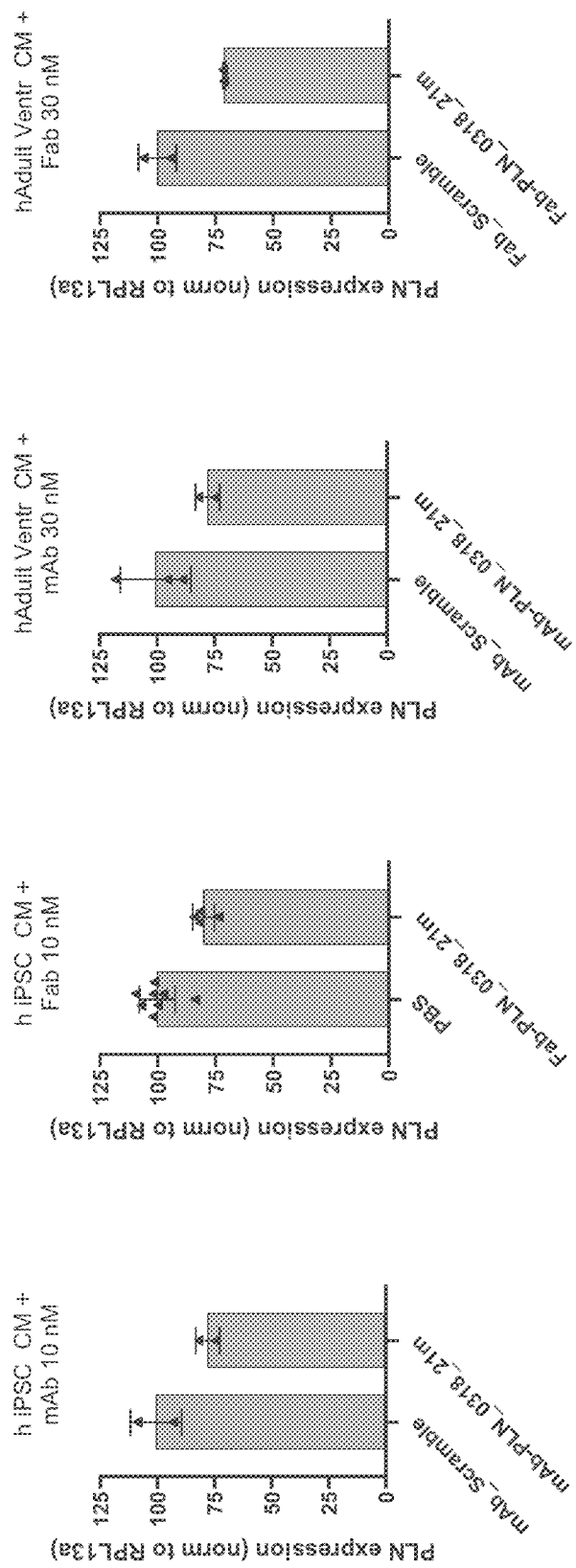
FIGS. 7A-7B are representative bar graphs showing in vitro PLN mRNA levels in human iPSC cardiomyocytes iCM2 treated with PLN siRNA conjugated to the full length monoclonal anti-transferrin receptor antibody (mAb anti-TfR1) at a concentration of 10 nM of mAb-AOC (FIG. 7A) or with PLN siRNA conjugate to the Fab fragment derived from an anti-transferrin receptor antibody (Fab-AOC) at a concentration of 10 nM at 3 days post-transfection (FIG. 7B).
FIGS. 7C-7D are representative bar graphs showing in vitro PLN mRNA levels in human adult ventricular cardiomyocytes treated with PLN siRNA conjugated to the full length monoclonal anti-transferrin receptor antibody (mAb anti-TfR1) at a concentration of 30 nM of mAb-AOC (FIG. 7C) or with PLN siRNA conjugate to the Fab fragment derived from an anti-transferrin receptor antibody (Fab-AOC) at a concentration of 30 nM at 3 days post-transfection (FIG. 7D).

PLN mRNA levels were knocked down (decreased) in iCM² cardiomyocyte cells transfected with 6 different PLN ASOs at a concentration of 1 μM for 72 hours (FIG. 6). The decreased PLN mRNA expression levels ranged from 25% knock down for ASO 1 to more than 90% knock down for ASO 5. These results indicate that PLN ASOs are able to decrease PLN mRNA levels in vitro.

Example 6: Conjugate Synthesis

Anti-Human Transferrin Receptor Antibody

Anti-human transferrin receptor antibody is a human IgG1 monoclonal antibody that binds to the human transferrin receptor 1. The antibody was produced as described in U.S. Pat. No. 10,913,800.

Anti-Transferrin Receptor Antibody

Anti-mouse transferrin receptor antibody or CD71 mAb is a rat IgG2a subclass monoclonal antibody that binds mouse CD71 or mouse transferrin receptor 1 (mTfR1). The antibody was produced by BioXcell and it is commercially available (Catalog #BE0175).

IgG2a Isotype Control Antibody

Rat IgG2a isotype control antibody was purchased from BioXcell (Clone 2A3, Catalog #BE0089). This antibody is specific to trinitrophenol and does not have any known antigens in mouse.

AOC Synthesis

Antibody Cys-MCC-siRNA Conjugation by Random Cysteine Conjugation siRNAs were synthesized on a solid support made of controlled pore glass (CPG) employing the conventional phosphoramidite oligomerization chemistry and purified by high-performance liquid chromatography (HPLC). The passenger strand of the siRNA used for conjugation was synthesized with a C6 amino linker at the 5'-end. Functionalized siRNA (maleimide Linker-siRNA) was obtained by the reaction of linker with siRNA in slightly basic conditions (pH 7.4) in 50% DMSO for 30 min at room temperature, and reaction completion was confirmed by MS. Excess linker and DMSO were removed by spin filtration using AMICON 3K MWCO filters or TFF and buffer exchange with pH 6 sodium acetate buffer. PLN AOC was generated using a standard random cysteine conjugation method of murine anti-TfR1 monoclonal antibody and PLN targeting siRNA. In practice, the interchain disulfides of the antibody are partially and mildly reduced with TCEP tris(2-carboxyethyl) phosphine) to reveal cysteines that are highly and selectively reactive with the maleimide linker on the siRNA. This reaction forms a covalent link between the two advanced intermediates. The remaining thiols were capped with N-ethylmaleimide (NEM) prior to purification.

The reaction mixture was purified using strong anion exchange chromatography (SAX) to separate unreacted Ab, a drug-antibody ratio (DAR) species (i.e., one siRNA per antibody is DAR1), and excess siRNA. DAR1 AOC and DAR2 AOC fractions were collected, concentrated, buffer exchanged into PBS, and sterile filtered using a 0.2 μm filter.

Step 1: Antibody Interchain Disulfide Reduction with TCEP and Conjugation

The reduced antibody was made by adding 2 mM EDTA and 4 equivalents (eq) of TCEP in PBS to a solution of antibody in PBS or 20 mM Histidine, 145 mM NaCl, pH 6 buffer. This solution was incubated for 4 hrs at 37° C. To the reduced antibody solution, 1.1 eq of MCC-C6-siRNA was added. Analysis of the reaction mixture by analytical SAX column chromatography showed antibody-siRNA conjugate along with unreacted antibody and siRNA.

Step 2: Purification

The crude reaction mixture was purified by AKTA Pure FPLC using strong anion exchange chromatography method-1. Fractions containing DAR1 and DAR>2 antibody-siRNA conjugates were separated, concentrated, buffer exchanged with pH 7.2 PBS, and sterile filtered using 0.2 μm filters.

Step-3: Analysis of the Purified Conjugate

The isolated conjugates were characterized by SEC, SAX chromatography. The purity of the conjugate was assessed by analytical HPLC using either anion exchange chromatography method-2 or anion exchange chromatography method-3 as described herein. Isolated DAR1 conjugates are typically eluted at 9.0±0.3 min on analytical SAX method and are greater than 90% pure. The typical DAR>2 cysteine conjugate contains more than 90% DAR2 and less than 10% DAR3.

Fab' Generation from mAb and Conjugation to siRNA

Figure 16:
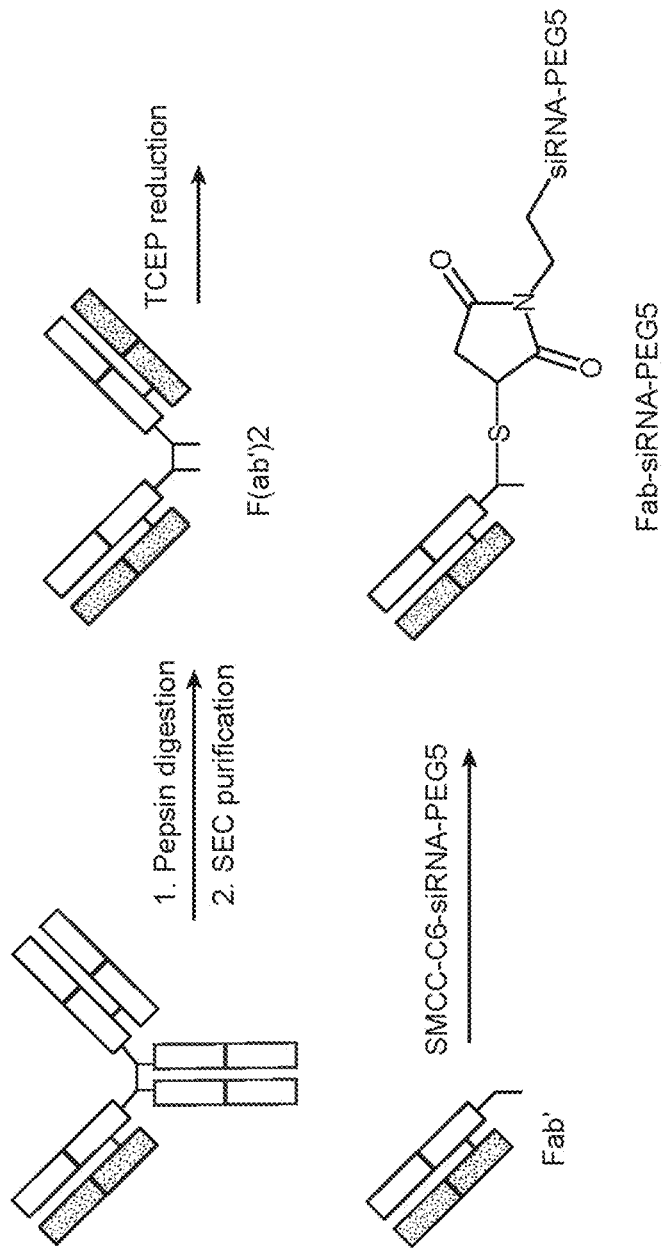
FIG. 16 shows a representative structure of Scheme-3: Fab-siRNA conjugate generation.

Scheme of Fab'-siRNA conjugate is described in FIG. 16.

The antibody was buffer exchanged with pH 4.0, 20 mM sodium acetate/acetic acid buffer and made up to 5 mg/ml concentration. Immobilized pepsin (Thermo Scientific, Prod #20343) was added and incubated for 3 hours at 37° C. The reaction mixture was filtered using 30 kDa MWCO Amicon spin filters and pH 7.4 PBS. The retentate was collected and purified using size exclusion chromatography to isolate F(ab')2. The collected F(ab')2 was then reduced by 10 equivalents of TCEP and conjugated with SMCC-C6-siRNA-PEG5 at room temperature in pH 7.4 PBS. Analysis of reaction mixture on SAX chromatography showed Fab-siRNA conjugate along with unreacted Fab and siRNA-PEG.

Fab' Oligonucleotide Conjugate Synthesis Method (FabOC)

Step 1: Fab Expression

Fab antibody fragments were synthesized in-house using CHO or HEK293 expression and purified by protein L. The sequences of the FabOC antibody fragments of human a-TfR1 antibody are provided in Table 13.

TABLE 13

| Compound | SEQ ID NO: | Sequence |
| --- | --- | --- |
| FabOC peptide | 465 | MEWSWVFLFFLSVTTGVHSQVQLVQSGAEVKKPGASVKVSCKA SGYTFTNYWMHWVRQAPGQGLEWMGEINPINGRSNYAQKFQG RVTLTVDTSISTAYMELSRLRSDDTAVYYCARGTRAMHYWGQG TLVTVSSASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKRVEPKSCDKTHTCG |
| FabOC nucleotide | 466 | ATGGAATGGTCATGGGTTTTTTGTTTTTCCTCTCAGTTACGAC TGGTGTCCATAGCCAAGTCCAACTGGTGCAGTCCGGTGCGGAG GTTAAGAAGCCCGGAGCGAGCGTAAAGGTGAGTTGTAAAGCG AGTGGATACACGTTCACGAACTATTGGATGCATTGGGTTCGAC AAGCACCGGGTCAGGGACTTGAGTGGATGGGAGAAATTAATC |

TABLE 13-continued

| Compound | SEQ ID NO: | Sequence |
|---|---|---|
| | | CGATTAACGGTCGCAGTAACTATGCGCAGAAATTCCAAGGCC<br>GAGTAACTCTCACCGTGGACACGTCCATCTCTACAGCGTACAT<br>GGAACTCAGCAGGTTGCGCTCTGACGATACCGCAGTTTATTAT<br>TGCGCGCGAGGGACGCGGGCTATGCACTATTGGGGGCAGGGC<br>ACCCTCGTCACCGTATCATCTGCGAGTACGAAGGGACCTTCTG<br>TGTTCCCATTGGCTCCCAGCAGCAAAAGTACCAGTGGTGGAAC<br>AGCTGCGCTTGGATGCCTGGTGAAAGATTATTTCCCCGAGCCG<br>GTGACAGTCAGCTGGAACAGCGGCGCACTCACCAGCGGTGTA<br>CATACGTTCCCGGCGGTTTTGCAATCTAGTGGCCTCTATTCCCT<br>TAGTTCCGTAGTTACCGTCCCATCTTCAAGCCTCGGAACCCAG<br>ACTTACATCTGCAACGTCAATCATAAGCCCAGTAACACAAAA<br>GTTGATAAGAGAGTAGAGCCGAAATCCTGTGATAAGACCCAC<br>ACATGTGGG |
| Light chain peptide | 467 | MSVPTQVLGLLLLWLTDARCDIQMTQSPSSLSASVGDRVTITCRT<br>SENIYNNLAWYQQKPGKAPKLLIYAATNLAEGVPSRFSGSGSGT<br>DYTLTISSLQPEDFATYYCQHFWGTPLTFGGGTKVEIKRTVAAPS<br>VFIFPPSDEQLKSGTASVVCLLNNFYPREAKVQWKVDNALQSGN<br>SQESVTEQDSKDSTYSLSSTLTLSKADYEKHKVYACEVTHQGLSS<br>PVTKSFNRGEC |
| Light chain nucleotide | 468 | GCCTCCGGACTCTAGAGCCGCCACCATGAGCGTACCAACCCA<br>GGTGCTCGGACTCCTGTTGTTGTGGCTCACCGATGCAAGATGC<br>GATATACAAATGACACAAAGCCCAAGTAGTTTGTCAGCCAGC<br>GTAGGGGATAGAGTTACTATAACTTGCCGAACGTCTGAAAAT<br>ATATATAATAACCTCGCGTGGTACCAGCAGAAGCCCGGCAAG<br>GCCCCTAAACTCCTCATTTATGCAGCTACTAACCTCGCTGAAG<br>GAGTACCATCAAGGTTCTCAGGCAGCGGGTCTGGAACTGACT<br>ACACATTGACTATTTCAAGCCTTCAGCCAGAGGACTTCGCTAC<br>ATACTACTGTCAACACTTCTGGGGGACTCCGCTTACTTTCGGA<br>GGCGGTACCAAAGTGGAGATAAAACGGACGGTTGCTGCTCCG<br>AGCGTTTTTATATTCCCGCCCTCTGATGAACAGCTGAAATCAG<br>GCACTGCGAGCGTTGTTTGCTTGCTGAATAACTTTTACCCCCG<br>CGAGGCGAAAGTACAATGGAAGGTAGACAACGCACTGCAATC<br>TGGGAATAGTCAAGAGAGTGTTACCGAACAAGATTCAAAAGA<br>TTCCACTTATTCCCTTAGTTCTACTTTGACACTGAGCAAAGCAG<br>ATTACGAGAAACATAAGGTCTACGCCTGCGAGGTGACGCACC<br>AGGGCCTGAGCAGCCCAGTTACAAAGTCCTTCAATCGAGGTG<br>AGTGTTAGGCGGCCGCTATAAGGGT |

Step 2: Fab Conjugation to Oligonucleotide

To the purified Fab, 2 mM of EDTA and 1 eq of TCEP in PBS was added. The solution was incubated at 37° C. for 4 hrs. Lyophilized siRNA was reconstituted in 50 mM PB, pH 7.6 and pH adjusted to pH 7.2 followed by the addition of 8 eq of SMCC in DMSO. The reaction mixture was incubated at room temperature (RT) for 40 min. The SMCC activation was verified by mass spectrometry (MS). The reaction mixture was treated and buffer exchanged with 10 mM Sodium Acetate buffer, pH 6.0 using 3K MWCO spin filters.

To the reduced Fab, 1 eq of SMCC activated siRNA solution was added and the reaction mixture was analyzed by analytical SAX.

Purification of FabOC

The crude reaction mixture was purified by AKTA explorerpure FPLC using anion exchange chromatography method-1. Fractions containing FabOC (DAR1 and DAR2 Fab-siRNA conjugates) were separated, concentrated and buffer exchanged with pH 7.4 PBS.

Step 3: Analysis of the Purified FabOC

The characterization and purity of the isolated conjugate was assessed by analytical HPLC using anion exchange chromatography method-2 or 3 as well as by SEC method-1.

Purification and Analytical Methods

Anion exchange chromatography method (SAX)-1

Column: Tosoh Bioscience, TSKGel SuperQ-5PW, 21.5 mm ID X 15 cm, 13 μm

Solvent A: 20 mM TRIS buffer, pH 8.0; Solvent B: 20 mM TRIS, 1.5M NaCl, pH 8.0;

Flow Rate: 6.0 ml/min

| Gradient: | | |
|---|---|---|
| % A | % B | Column Volume |
| 100 | 0 | 1.00 |
| 60 | 40 | 18.00 |
| 40 | 60 | 2.00 |
| 40 | 60 | 5.00 |
| 0 | 100 | 2.00 |
| 100 | 0 | 2.00 |

| Anion exchange chromatography (SAX) method-2 | | |
|---|---|---|

Column: Thermo Scientific, ProPac ™ SAX-10, Bio LCTM, 4 X 250 mm
Solvent A: 80% 10 mM TRIS pH 8, 20% ethanol; Solvent B: 80% 10 mM TRIS pH 8, 20% ethanol, 1.5M NaCl; Flow Rate: 0.75 ml/min

| Gradient: | | |
|---|---|---|
| Time | % A | % B |
| 0.0 | 90 | 10 |
| 3.00 | 90 | 10 |
| 11.00 | 40 | 60 |
| 13.00 | 40 | 60 |
| 15.00 | 90 | 10 |
| 20.00 | 90 | 10 |

| Anion exchange chromatography (SAX) method-3 | | |
|---|---|---|

Column: Thermo Scientific, ProPac ™TM SAX-10, Bio LCTM, 4 X 250 mm
Solvent A: 80% 10 mM TRIS pH 8, 20% ethanol; Solvent B: 80% 10 mM TRIS pH 8, 20% ethanol, 1.5M NaCl
Flow Rate: 0.75 ml/min

| Gradient: | | |
|---|---|---|
| Time | % A | % B |
| 0.0 | 90 | 10 |
| 3.00 | 90 | 10 |
| 11.00 | 40 | 60 |
| 23.00 | 40 | 60 |
| 25.00 | 90 | 10 |
| 30.00 | 90 | 10 |

Size Exclusion Chromatography (SEC) Method-1
   Column: TOSOH Biosciences, TSKgelG3000SW XL, 7.8×300 mm, 5 µM
   Mobile phase: 150 mM phosphate buffer
   Flow Rate: 1.0 ml/min for 15 mins Example 7: In Vitro Evaluation of Anti-TfR1 mAb Conjugated to PLN siRNA (mAb-AOC) and Anti-TfR1 Fab Conjugated to PLN siRNA (Fab-AOC) Activities Materials and Methods The synthesis of the siRNA described in Example 2. The siRNA sequences are described in Table 10, Table 11, Example 1, and Example 3. The synthesis and purification of the mAb AOC and Fab AOC are described in Example 6.

Human iPSC derived cardiomyocytes seeded at 25,000 cells per well (96 well format) were treated with PLN_0318_21m (guide strand: SEQ ID NO: 49; passenger strand: SEQ ID NO: 181) conjugated to an anti-TfR1 mAb (mAb-AOC) at a concentration of 10 nM or conjugated to an anti-TfR1 Fab (Fab-AOC) at a concentration of 10 nM. The mAb-AOC or Fab-AOC were added to culture media and cells were incubated for 72 hours. Cells were collected and gene expression was analyzed by qPCR as previously described in Example 2. Adult human primary ventricular cardiomyocytes from one ethically consented healthy heart donor were obtained from Anabios (San Diego, California). 200,000 viable cells were seeded per well of a 6 well plate and treated with mAb-AOC or Fab-AOC at 30 nM final concentration (or PBS control) and maintained in culture.

Results

Cells treated with mAb-AOC or Fab-AOC showed PLN mRNA knock down in vitro (FIGS. 7A-7D). Both mAb-AOC and Fab-AOC showed comparable knock down levels at around 25%. The results indicate that mAb-AOC or Fab-AOC are both able to successfully deliver PLN siRNAs into muscle cells (cardiac muscle cells, cardiomyocytes) and decrease mRNA levels in human iPSC cardiomyocytes and in human adult ventricular cardiomyocytes in vitro.

Example 8. In Vivo siRNA Testing in Wild-Type Mice

Materials and Methods

The synthesis of the siRNA described in Example 2. The siRNA sequences are described in Table 10, Table 11, Example 1, and Example 3. The synthesis and purification of the mouse anti-TfR1 antibody conjugated to the PLN siRNA (AOC-PLNs conjugates) are described in Example 6.

Animals

All animal studies were conducted following protocols in accordance with the Institutional Animal Care and Use Committee (IACUC) at Explora BioLabs, which adhere to the regulations outlined in the USDA Animal Welfare Act as well as the "Guide for the Care and Use of Laboratory Animals" (National Research Council publication, 8th Ed., revised in 2011). Mice were obtained from Charles River Laboratories or from Jackson Laboratories. Wild type C57BL/6J or 57BL6NCrl mice (8-10 week old) were dosed via intravenous (iv) infusion with the indicated AOCs and doses.

In Vivo siRNA Tissue Concentration Analysis

AOC-PLNs (PLN-siRNA antibody conjugates) were dosed in mice via tail vein injection at 3 mg/kg dose (by siRNA mass). At day 28 post dosing, the left ventricle of the heart was collected, and 20 mg tissue was homogenized in Trizol and analyzed by the stem-loop-assay. The methodology for the stem-loop RT-qPCR (SL-RT-qPCR) assay has been described previously (Chen, 2005, Real-time quantification of microRNAs by stem-loop RT-PCR. Nucleic Acids Res 33, e179). A specific SL-RT-qPCR assay was designed to quantify the amount of the guide strand of the PLN siRNA. The primers and probes for detecting PLN siRNAs are summarized in Table 14. Standard curves were generated by spiking different concentrations of siRNA into the appropriate matrix for comparison to the samples. Linear regressions of siRNA standard curves were performed in Prism and the slope and y-intercept values were used to interpolate tissue and plasma sample concentrations.

TABLE 14

| Reverse Transcription Primer (5'-3') | SEQ ID NO: | Forward Primer (5'-3') | SEQ ID NO: | Probe (5'-3') | SEQ ID NO: |
|---|---|---|---|---|---|
| GTCGTATCCAGTGCAGGG TCCGAGGTATTCGCACTG GATACGACAAGAATCT | 277 | GCCCGGGTAGAAAT TGATAAATAG | 283 | 6FAM- GCACTGGATACGAC AAGAAT-BNFQ | 289 |

TABLE 14-continued

| Reverse Transcription Primer (5'-3') | SEQ ID NO: | Forward Primer (5'-3') | SEQ ID NO: | Probe (5'-3') | SEQ ID NO: |
|---|---|---|---|---|---|
| GTCGTATCCAGTGCAGGG TCCGAGGTATTCGCACTG GATACGACAATATTT | 278 | GCGCGCCTGAGACA GAAATTGA | 284 | 6FAM-GCACTGGATACGAC AATATTTATC-BNFQ | 290 |
| GTCGTATCCAGTGCAGGG TCCGAGGTATTCGCACTG GATACGACAATTTATC | 279 | CCGGGCGTATGAGA CAGAAATT | 285 | 6FAM-GCACTGGATACGAC AATTTATC-BNFQ | 291 |
| GTCGTATCCAGTGCAGGG TCCGAGGTATTCGCACTG GATACGACAACTCTTG | 280 | GCGGGCGTATGATA CAGATCA | 286 | 6FAM-ACTGGATACGACA ACTCTT-BNFQ | 292 |
| GTCGTATCCAGTGCAGGG TCCGAGGTATTCGCACTG GATACGACAAGCTA | 281 | GCGCCGGTAGATCT AGAGGT | 287 | 6FAM-TGGATACGACAAG CTACA-BNFQ | 293 |
| GTCGTATCCAGTGCAGGG TCCGAGGTATTCGCACTG GATACGACAAGTATC | 282 | GCCGCGCTGTGTTA TTACTTTGATA | 288 | 6FAM-GCACTGGATACGAC AAGTA-BNFQ | 294 |

Assay for mRNA Levels

At day 28 post dosing, left ventricles of the heart were collected and 20 mg tissue was homogenized in Trizol. RNA was isolated from tissue homogenate supernatant using the Direct-zol-96 RNA kit (Zymo Research) according to the manufacturer's instructions and PLN gene expression was analyzed by qPCR as previously described in Example 2.

Results

Figure 8B:
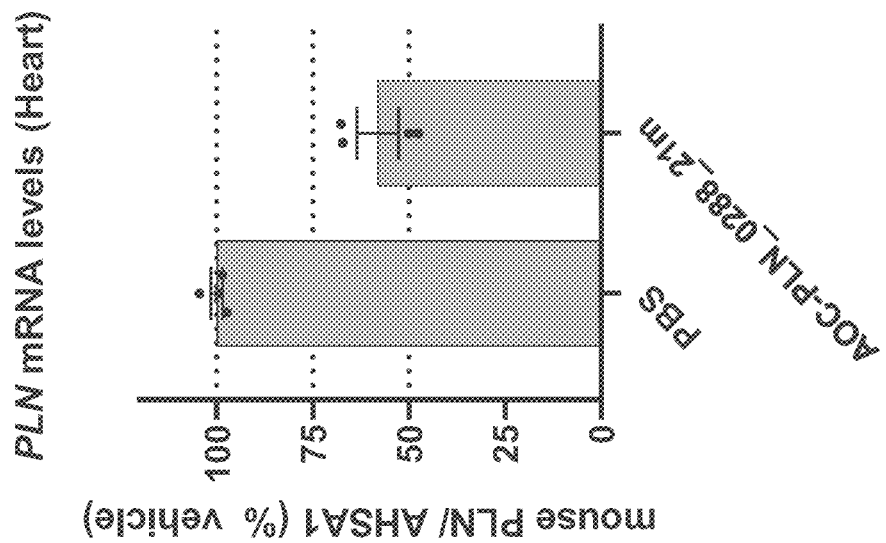
FIGS. 8A-8B are representative bar graphs showing siRNA concentrations and PLN mRNA expression levels in cardiac tissue of mice administered with CD71_PLN AOCs (PLN siRNA conjugated with mouse a-CD71 (a-transferrin receptor) antibody).
Figure 8A:
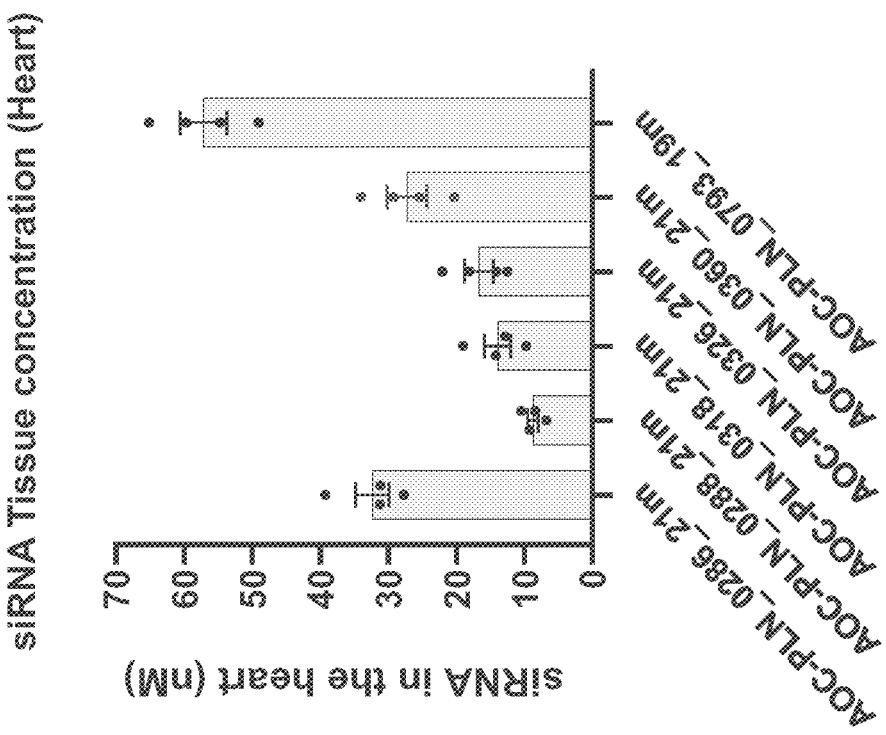

Analysis of the cardiac tissue showed that each siRNA delivered to the tissues and cells by conjugating with anti-TfR1 antibody was present at different tissue concentrations ranging from 10 nM to 60 nM (FIG. 8A). The highest tissue concentration of siRNA in the heart was obtained with the injection of the AOC-PLN_0793_19m (guide strand sequence: SEQ ID NO: 96) and the lowest tissue concentration was obtained with the injection of the AOC-PLN_0288_21m (guide strand sequence: SEQ ID NO: 37).

In addition, the AOC-PLN_0288_21m was used to determine the levels of PLN mRNA expression levels in the cardiac tissue since the siRNA sequence targeting the human PLN gene at position 288 is cross reactive to the murine PLN. Analysis PLN mRNA expression levels in the cardiac tissue revealed that the treatment with AOC-PLN_0288_21m induced approximately a 50% decrease of PLN mRNA levels in the cardiac tissue (FIG. 8B).

These results indicate that the murine anti-TfR1 antibody conjugated to PLN siRNA are able to successfully deliver siRNA to the cardiac tissue and reduce PLN mRNA levels in murine cardiac tissue.

Example 9: In Vitro Luciferase Assays in Cells Recombinantly Expressing PLN R14del Mutant Transfected with Increasing Concentrations of siRNA PLN_0318_21m Materials and Methods The synthesis of the siRNAs is described in Example 2. The siRNA sequences for the PLN_0318_21m siRNA are described in Table 11. The PLN siRNAs designed to target the R14del mutation of the PLN R14del transcript are described in Table 15A (19-mers) and Table 15B (21-mers). Table 15C summarizes the KD and IC50 for the PLN-R14d_0217_19m and PLN-R14d_0219_19m siRNAs.

TABLE 15A

| Compound | Target Transcript | Start | End | Antisense Strand/Guide Strand Sequence (5'-3') | SEQ ID NO: | Sense Strand/Passenger Strand Sequence (5'-3') | SEQ ID NO: |
|---|---|---|---|---|---|---|---|
| PLN-R14d_0216_19m | PLN-R14d | 216 | 234 | CUCUUAUAGCUGAGCGAGU | 300 | ACUCGCUCAGCUAUAAGAG | 314 |
| PLN-R14d_0217_19m | PLN-R14d | 217 | 235 | GCUCUUAUAGCUGAGCGAG | 301 | CUCGCUCAGCUAUAAGAGC | 315 |
| PLN-R14d_0218_19m | PLN-R14d | 218 | 236 | GGCUCUUAUAGCUGAGCGA | 302 | UCGCUCAGCUAUAAGAGCC | 316 |
| PLN-R14d_0219_19m | PLN-R14d | 219 | 237 | AGGCUCUUAUAGCUGAGCG | 303 | CGCUCAGCUAUAAGAGCCU | 317 |
| PLN-R14d_0220_19m | PLN-R14d | 220 | 238 | GAGGCUCUUAUAGCUGAGC | 304 | GCUCAGCUAUAAGAGCCUC | 318 |
| PLN-R14d_0221_19m | PLN-R14d | 221 | 239 | UGAGGCUCUUAUAGCUGAG | 305 | CUCAGCUAUAAGAGCCUCA | 319 |
| PLN-R14d_0222_19m | PLN-R14d | 222 | 240 | UUGAGGCUCUUAUAGCUGA | 306 | UCAGCUAUAAGAGCCUCAA | 320 |
| PLN-R14d_0223_19m | PLN-R14d | 223 | 241 | GUUGAGGCUCUUAUAGCUG | 307 | CAGCUAUAAGAGCCUCAAC | 321 |
| PLN-R14d_0224_19m | PLN-R14d | 224 | 242 | GGUUGAGGCUCUUAUAGCU | 308 | AGCUAUAAGAGCCUCAACC | 322 |
| PLN-R14d_0225_19m | PLN-R14d | 225 | 243 | UGGUUGAGGCUCUUAUAGC | 309 | GCUAUAAGAGCCUCAACCA | 323 |
| PLN-R14d_0226_19m | PLN-R14d | 226 | 244 | AUGGUUGAGGCUCUUAUAG | 310 | CUAUAAGAGCCUCAACCAU | 324 |
| PLN-R14d_0227_19m | PLN-R14d | 227 | 245 | AAUGGUUGAGGCUCUUAUA | 311 | UAUAAGAGCCUCAACCAUU | 325 |
| PLN-R14d_0228_19m | PLN-R14d | 228 | 246 | CAAUGGUUGAGGCUCUUAU | 312 | AUAAGAGCCUCAACCAUUG | 326 |
| PLN-R14d_0229_19m | PLN-R14d | 229 | 247 | UCAAUGGUUGAGGCUCUUA | 313 | UAAGAGCCUCAACCAUUGA | 327 |

TABLE 15B

| Compound | Target Transcript | Start | End | Antisense Strand/Guide Strand Sequence (5'-3') | SEQ ID NO: | Sense Strand/Passenger Strand Sequence (5'-3') | SEQ ID NO |
|---|---|---|---|---|---|---|---|
| PLN-R14d_0214_21m | PLN-R14d | 214 | 234 | CUCUUAUAGCUGAGCGAGUGA | 328 | UCACUCGCUCAGCUAUAAGAG | 344 |
| PLN-R14d_0215_21m | PLN-R14d | 215 | 235 | GCUCUUAUAGCUGAGCGAGUG | 329 | CACUCGCUCAGCUAUAAGAGC | 345 |
| PLN-R14d_0216_21m | PLN-R14d | 216 | 236 | GGCUCUUAUAGCUGAGCGAGU | 330 | ACUCGCUCAGCUAUAAGAGCC | 346 |
| PLN-R14d_0217_21m | PLN-R14d | 217 | 23 | AGGCUCUUAUAGCUGAGCGAG | 331 | CUCGCUCAGCUAUAAGAGCCU | 347 |
| PLN-R14d_0218_21m | PLN-R14d | 218 | 238 | GAGGCUCUUAUAGCUGAGCGA | 332 | UCGCUCAGCUAUAAGAGCCUC | 348 |
| PLN-R14d_0219_21m | PLN-R14d | 219 | 239 | UGAGGCUCUUAUAGCUGAGCG | 333 | CGCUCAGCUAUAAGAGCCUCA | 349 |
| PLN-R14d_0220_21m | PLN-R14d | 220 | 240 | UUGAGGCUCUUAUAGCUGAGC | 334 | GCUCAGCUAUAAGAGCCUCAA | 350 |
| PLN-R14d_0221_21m | PLN-R14d | 221 | 241 | GUUGAGGCUCUUAUAGCUGAG | 335 | CUCAGCUAUAAGAGCCUCAAC | 351 |
| PLN-R14d_0222_21m | PLN-R14d | 222 | 242 | GGUUGAGGCUCUUAUAGCUGA | 336 | UCAGCUAUAAGAGCCUCAACC | 352 |
| PLN-R14d_0223_21m | PLN-R14d | 223 | 243 | UGGUUGAGGCUCUUAUAGCUG | 337 | CAGCUAUAAGAGCCUCAACCA | 353 |
| PLN-R14d_0224_21m | PLN-R14d | 224 | 244 | AUGGUUGAGGCUCUUAUAGCU | 338 | AGCUAUAAGAGCCUCAACCAU | 354 |
| PLN-R14d_0225_21m | PLN-R14d | 225 | 245 | AAUGGUUGAGGCUCUUAUAGC | 339 | GCUAUAAGAGCCUCAACCAUU | 355 |
| PLN-R14d_0226_21m | PLN-R14d | 226 | 246 | CAAUGGUUGAGGCUCUUAUAG | 340 | CUAUAAGAGCCUCAACCAUUG | 356 |
| PLN-R14d_0227_21m | PLN-R14d | 227 | 247 | UCAAUGGUUGAGGCUCUUAUA | 341 | UAUAAGAGCCUCAACCAUUGA | 357 |
| PLN-R14d_0228_21m | PLN-R14d | 228 | 248 | UUCAAUGGUUGAGGCUCUUAU | 342 | AUAAGAGCCUCAACCAUUGAA | 358 |
| PLN-R14d_0229_21m | PLN-R14d | 228 | 249 | UUUCAAUGGUUGAGGCUCUUA | 343 | UAAGAGCCUCAACCAUUGAAA | 359 |

TABLE 15C

| Compound | Psicheck2 PLN Wildtype | | Psichecked PLN-R14Del | |
|---|---|---|---|---|
| | Max KD (%) | IC50 (pM) | Max KD (%) | IC50 (pM) |
| PLN-R14d_0217_19m | 77 | 272 | 79 | 152 |
| PLN-R14d_0219_19m | 61 | 1248 | 82 | 192 |

Full transcript of wild type human PLN or mutated human PLN R14del was inserted into the 3' end of the *renilla* cDNA in psiCheck2 plasmid (Promega) forming a fusion mRNA. Plasmid was transfected into HEK293 cells (AD-293 clone from Agilent) using Lipofectamine 3000. 24 hours after plasmid transfection, cells were transfected with increasing concentrations of PLN_0318_21m, PLN-R14d_0217_19m, or PLN-R14d_0219_19m (using lipofectamine RNAimax) and incubated for additional 48 hours. *Renilla* and firefly signal were measured using Dual-glo Luciferase assay system (Promega). Knock down (KD) of PLN mRNA transcript or PLN R14del mRNA transcript caused decreases in *renilla* signals. Firefly was present in the same plasmid under a different promoter and was used for normalization purposes.

Results

As shown in FIG. 9A, intensities of the *renilla* signals were decreased with treatment with increasing concentrations of PLN_0318_21m siRNA (the siRNA 21-mer targeting the PLN starting at position 318). The PLN_0318_21m siRNA was able to decrease mRNA expression levels of both wild type PLN and PLN variant R14del mRNA in a dose dependent manner.

In addition, the PLN-R14d_0217_19m and PLN-R14d_0219_19m siRNAs were both designed to target the PLN R14 deletion in the PLN mutant transcript and differ from one another by 2 nucleotides (see Table 15A). Both PLN-R14d_0217_19m and PLN-R14d_0219_19m siRNAs were able to decrease the mRNA levels of wild type PLN and PLN variant R14del in a dose dependent manner (FIGS. 9B-9C). Decreases in PLN mRNA levels induced by PLN-R14d_0217_19m siRNA were similar for both wild type PLN and PLN variant R14del transcripts (FIG. 9B). Unexpectedly, decreases in PLN mRNA levels induced by PLN-R14d_0219_19m siRNA were lower for the wild type PLN transcripts (max KD of 61%) than the ones for the PLN variant R14del (max KD of 82%) as shown in FIG. 9C. The IC50 of the PLN-R14d_0219_19m siRNA for the wild type PLN was 1248 pM while the one for mutant PLN-R14d was 192 pM. The PLN-R14d_0219_19m siRNA showed a 6-fold increase in IC50. The levels of PLN mRNA KD and IC50 for PLN-R14d_0217_19m and PLN-R14d_0219_19m siRNAs are summarized in Table 14C.

These results indicate that PLN siRNA could target and reduce wild type human PLN and genetic PLN variant mRNA levels in cells expressing PLN. More importantly, PLN siRNAs that target mutated transcripts could distinguish between wild type human PLN and genetic PLN variant mRNA levels and differentially reduce and genetic variant of PLN transcripts over the wild type transcripts.

Example 10: Screening of R14del siRNA Libraries In Vitro

To identify PLN-R14del selective siRNAs, a library of siRNAs that target PLN-R14del transcript to the region corresponding to nucleotides 214-249 (CUCGCUCAGCUAUAAGAAGAGCCUCAACCAUUGAA, SEQ ID NO: 469) was synthesized (Table 15A and Table 15B). The library was screened at 100 nM concentration using PLN wild type and PLN R14del Luciferase Reporter Assays. Full transcript human PLN cDNA was cloned in the multiple cloning site of psiCheck2 plasmid (Promega). One plasmid was generated for the wild type PLN sequence and another for the R14del sequence. 10,000 HEK cells (Strategene) were seeded at 10 k cells/well in 96 well format. After 24 hours, cells were transfected with 10 μg of plasmid using Lipofectamin 3000. One set of cells was treated with the wild type PLN plasmid and another set of cells on the same plate was treated with the R14del plasmid. Six hours later, culture media was replaced with 5% FBS in DMEM phenol red free and siRNAs were transfected at 100 nM final concentration using Lipofectamin RNAi max. After 48 hours after siRNA transfection, luciferase activities were measured using Dual Glo luciferase substrates (Promega) following manufacturer's protocol and Tecan plate reader (1 second integration time). For data analysis, *renilla*/firefly ratio for siRNA treated samples were normalized to the *renilla*/firefly ratio of mock treatment.

Next, to assess the activity of these siRNAs in a relevant disease cell model, 19-mer PLN siRNA library was screened in R14del iPSC patient derived cardiomyocytes. Cardiomyocyte cells were seeded at 10 k cells/well in 96 well plates previously coated with Matrigel. Seeding was done in RPMI media supplemented with B27 and 10% knock-out serum. Media was replaced 48 hours post-seeding with RPMI/B27 and replenished every two or three days thereafter. Three days post-seeding, cells were transfected with siRNAs using Lipofectamine RNAi max and collected with Tryzol 72 hours post-transfection. RNA extraction and RT reactions were performed as previously described. Wild type and mutant R14del PLN mRNA expression levels were quantified by qPCR using a duplexed Tagman assay containing one probe complementary to mutant allele and a second probe complementary to wild type allele PLN wt/R14del duplex assay (Forward primer: GAGAAAGTC-CAATACCTCACTCGCT (SEQ ID NO: 461); Reverse primer: TGTAGCTTTTGACGTGCTTGTTG (SEQ ID NO: 462); WT FAM probe: AGGCTCTTCTTATAGCTG (SEQ ID NO: 463) and R14d Mutant HEX probe: TGAGGCTCT-TATAGCTG (SEQ ID NO: 464)). PLN expression was normalized to RPL13a (Tagman Hs03043884_g1, Thermo Fisher) that was run in parallel wells using same cDNA input. Equal cDNA loading was used for all analyzed samples.

RNA sequencing was used as orthogonal method to quantify wild type and R14del allele expression in heterozygous cells. RNA-seq data was received as 150 bp-paired end reads. Reads were preprocessed using Trim Galore (version 0.6.7 and Cutadapt (version 3.4) to remove low quality portions of reads, and adapter content and quality controlled with FastQC (version 0.11.9). In order to quantify both wildtype and R14del transcripts, a reference transcriptome (Ensembl release 110 GRCh38, prepared via RSEM 1.3.3) was utilized by including a PLN transcript incorporating the R14del variant. The preprocessed signals against the modified reference transcriptome were quantified using Salmon 1.6.0.

The assays were performed in triplicates (N=3) and the results are presented as mean SD.

Results

Figure 10A:
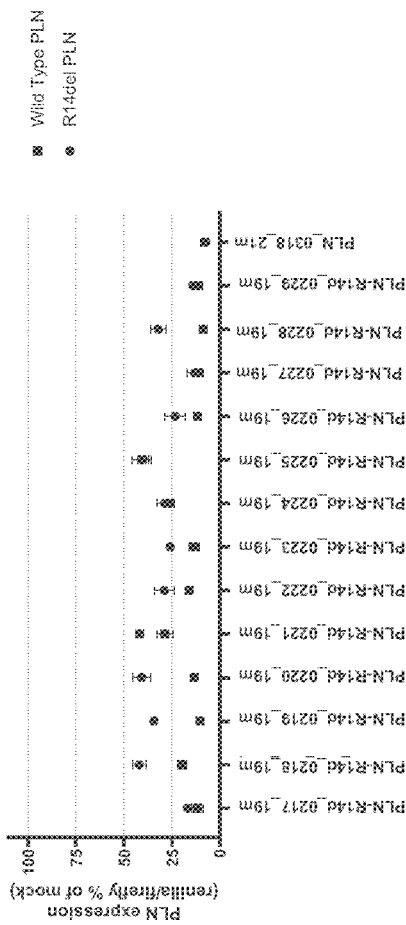
FIGS. 10A-10B are representative plots showing *renilla* intensity levels of allele-selective of siRNA (19-mer or 21-mer) library targeting the R14del allele using a R14del (circles) and wild-type PLN (squares) luciferase reporter assay.
Figure 10B:
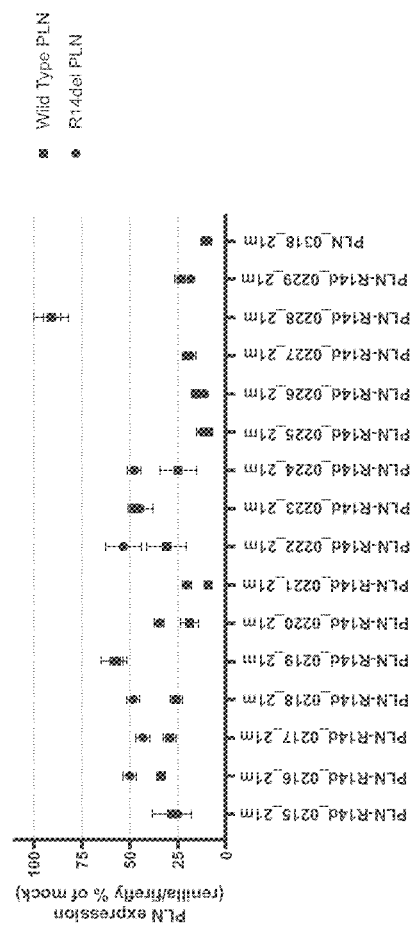

Libraries of 19-mer (Table 15A) and 21-mer (Table 15B) siRNAs specifically targeting the PLN R14del mutation were screened using a PLN Luciferase Reporter Assay (FIGS. 10A-10B). Several siRNAs in the 19-mer or 21-mer library resulted in different renilla/firefly activities for R14del PLN and wild-type PLN compared to the siRNA targeting PLN outside the R14del mutant region (PLN_0318_21m) which down-regulates both transcripts equally. Some R14del targeting siRNAs cause a more pronounced reduction in renilla activity for the R14del PLN reporter compared to the wild-type PLN reporter. As shown in FIG. 10A, several PLN R14del siRNAs in the 19-mer library (e.g., PLN-R14d_0218_19m, PLN-R14d_0219_19m, or PLN-R14d_0220_19m) showed selectivity for the R14del PLN reporter. In addition, several 21-mer R14del siRNAs, which differ from their counterpart 19-mer R14del siRNA sequences solely by the inclusion of two additional nucleotides, were observed to also show selectivity for the R14del PLN reporter (e.g., PLN-R14d_0217_21m and PLN-R14d_0218_21m) The PLN_0318_21m, which does not target the R14del mutation, was used as a control siRNA and reduced renilla activities in the R14del and wild type assay to similar level.

Overall, these results indicate that several R14del siRNAs show allelic selectivity for the mutant PLN transcript over the wild type PLN mRNA.

Figure 11:
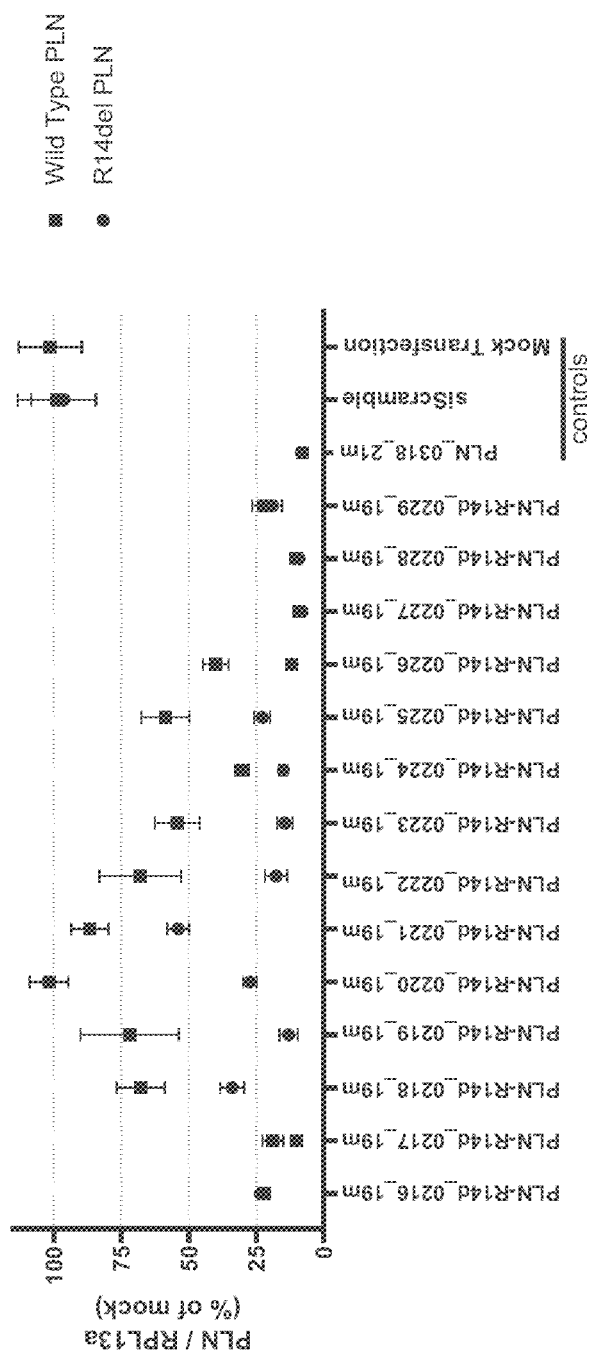
FIG. 11 is a representative plot showing relative PLN mRNA expression in R14del iPSC patient derived cardiomyocytes transfected with 19-mer siRNAs corresponding to siRNAs represented from top to bottom of Table 11, from left to right in FIG. 11, in order of appearance targeting the R14del allele at a concentration of 1 nM at 72 hours after transfection. Square data points represent the wild-type PLN allele transcript, and circle data points represent the PLN R14del transcript quantified by qPCR using an allele selective duplexed Taqman assay and normalized to RPL13a (N=3, mean±SD).

To investigate R14del siRNA selectivity in a more relevant cellular model, R14del siRNAs from the 19-mer siRNA library were transfected into R14del iPSC cardiomyocytes at a concentration of 1 nM for 72 hours (FIG. 11). R14del iPSC cardiomyocytes express endogenous PLN and are heterozygous for the R14del mutation. PLN expression levels were quantified by qPCR using a double Taqman assay. The results show that 2 R14del siRNAs, PLN-R14d_0219_19m and PLN-R14d_0220_19m, showed the highest selectivity in the assay, achieving over 90% and 70% decrease activities for R14del PLN compared to 30% and 0% decrease in activities of wild type PLN, respectively (FIG. 11). The PLN_318_21m could induce over 90% decrease activities for both forms of PLN.

Figure 12:
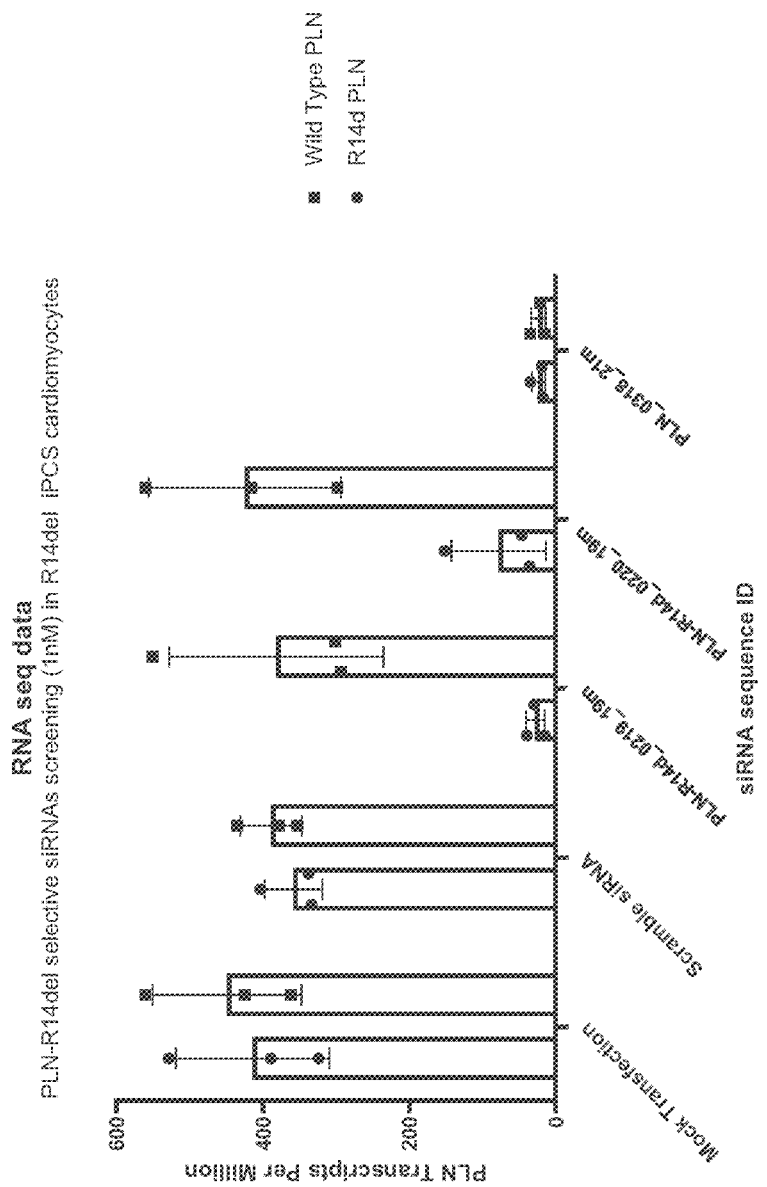
FIG. 12 is a representative bar graph illustrating the amount of PLN wild-type or R14del RNA transcripts in R14del iPSC patient derived cardiomyocytes (N=3, mean±SD) transfected with PLN R14del specific siRNAs (at a concentration of 1 nM at 72 hours after transfection. Square data points represent the wild-type PLN transcript, and circle data points represent the PLN R14del transcript quantified by RNA sequencing.

In addition, RNA sequencing as an orthogonal method was also utilized to quantify wild type and R14del transcripts. As shown in FIG. 12, RNA quantification results confirmed the activities of the qPCR data. The 2 R14del siRNA, PLN-R14d_0219_19m and PLN-R14d_0220_19m selectively decreased R14del transcripts levels while levels of the wild type transcripts remained unaffected. RNA sequencing data also indicated that wild type and R14del transcripts are equally expressed at baseline (mock treatment and Scramble siRNA).

Overall, these results indicate that the 2 R14del siRNAs, PLN-R14d_0219_19m and PLN-R14d_0220_19m and their equivalent 21 bp sequences (PLN-R14d_0217_21m and PLN-R14d_0218_21m) are among the best siRNA to selectively target R14del transcripts.

Dose Response Assay

Figure 13:
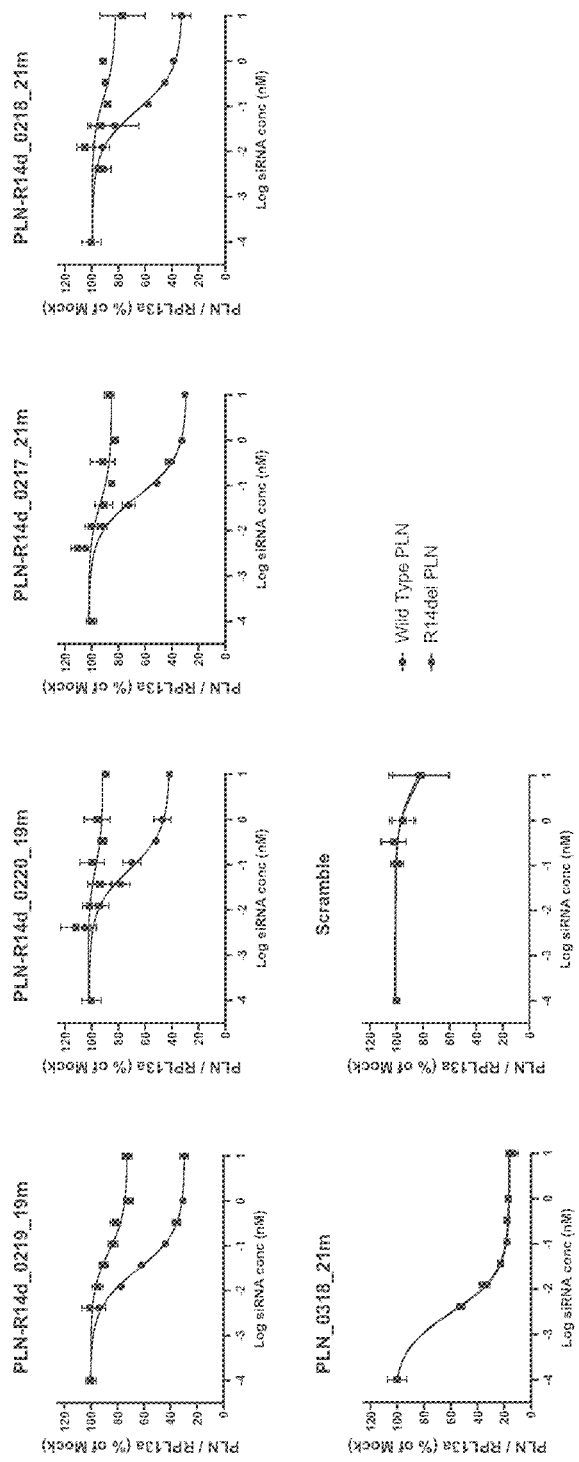
FIG. 13 shows representative plots of PLN mRNA expression in R14del iPSC patient derived cardiomyocytes transfected with increasing concentrations of four different siRNAs corresponding to (0.001-100 nM; 10-fold dilutions) against the R14del allele for 72 hours. Square data points represent the wild-type PLN allele transcript, and circle data points represent the PLN R14del allele transcript quantified by qPCR using an allele selective duplexed Taqman assay and normalized to RPL13a. (n=3, values represent mean±SD).

Two 19-mer R14del siRNAs, PLN-R14d_0219_19m and PLN-R14d_0220_19m two 21-mer R14del siRNAs (PLN-R14d_0217_21m and PLN-R14d_0218_21m) were then selected for a dose response assay. The R14del siRNAs were transfected into R14del iPSC cardiomyocytes with increasing concentrations (0.001-100 nM; 10-fold dilutions) for 72 hours (FIG. 13). Dose response curves of the 4 of R14del siRNAs show that the R14del siRNAs have high degree of selectivity for R14del transcript over a wide range of concentrations. Delta Emax for PLN-R14d_0219_19m, PLN-R14d_0220_19m, PLN-R14d_0217_21m, and PLN-R14d_0218_21m were 57%, 44%, 43% and 48%, respectively. In addition, the PLN_318_21m siRNA dose response curve for the Rd14 and wild type overlapped over one another indicating that the PLN_318_21m siRNA has no selectivity of the R14del transcripts over the PLN wild type transcripts. Finally, the scramble siRNA had no significant effect on PLN expression.

Overall, these results indicate that the 4 R14del siRNAs selectively target the R14del transcripts of the mutated allele of the PLN gene in a dose dependent manner.

Example 11: AOC-PLN Efficacy in a Cardiomyopathy Model Harboring Tropomyosin TM180 Mutation AOC-PLN AOCs were evaluated in a mouse model having a cardiomyopathy caused by increased calcium sensitivity due to mutation ET80G in the Tropomyosin 1 gene (Tpm1) (Gaffin et al. J Mol Cell Cardiol. 2011 November; 51(5): 812-820). This mutation in humans is associated with hypertrophic cardiomyopathy 3. Hemizygous mice exhibit hypertrophic cardiomyopathy and decreased heart function. TM180 mouse model was generated by Michael Kapiloff at Stanford university (Prabhakar et al., 2001 and Prabhakar et al., 2003) and were obtained from The Jackson Laboratory (Strain #035611, full name FVB/N-Tg(Myh6-Tpm1*E180G)57Dfw/MskfJ).

Male and female hemizygous mice and WT littermate controls were used for the study. Mice received 3 doses of vehicle (0 mg/kg) or 3 mg/Kg of siRNA conjugated to mouse TfR1 antibody via SMCC linker as summarized in Table 16. siRNA target position 431-451 of mouse PLN-transcript (ref. NM_001141927.1 (SEQ ID NO: 296)); guide strand sequence: 5'-UAGAAAUUGAUAAAUAG-GUUCUU-3' (SEQ ID NO: 297); passenger strand sequence: 5'-GAACCUAUUUAUCAAUUUCUA-3' (SEQ ID NO: 298). The guide strands were further modified with the addition (or substitution of the 5' end nucleotide of the base sequence) of the vinylphosophonate modified nucleotide VpUq at the 5'end of the guide strands. The synthesis of the siRNA described in Example 2. The synthesis and purification of the mouse anti-TfR1 antibody conjugated to the PLN siRNA (CD71_PLN siRNA conjugates) are described in Example 6.

Mice were dosed at 8, 16 and 24 weeks of age. Body weight was recorded weekly. Echocardiography measurements were performed at 6, 12 and 20 weeks after first dose. Animals were sacrificed 140 days after the 1$^{st}$ dose (week 22 of the study). Atria and ventricular weights were recorded at the end of the study and expressed as ratio to tibia length. Heart apex samples were analyzed for siRNA tissue concentration and mRNA expression. Tissue homogenization, RNA extraction, reverse transcription reaction and siRNA tissue concentration analysis were performed as previously described. Taqman assays used for qPCR analysis are Mm00452263_m1 (mouse PLN), Mm01201431_m1 (SERCA2A) and Mm00478295_m1 (PPIB, normalizer gene). PLN expression was calculated using formula: 100* [2^-($\Delta$Ct sample-$\Delta$Ct$_{WT}$)].

In Vivo Echocardiography (Echo) Measurement in Conscious Mice

All animal procedures were performed in accordance with the IACUC protocols. Mice were kept under identical housing conditions (12 hour light/dark cycle, standard diet ad libitum, 21° C. room temperature prior to echocardiographic assessment. Echo was performed using Vevo 3100 high-resolution Imaging System (Fujifilm VisualSonics, Toronto, Ontario, Canada). In order to obtain accurate cardiac measurements and avoid the cardio-suppressive effect of anesthesia, echo measurements were performed in conscious animals. Mice were restrained, naired and taped to a heated platform using surgical tape. A nose cone was used to flow air at 0.8 L/hr. Pre-warmed sonography gel was applied to the chest area and to the contact areas between the paws and the electrode surface. LAX B-mode was used to acquire EF %, SV and LV volume measurements. In the long axis measurement, the left ventricular outflow tract was aligned with the apex and images were acquired with wide open aorta and largest diameter of ventricles. After LAX image acquisition, the probe was moved on 90° to capture the SAX B-mode, to image along the short axis of the heart. Heart apex, papillary muscles and atria were localized and images were taken when the largest diameter was seen. Images were acquired when a posterior and the anterior wall were seen, without interfering with papillary muscles. SAX B-mode and M-mode were used for FS %, LV posterior wall thickness and LV diameter. After completion of acquisition, animals were wiped to remove gel, tape was removed, and animals were returned to home cage. All acquired images were digitally stored in raw format (DICOM) for further offline-analysis.

TABLE 16

Study Groups

| Group | Genotype | Test Article | siRNA Dose (mg/kg) | No. of mice |
|---|---|---|---|---|
| 1 | WT | Sterile Saline | 0 | 11 |
| 2 | TM180 | Sterile Saline | 0 | 13 |
| 3 | TM180 | AOC-mouse PLN siRNA | 3 | 12 |

Results

Figures 17A, 17B:
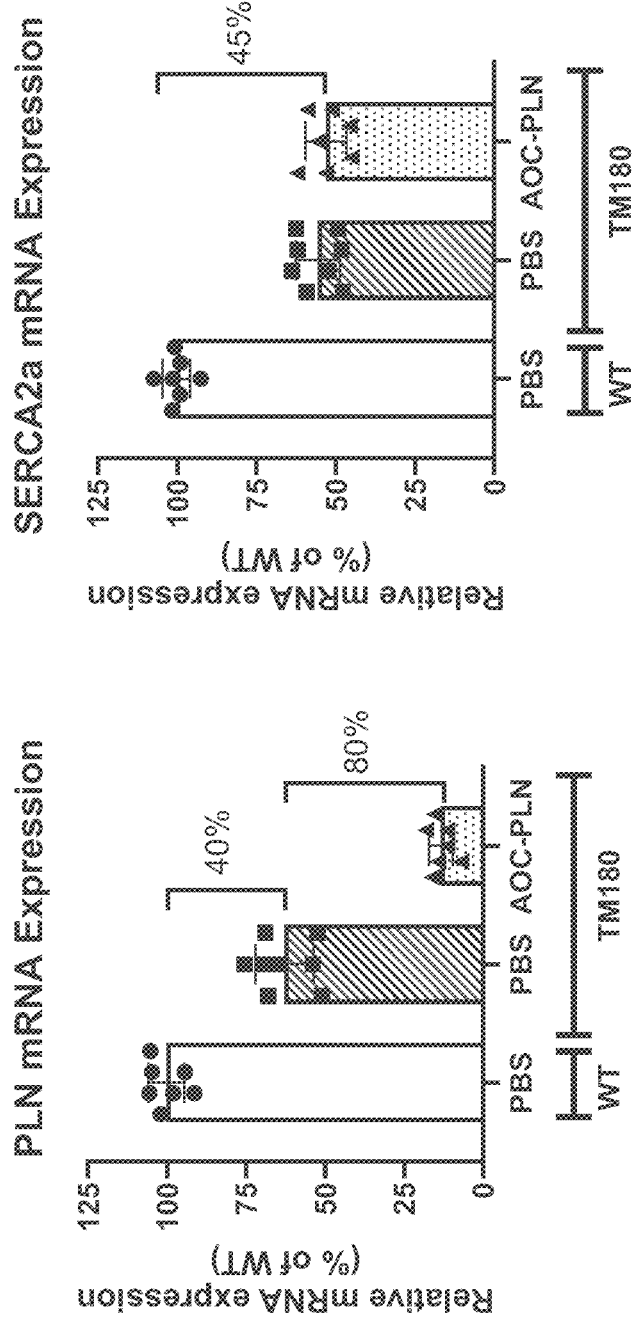
FIGS. 17A-17B are representative bar graphs illustrating mRNA expression levels of PLN (FIG. 17A) and SERCA2A (FIG. 17B) in hearts obtained from TM180 mice that have been administered AOC-PLN at a dose of 3 mg/kg on week 0, week 8 and week 16.

Heart tissues collected at the end of the study were investigated for mRNA expression and siRNA tissue concentration. Two weeks after the third AOC-PLN dose of 3 mg/kg, the siRNA tissue concentrations in the hearts were measured to be about 46 nM (data not shown). PLN mRNA expression levels, determined by qPCR, were about 40% lower in TM180 mutant mice compared to levels in WT mice (FIG. 17A). Interestingly, administration of AOC-PLN induced a further 80% decrease in PLN mRNA expression levels compared to levels of the PBS treated TM180 mutant mice (FIG. 17A).

In addition, SERCA2A mRNA expression levels were investigated in these mutant mice, since PLN is an inhibitor of SERCA that regulates calcium metabolism in cardiomyocytes. SERCA2A mRNA expression levels were reduced by 45% in TM180 mice compared to levels in WT mice, but doses of AOC-PLN did not affect SERCA2A mRNA expression levels in these mutant mice (FIG. 17B). The data suggests that lower PLN expression levels in AOC-PLN treated mutant mice decrease PLN mediated inhibition of SERCA.

Overall, these results indicate that mutant mice have lower PLN mRNA expression levels and lower SERCA2A mRNA expression levels than the levels in WT mice. Administration of AOC-PLN in these mice result in 80% further reduction of PLN mRNA levels compared to untreated mutant mice but the administration of AOC-PLN does not affect SERCA2A mRNA expression levels.

Figure 18A:
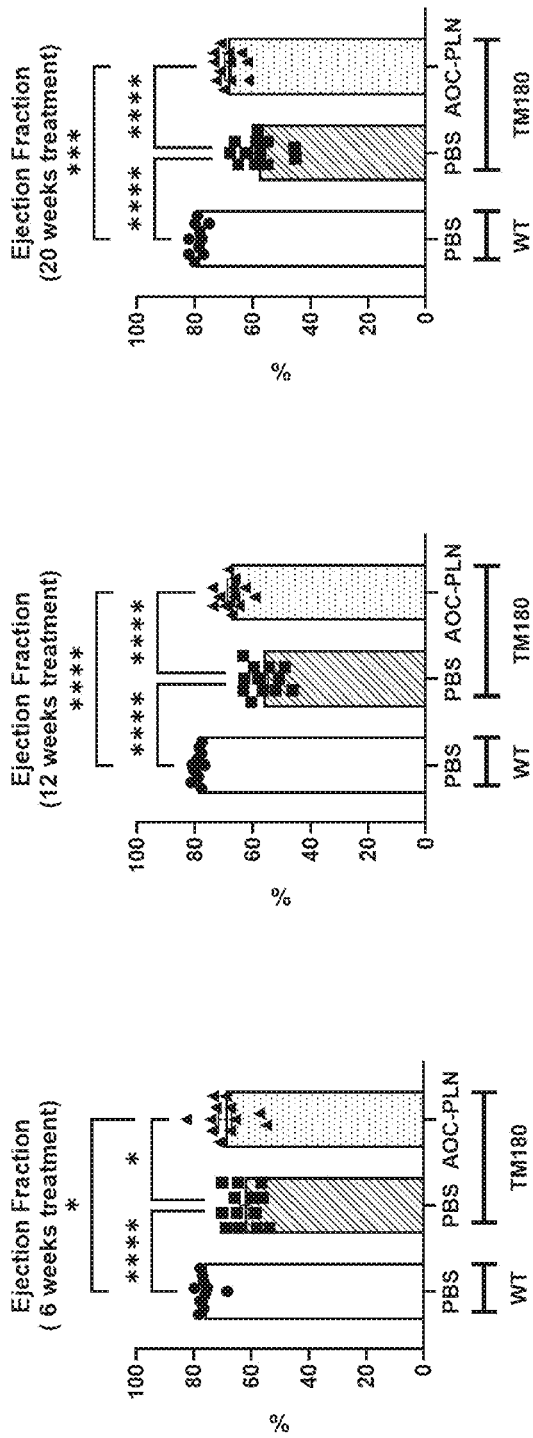

In addition, cardiac functions in the mutant mice were assessed by echocardiography. TM180 mice treated with PBS had reduced cardiac ejection fraction (FIG. 18A) and fractional shortening (not shown) compared to WT mice. Treatments of AOC-PLN in the TM180 mice were able to increase cardiac ejection fraction by reverting the decrease in cardiac function at all analyzed time points (6, 12, and 20 weeks of treatment). In addition, cardiac remodeling was also improved by AOC-PLN treatment in the mutant mice. TM180 PBS mice showed increased left ventricular diastolic diameter (FIG. 18B) and left ventricular mass (FIG. 18C) and both parameters were reduced by AOC-PLN. Impaired ventricular relaxation and reduced heart compliance can cause enlargement of the atria. The TM180 mice treated with PBS had a 4-fold increase in the size of left atrial of the heart when compared to the size in WT mice. However, the in the AOC-PLN treated group had a 2.7-fold increase in the size of the left atria of the heart compared to the one in WT mice (FIG. 18D). The size differences between the PBS treated mice and AOC-PLN treated mice can be visualized with pictures of the left atria of the hearts obtained from these mice (FIG. 18E).

Overall, TM180 mice treated with doses of AOC-PLN were able to partially revert cardiac abnormalities of the animal model by reducing left ventricular diameter, left ventricular mass, and atria size of hearts obtained from these animals.

Example 12: In Vivo Activity of AOC-PLN in Non-Human Primates

A non-human primate (NHP) study was performed to investigate AOC-PLN target engagement, pharmacodynamics, and pharmacokinetics in a species evolutionarily close to humans. The AOCs were composed of human transferrin receptor 1 (TfR1) antibody conjugated to a small interfering ribonucleic acid (siRNA) targeting human PLN (AOC-PLNs): AOC-PLN_0288_21m, AOC-PLN_0318_21m, and AOC-PLN_0360_19m. The NHP were administered AOC-PLN_0288_21m, AOC-PLN_0318_21m, or AOC-PLN_0360_19m at a dose of 3 mg/kg and the hearts were obtained at Day 29 as summarized in Table 17.

The study was performed following Institutional Animal Care and Use Committee (IACUC) protocols. Throughout the study, animals were housed individually in a stainless-steel wire cage (720W×700 L×800H mm). Animals had access to about 60 g of diet (Teklad Global Certified 20% Protein Primate Diet 2050C, Envigo, USA), twice daily. Animals had ad libitum access to filtered, ultraviolet light-irradiated municipal tap water at all times.

Male cynomolgus monkeys (*Macaca fascicularis*), approximately 2 to 4 years of age at receipt, and approximately 2 to 4 kg body weight at start of treatment received one single intravenous (IV) dose of vehicle control (0 mg/kg) or test article at 3 mg/kg siRNA dose on Day 1. Two animals were assigned per group. Body weights were measured weekly. Electrocardiograms were collected with a Cardio 10 (Bionet Co., Ltd., Korea) at day −6 and at the end of study. The evaluation consisted of a quantitative measurement of the HR, QT- and PR-interval from a QRS complex of each recording. QTc was derived at each time point using Bazett's formula. Heart weights were collected at necropsy and heart/body weight ratios were calculated for each animal. Hearts were collected at necropsy on Day 29.

TABLE 17

Study Design

| Group | Test Article | siRNA Dose (mg/kg) | No. of Males | Tissues |
|---|---|---|---|---|
| 1 | Sterile Saline | 0 | 2 | Hearts (apex) were |
| 2 | AOC-PLN_0288_21m | 3 | 2 | obtained at |

TABLE 17-continued

Study Design

| Group | Test Article | siRNA Dose (mg/kg) | No. of Males | Tissues |
|---|---|---|---|---|
| 3 | AOC-PLN_0318_21m | 3 | 2 | necropsy at Day 29 |
| 4 | AOC-PLN_0360_19m | 3 | 2 | |

Tissue samples were evaluated for mRNA expression using a comparative RT-qPCR assay. 25-50 mg of tissue were homogenized in 1 mL of TRIzol (Thermo Fisher) using OMNI Bead Ruptor Elite system (OMNI International). Total RNA was isolated from 200 µl tissue homogenate supernatant using the Direct-zol-96 RNA kit (Zymo Research) according to the manufacturer's instructions. 250 ng of purified RNA was reverse transcribed to cDNA using the High-Capacity cDNA Reverse Transcription Kit (Applied Biosystem) and SimpliAmp Thermal Cycler (Applied Biosystem). The amount of cDNA used per qPCR reaction was 20 ng. qPCR was performed using TaqMan Fast Universal Master Mix II (Thermo Fisher) and commercially available Taqman Assays (Mf04255299_s1 FAM for PLN and Mf04187362_g1 VIC for SSB normalizer). Each sample was run in technical duplicates in a Quant Studio instrument (Thermo Fisher). qPCR data was analyzed using the ΔΔCt method with gene of interest normalized to Small RNA Binding Exonuclease Protection Factor La gene (SSB) expression. PLN expression in heart was calculated using formula: $100*[2^{\wedge}-(\Delta Ct\ sample-\Delta Ct_{NHP\ Vehicle\ \#1})]$. PLN expression in skeletal muscle was calculated using formula: $100*[2^{\wedge}-(\Delta Ct\ sample-\Delta Ct_{Predose})]$. Taqman probe does not detect accurately PLN transcripts from NHP vehicle #2 control animal due to a SNP overlapping the probe binding site, and PLN data values from this animal were thus excluded from analysis. Data was analyzed using GraphPad Prism 10 and is expressed as mean±SD.

Additionally, cardiac PLN mRNA expression was quantified by RNA sequencing. Total RNA was enriched by ribosomal RNA depletion, RNA samples were subjected to library preparation with the Illumina unstranded Total RNA Prep and ligated with Ribo-Zero Plus kit. Derived libraries were qualified with the Agilent Fragment Analyzer 5300 and quantified with Qubit fluorometric assay. All libraries passed QC with acceptable yield and expected library smear size. Libraries were pooled and sequenced on NovaSeq 6000 with a S2 flow cell at 2×150 bp. For data analysis, RNAseq raw FASTQ files were trimmed for adapters with Trimmomatic (Bolger, A. M., M. Lohse, and B. Usadel, Trimmomatic: a flexible trimmer for Illumina sequence data. Bioinformatics, 2014. 30(15): p. 2114-20), then aligned to cynomolgus monkey genome (*Macaca fascicularis* 5.0) with STAR (Dobin, A., et al., STAR: ultrafast universal RNA-seq aligner. Bioinformatics, 2013. 29(1): p. 15-21). Gene-level expression was quantification by RSEM (Li, B. and C. N. Dewey, RSEM: accurate transcript quantification from RNA-Seq data with or without a reference genome. BMC Bioinformatics, 2011. 12: p. 323).

Quantification of PLN protein expression in heart was performed by capillary electrophoresis (Jess, Protein Simple). 50 mg of heart tissue (apex) was pulverized using CP02 cryoPREP (Covaris) and processed with 500 ul RIPA (containing protease and phosphatase inhibitors) using polytron and dounce homogenizers. Samples were centrifuged at 15,000 g for 10 minutes at 4° C. to remove insolubilized membrane. Total protein was quantified using BCA assay. 0.75 µg total protein was loaded per capillary in a 2-40 kDa Protein Simple module. Rabbit anti PLN antibody (ab85146, Abcam) was used at 1:50 dilution and anti-rabbit HRP conjugates 2ry antibody (042-206, Protein Simple) at 1:20 dilution.

To quantify the amount of siRNA guide strand concentration in tissues, a sequence specific stem-loop real-time quantitative polymerase chain reaction (SL-RT-qPCR) assay was designed for sequences PLN_0288_21m, PLN_0318_21m, and PLN_0360_19m (as shown in Table 10 and Table 11). The SL-RT-qPCR assay along with the general primer and TaqMan probe have been previously described (Chen, C et al. Real-time quantification of microRNAs by stem loop RT-PCR. Nucleic Acids Res 33, e179 (2005)). Briefly, calibration standards for an 8-point standard curve were generated by a 1:10 serial dilution of siRNAs PLN_0288_21m, PLN_0318_21m and PLN_0360_19m in TE Buffer with 0.1% Triton-X. Study samples were diluted in assay diluent up to the recommended MRD. The calibration standards were diluted in assay diluent. An siRNA-specific reverse transcription (RT) primer was added to the calibration standards and study samples, followed by an annealing and a reverse transcription step on a thermocycler. The RT products were quantified via conventional TaqMan RT-PCR which includes a siRNA-specific forward primer, a universal reverse primer, and a dye labeled siRNA-specific TaqMan probe. Raw Ct values were exported using the QuantStudio RealTime PCR and Excel software. The standard curve of Ct values vs. log base 10 of corresponding siRNA concentrations was generated in GraphPad Prism 9.3.1. A simple linear regression of the siRNA standard curve was performed in GraphPad Prism, and the linear equation was used to interpolate study sample plasma concentrations in Excel. The lower limit of quantification was 5 pM.

Results

Figure 19C:
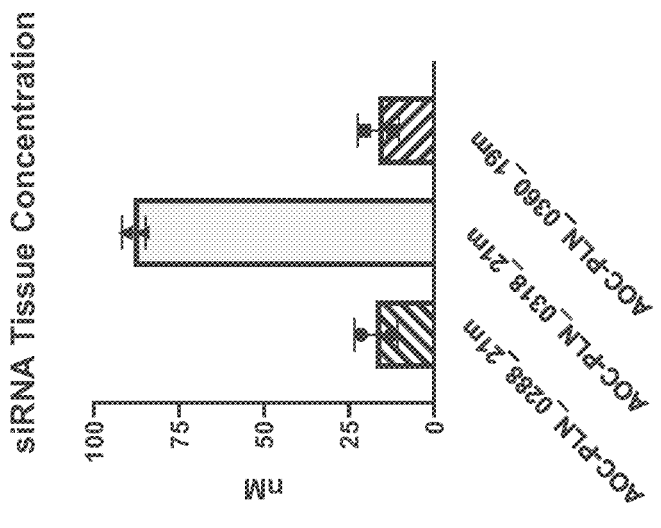
FIGS. 19A-19C show representative bar graphs of PLN mRNA expression levels and siRNA tissue concentrations in hearts of cynomolgus monkeys that have been administered a single injection of AOC-PLNs (a-TfR1 antibody conjugated with PLN targeting siRNAs): AOC-PLN_0288_21m, AOC-PLN_0318_21m, or AOC-PLN_0360_19m at a dose of 3 mg/kg.
Figure 19B:
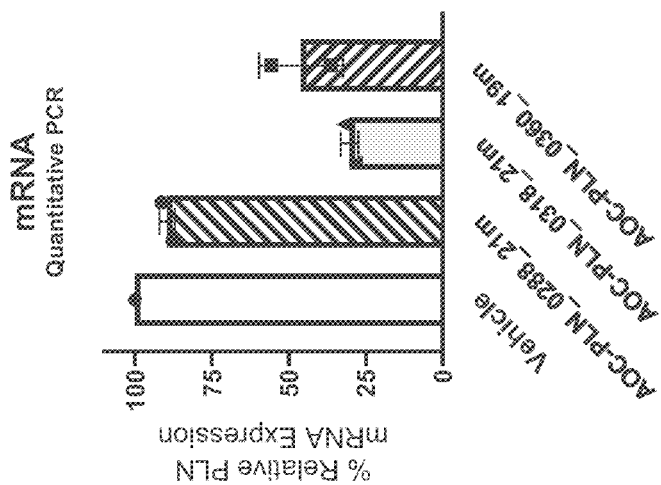
Figure 19A:
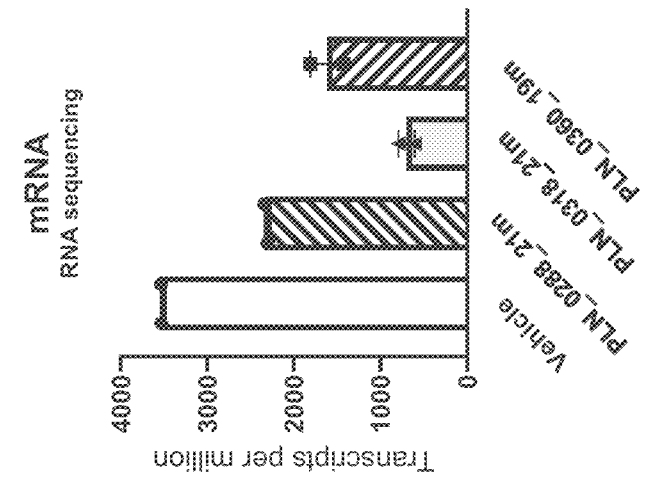

To investigate the effects of AOC-PLNs in hearts of NHP, animals were administered a single injection of 3 different AOC-PLNs: AOC-PLN_0288_21m, AOC-PLN_0318_21m, or AOC-PLN_0360_19m, at a dose of 3 mg/kg. 28 days after one dose of AOC-PLN_0288_21m, AOC-PLN_0318_21m, or AOC-PLN_0318_21m, quantification of PLN transcripts by RNA sequencing in hearts of NHP showed that the highest reduction in PLN transcript levels was over 85% for the AOC-PLN_0318_21m treated group and both the AOC-PLN_0288_21m and AOC-PLN_0360_19m treated groups also had significant reduction in PLN transcript levels compared to PLN transcript levels in the control group (FIG. 19A). Similarly, PLN mRNA expression levels analyzed by quantitative PCR showed that the group treated with AOC-PLN_0318_21m with over 75% reduction in mRNA levels had the highest decrease in mRNA levels among the groups treated with other AOC-PLNs (FIG. 19B). Moreover, PLN siRNA tissue concentrations in the hearts of NHP were the highest for AOC-PLN_0318_21m with 88 nM while the concentrations were 17 nM for AOC-PLN_0288_21m and 16 nM for AOC-PLN_0360_19m (FIG. 19C). At the protein level, the 3 AOC-PLNs, AOC-PLN_0288_21m, AOC-PLN_0318_21m, and AOC-PLN_0360_19m, administered to NHP were able to reduce signals for PLN proteins (monomers and oligomers) as detected by Jess protein electrophoresis (FIG. 20A). Quantification of band intensities of the PLN proteins (monomers and oligomers) indicated that the AOC-PLN_0318_21m treated group had a reduction over 70% in PLN protein levels while the AOC-PLN_0288_21m and AOC-PLN_0360_19m groups had over 45% reduction in PLN protein levels (FIG. 20B). The results show that PLN expression levels in hearts of NHP both at the mRNA and protein levels suggest that administration of PLN AOC to NHP result in significant decreases in PLN mRNA and protein expression levels. In addition, AOC-PLN_0318_21m had the best activities in decreasing PLN levels among the 3 AOC-PLNs administered to NHP.

Overall, administration of PLN AOCs administered to NHP results in lower PLN mRNA and protein levels hearts.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

---

What is claimed is:

1. A polynucleotide conjugate comprising an anti-transferrin receptor antibody or antigen-binding fragment thereof conjugated to a polynucleotide that hybridizes to a target sequence of PLN mRNA and mediates downregulation of the PLN mRNA in a cardiac muscle cell, wherein the polynucleotide hybridizes to a nucleic acid sequence at positions 195-213, 242-379, 449-546, 780-811, 967-1002, 1072-1099, 1119-1138, and 1234-1253 of the PLN mRNA (NM 002667.5).

2. The polynucleotide conjugate of claim 1, wherein the target sequence of the PLN mRNA is a genetic PLN variant having a genetic mutation selected from Arg14del (R14del), Arg9Cys (R9C), and Arg25Cys (R25C).

3. The polynucleotide conjugate of claim 1, wherein the polynucleotide is an antisense oligonucleotide (ASO) or a double-stranded small interfering RNA (siRNA) comprising a guide strand and a passenger strand.

4. The polynucleotide conjugate of claim 3, wherein the ASO comprises a nucleic acid sequence selected from SEQ ID NOs: 265-276.

5. The polynucleotide conjugate of claim 3, wherein the ASO comprises a nucleic acid sequence having at least 14, 15, 16, 17, or 18 consecutive nucleotides from a sequence selected from SEQ ID NOs: 265-276.

6. The polynucleotide conjugate of claim 3, wherein the passenger strand comprises a nucleic acid sequence selected from SEQ ID NOs: 144, 152, 155, 158-160, 162-166, 168-170, 172-177, 181, 187-188, 191-192, 196, 198, 200, 203, 206, 210-216, 225-228, 230, 232, 235-238, 241, 245-247, 254-255, 315, and 317.

7. The polynucleotide conjugate of claim 3, wherein the guide strand comprises a nucleic acid sequence selected from SEQ ID NOs: 12, 20, 23, 26-28, 30-34, 36-38, 40-45, 49, 55-56, 59-60, 64, 66, 68, 71, 74, 78-84, 93-96, 98, 100, 103-106, 109, 113-115, 122-123, 301, and 303.

8. The polynucleotide conjugate of claim 3, wherein the passenger strand comprises a nucleic acid sequence having at least 16, 17, 18, 19, 20, or 21 consecutive nucleotides from a sequence selected from SEQ ID NOs: 144, 152, 155, 158-160, 162-166, 168-170, 172-177, 181, 187-188, 191-192, 196, 198, 200, 203, 206, 210-216, 225-228, 230, 232, 235-238, 241, 245-247, 254-255, 315, and 317.

9. The polynucleotide conjugate of claim 3, wherein the guide strand comprises a nucleic acid sequence having at least 16, 17, 18, 19, 20, or 21 consecutive nucleotides from a sequence selected from SEQ ID NOs: 12, 20, 23, 26-28, 30-34, 36-38, 40-45, 49, 55-56, 59-60, 64, 66, 68, 71, 74, 78-84, 93-96, 98, 100, 103-106, 109, 113-115, 122-123, 301, and 303.

10. The polynucleotide conjugate of claim 1, wherein the polynucleotide comprises at least one 2'-modified nucleotide, at least one modified internucleotide linkage, or at least one inverted abasic moiety.

11. The polynucleotide conjugate of claim 10, wherein the at least one 2'-modified nucleotide comprises:
2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA) modified nucleotide, locked nucleic acid (LNA), or ethylene nucleic acid (ENA), or a combination thereof.

12. The polynucleotide conjugate of claim 10, wherein the at least one modified internucleotide linkage comprises a phosphorothioate linkage or a phosphorodithioate linkage.

13. The polynucleotide conjugate of claim 1, wherein the polynucleotide comprises a 5'-terminal vinylphosphonate-modified nucleotide.

14. The polynucleotide conjugate of claim 1, wherein the anti-transferrin receptor antibody or antigen binding fragment thereof comprises a non-human antibody or antigen binding fragment thereof, a human antibody or antigen binding fragment thereof, a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), or a camelid antibody or antigen binding fragment thereof.

15. The polynucleotide conjugate of claim 1, wherein the polynucleotide conjugate has a polynucleotide to antibody ratio of from about 1 to about 4.

16. The polynucleotide conjugate of claim 1, wherein polynucleotide conjugate comprises a linker connecting the anti-transferrin receptor antibody or antigen-binding fragment thereof to the polynucleotide.

17. A polynucleotide molecule for modulating PLN mRNA expression, wherein the polynucleotide molecule is a single stranded ASO comprising a nucleic acid sequence selected from SEQ ID NOs: 265-276, or the polynucleotide molecule is a double stranded siRNA comprising a guide strand and a passenger strand, wherein the guide strand comprises a nucleic acid sequence selected from SEQ ID NOs: 12, 20, 23, 26-28, 30-34, 36-38, 40-45, 49, 55-56, 59-60, 64, 66, 68, 71, 74, 78-84, 93-96, 98, 100, 103-106, 109, 113-115, 122-123, 301, and 303.

18. A conjugate comprising an anti-transferrin receptor antibody or antigen-binding fragment thereof conjugated to an siRNA or an ASO that decreases PLN mRNA levels in a cardiac muscle cell, wherein the anti-transferrin receptor antibody or antigen-binding fragment thereof comprises a VH sequence of SEQ ID NO: 376, 377, 378, 379, or 380, and a VL sequence of SEQ ID NOs: 381, 382, 383, 384, or 385, and wherein the ASO comprises a nucleic acid sequence selected from SEQ ID NOs: 265-276, and wherein a guide strand sequence of the siRNA comprises a nucleic acid sequence selected from the group consisting of SEQ ID NOs: 12, 20, 23, 26-28, 30-34, 36-38, 40-45, 49, 55-56, 59-60, 64, 66, 68, 71, 74, 78-84, 93-96, 98, 100, 103-106, 109, 113-115, 122-123, 301, and 303 and a passenger strand sequence of the siRNA comprises a nucleic acid sequence selected from the group consisting of SEQ ID NOs: 144, 152, 155, 158-160, 162-166, 168-170, 172-177, 181, 187-188, 191-192, 196, 198, 200, 203, 206, 210-216, 225-228, 230, 232, 235-238, 241, 245-247, 254-255, 315, and 317.

19. The conjugate of claim 18, wherein the passenger stand or the guide strand of the siRNA comprises a 5'-terminal vinylphosphonate-modified nucleotide.

20. The conjugate of claim 18, wherein the conjugate comprises a linker connecting the anti-transferrin receptor antibody or antigen-binding fragment thereof to the siRNA.

21. The conjugate of claim 20, wherein the linker comprises a maleimide group.

22. The conjugate of claim 18, wherein the siRNA is selected from the group consisting of the guide strand sequence of SEQ ID NO: 31 and the passenger strand sequence of SEQ ID NO: 163; the guide strand sequence of SEQ ID NO: 36 and the passenger strand sequence of SEQ ID NO: 168; the guide strand sequence of SEQ ID NO: 37 and the passenger sequence of SEQ ID NO: 169; the guide strand sequence of SEQ ID NO: 49 and the passenger strand sequence of SEQ ID NO: 181; the guide strand sequence of SEQ ID NO: 59 and the passenger strand sequence of SEQ ID NO: 191; the guide strand sequence of SEQ ID NO: 74 and the passenger strand sequence of SEQ ID NO: 206; the guide strand sequence of SEQ ID NO: 96 and the passenger strand sequence of SEQ ID NO: 228; the guide strand sequence of SEQ ID NO: 301 and the passenger strand sequence of SEQ ID NO: 315; and the guide strand sequence of SEQ ID NO: 303 and the passenger strand sequence of SEQ ID NO: 317.

23. A method of treating a cardiomyopathy associated with PLN in a subject in need thereof comprising administering to said subject a polynucleotide conjugate comprising an anti-transferrin receptor antibody or antigen-binding fragment thereof conjugated to a polynucleotide that hybridizes to a target sequence of PLN mRNA, thereby treating the cardiomyopathy in said subject, wherein the polynucleotide hybridizes to a nucleic acid sequence at positions 195-213, 242-379, 449-546, 780-811, 967-1002, 1072-1099, 1119-1138 and 1234-1253 of the PLN mRNA (NM_002667.5).

24. The method of claim 23, wherein the cardiomyopathy associated with PLN is a genetic cardiomyopathy associated with a genetic PLN variant comprising a genetic mutation selected from Arg14del (R14del), Arg9Cys (R9C), and Arg25Cys (R25C).

25. The method of claim 23, wherein the cardiomyopathy associated with PLN is a dilated cardiomyopathy or a hypertrophic cardiomyopathy.

26. The method of claim 25, wherein the dilated cardiomyopathy is a genetic dilated cardiomyopathy associated with TTN, LMNA, RI3M20, SCN5A, MYH7, TNNT2, and TPMI mutations.

27. The method of claim 25, wherein the hypertrophic cardiomyopathy is associated with MYH7, MYBPC3, TNNT2, TNNC, and TPM1 mutations.

* * * * *

SEQUENCE LISTING

```
Sequence total quantity: 469
SEQ ID NO: 1             moltype = RNA  length = 19
FEATURE                  Location/Qualifiers
source                   1..19
                         mol_type = other RNA
                         organism = synthetic construct
SEQUENCE: 1
ttgtgttgta tgaagtctt                                                 19

SEQ ID NO: 2             moltype = RNA  length = 19
FEATURE                  Location/Qualifiers
source                   1..19
                         mol_type = other RNA
                         organism = synthetic construct
SEQUENCE: 2
attgtgttgt atgaagtct                                                 19

SEQ ID NO: 3             moltype = RNA  length = 19
FEATURE                  Location/Qualifiers
source                   1..19
                         mol_type = other RNA
                         organism = synthetic construct
SEQUENCE: 3
agtattgtgt tgtatgaag                                                 19

SEQ ID NO: 4             moltype = RNA  length = 19
FEATURE                  Location/Qualifiers
source                   1..19
                         mol_type = other RNA
                         organism = synthetic construct
SEQUENCE: 4
tagagtattg tgttgtatg                                                 19

SEQ ID NO: 5             moltype = RNA  length = 19
FEATURE                  Location/Qualifiers
source                   1..19
                         mol_type = other RNA
                         organism = synthetic construct
SEQUENCE: 5
tcttttaggt agccttggc                                                 19

SEQ ID NO: 6             moltype = RNA  length = 19
FEATURE                  Location/Qualifiers
source                   1..19
                         mol_type = other RNA
                         organism = synthetic construct
SEQUENCE: 6
ttctttagg tagccttgg                                                  19

SEQ ID NO: 7             moltype = RNA  length = 19
FEATURE                  Location/Qualifiers
source                   1..19
                         mol_type = other RNA
                         organism = synthetic construct
SEQUENCE: 7
cttctttag gtagccttg                                                  19

SEQ ID NO: 8             moltype = RNA  length = 19
FEATURE                  Location/Qualifiers
source                   1..19
                         mol_type = other RNA
                         organism = synthetic construct
SEQUENCE: 8
tcttctttta ggtagcctt                                                 19
```

| | | |
|---|---|---|
| SEQ ID NO: 9<br>FEATURE<br>source | moltype = RNA   length = 19<br>Location/Qualifiers<br>1..19<br>mol_type = other RNA<br>organism = synthetic construct | |
| SEQUENCE: 9<br>tatgagataa ctgtcttct | | 19 |
| SEQ ID NO: 10<br>FEATURE<br>source | moltype = RNA   length = 19<br>Location/Qualifiers<br>1..19<br>mol_type = other RNA<br>organism = synthetic construct | |
| SEQUENCE: 10<br>aatatgagat aactgtctt | | 19 |
| SEQ ID NO: 11<br>FEATURE<br>source | moltype = RNA   length = 19<br>Location/Qualifiers<br>1..19<br>mol_type = other RNA<br>organism = synthetic construct | |
| SEQUENCE: 11<br>aaatatgaga taactgtct | | 19 |
| SEQ ID NO: 12<br>FEATURE<br>source | moltype = RNA   length = 19<br>Location/Qualifiers<br>1..19<br>mol_type = other RNA<br>organism = synthetic construct | |
| SEQUENCE: 12<br>ggtattggac tttctccat | | 19 |
| SEQ ID NO: 13<br>FEATURE<br>source | moltype = RNA   length = 19<br>Location/Qualifiers<br>1..19<br>mol_type = other RNA<br>organism = synthetic construct | |
| SEQUENCE: 13<br>aggtattgga ctttctcca | | 19 |
| SEQ ID NO: 14<br>FEATURE<br>source | moltype = RNA   length = 19<br>Location/Qualifiers<br>1..19<br>mol_type = other RNA<br>organism = synthetic construct | |
| SEQUENCE: 14<br>ttcaatggtt gaggctctt | | 19 |
| SEQ ID NO: 15<br>FEATURE<br>source | moltype = RNA   length = 21<br>Location/Qualifiers<br>1..21<br>mol_type = other RNA<br>organism = synthetic construct | |
| SEQUENCE: 15<br>atttcaatgg ttgaggctct t | | 21 |
| SEQ ID NO: 16<br>FEATURE<br>source | moltype = RNA   length = 19<br>Location/Qualifiers<br>1..19<br>mol_type = other RNA<br>organism = synthetic construct | |
| SEQUENCE: 16<br>tttcaatggt tgaggctct | | 19 |
| SEQ ID NO: 17<br>FEATURE<br>source | moltype = RNA   length = 21<br>Location/Qualifiers<br>1..21<br>mol_type = other RNA<br>organism = synthetic construct | |
| SEQUENCE: 17<br>catttcaatg gttgaggctc t | | 21 |
| SEQ ID NO: 18<br>FEATURE<br>source | moltype = RNA   length = 19<br>Location/Qualifiers<br>1..19<br>mol_type = other RNA<br>organism = synthetic construct | |
| SEQUENCE: 18 | | |

```
catttcaatg gttgaggct                                                 19

SEQ ID NO: 19          moltype = RNA   length = 21
FEATURE                Location/Qualifiers
source                 1..21
                       mol_type = other RNA
                       organism = synthetic construct
SEQUENCE: 19
gttgaggcat ttcaatggtt g                                              21

SEQ ID NO: 20          moltype = RNA   length = 21
FEATURE                Location/Qualifiers
source                 1..21
                       mol_type = other RNA
                       organism = synthetic construct
SEQUENCE: 20
tgttgaggca tttcaatggt t                                              21

SEQ ID NO: 21          moltype = RNA   length = 19
FEATURE                Location/Qualifiers
source                 1..19
                       mol_type = other RNA
                       organism = synthetic construct
SEQUENCE: 21
gttgaggcat ttcaatggt                                                 19

SEQ ID NO: 22          moltype = RNA   length = 21
FEATURE                Location/Qualifiers
source                 1..21
                       mol_type = other RNA
                       organism = synthetic construct
SEQUENCE: 22
ttgttgaggc atttcaatgg t                                              21

SEQ ID NO: 23          moltype = RNA   length = 19
FEATURE                Location/Qualifiers
source                 1..19
                       mol_type = other RNA
                       organism = synthetic construct
SEQUENCE: 23
tgttgaggca tttcaatgg                                                 19

SEQ ID NO: 24          moltype = RNA   length = 21
FEATURE                Location/Qualifiers
source                 1..21
                       mol_type = other RNA
                       organism = synthetic construct
SEQUENCE: 24
cttgttgagg catttcaatg g                                              21

SEQ ID NO: 25          moltype = RNA   length = 19
FEATURE                Location/Qualifiers
source                 1..19
                       mol_type = other RNA
                       organism = synthetic construct
SEQUENCE: 25
ttgttgaggc atttcaatg                                                 19

SEQ ID NO: 26          moltype = RNA   length = 21
FEATURE                Location/Qualifiers
source                 1..21
                       mol_type = other RNA
                       organism = synthetic construct
SEQUENCE: 26
gcttgttgag gcatttcaat g                                              21

SEQ ID NO: 27          moltype = RNA   length = 21
FEATURE                Location/Qualifiers
source                 1..21
                       mol_type = other RNA
                       organism = synthetic construct
SEQUENCE: 27
attgataaat agattctgta g                                              21

SEQ ID NO: 28          moltype = RNA   length = 19
FEATURE                Location/Qualifiers
source                 1..19
                       mol_type = other RNA
                       organism = synthetic construct
```

```
SEQUENCE: 28
ttgataaata gattctgta                                                    19

SEQ ID NO: 29          moltype = RNA   length = 21
FEATURE                Location/Qualifiers
source                 1..21
                       mol_type = other RNA
                       organism = synthetic construct
SEQUENCE: 29
aattgataaa tagattctgt a                                                 21

SEQ ID NO: 30          moltype = RNA   length = 21
FEATURE                Location/Qualifiers
source                 1..21
                       mol_type = other RNA
                       organism = synthetic construct
SEQUENCE: 30
agaaattgat aaatagattc t                                                 21

SEQ ID NO: 31          moltype = RNA   length = 21
FEATURE                Location/Qualifiers
source                 1..21
                       mol_type = other RNA
                       organism = synthetic construct
SEQUENCE: 31
cagaaattga taaatagatt c                                                 21

SEQ ID NO: 32          moltype = RNA   length = 19
FEATURE                Location/Qualifiers
source                 1..19
                       mol_type = other RNA
                       organism = synthetic construct
SEQUENCE: 32
agaaattgat aaatagatt                                                    19

SEQ ID NO: 33          moltype = RNA   length = 21
FEATURE                Location/Qualifiers
source                 1..21
                       mol_type = other RNA
                       organism = synthetic construct
SEQUENCE: 33
acagaaattg ataaatagat t                                                 21

SEQ ID NO: 34          moltype = RNA   length = 21
FEATURE                Location/Qualifiers
source                 1..21
                       mol_type = other RNA
                       organism = synthetic construct
SEQUENCE: 34
gacagaaatt gataaataga t                                                 21

SEQ ID NO: 35          moltype = RNA   length = 19
FEATURE                Location/Qualifiers
source                 1..19
                       mol_type = other RNA
                       organism = synthetic construct
SEQUENCE: 35
acagaaattg ataaataga                                                    19

SEQ ID NO: 36          moltype = RNA   length = 21
FEATURE                Location/Qualifiers
source                 1..21
                       mol_type = other RNA
                       organism = synthetic construct
SEQUENCE: 36
tgagacagaa attgataaat a                                                 21

SEQ ID NO: 37          moltype = RNA   length = 21
FEATURE                Location/Qualifiers
source                 1..21
                       mol_type = other RNA
                       organism = synthetic construct
SEQUENCE: 37
gatgagacag aaattgataa a                                                 21

SEQ ID NO: 38          moltype = RNA   length = 21
FEATURE                Location/Qualifiers
source                 1..21
                       mol_type = other RNA
```

```
                       organism = synthetic construct
SEQUENCE: 38
agatgagaca gaaattgata a                                              21

SEQ ID NO: 39          moltype = RNA   length = 19
FEATURE                Location/Qualifiers
source                 1..19
                       mol_type = other RNA
                       organism = synthetic construct
SEQUENCE: 39
gatgagacag aaattgata                                                 19

SEQ ID NO: 40          moltype = RNA   length = 21
FEATURE                Location/Qualifiers
source                 1..21
                       mol_type = other RNA
                       organism = synthetic construct
SEQUENCE: 40
cagatcagca agagacatat t                                              21

SEQ ID NO: 41          moltype = RNA   length = 19
FEATURE                Location/Qualifiers
source                 1..19
                       mol_type = other RNA
                       organism = synthetic construct
SEQUENCE: 41
cagatcagca agagacata                                                 19

SEQ ID NO: 42          moltype = RNA   length = 21
FEATURE                Location/Qualifiers
source                 1..21
                       mol_type = other RNA
                       organism = synthetic construct
SEQUENCE: 42
atacagatca gcaagagaca t                                              21

SEQ ID NO: 43          moltype = RNA   length = 21
FEATURE                Location/Qualifiers
source                 1..21
                       mol_type = other RNA
                       organism = synthetic construct
SEQUENCE: 43
gatacagatc agcaagagac a                                              21

SEQ ID NO: 44          moltype = RNA   length = 19
FEATURE                Location/Qualifiers
source                 1..19
                       mol_type = other RNA
                       organism = synthetic construct
SEQUENCE: 44
atacagatca gcaagagac                                                 19

SEQ ID NO: 45          moltype = RNA   length = 21
FEATURE                Location/Qualifiers
source                 1..21
                       mol_type = other RNA
                       organism = synthetic construct
SEQUENCE: 45
tgatacagat cagcaagaga c                                              21

SEQ ID NO: 46          moltype = RNA   length = 19
FEATURE                Location/Qualifiers
source                 1..19
                       mol_type = other RNA
                       organism = synthetic construct
SEQUENCE: 46
gatacagatc agcaagaga                                                 19

SEQ ID NO: 47          moltype = RNA   length = 21
FEATURE                Location/Qualifiers
source                 1..21
                       mol_type = other RNA
                       organism = synthetic construct
SEQUENCE: 47
atgatacaga tcagcaagag a                                              21

SEQ ID NO: 48          moltype = RNA   length = 19
FEATURE                Location/Qualifiers
source                 1..19
```

```
                            mol_type = other RNA
                            organism = synthetic construct
SEQUENCE: 48
tgatacagat cagcaagag                                                  19

SEQ ID NO: 49               moltype = RNA  length = 21
FEATURE                     Location/Qualifiers
source                      1..21
                            mol_type = other RNA
                            organism = synthetic construct
SEQUENCE: 49
gatgatacag atcagcaaga g                                               21

SEQ ID NO: 50               moltype = RNA  length = 19
FEATURE                     Location/Qualifiers
source                      1..19
                            mol_type = other RNA
                            organism = synthetic construct
SEQUENCE: 50
atgatacaga tcagcaaga                                                  19

SEQ ID NO: 51               moltype = RNA  length = 21
FEATURE                     Location/Qualifiers
source                      1..21
                            mol_type = other RNA
                            organism = synthetic construct
SEQUENCE: 51
acgatgatac agatcagcaa g                                               21

SEQ ID NO: 52               moltype = RNA  length = 21
FEATURE                     Location/Qualifiers
source                      1..21
                            mol_type = other RNA
                            organism = synthetic construct
SEQUENCE: 52
cacgatgata cagatcagca a                                               21

SEQ ID NO: 53               moltype = RNA  length = 19
FEATURE                     Location/Qualifiers
source                      1..19
                            mol_type = other RNA
                            organism = synthetic construct
SEQUENCE: 53
acgatgatac agatcagca                                                  19

SEQ ID NO: 54               moltype = RNA  length = 21
FEATURE                     Location/Qualifiers
source                      1..21
                            mol_type = other RNA
                            organism = synthetic construct
SEQUENCE: 54
tcacgatgat acagatcagc a                                               21

SEQ ID NO: 55               moltype = RNA  length = 19
FEATURE                     Location/Qualifiers
source                      1..19
                            mol_type = other RNA
                            organism = synthetic construct
SEQUENCE: 55
cacgatgata cagatcagc                                                  19

SEQ ID NO: 56               moltype = RNA  length = 21
FEATURE                     Location/Qualifiers
source                      1..21
                            mol_type = other RNA
                            organism = synthetic construct
SEQUENCE: 56
atcacgatga tacagatcag c                                               21

SEQ ID NO: 57               moltype = RNA  length = 21
FEATURE                     Location/Qualifiers
source                      1..21
                            mol_type = other RNA
                            organism = synthetic construct
SEQUENCE: 57
catcacgatg atacagatca g                                               21

SEQ ID NO: 58               moltype = RNA  length = 19
FEATURE                     Location/Qualifiers
```

```
                              source              1..19
                                                  mol_type = other RNA
                                                  organism = synthetic construct
                      SEQUENCE: 58
                      atcacgatga tacagatca                                                    19

SEQ ID NO: 59           moltype = RNA  length = 21
                      FEATURE                 Location/Qualifiers
                      source                  1..21
                                              mol_type = other RNA
                                              organism = synthetic construct
                      SEQUENCE: 59
                      agcatcacga tgatacagat c                                                 21

SEQ ID NO: 60           moltype = RNA  length = 21
                      FEATURE                 Location/Qualifiers
                      source                  1..21
                                              mol_type = other RNA
                                              organism = synthetic construct
                      SEQUENCE: 60
                      agcatcacga tgatacagat c                                                 21

SEQ ID NO: 61           moltype = RNA  length = 21
                      FEATURE                 Location/Qualifiers
                      source                  1..21
                                              mol_type = other RNA
                                              organism = synthetic construct
                      SEQUENCE: 61
                      aagcatcacg atgatacaga t                                                 21

SEQ ID NO: 62           moltype = RNA  length = 21
                      FEATURE                 Location/Qualifiers
                      source                  1..21
                                              mol_type = other RNA
                                              organism = synthetic construct
                      SEQUENCE: 62
                      gaagcatcac gatgatacag a                                                 21

SEQ ID NO: 63           moltype = RNA  length = 19
                      FEATURE                 Location/Qualifiers
                      source                  1..19
                                              mol_type = other RNA
                                              organism = synthetic construct
                      SEQUENCE: 63
                      aagcatcacg atgatacag                                                    19

SEQ ID NO: 64           moltype = RNA  length = 21
                      FEATURE                 Location/Qualifiers
                      source                  1..21
                                              mol_type = other RNA
                                              organism = synthetic construct
                      SEQUENCE: 64
                      agaagcatca cgatgataca g                                                 21

SEQ ID NO: 65           moltype = RNA  length = 19
                      FEATURE                 Location/Qualifiers
                      source                  1..19
                                              mol_type = other RNA
                                              organism = synthetic construct
                      SEQUENCE: 65
                      gaagcatcac gatgataca                                                    19

SEQ ID NO: 66           moltype = RNA  length = 19
                      FEATURE                 Location/Qualifiers
                      source                  1..19
                                              mol_type = other RNA
                                              organism = synthetic construct
                      SEQUENCE: 66
                      agaagcatca cgatgatac                                                    19

SEQ ID NO: 67           moltype = RNA  length = 21
                      FEATURE                 Location/Qualifiers
                      source                  1..21
                                              mol_type = other RNA
                                              organism = synthetic construct
                      SEQUENCE: 67
                      agagaagcat cacgatgata c                                                 21

SEQ ID NO: 68           moltype = RNA  length = 21
```

```
FEATURE              Location/Qualifiers
source               1..21
                     mol_type = other RNA
                     organism = synthetic construct
SEQUENCE: 68
cagagaagca tcacgatgat a                                              21

SEQ ID NO: 69        moltype = RNA   length = 19
FEATURE              Location/Qualifiers
source               1..19
                     mol_type = other RNA
                     organism = synthetic construct
SEQUENCE: 69
agagaagcat cacgatgat                                                 19

SEQ ID NO: 70        moltype = RNA   length = 21
FEATURE              Location/Qualifiers
source               1..21
                     mol_type = other RNA
                     organism = synthetic construct
SEQUENCE: 70
tcagagaagc atcacgatga t                                              21

SEQ ID NO: 71        moltype = RNA   length = 19
FEATURE              Location/Qualifiers
source               1..19
                     mol_type = other RNA
                     organism = synthetic construct
SEQUENCE: 71
cagagaagca tcacgatga                                                 19

SEQ ID NO: 72        moltype = RNA   length = 19
FEATURE              Location/Qualifiers
source               1..19
                     mol_type = other RNA
                     organism = synthetic construct
SEQUENCE: 72
tgtagcagaa cttcagaga                                                 19

SEQ ID NO: 73        moltype = RNA   length = 19
FEATURE              Location/Qualifiers
source               1..19
                     mol_type = other RNA
                     organism = synthetic construct
SEQUENCE: 73
gatctagagg ttgtagcag                                                 19

SEQ ID NO: 74        moltype = RNA   length = 19
FEATURE              Location/Qualifiers
source               1..19
                     mol_type = other RNA
                     organism = synthetic construct
SEQUENCE: 74
cagatctaga ggttgtagc                                                 19

SEQ ID NO: 75        moltype = RNA   length = 19
FEATURE              Location/Qualifiers
source               1..19
                     mol_type = other RNA
                     organism = synthetic construct
SEQUENCE: 75
attttaagct gatgtggca                                                 19

SEQ ID NO: 76        moltype = RNA   length = 19
FEATURE              Location/Qualifiers
source               1..19
                     mol_type = other RNA
                     organism = synthetic construct
SEQUENCE: 76
cagattttaa gctgatgtg                                                 19

SEQ ID NO: 77        moltype = RNA   length = 19
FEATURE              Location/Qualifiers
source               1..19
                     mol_type = other RNA
                     organism = synthetic construct
SEQUENCE: 77
gtctgcatgg gatgacaga                                                 19
```

```
SEQ ID NO: 78           moltype = RNA  length = 19
FEATURE                 Location/Qualifiers
source                  1..19
                        mol_type = other RNA
                        organism = synthetic construct
SEQUENCE: 78
aaactcttct actcaggaa                                                     19

SEQ ID NO: 79           moltype = RNA  length = 19
FEATURE                 Location/Qualifiers
source                  1..19
                        mol_type = other RNA
                        organism = synthetic construct
SEQUENCE: 79
gaaactcttc tactcagga                                                     19

SEQ ID NO: 80           moltype = RNA  length = 19
FEATURE                 Location/Qualifiers
source                  1..19
                        mol_type = other RNA
                        organism = synthetic construct
SEQUENCE: 80
aagaaactct tctactcag                                                     19

SEQ ID NO: 81           moltype = RNA  length = 19
FEATURE                 Location/Qualifiers
source                  1..19
                        mol_type = other RNA
                        organism = synthetic construct
SEQUENCE: 81
ttagtcttaa tcttgacct                                                     19

SEQ ID NO: 82           moltype = RNA  length = 19
FEATURE                 Location/Qualifiers
source                  1..19
                        mol_type = other RNA
                        organism = synthetic construct
SEQUENCE: 82
tttagtctta atcttgacc                                                     19

SEQ ID NO: 83           moltype = RNA  length = 19
FEATURE                 Location/Qualifiers
source                  1..19
                        mol_type = other RNA
                        organism = synthetic construct
SEQUENCE: 83
taacaataag ttttagtct                                                     19

SEQ ID NO: 84           moltype = RNA  length = 19
FEATURE                 Location/Qualifiers
source                  1..19
                        mol_type = other RNA
                        organism = synthetic construct
SEQUENCE: 84
tttcatgttt acaagatcc                                                     19

SEQ ID NO: 85           moltype = RNA  length = 19
FEATURE                 Location/Qualifiers
source                  1..19
                        mol_type = other RNA
                        organism = synthetic construct
SEQUENCE: 85
ttgtgagcca tgttgagga                                                     19

SEQ ID NO: 86           moltype = RNA  length = 19
FEATURE                 Location/Qualifiers
source                  1..19
                        mol_type = other RNA
                        organism = synthetic construct
SEQUENCE: 86
aaatttgtga gccatgttg                                                     19

SEQ ID NO: 87           moltype = RNA  length = 19
FEATURE                 Location/Qualifiers
source                  1..19
                        mol_type = other RNA
                        organism = synthetic construct
SEQUENCE: 87
gaacttgttg gcagtgcag                                                     19
```

```
SEQ ID NO: 88              moltype = RNA   length = 19
FEATURE                    Location/Qualifiers
source                     1..19
                           mol_type = other RNA
                           organism = synthetic construct
SEQUENCE: 88
tatgaagtga acttgttgg                                                     19

SEQ ID NO: 89              moltype = RNA   length = 19
FEATURE                    Location/Qualifiers
source                     1..19
                           mol_type = other RNA
                           organism = synthetic construct
SEQUENCE: 89
tatatgaagt gaacttgtt                                                     19

SEQ ID NO: 90              moltype = RNA   length = 19
FEATURE                    Location/Qualifiers
source                     1..19
                           mol_type = other RNA
                           organism = synthetic construct
SEQUENCE: 90
tttatatatg aagtgaact                                                     19

SEQ ID NO: 91              moltype = RNA   length = 19
FEATURE                    Location/Qualifiers
source                     1..19
                           mol_type = other RNA
                           organism = synthetic construct
SEQUENCE: 91
ttcacctcaa aagagtaaa                                                     19

SEQ ID NO: 92              moltype = RNA   length = 19
FEATURE                    Location/Qualifiers
source                     1..19
                           mol_type = other RNA
                           organism = synthetic construct
SEQUENCE: 92
tattcacctc aaaagagta                                                     19

SEQ ID NO: 93              moltype = RNA   length = 19
FEATURE                    Location/Qualifiers
source                     1..19
                           mol_type = other RNA
                           organism = synthetic construct
SEQUENCE: 93
tttgatactt ggtgaagac                                                     19

SEQ ID NO: 94              moltype = RNA   length = 19
FEATURE                    Location/Qualifiers
source                     1..19
                           mol_type = other RNA
                           organism = synthetic construct
SEQUENCE: 94
ctttgatact tggtgaaga                                                     19

SEQ ID NO: 95              moltype = RNA   length = 19
FEATURE                    Location/Qualifiers
source                     1..19
                           mol_type = other RNA
                           organism = synthetic construct
SEQUENCE: 95
attactttga tacttggtg                                                     19

SEQ ID NO: 96              moltype = RNA   length = 19
FEATURE                    Location/Qualifiers
source                     1..19
                           mol_type = other RNA
                           organism = synthetic construct
SEQUENCE: 96
tgtgttatta ctttgatac                                                     19

SEQ ID NO: 97              moltype = RNA   length = 19
FEATURE                    Location/Qualifiers
source                     1..19
                           mol_type = other RNA
                           organism = synthetic construct
SEQUENCE: 97
```
tacttgattc tcatcaact                                                      19

SEQ ID NO: 98           moltype = RNA   length = 19
FEATURE                 Location/Qualifiers
source                  1..19
                        mol_type = other RNA
                        organism = synthetic construct
SEQUENCE: 98
gccttacttt tccatactt                                                      19

SEQ ID NO: 99           moltype = RNA   length = 19
FEATURE                 Location/Qualifiers
source                  1..19
                        mol_type = other RNA
                        organism = synthetic construct
SEQUENCE: 99
gtatggcctt acttttcca                                                      19

SEQ ID NO: 100          moltype = RNA   length = 19
FEATURE                 Location/Qualifiers
source                  1..19
                        mol_type = other RNA
                        organism = synthetic construct
SEQUENCE: 100
taagagtatg gccttactt                                                      19

SEQ ID NO: 101          moltype = RNA   length = 19
FEATURE                 Location/Qualifiers
source                  1..19
                        mol_type = other RNA
                        organism = synthetic construct
SEQUENCE: 101
gtaagagtat ggccttact                                                      19

SEQ ID NO: 102          moltype = RNA   length = 19
FEATURE                 Location/Qualifiers
source                  1..19
                        mol_type = other RNA
                        organism = synthetic construct
SEQUENCE: 102
tgtaagagta tggccttac                                                      19

SEQ ID NO: 103          moltype = RNA   length = 19
FEATURE                 Location/Qualifiers
source                  1..19
                        mol_type = other RNA
                        organism = synthetic construct
SEQUENCE: 103
atgtaagagt atggcctta                                                      19

SEQ ID NO: 104          moltype = RNA   length = 19
FEATURE                 Location/Qualifiers
source                  1..19
                        mol_type = other RNA
                        organism = synthetic construct
SEQUENCE: 104
ttatgtaaga gtatggcct                                                      19

SEQ ID NO: 105          moltype = RNA   length = 19
FEATURE                 Location/Qualifiers
source                  1..19
                        mol_type = other RNA
                        organism = synthetic construct
SEQUENCE: 105
attatgtaag agtatggcc                                                      19

SEQ ID NO: 106          moltype = RNA   length = 19
FEATURE                 Location/Qualifiers
source                  1..19
                        mol_type = other RNA
                        organism = synthetic construct
SEQUENCE: 106
tattatgtaa gagtatggc                                                      19

SEQ ID NO: 107          moltype = RNA   length = 19
FEATURE                 Location/Qualifiers
source                  1..19
                        mol_type = other RNA
                        organism = synthetic construct SEQUENCE: 107
tttattatgt aagagtatg                                                      19

SEQ ID NO: 108        moltype = RNA  length = 19
FEATURE               Location/Qualifiers
source                1..19
                      mol_type = other RNA
                      organism = synthetic construct
SEQUENCE: 108
gatcatatgt cttagaaca                                                      19

SEQ ID NO: 109        moltype = RNA  length = 19
FEATURE               Location/Qualifiers
source                1..19
                      mol_type = other RNA
                      organism = synthetic construct
SEQUENCE: 109
ttgatcatat gtcttagaa                                                      19

SEQ ID NO: 110        moltype = RNA  length = 19
FEATURE               Location/Qualifiers
source                1..19
                      mol_type = other RNA
                      organism = synthetic construct
SEQUENCE: 110
atctgttgat catatgtct                                                      19

SEQ ID NO: 111        moltype = RNA  length = 19
FEATURE               Location/Qualifiers
source                1..19
                      mol_type = other RNA
                      organism = synthetic construct
SEQUENCE: 111
catctgttga tcatatgtc                                                      19

SEQ ID NO: 112        moltype = RNA  length = 19
FEATURE               Location/Qualifiers
source                1..19
                      mol_type = other RNA
                      organism = synthetic construct
SEQUENCE: 112
tcatctgttg atcatatgt                                                      19

SEQ ID NO: 113        moltype = RNA  length = 19
FEATURE               Location/Qualifiers
source                1..19
                      mol_type = other RNA
                      organism = synthetic construct
SEQUENCE: 113
tctcatctgt tgatcatat                                                      19

SEQ ID NO: 114        moltype = RNA  length = 19
FEATURE               Location/Qualifiers
source                1..19
                      mol_type = other RNA
                      organism = synthetic construct
SEQUENCE: 114
gatatgacta atctcactg                                                      19

SEQ ID NO: 115        moltype = RNA  length = 19
FEATURE               Location/Qualifiers
source                1..19
                      mol_type = other RNA
                      organism = synthetic construct
SEQUENCE: 115
tgatatgact aatctcact                                                      19

SEQ ID NO: 116        moltype = RNA  length = 19
FEATURE               Location/Qualifiers
source                1..19
                      mol_type = other RNA
                      organism = synthetic construct
SEQUENCE: 116
gtgatatgac taatctcac                                                      19

SEQ ID NO: 117        moltype = RNA  length = 19
FEATURE               Location/Qualifiers
source                1..19
                      mol_type = other RNA

```
                                 organism = synthetic construct
SEQUENCE: 117
tattagtgat atgactaat                                                          19

SEQ ID NO: 118          moltype = RNA  length = 19
FEATURE                 Location/Qualifiers
source                  1..19
                        mol_type = other RNA
                        organism = synthetic construct
SEQUENCE: 118
gtatattagt gatatgact                                                          19

SEQ ID NO: 119          moltype = RNA  length = 19
FEATURE                 Location/Qualifiers
source                  1..19
                        mol_type = other RNA
                        organism = synthetic construct
SEQUENCE: 119
agtatattag tgatatgac                                                          19

SEQ ID NO: 120          moltype = RNA  length = 19
FEATURE                 Location/Qualifiers
source                  1..19
                        mol_type = other RNA
                        organism = synthetic construct
SEQUENCE: 120
ttagtatatt agtgatatg                                                          19

SEQ ID NO: 121          moltype = RNA  length = 19
FEATURE                 Location/Qualifiers
source                  1..19
                        mol_type = other RNA
                        organism = synthetic construct
SEQUENCE: 121
tgttagtata ttagtgata                                                          19

SEQ ID NO: 122          moltype = RNA  length = 19
FEATURE                 Location/Qualifiers
source                  1..19
                        mol_type = other RNA
                        organism = synthetic construct
SEQUENCE: 122
agtcttaagg tttcatgat                                                          19

SEQ ID NO: 123          moltype = RNA  length = 19
FEATURE                 Location/Qualifiers
source                  1..19
                        mol_type = other RNA
                        organism = synthetic construct
SEQUENCE: 123
aagtcttaag gtttcatga                                                          19

SEQ ID NO: 124          moltype = RNA  length = 19
FEATURE                 Location/Qualifiers
source                  1..19
                        mol_type = other RNA
                        organism = synthetic construct
SEQUENCE: 124
gcctgcattg gatgttagg                                                          19

SEQ ID NO: 125          moltype = RNA  length = 19
FEATURE                 Location/Qualifiers
source                  1..19
                        mol_type = other RNA
                        organism = synthetic construct
SEQUENCE: 125
tagatgggcc aacaagttc                                                          19

SEQ ID NO: 126          moltype = RNA  length = 19
FEATURE                 Location/Qualifiers
source                  1..19
                        mol_type = other RNA
                        organism = synthetic construct
SEQUENCE: 126
atagatgggc caacaagtt                                                          19

SEQ ID NO: 127          moltype = RNA  length = 19
FEATURE                 Location/Qualifiers
source                  1..19
```

```
                              mol_type = other RNA
                              organism = synthetic construct
SEQUENCE: 127
aatagatggg ccaacaagt                                              19

SEQ ID NO: 128               moltype = RNA  length = 19
FEATURE                      Location/Qualifiers
source                       1..19
                              mol_type = other RNA
                              organism = synthetic construct
SEQUENCE: 128
taatagatgg gccaacaag                                              19

SEQ ID NO: 129               moltype = RNA  length = 19
FEATURE                      Location/Qualifiers
source                       1..19
                              mol_type = other RNA
                              organism = synthetic construct
SEQUENCE: 129
gtaatagatg ggccaacaa                                              19

SEQ ID NO: 130               moltype = RNA  length = 19
FEATURE                      Location/Qualifiers
source                       1..19
                              mol_type = other RNA
                              organism = synthetic construct
SEQUENCE: 130
tgtaatagat gggccaaca                                              19

SEQ ID NO: 131               moltype = RNA  length = 19
FEATURE                      Location/Qualifiers
source                       1..19
                              mol_type = other RNA
                              organism = synthetic construct
SEQUENCE: 131
atgtaataga tgggccaac                                              19

SEQ ID NO: 132               moltype = RNA  length = 19
FEATURE                      Location/Qualifiers
source                       1..19
                              mol_type = other RNA
                              organism = synthetic construct
SEQUENCE: 132
gatgtaatag atgggccaa                                              19

SEQ ID NO: 133               moltype = RNA  length = 19
FEATURE                      Location/Qualifiers
source                       1..19
                              mol_type = other RNA
                              organism = synthetic construct
SEQUENCE: 133
aagacttcat acaacacaa                                              19

SEQ ID NO: 134               moltype = RNA  length = 19
FEATURE                      Location/Qualifiers
source                       1..19
                              mol_type = other RNA
                              organism = synthetic construct
SEQUENCE: 134
agacttcata caacacaat                                              19

SEQ ID NO: 135               moltype = RNA  length = 19
FEATURE                      Location/Qualifiers
source                       1..19
                              mol_type = other RNA
                              organism = synthetic construct
SEQUENCE: 135
cttcatacaa cacaatact                                              19

SEQ ID NO: 136               moltype = RNA  length = 19
FEATURE                      Location/Qualifiers
source                       1..19
                              mol_type = other RNA
                              organism = synthetic construct
SEQUENCE: 136
catacaacac aatactcta                                              19

SEQ ID NO: 137               moltype = RNA  length = 19
FEATURE                      Location/Qualifiers
```

```
                            -continued source              1..19
                    mol_type = other RNA
                    organism = synthetic construct
SEQUENCE: 137
gccaaggcta cctaaaaga                                                19

SEQ ID NO: 138      moltype = RNA   length = 19
FEATURE             Location/Qualifiers
source              1..19
                    mol_type = other RNA
                    organism = synthetic construct
SEQUENCE: 138
ccaaggctac ctaaaagaa                                                19

SEQ ID NO: 139      moltype = RNA   length = 19
FEATURE             Location/Qualifiers
source              1..19
                    mol_type = other RNA
                    organism = synthetic construct
SEQUENCE: 139
caaggctacc taaaagaag                                                19

SEQ ID NO: 140      moltype = RNA   length = 19
FEATURE             Location/Qualifiers
source              1..19
                    mol_type = other RNA
                    organism = synthetic construct
SEQUENCE: 140
aaggctacct aaaagaaga                                                19

SEQ ID NO: 141      moltype = RNA   length = 19
FEATURE             Location/Qualifiers
source              1..19
                    mol_type = other RNA
                    organism = synthetic construct
SEQUENCE: 141
agaagacagt tatctcata                                                19

SEQ ID NO: 142      moltype = RNA   length = 19
FEATURE             Location/Qualifiers
source              1..19
                    mol_type = other RNA
                    organism = synthetic construct
SEQUENCE: 142
aagacagtta tctcatatt                                                19

SEQ ID NO: 143      moltype = RNA   length = 19
FEATURE             Location/Qualifiers
source              1..19
                    mol_type = other RNA
                    organism = synthetic construct
SEQUENCE: 143
agacagttat ctcatattt                                                19

SEQ ID NO: 144      moltype = RNA   length = 19
FEATURE             Location/Qualifiers
source              1..19
                    mol_type = other RNA
                    organism = synthetic construct
SEQUENCE: 144
atggagaaag tccaatacc                                                19

SEQ ID NO: 145      moltype = RNA   length = 19
FEATURE             Location/Qualifiers
source              1..19
                    mol_type = other RNA
                    organism = synthetic construct
SEQUENCE: 145
tggagaaagt ccaatacct                                                19

SEQ ID NO: 146      moltype = RNA   length = 19
FEATURE             Location/Qualifiers
source              1..19
                    mol_type = other RNA
                    organism = synthetic construct
SEQUENCE: 146
aagagcctca accattgaa                                                19

SEQ ID NO: 147      moltype = RNA   length = 21
```

```
FEATURE               Location/Qualifiers
source                1..21
                      mol_type = other RNA
                      organism = synthetic construct
SEQUENCE: 147
aagagcctca accattgaaa t                                                   21

SEQ ID NO: 148        moltype = RNA   length = 19
FEATURE               Location/Qualifiers
source                1..19
                      mol_type = other RNA
                      organism = synthetic construct
SEQUENCE: 148
agagcctcaa ccattgaaa                                                      19

SEQ ID NO: 149        moltype = RNA   length = 21
FEATURE               Location/Qualifiers
source                1..21
                      mol_type = other RNA
                      organism = synthetic construct
SEQUENCE: 149
agagcctcaa ccattgaaat g                                                   21

SEQ ID NO: 150        moltype = RNA   length = 19
FEATURE               Location/Qualifiers
source                1..19
                      mol_type = other RNA
                      organism = synthetic construct
SEQUENCE: 150
agcctcaacc attgaaatg                                                      19

SEQ ID NO: 151        moltype = RNA   length = 21
FEATURE               Location/Qualifiers
source                1..21
                      mol_type = other RNA
                      organism = synthetic construct
SEQUENCE: 151
caaccattga aatgcctcaa c                                                   21

SEQ ID NO: 152        moltype = RNA   length = 21
FEATURE               Location/Qualifiers
source                1..21
                      mol_type = other RNA
                      organism = synthetic construct
SEQUENCE: 152
aaccattgaa atgcctcaac a                                                   21

SEQ ID NO: 153        moltype = RNA   length = 19
FEATURE               Location/Qualifiers
source                1..19
                      mol_type = other RNA
                      organism = synthetic construct
SEQUENCE: 153
accattgaaa tgcctcaac                                                      19

SEQ ID NO: 154        moltype = RNA   length = 21
FEATURE               Location/Qualifiers
source                1..21
                      mol_type = other RNA
                      organism = synthetic construct
SEQUENCE: 154
accattgaaa tgcctcaaca a                                                   21

SEQ ID NO: 155        moltype = RNA   length = 19
FEATURE               Location/Qualifiers
source                1..19
                      mol_type = other RNA
                      organism = synthetic construct
SEQUENCE: 155
ccattgaaat gcctcaaca                                                      19

SEQ ID NO: 156        moltype = RNA   length = 21
FEATURE               Location/Qualifiers
source                1..21
                      mol_type = other RNA
                      organism = synthetic construct
SEQUENCE: 156
ccattgaaat gcctcaacaa g                                                   21
```

```
SEQ ID NO: 157           moltype = RNA   length = 19
FEATURE                  Location/Qualifiers
source                   1..19
                         mol_type = other RNA
                         organism = synthetic construct
SEQUENCE: 157
cattgaaatg cctcaacaa                                                      19

SEQ ID NO: 158           moltype = RNA   length = 21
FEATURE                  Location/Qualifiers
source                   1..21
                         mol_type = other RNA
                         organism = synthetic construct
SEQUENCE: 158
cattgaaatg cctcaacaag c                                                   21

SEQ ID NO: 159           moltype = RNA   length = 21
FEATURE                  Location/Qualifiers
source                   1..21
                         mol_type = other RNA
                         organism = synthetic construct
SEQUENCE: 159
ctacagaatc tatttatcaa t                                                   21

SEQ ID NO: 160           moltype = RNA   length = 19
FEATURE                  Location/Qualifiers
source                   1..19
                         mol_type = other RNA
                         organism = synthetic construct
SEQUENCE: 160
tacagaatct atttatcaa                                                      19

SEQ ID NO: 161           moltype = RNA   length = 21
FEATURE                  Location/Qualifiers
source                   1..21
                         mol_type = other RNA
                         organism = synthetic construct
SEQUENCE: 161
tacagaatct atttatcaat t                                                   21

SEQ ID NO: 162           moltype = RNA   length = 21
FEATURE                  Location/Qualifiers
source                   1..21
                         mol_type = other RNA
                         organism = synthetic construct
SEQUENCE: 162
agaatctatt tatcaatttc t                                                   21

SEQ ID NO: 163           moltype = RNA   length = 21
FEATURE                  Location/Qualifiers
source                   1..21
                         mol_type = other RNA
                         organism = synthetic construct
SEQUENCE: 163
gaatctattt atcaatttct g                                                   21

SEQ ID NO: 164           moltype = RNA   length = 19
FEATURE                  Location/Qualifiers
source                   1..19
                         mol_type = other RNA
                         organism = synthetic construct
SEQUENCE: 164
aatctattta tcaatttct                                                      19

SEQ ID NO: 165           moltype = RNA   length = 21
FEATURE                  Location/Qualifiers
source                   1..21
                         mol_type = other RNA
                         organism = synthetic construct
SEQUENCE: 165
aatctattta tcaatttctg t                                                   21

SEQ ID NO: 166           moltype = RNA   length = 21
FEATURE                  Location/Qualifiers
source                   1..21
                         mol_type = other RNA
                         organism = synthetic construct
SEQUENCE: 166
atctatttat caatttctgt c                                                   21
```

```
SEQ ID NO: 167         moltype = RNA   length = 19
FEATURE                Location/Qualifiers
source                 1..19
                       mol_type = other RNA
                       organism = synthetic construct
SEQUENCE: 167
tctatttatc aatttctgt                                                   19

SEQ ID NO: 168         moltype = RNA   length = 21
FEATURE                Location/Qualifiers
source                 1..21
                       mol_type = other RNA
                       organism = synthetic construct
SEQUENCE: 168
tatttatcaa tttctgtctc a                                                21

SEQ ID NO: 169         moltype = RNA   length = 21
FEATURE                Location/Qualifiers
source                 1..21
                       mol_type = other RNA
                       organism = synthetic construct
SEQUENCE: 169
tttatcaatt tctgtctcat c                                                21

SEQ ID NO: 170         moltype = RNA   length = 21
FEATURE                Location/Qualifiers
source                 1..21
                       mol_type = other RNA
                       organism = synthetic construct
SEQUENCE: 170
ttatcaattt ctgtctcatc t                                                21

SEQ ID NO: 171         moltype = RNA   length = 19
FEATURE                Location/Qualifiers
source                 1..19
                       mol_type = other RNA
                       organism = synthetic construct
SEQUENCE: 171
tatcaatttc tgtctcatc                                                   19

SEQ ID NO: 172         moltype = RNA   length = 21
FEATURE                Location/Qualifiers
source                 1..21
                       mol_type = other RNA
                       organism = synthetic construct
SEQUENCE: 172
aatatgtctc ttgctgatct g                                                21

SEQ ID NO: 173         moltype = RNA   length = 19
FEATURE                Location/Qualifiers
source                 1..19
                       mol_type = other RNA
                       organism = synthetic construct
SEQUENCE: 173
tatgtctctt gctgatctg                                                   19

SEQ ID NO: 174         moltype = RNA   length = 21
FEATURE                Location/Qualifiers
source                 1..21
                       mol_type = other RNA
                       organism = synthetic construct
SEQUENCE: 174
atgtctcttg ctgatctgta t                                                21

SEQ ID NO: 175         moltype = RNA   length = 21
FEATURE                Location/Qualifiers
source                 1..21
                       mol_type = other RNA
                       organism = synthetic construct
SEQUENCE: 175
tgtctcttgc tgatctgtat c                                                21

SEQ ID NO: 176         moltype = RNA   length = 19
FEATURE                Location/Qualifiers
source                 1..19
                       mol_type = other RNA
                       organism = synthetic construct
SEQUENCE: 176
```

-continued

```
gtctcttgct gatctgtat                                              19

SEQ ID NO: 177          moltype = RNA   length = 21
FEATURE                 Location/Qualifiers
source                  1..21
                        mol_type = other RNA
                        organism = synthetic construct
SEQUENCE: 177
gtctcttgct gatctgtatc a                                           21

SEQ ID NO: 178          moltype = RNA   length = 19
FEATURE                 Location/Qualifiers
source                  1..19
                        mol_type = other RNA
                        organism = synthetic construct
SEQUENCE: 178
tctcttgctg atctgtatc                                              19

SEQ ID NO: 179          moltype = RNA   length = 21
FEATURE                 Location/Qualifiers
source                  1..21
                        mol_type = other RNA
                        organism = synthetic construct
SEQUENCE: 179
tctcttgctg atctgtatca t                                           21

SEQ ID NO: 180          moltype = RNA   length = 19
FEATURE                 Location/Qualifiers
source                  1..19
                        mol_type = other RNA
                        organism = synthetic construct
SEQUENCE: 180
ctcttgctga tctgtatca                                              19

SEQ ID NO: 181          moltype = RNA   length = 21
FEATURE                 Location/Qualifiers
source                  1..21
                        mol_type = other RNA
                        organism = synthetic construct
SEQUENCE: 181
ctcttgctga tctgtatcat c                                           21

SEQ ID NO: 182          moltype = RNA   length = 19
FEATURE                 Location/Qualifiers
source                  1..19
                        mol_type = other RNA
                        organism = synthetic construct
SEQUENCE: 182
tcttgctgat ctgtatcat                                              19

SEQ ID NO: 183          moltype = RNA   length = 21
FEATURE                 Location/Qualifiers
source                  1..21
                        mol_type = other RNA
                        organism = synthetic construct
SEQUENCE: 183
cttgctgatc tgtatcatcg t                                           21

SEQ ID NO: 184          moltype = RNA   length = 21
FEATURE                 Location/Qualifiers
source                  1..21
                        mol_type = other RNA
                        organism = synthetic construct
SEQUENCE: 184
ttgctgatct gtatcatcgt g                                           21

SEQ ID NO: 185          moltype = RNA   length = 19
FEATURE                 Location/Qualifiers
source                  1..19
                        mol_type = other RNA
                        organism = synthetic construct
SEQUENCE: 185
tgctgatctg tatcatcgt                                              19

SEQ ID NO: 186          moltype = RNA   length = 21
FEATURE                 Location/Qualifiers
source                  1..21
                        mol_type = other RNA
                        organism = synthetic construct
```

```
SEQUENCE: 186
tgctgatctg tatcatcgtg a                                                     21

SEQ ID NO: 187          moltype = RNA   length = 19
FEATURE                 Location/Qualifiers
source                  1..19
                        mol_type = other RNA
                        organism = synthetic construct
SEQUENCE: 187
gctgatctgt atcatcgtg                                                        19

SEQ ID NO: 188          moltype = RNA   length = 21
FEATURE                 Location/Qualifiers
source                  1..21
                        mol_type = other RNA
                        organism = synthetic construct
SEQUENCE: 188
gctgatctgt atcatcgtga t                                                     21

SEQ ID NO: 189          moltype = RNA   length = 21
FEATURE                 Location/Qualifiers
source                  1..21
                        mol_type = other RNA
                        organism = synthetic construct
SEQUENCE: 189
ctgatctgta tcatcgtgat g                                                     21

SEQ ID NO: 190          moltype = RNA   length = 19
FEATURE                 Location/Qualifiers
source                  1..19
                        mol_type = other RNA
                        organism = synthetic construct
SEQUENCE: 190
tgatctgtat catcgtgat                                                        19

SEQ ID NO: 191          moltype = RNA   length = 19
FEATURE                 Location/Qualifiers
source                  1..19
                        mol_type = other RNA
                        organism = synthetic construct
SEQUENCE: 191
gatctgtatc atcgtgatg                                                        19

SEQ ID NO: 192          moltype = RNA   length = 21
FEATURE                 Location/Qualifiers
source                  1..21
                        mol_type = other RNA
                        organism = synthetic construct
SEQUENCE: 192
gatctgtatc atcgtgatgc t                                                     21

SEQ ID NO: 193          moltype = RNA   length = 21
FEATURE                 Location/Qualifiers
source                  1..21
                        mol_type = other RNA
                        organism = synthetic construct
SEQUENCE: 193
atctgtatca tcgtgatgct t                                                     21

SEQ ID NO: 194          moltype = RNA   length = 21
FEATURE                 Location/Qualifiers
source                  1..21
                        mol_type = other RNA
                        organism = synthetic construct
SEQUENCE: 194
tctgtatcat cgtgatgctt c                                                     21

SEQ ID NO: 195          moltype = RNA   length = 19
FEATURE                 Location/Qualifiers
source                  1..19
                        mol_type = other RNA
                        organism = synthetic construct
SEQUENCE: 195
ctgtatcatc gtgatgctt                                                        19

SEQ ID NO: 196          moltype = RNA   length = 21
FEATURE                 Location/Qualifiers
source                  1..21
                        mol_type = other RNA
```

-continued

```
                        organism = synthetic construct
SEQUENCE: 196
ctgtatcatc gtgatgcttc t                                              21

SEQ ID NO: 197          moltype = RNA   length = 19
FEATURE                 Location/Qualifiers
source                  1..19
                        mol_type = other RNA
                        organism = synthetic construct
SEQUENCE: 197
tgtatcatcg tgatgcttc                                                 19

SEQ ID NO: 198          moltype = RNA   length = 19
FEATURE                 Location/Qualifiers
source                  1..19
                        mol_type = other RNA
                        organism = synthetic construct
SEQUENCE: 198
gtatcatcgt gatgcttct                                                 19

SEQ ID NO: 199          moltype = RNA   length = 21
FEATURE                 Location/Qualifiers
source                  1..21
                        mol_type = other RNA
                        organism = synthetic construct
SEQUENCE: 199
gtatcatcgt gatgcttctc t                                              21

SEQ ID NO: 200          moltype = RNA   length = 21
FEATURE                 Location/Qualifiers
source                  1..21
                        mol_type = other RNA
                        organism = synthetic construct
SEQUENCE: 200
tatcatcgtg atgcttctct g                                              21

SEQ ID NO: 201          moltype = RNA   length = 19
FEATURE                 Location/Qualifiers
source                  1..19
                        mol_type = other RNA
                        organism = synthetic construct
SEQUENCE: 201
atcatcgtga tgcttctct                                                 19

SEQ ID NO: 202          moltype = RNA   length = 21
FEATURE                 Location/Qualifiers
source                  1..21
                        mol_type = other RNA
                        organism = synthetic construct
SEQUENCE: 202
atcatcgtga tgcttctctg a                                              21

SEQ ID NO: 203          moltype = RNA   length = 19
FEATURE                 Location/Qualifiers
source                  1..19
                        mol_type = other RNA
                        organism = synthetic construct
SEQUENCE: 203
tcatcgtgat gcttctctg                                                 19

SEQ ID NO: 204          moltype = RNA   length = 19
FEATURE                 Location/Qualifiers
source                  1..19
                        mol_type = other RNA
                        organism = synthetic construct
SEQUENCE: 204
tctctgaagt tctgctaca                                                 19

SEQ ID NO: 205          moltype = RNA   length = 19
FEATURE                 Location/Qualifiers
source                  1..19
                        mol_type = other RNA
                        organism = synthetic construct
SEQUENCE: 205
ctgctacaac ctctagatc                                                 19

SEQ ID NO: 206          moltype = RNA   length = 19
FEATURE                 Location/Qualifiers
source                  1..19
```

```
                            mol_type = other RNA
                            organism = synthetic construct
SEQUENCE: 206
gctacaacct ctagatctg                                                   19

SEQ ID NO: 207              moltype = RNA   length = 19
FEATURE                     Location/Qualifiers
source                      1..19
                            mol_type = other RNA
                            organism = synthetic construct
SEQUENCE: 207
tgccacatca gcttaaaat                                                   19

SEQ ID NO: 208              moltype = RNA   length = 19
FEATURE                     Location/Qualifiers
source                      1..19
                            mol_type = other RNA
                            organism = synthetic construct
SEQUENCE: 208
cacatcagct taaaatctg                                                   19

SEQ ID NO: 209              moltype = RNA   length = 19
FEATURE                     Location/Qualifiers
source                      1..19
                            mol_type = other RNA
                            organism = synthetic construct
SEQUENCE: 209
tctgtcatcc catgcagac                                                   19

SEQ ID NO: 210              moltype = RNA   length = 19
FEATURE                     Location/Qualifiers
source                      1..19
                            mol_type = other RNA
                            organism = synthetic construct
SEQUENCE: 210
ttcctgagta gaaagagttt                                                  19

SEQ ID NO: 211              moltype = RNA   length = 19
FEATURE                     Location/Qualifiers
source                      1..19
                            mol_type = other RNA
                            organism = synthetic construct
SEQUENCE: 211
tcctgagtag aagagtttc                                                   19

SEQ ID NO: 212              moltype = RNA   length = 19
FEATURE                     Location/Qualifiers
source                      1..19
                            mol_type = other RNA
                            organism = synthetic construct
SEQUENCE: 212
ctgagtagaa gagtttctt                                                   19

SEQ ID NO: 213              moltype = RNA   length = 19
FEATURE                     Location/Qualifiers
source                      1..19
                            mol_type = other RNA
                            organism = synthetic construct
SEQUENCE: 213
aggtcaagat taagactaa                                                   19

SEQ ID NO: 214              moltype = RNA   length = 19
FEATURE                     Location/Qualifiers
source                      1..19
                            mol_type = other RNA
                            organism = synthetic construct
SEQUENCE: 214
ggtcaagatt aagactaaa                                                   19

SEQ ID NO: 215              moltype = RNA   length = 19
FEATURE                     Location/Qualifiers
source                      1..19
                            mol_type = other RNA
                            organism = synthetic construct
SEQUENCE: 215
agactaaaac ttattgtta                                                   19

SEQ ID NO: 216              moltype = RNA   length = 19
FEATURE                     Location/Qualifiers
```

```
source                  1..19
                        mol_type = other RNA
                        organism = synthetic construct
SEQUENCE: 216
ggatcttgta aacatgaaa                                                    19

SEQ ID NO: 217          moltype = RNA   length = 19
FEATURE                 Location/Qualifiers
source                  1..19
                        mol_type = other RNA
                        organism = synthetic construct
SEQUENCE: 217
tcctcaacat ggctcacaa                                                    19

SEQ ID NO: 218          moltype = RNA   length = 19
FEATURE                 Location/Qualifiers
source                  1..19
                        mol_type = other RNA
                        organism = synthetic construct
SEQUENCE: 218
caacatggct cacaaattt                                                    19

SEQ ID NO: 219          moltype = RNA   length = 19
FEATURE                 Location/Qualifiers
source                  1..19
                        mol_type = other RNA
                        organism = synthetic construct
SEQUENCE: 219
ctgcactgcc aacaagttc                                                    19

SEQ ID NO: 220          moltype = RNA   length = 19
FEATURE                 Location/Qualifiers
source                  1..19
                        mol_type = other RNA
                        organism = synthetic construct
SEQUENCE: 220
ccaacaagtt cacttcata                                                    19

SEQ ID NO: 221          moltype = RNA   length = 19
FEATURE                 Location/Qualifiers
source                  1..19
                        mol_type = other RNA
                        organism = synthetic construct
SEQUENCE: 221
aacaagttca cttcatata                                                    19

SEQ ID NO: 222          moltype = RNA   length = 19
FEATURE                 Location/Qualifiers
source                  1..19
                        mol_type = other RNA
                        organism = synthetic construct
SEQUENCE: 222
agttcacttc atatataaa                                                    19

SEQ ID NO: 223          moltype = RNA   length = 19
FEATURE                 Location/Qualifiers
source                  1..19
                        mol_type = other RNA
                        organism = synthetic construct
SEQUENCE: 223
tttactcttt tgaggtgaa                                                    19

SEQ ID NO: 224          moltype = RNA   length = 19
FEATURE                 Location/Qualifiers
source                  1..19
                        mol_type = other RNA
                        organism = synthetic construct
SEQUENCE: 224
tactcttttg aggtgaata                                                    19

SEQ ID NO: 225          moltype = RNA   length = 19
FEATURE                 Location/Qualifiers
source                  1..19
                        mol_type = other RNA
                        organism = synthetic construct
SEQUENCE: 225
gtcttcacca agtatcaaa                                                    19

SEQ ID NO: 226          moltype = RNA   length = 19
```

-continued

| FEATURE | Location/Qualifiers |
|---|---|
| source | 1..19<br>mol_type = other RNA<br>organism = synthetic construct |

SEQUENCE: 226
tcttcaccaa gtatcaaag                                                    19

SEQ ID NO: 227     moltype = RNA   length = 19
FEATURE            Location/Qualifiers
source             1..19
                   mol_type = other RNA
                   organism = synthetic construct SEQUENCE: 227
caccaagtat caaagtaat                                                    19

SEQ ID NO: 228     moltype = RNA   length = 19
FEATURE            Location/Qualifiers
source             1..19
                   mol_type = other RNA
                   organism = synthetic construct SEQUENCE: 228
gtatcaaagt aataacaca                                                    19

SEQ ID NO: 229     moltype = RNA   length = 19
FEATURE            Location/Qualifiers
source             1..19
                   mol_type = other RNA
                   organism = synthetic construct SEQUENCE: 229
agttgatgag aatcaagta                                                    19

SEQ ID NO: 230     moltype = RNA   length = 19
FEATURE            Location/Qualifiers
source             1..19
                   mol_type = other RNA
                   organism = synthetic construct SEQUENCE: 230
aagtatggaa aagtaaggc                                                    19

SEQ ID NO: 231     moltype = RNA   length = 19
FEATURE            Location/Qualifiers
source             1..19
                   mol_type = other RNA
                   organism = synthetic construct SEQUENCE: 231
tggaaaagta aggccatac                                                    19

SEQ ID NO: 232     moltype = RNA   length = 19
FEATURE            Location/Qualifiers
source             1..19
                   mol_type = other RNA
                   organism = synthetic construct SEQUENCE: 232
aagtaaggcc atactctta                                                    19

SEQ ID NO: 233     moltype = RNA   length = 19
FEATURE            Location/Qualifiers
source             1..19
                   mol_type = other RNA
                   organism = synthetic construct SEQUENCE: 233
agtaaggcca tactcttac                                                    19

SEQ ID NO: 234     moltype = RNA   length = 19
FEATURE            Location/Qualifiers
source             1..19
                   mol_type = other RNA
                   organism = synthetic construct SEQUENCE: 234
gtaaggccat actcttaca                                                    19

SEQ ID NO: 235     moltype = RNA   length = 19
FEATURE            Location/Qualifiers
source             1..19
                   mol_type = other RNA
                   organism = synthetic construct SEQUENCE: 235
taaggccata ctcttacat                                                    19

```
SEQ ID NO: 236         moltype = RNA   length = 19
FEATURE                Location/Qualifiers
source                 1..19
                       mol_type = other RNA
                       organism = synthetic construct
SEQUENCE: 236
aggccatact cttacataa                                                       19

SEQ ID NO: 237         moltype = RNA   length = 19
FEATURE                Location/Qualifiers
source                 1..19
                       mol_type = other RNA
                       organism = synthetic construct
SEQUENCE: 237
ggccatactc ttacataat                                                       19

SEQ ID NO: 238         moltype = RNA   length = 19
FEATURE                Location/Qualifiers
source                 1..19
                       mol_type = other RNA
                       organism = synthetic construct
SEQUENCE: 238
gccatactct tacataata                                                       19

SEQ ID NO: 239         moltype = RNA   length = 19
FEATURE                Location/Qualifiers
source                 1..19
                       mol_type = other RNA
                       organism = synthetic construct
SEQUENCE: 239
catactctta cataataaa                                                       19

SEQ ID NO: 240         moltype = RNA   length = 19
FEATURE                Location/Qualifiers
source                 1..19
                       mol_type = other RNA
                       organism = synthetic construct
SEQUENCE: 240
tgttctaaga catatgatc                                                       19

SEQ ID NO: 241         moltype = RNA   length = 19
FEATURE                Location/Qualifiers
source                 1..19
                       mol_type = other RNA
                       organism = synthetic construct
SEQUENCE: 241
ttctaagaca tatgatcaa                                                       19

SEQ ID NO: 242         moltype = RNA   length = 19
FEATURE                Location/Qualifiers
source                 1..19
                       mol_type = other RNA
                       organism = synthetic construct
SEQUENCE: 242
agacatatga tcaacagat                                                       19

SEQ ID NO: 243         moltype = RNA   length = 19
FEATURE                Location/Qualifiers
source                 1..19
                       mol_type = other RNA
                       organism = synthetic construct
SEQUENCE: 243
gacatatgat caacagatg                                                       19

SEQ ID NO: 244         moltype = RNA   length = 19
FEATURE                Location/Qualifiers
source                 1..19
                       mol_type = other RNA
                       organism = synthetic construct
SEQUENCE: 244
acatatgatc aacagatga                                                       19

SEQ ID NO: 245         moltype = RNA   length = 19
FEATURE                Location/Qualifiers
source                 1..19
                       mol_type = other RNA
                       organism = synthetic construct
SEQUENCE: 245
atatgatcaa cagatgaga                                                       19
```

| | | |
|---|---|---|
| SEQ ID NO: 246<br>FEATURE<br>source | moltype = RNA length = 19<br>Location/Qualifiers<br>1..19<br>mol_type = other RNA<br>organism = synthetic construct | |
| SEQUENCE: 246<br>cagtgagatt agtcatatc | | 19 |
| SEQ ID NO: 247<br>FEATURE<br>source | moltype = RNA length = 19<br>Location/Qualifiers<br>1..19<br>mol_type = other RNA<br>organism = synthetic construct | |
| SEQUENCE: 247<br>agtgagatta gtcatatca | | 19 |
| SEQ ID NO: 248<br>FEATURE<br>source | moltype = RNA length = 19<br>Location/Qualifiers<br>1..19<br>mol_type = other RNA<br>organism = synthetic construct | |
| SEQUENCE: 248<br>gtgagattag tcatatcac | | 19 |
| SEQ ID NO: 249<br>FEATURE<br>source | moltype = RNA length = 19<br>Location/Qualifiers<br>1..19<br>mol_type = other RNA<br>organism = synthetic construct | |
| SEQUENCE: 249<br>attagtcata tcactaata | | 19 |
| SEQ ID NO: 250<br>FEATURE<br>source | moltype = RNA length = 19<br>Location/Qualifiers<br>1..19<br>mol_type = other RNA<br>organism = synthetic construct | |
| SEQUENCE: 250<br>agtcatatca ctaatatac | | 19 |
| SEQ ID NO: 251<br>FEATURE<br>source | moltype = RNA length = 19<br>Location/Qualifiers<br>1..19<br>mol_type = other RNA<br>organism = synthetic construct | |
| SEQUENCE: 251<br>gtcatatcac taatatact | | 19 |
| SEQ ID NO: 252<br>FEATURE<br>source | moltype = RNA length = 19<br>Location/Qualifiers<br>1..19<br>mol_type = other RNA<br>organism = synthetic construct | |
| SEQUENCE: 252<br>catatcacta atatactaa | | 19 |
| SEQ ID NO: 253<br>FEATURE<br>source | moltype = RNA length = 19<br>Location/Qualifiers<br>1..19<br>mol_type = other RNA<br>organism = synthetic construct | |
| SEQUENCE: 253<br>tatcactaat atactaaca | | 19 |
| SEQ ID NO: 254<br>FEATURE<br>source | moltype = RNA length = 19<br>Location/Qualifiers<br>1..19<br>mol_type = other RNA<br>organism = synthetic construct | |
| SEQUENCE: 254<br>atcatgaaac cttaagact | | 19 |
| SEQ ID NO: 255<br>FEATURE<br>source | moltype = RNA length = 19<br>Location/Qualifiers<br>1..19<br>mol_type = other RNA<br>organism = synthetic construct | |
| SEQUENCE: 255 | | |

```
tcatgaaacc ttaagactt                                                     19

SEQ ID NO: 256          moltype = RNA   length = 19
FEATURE                 Location/Qualifiers
source                  1..19
                        mol_type = other RNA
                        organism = synthetic construct SEQUENCE: 256
cctaacatcc aatgcaggc                                                     19

SEQ ID NO: 257          moltype = RNA   length = 19
FEATURE                 Location/Qualifiers
source                  1..19
                        mol_type = other RNA
                        organism = synthetic construct SEQUENCE: 257
gaacttgttg gcccatcta                                                     19

SEQ ID NO: 258          moltype = RNA   length = 19
FEATURE                 Location/Qualifiers
source                  1..19
                        mol_type = other RNA
                        organism = synthetic construct SEQUENCE: 258
aacttgttgg cccatctat                                                     19

SEQ ID NO: 259          moltype = RNA   length = 19
FEATURE                 Location/Qualifiers
source                  1..19
                        mol_type = other RNA
                        organism = synthetic construct SEQUENCE: 259
acttgttggc ccatctatt                                                     19

SEQ ID NO: 260          moltype = RNA   length = 19
FEATURE                 Location/Qualifiers
source                  1..19
                        mol_type = other RNA
                        organism = synthetic construct SEQUENCE: 260
cttgttggcc catctatta                                                     19

SEQ ID NO: 261          moltype = RNA   length = 19
FEATURE                 Location/Qualifiers
source                  1..19
                        mol_type = other RNA
                        organism = synthetic construct SEQUENCE: 261
ttgttggccc atctattac                                                     19

SEQ ID NO: 262          moltype = RNA   length = 19
FEATURE                 Location/Qualifiers
source                  1..19
                        mol_type = other RNA
                        organism = synthetic construct SEQUENCE: 262
tgttggccca tctattaca                                                     19

SEQ ID NO: 263          moltype = RNA   length = 19
FEATURE                 Location/Qualifiers
source                  1..19
                        mol_type = other RNA
                        organism = synthetic construct SEQUENCE: 263
gttggcccat ctattacat                                                     19

SEQ ID NO: 264          moltype = RNA   length = 19
FEATURE                 Location/Qualifiers
source                  1..19
                        mol_type = other RNA
                        organism = synthetic construct SEQUENCE: 264
ttggcccatc tattacatc                                                     19

SEQ ID NO: 265          moltype = DNA   length = 20
FEATURE                 Location/Qualifiers
source                  1..20
                        mol_type = other DNA
                        organism = synthetic construct
```

```
misc_feature           1..5
                       note = RNA
misc_feature           6..15
                       note = DNA
misc_feature           16..20
                       note = RNA
SEQUENCE: 265
cagaaattga taaatagatt                                                       20

SEQ ID NO: 266         moltype = DNA  length = 20
FEATURE                Location/Qualifiers
source                 1..20
                       mol_type = other DNA
                       organism = synthetic construct
misc_feature           1..5
                       note = RNA
misc_feature           6..15
                       note = DNA
misc_feature           16..20
                       note = RNA
SEQUENCE: 266
atgatacaga tcagcaagag                                                       20

SEQ ID NO: 267         moltype = DNA  length = 20
FEATURE                Location/Qualifiers
source                 1..20
                       mol_type = other DNA
                       organism = synthetic construct
misc_feature           1..5
                       note = RNA
misc_feature           6..15
                       note = DNA
misc_feature           16..20
                       note = RNA
SEQUENCE: 267
atcacgatga tacagatcag                                                       20

SEQ ID NO: 268         moltype = DNA  length = 20
FEATURE                Location/Qualifiers
source                 1..20
                       mol_type = other DNA
                       organism = synthetic construct
misc_feature           1..5
                       note = RNA
misc_feature           6..15
                       note = DNA
misc_feature           16..20
                       note = RNA
SEQUENCE: 268
cagatctaga ggttgtagca                                                       20

SEQ ID NO: 269         moltype = DNA  length = 20
FEATURE                Location/Qualifiers
source                 1..20
                       mol_type = other DNA
                       organism = synthetic construct
misc_feature           1..5
                       note = RNA
misc_feature           6..15
                       note = DNA
misc_feature           16..20
                       note = RNA
SEQUENCE: 269
gcagatctag aggttgtagc                                                       20

SEQ ID NO: 270         moltype = DNA  length = 20
FEATURE                Location/Qualifiers
source                 1..20
                       mol_type = other DNA
                       organism = synthetic construct
misc_feature           1..5
                       note = RNA
misc_feature           6..15
                       note = DNA
misc_feature           16..20
                       note = RNA
SEQUENCE: 270
tttgatactt ggtgaagacc                                                       20
```

```
SEQ ID NO: 271            moltype = DNA  length = 20
FEATURE                   Location/Qualifiers
source                    1..20
                          mol_type = other DNA
                          organism = synthetic construct
modified_base             1..5
                          mod_base = OTHER
                          note = 2'-O-methyl ribonucleotide
modified_base             16..20
                          mod_base = OTHER
                          note = 2'-O-methyl ribonucleotide
modified_base             1..20
                          mod_base = OTHER
                          note = phosphorothioate linkage
misc_feature              1..5
                          note = RNA
misc_feature              6..15
                          note = DNA
misc_feature              16..20
                          note = RNA
SEQUENCE: 271
cagaaattga taaatagatt                                                  20

SEQ ID NO: 272            moltype = DNA  length = 20
FEATURE                   Location/Qualifiers
source                    1..20
                          mol_type = other DNA
                          organism = synthetic construct
modified_base             1..5
                          mod_base = OTHER
                          note = 2'-O-methyl ribonucleotide
modified_base             16..20
                          mod_base = OTHER
                          note = 2'-O-methyl ribonucleotide
modified_base             1..20
                          mod_base = OTHER
                          note = phosphorothioate linkage
misc_feature              1..5
                          note = RNA
misc_feature              6..15
                          note = DNA
misc_feature              16..20
                          note = RNA
SEQUENCE: 272
atgatacaga tcagcaagag                                                  20

SEQ ID NO: 273            moltype = DNA  length = 20
FEATURE                   Location/Qualifiers
source                    1..20
                          mol_type = other DNA
                          organism = synthetic construct
modified_base             1..5
                          mod_base = OTHER
                          note = 2'-O-methyl ribonucleotide
modified_base             16..20
                          mod_base = OTHER
                          note = 2'-O-methyl ribonucleotide
modified_base             1..20
                          mod_base = OTHER
                          note = phosphorothioate linkage
misc_feature              1..5
                          note = RNA
misc_feature              6..15
                          note = DNA
misc_feature              16..20
                          note = RNA
SEQUENCE: 273
atcacgatga tacagatcag                                                  20

SEQ ID NO: 274            moltype = DNA  length = 20
FEATURE                   Location/Qualifiers
source                    1..20
                          mol_type = other DNA
                          organism = synthetic construct
modified_base             1..5
                          mod_base = OTHER
                          note = 2'-O-methyl ribonucleotide
modified_base             16..20
                          mod_base = OTHER
```

```
                        note = 2'-O-methyl ribonucleotide
modified_base           1..20
                        mod_base = OTHER
                        note = phosphorothioate linkage
misc_feature            1..5
                        note = RNA
misc_feature            6..15
                        note = DNA
misc_feature            16..20
                        note = RNA
SEQUENCE: 274
cagatctaga ggttgtagca                                                      20

SEQ ID NO: 275          moltype = DNA  length = 20
FEATURE                 Location/Qualifiers
source                  1..20
                        mol_type = other DNA
                        organism = synthetic construct
modified_base           1..5
                        mod_base = OTHER
                        note = 2'-O-methyl ribonucleotide
modified_base           16..20
                        mod_base = OTHER
                        note = 2'-O-methyl ribonucleotide
modified_base           1..20
                        mod_base = OTHER
                        note = phosphorothioate linkage
misc_feature            1..5
                        note = RNA
misc_feature            6..15
                        note = DNA
misc_feature            16..20
                        note = RNA
SEQUENCE: 275
gcagatctag aggttgtagc                                                      20

SEQ ID NO: 276          moltype = DNA  length = 20
FEATURE                 Location/Qualifiers
source                  1..20
                        mol_type = other DNA
                        organism = synthetic construct
modified_base           1..5
                        mod_base = OTHER
                        note = 2'-O-methyl ribonucleotide
modified_base           16..20
                        mod_base = OTHER
                        note = 2'-O-methyl ribonucleotide
modified_base           1..20
                        mod_base = OTHER
                        note = phosphorothioate linkage
misc_feature            1..5
                        note = RNA
misc_feature            6..15
                        note = DNA
misc_feature            16..20
                        note = RNA
SEQUENCE: 276
tttgatactt ggtgaagacc                                                      20

SEQ ID NO: 277          moltype = DNA  length = 52
FEATURE                 Location/Qualifiers
source                  1..52
                        mol_type = other DNA
                        organism = synthetic construct
SEQUENCE: 277
gtcgtatcca gtgcagggtc cgaggtattc gcactggata cgacaagaat ct                  52

SEQ ID NO: 278          moltype = DNA  length = 51
FEATURE                 Location/Qualifiers
source                  1..51
                        mol_type = other DNA
                        organism = synthetic construct
SEQUENCE: 278
gtcgtatcca gtgcagggtc cgaggtattc gcactggata cgacaatatt t                   51

SEQ ID NO: 279          moltype = DNA  length = 52
FEATURE                 Location/Qualifiers
source                  1..52
                        mol_type = other DNA
```

```
                        organism = synthetic construct
SEQUENCE: 279
gtcgtatcca gtgcagggtc cgaggtattc gcactggata cgacaattta tc          52

SEQ ID NO: 280          moltype = DNA  length = 52
FEATURE                 Location/Qualifiers
source                  1..52
                        mol_type = other DNA
                        organism = synthetic construct
SEQUENCE: 280
gtcgtatcca gtgcagggtc cgaggtattc gcactggata cgacaactct tg          52

SEQ ID NO: 281          moltype = DNA  length = 50
FEATURE                 Location/Qualifiers
source                  1..50
                        mol_type = other DNA
                        organism = synthetic construct
SEQUENCE: 281
gtcgtatcca gtgcagggtc cgaggtattc gcactggata cgacaagcta             50

SEQ ID NO: 282          moltype = DNA  length = 51
FEATURE                 Location/Qualifiers
source                  1..51
                        mol_type = other DNA
                        organism = synthetic construct
SEQUENCE: 282
gtcgtatcca gtgcagggtc cgaggtattc gcactggata cgacaagtat c           51

SEQ ID NO: 283          moltype = DNA  length = 24
FEATURE                 Location/Qualifiers
source                  1..24
                        mol_type = other DNA
                        organism = synthetic construct
SEQUENCE: 283
gcccgggtag aaattgataa atag                                         24

SEQ ID NO: 284          moltype = DNA  length = 22
FEATURE                 Location/Qualifiers
source                  1..22
                        mol_type = other DNA
                        organism = synthetic construct
SEQUENCE: 284
gcgcgcctga gacagaaatt ga                                           22

SEQ ID NO: 285          moltype = DNA  length = 22
FEATURE                 Location/Qualifiers
source                  1..22
                        mol_type = other DNA
                        organism = synthetic construct
SEQUENCE: 285
ccgggcgtat gagacagaaa tt                                           22

SEQ ID NO: 286          moltype = DNA  length = 21
FEATURE                 Location/Qualifiers
source                  1..21
                        mol_type = other DNA
                        organism = synthetic construct
SEQUENCE: 286
gcgggcgtat gatacagatc a                                            21

SEQ ID NO: 287          moltype = DNA  length = 20
FEATURE                 Location/Qualifiers
source                  1..20
                        mol_type = other DNA
                        organism = synthetic construct
SEQUENCE: 287
gcgccggtag atctagaggt                                              20

SEQ ID NO: 288          moltype = DNA  length = 25
FEATURE                 Location/Qualifiers
source                  1..25
                        mol_type = other DNA
                        organism = synthetic construct
SEQUENCE: 288
gccgcgctgt gttattactt tgata                                        25

SEQ ID NO: 289          moltype = DNA  length = 20
FEATURE                 Location/Qualifiers
source                  1..20
```

```
                        mol_type = other DNA
                        organism = synthetic construct
SEQUENCE: 289
gcactggata cgacaagaat                                                    20

SEQ ID NO: 290          moltype = DNA   length = 24
FEATURE                 Location/Qualifiers
source                  1..24
                        mol_type = other DNA
                        organism = synthetic construct
SEQUENCE: 290
gcactggata cgacaatatt tatc                                               24

SEQ ID NO: 291          moltype = DNA   length = 22
FEATURE                 Location/Qualifiers
source                  1..22
                        mol_type = other DNA
                        organism = synthetic construct
SEQUENCE: 291
gcactggata cgacaattta tc                                                 22

SEQ ID NO: 292          moltype = DNA   length = 19
FEATURE                 Location/Qualifiers
source                  1..19
                        mol_type = other DNA
                        organism = synthetic construct
SEQUENCE: 292
actggatacg acaactctt                                                     19

SEQ ID NO: 293          moltype = DNA   length = 18
FEATURE                 Location/Qualifiers
source                  1..18
                        mol_type = other DNA
                        organism = synthetic construct
SEQUENCE: 293
tggatacgac aagctaca                                                      18

SEQ ID NO: 294          moltype = DNA   length = 19
FEATURE                 Location/Qualifiers
source                  1..19
                        mol_type = other DNA
                        organism = synthetic construct
SEQUENCE: 294
gcactggata cgacaagta                                                     19

SEQ ID NO: 295          moltype =     length =
SEQUENCE: 295
000

SEQ ID NO: 296          moltype =     length =
SEQUENCE: 296
000

SEQ ID NO: 297          moltype = RNA   length = 23
FEATURE                 Location/Qualifiers
source                  1..23
                        mol_type = other RNA
                        organism = synthetic construct
SEQUENCE: 297
tagaaattga taaataggtt ctt                                                23

SEQ ID NO: 298          moltype = RNA   length = 21
FEATURE                 Location/Qualifiers
source                  1..21
                        mol_type = other RNA
                        organism = synthetic construct
SEQUENCE: 298
gaacctattt atcaatttct a                                                  21

SEQ ID NO: 299          moltype =     length =
SEQUENCE: 299
000

SEQ ID NO: 300          moltype = RNA   length = 19
FEATURE                 Location/Qualifiers
source                  1..19
                        mol_type = other RNA
                        organism = synthetic construct
SEQUENCE: 300
```

```
ctcttatagc tgagcgagt                                              19

SEQ ID NO: 301        moltype = RNA   length = 19
FEATURE               Location/Qualifiers
source                1..19
                      mol_type = other RNA
                      organism = synthetic construct SEQUENCE: 301
gctcttatag ctgagcgag                                              19

SEQ ID NO: 302        moltype = RNA   length = 19
FEATURE               Location/Qualifiers
source                1..19
                      mol_type = other RNA
                      organism = synthetic construct SEQUENCE: 302
ggctcttata gctgagcga                                              19

SEQ ID NO: 303        moltype = RNA   length = 19
FEATURE               Location/Qualifiers
source                1..19
                      mol_type = other RNA
                      organism = synthetic construct SEQUENCE: 303
aggctcttat agctgagcg                                              19

SEQ ID NO: 304        moltype = RNA   length = 19
FEATURE               Location/Qualifiers
source                1..19
                      mol_type = other RNA
                      organism = synthetic construct SEQUENCE: 304
gaggctctta tagctgagc                                              19

SEQ ID NO: 305        moltype = RNA   length = 19
FEATURE               Location/Qualifiers
source                1..19
                      mol_type = other RNA
                      organism = synthetic construct SEQUENCE: 305
tgaggctctt atagctgag                                              19

SEQ ID NO: 306        moltype = RNA   length = 19
FEATURE               Location/Qualifiers
source                1..19
                      mol_type = other RNA
                      organism = synthetic construct SEQUENCE: 306
ttgaggctct tatagctga                                              19

SEQ ID NO: 307        moltype = RNA   length = 19
FEATURE               Location/Qualifiers
source                1..19
                      mol_type = other RNA
                      organism = synthetic construct SEQUENCE: 307
gttgaggctc ttatagctg                                              19

SEQ ID NO: 308        moltype = RNA   length = 19
FEATURE               Location/Qualifiers
source                1..19
                      mol_type = other RNA
                      organism = synthetic construct SEQUENCE: 308
ggttgaggct cttatagct                                              19

SEQ ID NO: 309        moltype = RNA   length = 19
FEATURE               Location/Qualifiers
source                1..19
                      mol_type = other RNA
                      organism = synthetic construct SEQUENCE: 309
tggttgaggc tcttatagc                                              19

SEQ ID NO: 310        moltype = RNA   length = 19
FEATURE               Location/Qualifiers
source                1..19
                      mol_type = other RNA
                      organism = synthetic construct
```

```
SEQUENCE: 310
atggttgagg ctcttatag                                                                    19

SEQ ID NO: 311         moltype = RNA  length = 19
FEATURE                Location/Qualifiers
source                 1..19
                       mol_type = other RNA
                       organism = synthetic construct
SEQUENCE: 311
aatggttgag gctcttata                                                                    19

SEQ ID NO: 312         moltype = RNA  length = 19
FEATURE                Location/Qualifiers
source                 1..19
                       mol_type = other RNA
                       organism = synthetic construct
SEQUENCE: 312
caatggttga ggctcttat                                                                    19

SEQ ID NO: 313         moltype = RNA  length = 19
FEATURE                Location/Qualifiers
source                 1..19
                       mol_type = other RNA
                       organism = synthetic construct
SEQUENCE: 313
tcaatggttg aggctctta                                                                    19

SEQ ID NO: 314         moltype = RNA  length = 19
FEATURE                Location/Qualifiers
source                 1..19
                       mol_type = other RNA
                       organism = synthetic construct
SEQUENCE: 314
actcgctcag ctataagag                                                                    19

SEQ ID NO: 315         moltype = RNA  length = 19
FEATURE                Location/Qualifiers
source                 1..19
                       mol_type = other RNA
                       organism = synthetic construct
SEQUENCE: 315
ctcgctcagc tataagagc                                                                    19

SEQ ID NO: 316         moltype = RNA  length = 19
FEATURE                Location/Qualifiers
source                 1..19
                       mol_type = other RNA
                       organism = synthetic construct
SEQUENCE: 316
tcgctcagct ataagagcc                                                                    19

SEQ ID NO: 317         moltype = RNA  length = 19
FEATURE                Location/Qualifiers
source                 1..19
                       mol_type = other RNA
                       organism = synthetic construct
SEQUENCE: 317
cgctcagcta taagagcct                                                                    19

SEQ ID NO: 318         moltype = RNA  length = 19
FEATURE                Location/Qualifiers
source                 1..19
                       mol_type = other RNA
                       organism = synthetic construct
SEQUENCE: 318
gctcagctat aagagcctc                                                                    19

SEQ ID NO: 319         moltype = RNA  length = 19
FEATURE                Location/Qualifiers
source                 1..19
                       mol_type = other RNA
                       organism = synthetic construct
SEQUENCE: 319
ctcagctata agagcctca                                                                    19

SEQ ID NO: 320         moltype = RNA  length = 19
FEATURE                Location/Qualifiers
source                 1..19
                       mol_type = other RNA
```

```
                         organism = synthetic construct
SEQUENCE: 320
tcagctataa gagcctcaa                                                    19

SEQ ID NO: 321          moltype = RNA  length = 19
FEATURE                 Location/Qualifiers
source                  1..19
                        mol_type = other RNA
                        organism = synthetic construct
SEQUENCE: 321
cagctataag agcctcaac                                                    19

SEQ ID NO: 322          moltype = RNA  length = 19
FEATURE                 Location/Qualifiers
source                  1..19
                        mol_type = other RNA
                        organism = synthetic construct
SEQUENCE: 322
agctataaga gcctcaacc                                                    19

SEQ ID NO: 323          moltype = RNA  length = 19
FEATURE                 Location/Qualifiers
source                  1..19
                        mol_type = other RNA
                        organism = synthetic construct
SEQUENCE: 323
gctataagag cctcaacca                                                    19

SEQ ID NO: 324          moltype = RNA  length = 19
FEATURE                 Location/Qualifiers
source                  1..19
                        mol_type = other RNA
                        organism = synthetic construct
SEQUENCE: 324
ctataagagc ctcaaccat                                                    19

SEQ ID NO: 325          moltype = RNA  length = 19
FEATURE                 Location/Qualifiers
source                  1..19
                        mol_type = other RNA
                        organism = synthetic construct
SEQUENCE: 325
tataagagcc tcaaccatt                                                    19

SEQ ID NO: 326          moltype = RNA  length = 19
FEATURE                 Location/Qualifiers
source                  1..19
                        mol_type = other RNA
                        organism = synthetic construct
SEQUENCE: 326
ataagagcct caaccattg                                                    19

SEQ ID NO: 327          moltype = RNA  length = 19
FEATURE                 Location/Qualifiers
source                  1..19
                        mol_type = other RNA
                        organism = synthetic construct
SEQUENCE: 327
taagagcctc aaccattga                                                    19

SEQ ID NO: 328          moltype = RNA  length = 21
FEATURE                 Location/Qualifiers
source                  1..21
                        mol_type = other RNA
                        organism = synthetic construct
SEQUENCE: 328
ctcttatagc tgagcgagtg a                                                 21

SEQ ID NO: 329          moltype = RNA  length = 21
FEATURE                 Location/Qualifiers
source                  1..21
                        mol_type = other RNA
                        organism = synthetic construct
SEQUENCE: 329
gctcttatag ctgagcgagt g                                                 21

SEQ ID NO: 330          moltype = RNA  length = 21
FEATURE                 Location/Qualifiers
source                  1..21
```

```
                              mol_type = other RNA
                              organism = synthetic construct
SEQUENCE: 330
ggctcttata gctgagcgag t                                              21

SEQ ID NO: 331                moltype = RNA  length = 21
FEATURE                       Location/Qualifiers
source                        1..21
                              mol_type = other RNA
                              organism = synthetic construct
SEQUENCE: 331
aggctcttat agctgagcga g                                              21

SEQ ID NO: 332                moltype = RNA  length = 21
FEATURE                       Location/Qualifiers
source                        1..21
                              mol_type = other RNA
                              organism = synthetic construct
SEQUENCE: 332
gaggctctta tagctgagcg a                                              21

SEQ ID NO: 333                moltype = RNA  length = 21
FEATURE                       Location/Qualifiers
source                        1..21
                              mol_type = other RNA
                              organism = synthetic construct
SEQUENCE: 333
tgaggctctt atagctgagc g                                              21

SEQ ID NO: 334                moltype = RNA  length = 21
FEATURE                       Location/Qualifiers
source                        1..21
                              mol_type = other RNA
                              organism = synthetic construct
SEQUENCE: 334
ttgaggctct tatagctgag c                                              21

SEQ ID NO: 335                moltype = RNA  length = 21
FEATURE                       Location/Qualifiers
source                        1..21
                              mol_type = other RNA
                              organism = synthetic construct
SEQUENCE: 335
gttgaggctc ttatagctga g                                              21

SEQ ID NO: 336                moltype = RNA  length = 21
FEATURE                       Location/Qualifiers
source                        1..21
                              mol_type = other RNA
                              organism = synthetic construct
SEQUENCE: 336
ggttgaggct cttatagctg a                                              21

SEQ ID NO: 337                moltype = RNA  length = 21
FEATURE                       Location/Qualifiers
source                        1..21
                              mol_type = other RNA
                              organism = synthetic construct
SEQUENCE: 337
tggttgaggc tcttatagct g                                              21

SEQ ID NO: 338                moltype = RNA  length = 21
FEATURE                       Location/Qualifiers
source                        1..21
                              mol_type = other RNA
                              organism = synthetic construct
SEQUENCE: 338
atggttgagg ctcttatagc t                                              21

SEQ ID NO: 339                moltype = RNA  length = 21
FEATURE                       Location/Qualifiers
source                        1..21
                              mol_type = other RNA
                              organism = synthetic construct
SEQUENCE: 339
aatggttgag gctcttatag c                                              21

SEQ ID NO: 340                moltype = RNA  length = 21
FEATURE                       Location/Qualifiers
```

```
source                   1..21
                         mol_type = other RNA
                         organism = synthetic construct
SEQUENCE: 340
caatggttga ggctcttata g                                              21

SEQ ID NO: 341           moltype = RNA   length = 21
FEATURE                  Location/Qualifiers
source                   1..21
                         mol_type = other RNA
                         organism = synthetic construct
SEQUENCE: 341
tcaatggttg aggctcttat a                                              21

SEQ ID NO: 342           moltype = RNA   length = 21
FEATURE                  Location/Qualifiers
source                   1..21
                         mol_type = other RNA
                         organism = synthetic construct
SEQUENCE: 342
ttcaatggtt gaggctctta t                                              21

SEQ ID NO: 343           moltype = RNA   length = 21
FEATURE                  Location/Qualifiers
source                   1..21
                         mol_type = other RNA
                         organism = synthetic construct
SEQUENCE: 343
tttcaatggt tgaggctctt a                                              21

SEQ ID NO: 344           moltype = RNA   length = 21
FEATURE                  Location/Qualifiers
source                   1..21
                         mol_type = other RNA
                         organism = synthetic construct
SEQUENCE: 344
tcactcgctc agctataaga g                                              21

SEQ ID NO: 345           moltype = RNA   length = 21
FEATURE                  Location/Qualifiers
source                   1..21
                         mol_type = other RNA
                         organism = synthetic construct
SEQUENCE: 345
cactcgctca gctataagag c                                              21

SEQ ID NO: 346           moltype = RNA   length = 21
FEATURE                  Location/Qualifiers
source                   1..21
                         mol_type = other RNA
                         organism = synthetic construct
SEQUENCE: 346
actcgctcag ctataagagc c                                              21

SEQ ID NO: 347           moltype = RNA   length = 21
FEATURE                  Location/Qualifiers
source                   1..21
                         mol_type = other RNA
                         organism = synthetic construct
SEQUENCE: 347
ctcgctcagc tataagagcc t                                              21

SEQ ID NO: 348           moltype = RNA   length = 21
FEATURE                  Location/Qualifiers
source                   1..21
                         mol_type = other RNA
                         organism = synthetic construct
SEQUENCE: 348
tcgctcagct ataagagcct c                                              21

SEQ ID NO: 349           moltype = RNA   length = 21
FEATURE                  Location/Qualifiers
source                   1..21
                         mol_type = other RNA
                         organism = synthetic construct
SEQUENCE: 349
cgctcagcta taagagcctc a                                              21

SEQ ID NO: 350           moltype = RNA   length = 21
```

```
                          -continued

FEATURE                Location/Qualifiers
source                 1..21
                       mol_type = other RNA
                       organism = synthetic construct
SEQUENCE: 350
gctcagctat aagagcctca a                                        21

SEQ ID NO: 351         moltype = RNA   length = 21
FEATURE                Location/Qualifiers
source                 1..21
                       mol_type = other RNA
                       organism = synthetic construct
SEQUENCE: 351
ctcagctata agagcctcaa c                                        21

SEQ ID NO: 352         moltype = RNA   length = 21
FEATURE                Location/Qualifiers
source                 1..21
                       mol_type = other RNA
                       organism = synthetic construct
SEQUENCE: 352
tcagctataa gagcctcaac c                                        21

SEQ ID NO: 353         moltype = RNA   length = 21
FEATURE                Location/Qualifiers
source                 1..21
                       mol_type = other RNA
                       organism = synthetic construct
SEQUENCE: 353
cagctataag agcctcaacc a                                        21

SEQ ID NO: 354         moltype = RNA   length = 21
FEATURE                Location/Qualifiers
source                 1..21
                       mol_type = other RNA
                       organism = synthetic construct
SEQUENCE: 354
agctataaga gcctcaacca t                                        21

SEQ ID NO: 355         moltype = RNA   length = 21
FEATURE                Location/Qualifiers
source                 1..21
                       mol_type = other RNA
                       organism = synthetic construct
SEQUENCE: 355
gctataagag cctcaaccat t                                        21

SEQ ID NO: 356         moltype = RNA   length = 21
FEATURE                Location/Qualifiers
source                 1..21
                       mol_type = other RNA
                       organism = synthetic construct
SEQUENCE: 356
ctataagagc ctcaaccatt g                                        21

SEQ ID NO: 357         moltype = RNA   length = 21
FEATURE                Location/Qualifiers
source                 1..21
                       mol_type = other RNA
                       organism = synthetic construct
SEQUENCE: 357
tataagagcc tcaaccattg a                                        21

SEQ ID NO: 358         moltype = RNA   length = 21
FEATURE                Location/Qualifiers
source                 1..21
                       mol_type = other RNA
                       organism = synthetic construct
SEQUENCE: 358
ataagagcct caaccattga a                                        21

SEQ ID NO: 359         moltype = RNA   length = 21
FEATURE                Location/Qualifiers
source                 1..21
                       mol_type = other RNA
                       organism = synthetic construct
SEQUENCE: 359
taagagcctc aaccattgaa a                                        21
```

```
SEQ ID NO: 360              moltype = AA   length = 9
FEATURE                     Location/Qualifiers
source                      1..9
                            mol_type = protein
                            organism = synthetic construct
SEQUENCE: 360
YTFTNYWMH                                                                    9

SEQ ID NO: 361              moltype = AA   length = 17
FEATURE                     Location/Qualifiers
source                      1..17
                            mol_type = protein
                            organism = synthetic construct
VARIANT                     6
                            note = N or Q
SEQUENCE: 361
EINPIXGRSN YAZKFQG                                                          17

SEQ ID NO: 362              moltype = AA   length = 17
FEATURE                     Location/Qualifiers
source                      1..17
                            mol_type = protein
                            organism = synthetic construct
SEQUENCE: 362
EINPINGRSN YAQKFQG                                                          17

SEQ ID NO: 363              moltype = AA   length = 17
FEATURE                     Location/Qualifiers
source                      1..17
                            mol_type = protein
                            organism = synthetic construct
SEQUENCE: 363
EINPINGRSN YAEKFQG                                                          17

SEQ ID NO: 364              moltype = AA   length = 17
FEATURE                     Location/Qualifiers
source                      1..17
                            mol_type = protein
                            organism = synthetic construct
SEQUENCE: 364
EINPIQGRSN YAEKFQG                                                          17

SEQ ID NO: 365              moltype = AA   length = 7
FEATURE                     Location/Qualifiers
source                      1..7
                            mol_type = protein
                            organism = synthetic construct
SEQUENCE: 365
GTRAMHY                                                                      7

SEQ ID NO: 366              moltype = AA   length = 11
FEATURE                     Location/Qualifiers
source                      1..11
                            mol_type = protein
                            organism = synthetic construct
VARIANT                     8
                            note = N or S
SEQUENCE: 366
RTSENIYXNL A                                                                11

SEQ ID NO: 367              moltype = AA   length = 11
FEATURE                     Location/Qualifiers
source                      1..11
                            mol_type = protein
                            organism = synthetic construct
SEQUENCE: 367
RTSENIYNNL A                                                                11

SEQ ID NO: 368              moltype = AA   length = 11
FEATURE                     Location/Qualifiers
source                      1..11
                            mol_type = protein
                            organism = synthetic construct
SEQUENCE: 368
RTSENIYSNL A                                                                11

SEQ ID NO: 369              moltype = AA   length = 7
FEATURE                     Location/Qualifiers
source                      1..7
```

```
                            mol_type = protein
                            organism = synthetic construct
VARIANT                     2
                            note = A or G
VARIANT                     7
                            note = D or E
SEQUENCE: 369
AXTNLAX                                                                       7

SEQ ID NO: 370              moltype = AA   length = 7
FEATURE                     Location/Qualifiers
source                      1..7
                            mol_type = protein
                            organism = synthetic construct
SEQUENCE: 370
AATNLAD                                                                       7

SEQ ID NO: 371              moltype = AA   length = 7
FEATURE                     Location/Qualifiers
source                      1..7
                            mol_type = protein
                            organism = synthetic construct
SEQUENCE: 371
AATNLAE                                                                       7

SEQ ID NO: 372              moltype = AA   length = 7
FEATURE                     Location/Qualifiers
source                      1..7
                            mol_type = protein
                            organism = synthetic construct
SEQUENCE: 372
AGTNLAD                                                                       7

SEQ ID NO: 373              moltype = AA   length = 10
FEATURE                     Location/Qualifiers
source                      1..10
                            mol_type = protein
                            organism = synthetic construct
VARIANT                     10
                            note = May be deleted
SEQUENCE: 373
QHFWGTPLTF                                                                   10

SEQ ID NO: 374              moltype = AA   length = 9
FEATURE                     Location/Qualifiers
source                      1..9
                            mol_type = protein
                            organism = synthetic construct
SEQUENCE: 374
QHFWGTPLT                                                                     9

SEQ ID NO: 375              moltype = AA   length = 10
FEATURE                     Location/Qualifiers
source                      1..10
                            mol_type = protein
                            organism = synthetic construct
SEQUENCE: 375
QHFWGTPLTF                                                                   10

SEQ ID NO: 376              moltype = AA   length = 116
FEATURE                     Location/Qualifiers
source                      1..116
                            mol_type = protein
                            organism = synthetic construct
SEQUENCE: 376
QVQLVQSGAE VKKPGASVKV SCKASGYTFT NYWMHWVRQA PGQGLEWMGE INPINGRSNY             60
AQKFQGRVTL TVDTSISTAY MELSRLRSDD TAVYYCARGT RAMHYWGQGT LVTVSS                116

SEQ ID NO: 377              moltype = AA   length = 116
FEATURE                     Location/Qualifiers
source                      1..116
                            mol_type = protein
                            organism = synthetic construct
SEQUENCE: 377
QVQLVQSGAE VKKPGASVKV SCKASGYTFT NYWMHWVRQA PGQGLEWIGE INPINGRSNY             60
AEKFQGRVTL TVDTSSSTAY MELSRLRSDD TAVYYCARGT RAMHYWGQGT LVTVSS                116

SEQ ID NO: 378              moltype = AA   length = 116
FEATURE                     Location/Qualifiers
```

```
                           source          1..116
                                           mol_type = protein
                                           organism = synthetic construct
SEQUENCE: 378
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSS       116

SEQ ID NO: 379          moltype = AA   length = 116
FEATURE                 Location/Qualifiers
source                  1..116
                        mol_type = protein
                        organism = synthetic construct
SEQUENCE: 379
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSS       116

SEQ ID NO: 380          moltype = AA   length = 116
FEATURE                 Location/Qualifiers
source                  1..116
                        mol_type = protein
                        organism = synthetic construct
SEQUENCE: 380
QVQLQQPGAE LVKPGASVKL SCKASGYTFT NYWMHWVKQR PGQGLEWIGE INPINGRSNY    60
GERFKTKATL TVDKSSSTAY MQLSSLTSED SAVYYCARGT RAMHYWGQGT SVTVSS       116

SEQ ID NO: 381          moltype = AA   length = 107
FEATURE                 Location/Qualifiers
source                  1..107
                        mol_type = protein
                        organism = synthetic construct
SEQUENCE: 381
DIQMTQSPSS LSASVGDRVT ITCRTSENIY NNLAWYQQKP GKSPKLLIYA ATNLADGVPS    60
RFSGSGSGTD YTLTISSLQP EDFATYYCQH FWGTPLTFGG GTKVEIK                 107

SEQ ID NO: 382          moltype = AA   length = 107
FEATURE                 Location/Qualifiers
source                  1..107
                        mol_type = protein
                        organism = synthetic construct
SEQUENCE: 382
DIQMTQSPSS LSASVGDRVT ITCRTSENIY NNLAWYQQKP GKAPKLLIYA ATNLADGVPS    60
RFSGSGSGTD YTLTISSLQP EDFATYYCQH FWGTPLTFGG GTKVEIK                 107

SEQ ID NO: 383          moltype = AA   length = 107
FEATURE                 Location/Qualifiers
source                  1..107
                        mol_type = protein
                        organism = synthetic construct
SEQUENCE: 383
DIQMTQSPSS LSASVGDRVT ITCRTSENIY NNLAWYQQKP GKAPKLLIYA ATNLAEGVPS    60
RFSGSGSGTD YTLTISSLQP EDFATYYCQH FWGTPLTFGG GTKVEIK                 107

SEQ ID NO: 384          moltype = AA   length = 107
FEATURE                 Location/Qualifiers
source                  1..107
                        mol_type = protein
                        organism = synthetic construct
SEQUENCE: 384
DIQMTQSPSS LSASVGDRVT ITCRTSENIY SNLAWYQQKP GKAPKLLIYA GTNLADGVPS    60
RFSGSGSGTD YTLTISSLQP EDFANYYCQH FWGTPLTFGG GTKVEIK                 107

SEQ ID NO: 385          moltype = AA   length = 107
FEATURE                 Location/Qualifiers
source                  1..107
                        mol_type = protein
                        organism = synthetic construct
SEQUENCE: 385
DIQMTQSPAS LSVSVGETVT ITCRTSENIY NNLAWYQQKQ GKSPQLLVYA ATNLADGVPS    60
RFSGSGSGTQ YSLKINSLQS EDFGNYYCQH FWGTPLTFGA GTKLELK                 107

SEQ ID NO: 386          moltype =      length =
SEQUENCE: 386
000

SEQ ID NO: 387          moltype =      length =
SEQUENCE: 387
000

SEQ ID NO: 388          moltype =      length =
```

```
SEQUENCE: 388
000

SEQ ID NO: 389         moltype =    length =
SEQUENCE: 389
000

SEQ ID NO: 390         moltype = AA   length = 445
FEATURE                Location/Qualifiers
source                 1..445
                       mol_type = protein
                       organism = synthetic construct
SEQUENCE: 390
QVQLVQSGAE VKKPGASVKV SCKASGYTFT NYWMHWVRQA PGQGLEWMGE INPINGRSNY   60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 391         moltype = AA   length = 445
FEATURE                Location/Qualifiers
source                 1..445
                       mol_type = protein
                       organism = synthetic construct
SEQUENCE: 391
QVQLVQSGAE VKKPGASVKV SCKASGYTFT NYWMHWVRQA PGQGLEWMGE INPINGRSNY   60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 392         moltype = AA   length = 445
FEATURE                Location/Qualifiers
source                 1..445
                       mol_type = protein
                       organism = synthetic construct
SEQUENCE: 392
QVQLVQSGAE VKKPGASVKV SCKASGYTFT NYWMHWVRQA PGQGLEWMGE INPINGRSNY   60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 393         moltype = AA   length = 445
FEATURE                Location/Qualifiers
source                 1..445
                       mol_type = protein
                       organism = synthetic construct
SEQUENCE: 393
QVQLVQSGAE VKKPGASVKV SCKASGYTFT NYWMHWVRQA PGQGLEWMGE INPINGRSNY   60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 394         moltype = AA   length = 445
FEATURE                Location/Qualifiers
source                 1..445
                       mol_type = protein
                       organism = synthetic construct
SEQUENCE: 394
QVQLVQSGAE VKKPGASVKV SCKASGYTFT NYWMHWVRQA PGQGLEWMGE INPINGRSNY   60
AQKFQGRVTL TVDTSISTAY MELSRLRSDD TAVYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
```

```
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 395           moltype = AA  length = 445
FEATURE                  Location/Qualifiers
source                   1..445
                         mol_type = protein
                         organism = synthetic construct
SEQUENCE: 395
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVAVSHEDP EVKFNWYVDG VEVHNAKTKP REEQYGSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 396           moltype = AA  length = 445
FEATURE                  Location/Qualifiers
source                   1..445
                         mol_type = protein
                         organism = synthetic construct
SEQUENCE: 396
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 397           moltype = AA  length = 445
FEATURE                  Location/Qualifiers
source                   1..445
                         mol_type = protein
                         organism = synthetic construct
SEQUENCE: 397
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 398           moltype = AA  length = 445
FEATURE                  Location/Qualifiers
source                   1..445
                         mol_type = protein
                         organism = synthetic construct
SEQUENCE: 398
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC GVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 399           moltype = AA  length = 445
FEATURE                  Location/Qualifiers
source                   1..445
                         mol_type = protein
                         organism = synthetic construct
SEQUENCE: 399
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 400           moltype = AA  length = 445
```

```
FEATURE                 Location/Qualifiers
source                  1..445
                        mol_type = protein
                        organism = synthetic construct
SEQUENCE: 400
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALGAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 401          moltype = AA   length = 445
FEATURE                 Location/Qualifiers
source                  1..445
                        mol_type = protein
                        organism = synthetic construct
SEQUENCE: 401
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVAVSHEDP EVKFNWYVDG VEVHNAKTKP REEQYGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 402          moltype = AA   length = 445
FEATURE                 Location/Qualifiers
source                  1..445
                        mol_type = protein
                        organism = synthetic construct
SEQUENCE: 402
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 403          moltype = AA   length = 445
FEATURE                 Location/Qualifiers
source                  1..445
                        mol_type = protein
                        organism = synthetic construct
SEQUENCE: 403
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 404          moltype = AA   length = 445
FEATURE                 Location/Qualifiers
source                  1..445
                        mol_type = protein
                        organism = synthetic construct
SEQUENCE: 404
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC GVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 405          moltype = AA   length = 445
FEATURE                 Location/Qualifiers
source                  1..445
                        mol_type = protein
                        organism = synthetic construct
```

```
SEQUENCE: 405
QVQLVQSGAE VKKPGASVKV SCKASGYTFT NYWMHWVRQA PGQGLEWMGE INPIQGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKARPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 406         moltype = AA  length = 445
FEATURE                Location/Qualifiers
source                 1..445
                       mol_type = protein
                       organism = synthetic construct
SEQUENCE: 406
QVQLVQSGAE VKKPGASVKV SCKASGYTFT NYWMHWVRQA PGQGLEWMGE INPIQGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 407         moltype = AA  length = 445
FEATURE                Location/Qualifiers
source                 1..445
                       mol_type = protein
                       organism = synthetic construct
SEQUENCE: 407
QVQLVQSGAE VKKPGASVKV SCKASGYTFT NYWMHWVRQA PGQGLEWMGE INPIQGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 408         moltype = AA  length = 445
FEATURE                Location/Qualifiers
source                 1..445
                       mol_type = protein
                       organism = synthetic construct
SEQUENCE: 408
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 409         moltype = AA  length = 445
FEATURE                Location/Qualifiers
source                 1..445
                       mol_type = protein
                       organism = synthetic construct
SEQUENCE: 409
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 410         moltype = AA  length = 445
FEATURE                Location/Qualifiers
source                 1..445
                       mol_type = protein
                       organism = synthetic construct
SEQUENCE: 410
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
```

```
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC GVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 411          moltype = AA  length = 445
FEATURE                 Location/Qualifiers
source                  1..445
                        mol_type = protein
                        organism = synthetic construct
SEQUENCE: 411
QVQLVQSGAE VKKPGASVKV SCKASGYTFT NYWMHWVRQA PGQGLEWMGE INPINGRSNY     60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 412          moltype = AA  length = 445
FEATURE                 Location/Qualifiers
source                  1..445
                        mol_type = protein
                        organism = synthetic construct
SEQUENCE: 412
QVQLVQSGAE VKKPGASVKV SCKASGYTFT NYWMHWVRQA PGQGLEWMGE INPINGRSNY     60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALGAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 413          moltype = AA  length = 445
FEATURE                 Location/Qualifiers
source                  1..445
                        mol_type = protein
                        organism = synthetic construct
SEQUENCE: 413
QVQLVQSGAE VKKPGASVKV SCKASGYTFT NYWMHWVRQA PGQGLEWMGE INPINGRSNY     60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVAVSHEDP EVKFNWYVDG VEVHNAKTKP REEQYGSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 414          moltype = AA  length = 214
FEATURE                 Location/Qualifiers
source                  1..214
                        mol_type = protein
                        organism = synthetic construct
SEQUENCE: 414
DIQMTQSPSS LSASVGDRVT ITCRTSENIY NNLAWYQQKP GKSPKLLIYA ATNLADGVPS     60
RFSGSGSGTD YTLTISSLQP EDFATYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 415          moltype = AA  length = 214
FEATURE                 Location/Qualifiers
source                  1..214
                        mol_type = protein
                        organism = synthetic construct
SEQUENCE: 415
DIQMTQSPSS LSASVGDRVT ITCRTSENIY NNLAWYQQKP GKAPKLLIYA ATNLADGVPS     60
RFSGSGSGTD YTLTISSLQP EDFATYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 416          moltype = AA  length = 214
FEATURE                 Location/Qualifiers
source                  1..214
                        mol_type = protein
                        organism = synthetic construct
SEQUENCE: 416
```

```
DIQMTQSPSS LSASVGDRVT ITCRTSENIY NNLAWYQQKP GKAPKLLIYA ATNLAEGVPS    60
RFSGSGSGTD YTLTISSLQP EDFATYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 417          moltype = AA   length = 214
FEATURE                 Location/Qualifiers
source                  1..214
                        mol_type = protein
                        organism = synthetic construct
SEQUENCE: 417
DIQMTQSPSS LSASVGDRVT ITCRTSENIY SNLAWYQQKP GKAPKLLIYA GTNLADGVPS    60
RFSGSGSGTD YTLTISSLQP EDFANYYCQH FWGTPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 418          moltype = AA   length = 24
FEATURE                 Location/Qualifiers
source                  1..24
                        mol_type = protein
                        organism = synthetic construct
SEQUENCE: 418
CGIFGEIEEL IEEGLENLID WGNA                                           24

SEQ ID NO: 419          moltype = AA   length = 24
FEATURE                 Location/Qualifiers
source                  1..24
                        mol_type = protein
                        organism = synthetic construct
SEQUENCE: 419
GLFEAIEGFI ENGWEGMIDG WYGC                                           24

SEQ ID NO: 420          moltype = AA   length = 27
FEATURE                 Location/Qualifiers
source                  1..27
                        mol_type = protein
                        organism = synthetic construct
SEQUENCE: 420
GLFEAIEGFI ENGWEGMIWD YGSGSCG                                        27

SEQ ID NO: 421          moltype = AA   length = 23
FEATURE                 Location/Qualifiers
source                  1..23
                        mol_type = protein
                        organism = synthetic construct
SEQUENCE: 421
GLFEAIEGFI ENGWEGMIDG WYG                                            23

SEQ ID NO: 422          moltype = AA   length = 27
FEATURE                 Location/Qualifiers
source                  1..27
                        mol_type = protein
                        organism = synthetic construct
SEQUENCE: 422
GLFEAIEGFI ENGWEGMIWD YGSGSCK                                        27

SEQ ID NO: 423          moltype = AA   length = 27
FEATURE                 Location/Qualifiers
source                  1..27
                        mol_type = protein
                        organism = synthetic construct
SEQUENCE: 423
CLIGAILKVL ATGLPTLISW IKNKRKQ                                        27

SEQ ID NO: 424          moltype = AA   length = 26
FEATURE                 Location/Qualifiers
source                  1..26
                        mol_type = protein
                        organism = synthetic construct
SEQUENCE: 424
GIGAVLKVLT TGLPALISWI KRKRQQ                                         26

SEQ ID NO: 425          moltype = AA   length = 13
FEATURE                 Location/Qualifiers
source                  1..13
                        mol_type = protein
                        organism = synthetic construct
SITE                    13
                        note = amidated phenylalanine
```

```
SEQUENCE: 425
IFGAIAGLLK NIF                                                                    13

SEQ ID NO: 426           moltype = AA   length = 18
FEATURE                  Location/Qualifiers
source                   1..18
                         mol_type = protein
                         organism = synthetic construct
SEQUENCE: 426
FFGHLFKLAT KIIPSLFQ                                                               18

SEQ ID NO: 427           moltype = AA   length = 21
FEATURE                  Location/Qualifiers
source                   1..21
                         mol_type = protein
                         organism = synthetic construct
SEQUENCE: 427
KETWWETWWT EWSQPKKKRK V                                                           21

SEQ ID NO: 428           moltype = AA   length = 19
FEATURE                  Location/Qualifiers
source                   1..19
                         mol_type = protein
                         organism = synthetic construct
SEQUENCE: 428
LLIILRRRRI RKQAHAHSK                                                              19

SEQ ID NO: 429           moltype = AA   length = 26
FEATURE                  Location/Qualifiers
source                   1..26
                         mol_type = protein
                         organism = synthetic construct
SEQUENCE: 429
DPKGDPKGVT VTVTVTVTGK GDPKPD                                                      26

SEQ ID NO: 430           moltype = AA   length = 17
FEATURE                  Location/Qualifiers
source                   1..17
                         mol_type = protein
                         organism = synthetic construct
SEQUENCE: 430
CSIPPEVKFN KPFVYLI                                                                17

SEQ ID NO: 431           moltype = AA   length = 27
FEATURE                  Location/Qualifiers
source                   1..27
                         mol_type = protein
                         organism = synthetic construct
SEQUENCE: 431
GWTLNSAGYL LGKINLKALA ALAKKIL                                                     27

SEQ ID NO: 432           moltype = AA   length = 21
FEATURE                  Location/Qualifiers
source                   1..21
                         mol_type = protein
                         organism = synthetic construct
SEQUENCE: 432
AGYLLGKINL KALAALAKKI L                                                           21

SEQ ID NO: 433           moltype = AA   length = 17
FEATURE                  Location/Qualifiers
source                   1..17
                         mol_type = protein
                         organism = synthetic construct
SEQUENCE: 433
GALFLGFLGA AGSTMGA                                                                17

SEQ ID NO: 434           moltype = AA   length = 20
FEATURE                  Location/Qualifiers
source                   1..20
                         mol_type = protein
                         organism = synthetic construct
SEQUENCE: 434
HGLASTLTRW AHYNALIRAF                                                             20

SEQ ID NO: 435           moltype = AA   length = 20
FEATURE                  Location/Qualifiers
source                   1..20
                         mol_type = protein
```

```
                            organism = synthetic construct
SEQUENCE: 435
GLWRALWRLL RSLWRLLWRA                                               20

SEQ ID NO: 436          moltype = AA   length = 30
FEATURE                 Location/Qualifiers
source                  1..30
                        mol_type = protein
                        organism = synthetic construct
SEQUENCE: 436
WEAALAEALA EALAEHLAEA LAEALEALAA                                    30

SEQ ID NO: 437          moltype = AA   length = 24
FEATURE                 Location/Qualifiers
source                  1..24
                        mol_type = protein
                        organism = synthetic construct
SEQUENCE: 437
GLFEAIEGFI ENGWEGMIDG WYGC                                          24

SEQ ID NO: 438          moltype = AA   length = 23
FEATURE                 Location/Qualifiers
source                  1..23
                        mol_type = protein
                        organism = synthetic construct
SEQUENCE: 438
GLFGAIAGFI ENGWEGMIDG WYG                                           23

SEQ ID NO: 439          moltype = AA   length = 36
FEATURE                 Location/Qualifiers
source                  1..36
                        mol_type = protein
                        organism = synthetic construct
SITE                    36
                        note = amidated lysine
SEQUENCE: 439
GLFGAIAGFI ENGWEGMIDG RQIKIWFQNR RMKWKK                             36

SEQ ID NO: 440          moltype = AA   length = 26
FEATURE                 Location/Qualifiers
source                  1..26
                        mol_type = protein
                        organism = synthetic construct
SEQUENCE: 440
GLFGAIAGFI ENGWEGMIDG SSKKKK                                        26

SEQ ID NO: 441          moltype = AA   length = 24
FEATURE                 Location/Qualifiers
source                  1..24
                        mol_type = protein
                        organism = synthetic construct
SEQUENCE: 441
GLFEAIAGFI ENGWEGMIDG GGYC                                          24

SEQ ID NO: 442          moltype = AA   length = 23
FEATURE                 Location/Qualifiers
source                  1..23
                        mol_type = protein
                        organism = synthetic construct
SEQUENCE: 442
GLFHAIAHFI HGGWHGLIHG WYG                                           23

SEQ ID NO: 443          moltype = AA   length = 30
FEATURE                 Location/Qualifiers
source                  1..30
                        mol_type = protein
                        organism = synthetic construct
SEQUENCE: 443
GLFEAIEGFI ENGWEGLAEA LAEALEALAA                                    30

SEQ ID NO: 444          moltype = AA   length = 29
FEATURE                 Location/Qualifiers
source                  1..29
                        mol_type = protein
                        organism = synthetic construct
SEQUENCE: 444
KWKLFKKIGA VLKVLTTGYG RKKRRQRRR                                     29

SEQ ID NO: 445          moltype = AA   length = 16
```

```
FEATURE              Location/Qualifiers
source               1..16
                     mol_type = protein
                     organism = synthetic construct
SEQUENCE: 445
RQIKIWFQNR RMKWKK                                                        16

SEQ ID NO: 446       moltype = AA   length = 13
FEATURE              Location/Qualifiers
source               1..13
                     mol_type = protein
                     organism = synthetic construct
SEQUENCE: 446
GRKKRRQRRR PPQ                                                           13

SEQ ID NO: 447       moltype = AA   length = 18
FEATURE              Location/Qualifiers
source               1..18
                     mol_type = protein
                     organism = synthetic construct
SEQUENCE: 447
LLIILRRRIR KQAHAHSK                                                      18

SEQ ID NO: 448       moltype = AA   length = 27
FEATURE              Location/Qualifiers
source               1..27
                     mol_type = protein
                     organism = synthetic construct
SEQUENCE: 448
GWTLNSAGYL LGKINLKALA ALAKKIL                                            27

SEQ ID NO: 449       moltype = AA   length = 27
FEATURE              Location/Qualifiers
source               1..27
                     mol_type = protein
                     organism = synthetic construct
SEQUENCE: 449
GALFLGFLGA AGSTMGAWSQ PKKKRKV                                            27

SEQ ID NO: 450       moltype = AA   length = 21
FEATURE              Location/Qualifiers
source               1..21
                     mol_type = protein
                     organism = synthetic construct
SEQUENCE: 450
KETWWETWWT EWSQPKKKRK V                                                  21

SEQ ID NO: 451       moltype = AA   length = 11
FEATURE              Location/Qualifiers
source               1..11
                     mol_type = protein
                     organism = synthetic construct
VARIANT              8..11
                     note = Residues may be deleted
SEQUENCE: 451
RRRRRRRRRR R                                                             11

SEQ ID NO: 452       moltype = AA   length = 18
FEATURE              Location/Qualifiers
source               1..18
                     mol_type = protein
                     organism = synthetic construct
SEQUENCE: 452
KLALKLALKA LKAALKLA                                                      18

SEQ ID NO: 453       moltype = AA   length = 9
FEATURE              Location/Qualifiers
source               1..9
                     mol_type = protein
                     organism = synthetic construct
SEQUENCE: 453
RRWWRRWRR                                                                 9

SEQ ID NO: 454       moltype = AA   length = 13
FEATURE              Location/Qualifiers
source               1..13
                     mol_type = protein
                     organism = synthetic construct
SEQUENCE: 454
```

```
CGYGPKKKRK VGG                                                          13

SEQ ID NO: 455          moltype = AA  length = 8
FEATURE                 Location/Qualifiers
source                  1..8
                        mol_type = protein
                        organism = synthetic construct
SEQUENCE: 455
KKKKKKKK                                                                8

SEQ ID NO: 456          moltype = AA  length = 22
FEATURE                 Location/Qualifiers
source                  1..22
                        mol_type = protein
                        organism = synthetic construct
SEQUENCE: 456
MVRRFLVTLR IRRACGPPRV RV                                                22

SEQ ID NO: 457          moltype = AA  length = 28
FEATURE                 Location/Qualifiers
source                  1..28
                        mol_type = protein
                        organism = synthetic construct
SEQUENCE: 457
LSTAADMQGV VTDGMASGLD KDYLKPDD                                          28

SEQ ID NO: 458          moltype = AA  length = 4
FEATURE                 Location/Qualifiers
source                  1..4
                        mol_type = protein
                        organism = synthetic construct
SEQUENCE: 458
GGFG                                                                    4

SEQ ID NO: 459          moltype = AA  length = 4
FEATURE                 Location/Qualifiers
source                  1..4
                        mol_type = protein
                        organism = synthetic construct
SEQUENCE: 459
ALAL                                                                    4

SEQ ID NO: 460          moltype = AA  length = 4
FEATURE                 Location/Qualifiers
source                  1..4
                        mol_type = protein
                        organism = synthetic construct
SEQUENCE: 460
GFLG                                                                    4

SEQ ID NO: 461          moltype = DNA  length = 25
FEATURE                 Location/Qualifiers
source                  1..25
                        mol_type = other DNA
                        organism = synthetic construct
SEQUENCE: 461
gagaaagtcc aatacctcac tcgct                                             25

SEQ ID NO: 462          moltype = DNA  length = 23
FEATURE                 Location/Qualifiers
source                  1..23
                        mol_type = other DNA
                        organism = synthetic construct
SEQUENCE: 462
tgtagctttt gacgtgcttg ttg                                               23

SEQ ID NO: 463          moltype = DNA  length = 18
FEATURE                 Location/Qualifiers
source                  1..18
                        mol_type = other DNA
                        organism = synthetic construct
SEQUENCE: 463
aggctcttct tatagctg                                                     18

SEQ ID NO: 464          moltype = DNA  length = 17
FEATURE                 Location/Qualifiers
source                  1..17
                        mol_type = other DNA
                        organism = synthetic construct
```

```
SEQUENCE: 464
tgaggctctt atagctg                                                      17

SEQ ID NO: 465          moltype = AA  length = 245
FEATURE                 Location/Qualifiers
source                  1..245
                        mol_type = protein
                        organism = synthetic construct
SEQUENCE: 465
MEWSWVFLFF LSVTTGVHSQ VQLVQSGAEV KKPGASVKVS CKASGYTFTN YWMHWVRQAP   60
GQGLEWMGEI NPINGRSNYA QKFQGRVTLT VDTSISTAYM ELSRLRSDDT AVYYCARGTR  120
AMHYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCG                                                              245

SEQ ID NO: 466          moltype = DNA  length = 735
FEATURE                 Location/Qualifiers
source                  1..735
                        mol_type = other DNA
                        organism = synthetic construct
SEQUENCE: 466
atggaatggt catgggtttt tttgttttc ctctcagtta cgactggtgt ccatagccaa    60
gtccaactgg tgcagtccgg tgcggaggtt aagaagcccg gagcgagcgt aaaggtgagt  120
tgtaaagcga gtggatacac gttcacgaac tattggatgc attgggttcg acaagcaccg  180
ggtcagggac ttgagtggat gggagaaatt aatccgatta acgtcgcag taactatgcg   240
cagaaattcc aaggccgagt aactctcacc gtggacacgt ccatctctac agcgtacatg  300
gaactcagca ggttgcgctc tgacgatacc gcagtttatt attgcgcgcg agggacgcgg  360
gctatgcact attggggca gggcaccctc gtcaccgtat catctgcgag tacgaaggga   420
ccttctgtgt tcccattggc tcccagcagc aaaagtacca gtggtggaac agctgcgctt  480
ggatgcctgg tgaaagatta tttccccgag ccggtgacag tcagctggaa cagcggcgca  540
ctcaccagcg gtgtacatac gttccggcg gttttgcaat ctagtggcct ctattccctt   600
agttccgtag ttaccgtccc atcttcaagc tcggaaccc agacttacat ctgcaacgtc   660
aatcataagc ccagtaacac aaaagttgat aagagagtag agccgaaatc ctgtgataag  720
acccacacat gtggg                                                   735

SEQ ID NO: 467          moltype = AA  length = 234
FEATURE                 Location/Qualifiers
source                  1..234
                        mol_type = protein
                        organism = synthetic construct
SEQUENCE: 467
MSVPTQVLGL LLLWLTDARC DIQMTQSPSS LSASVGDRVT ITCRTSENIY NNLAWYQQKP   60
GKAPKLLIYA ATNLAEGVPS RFSGSGSGTD YTLTISSLQP EDFATYYCQH FWGTPLTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 468          moltype = DNA  length = 747
FEATURE                 Location/Qualifiers
source                  1..747
                        mol_type = other DNA
                        organism = synthetic construct
SEQUENCE: 468
gcctccggac tctagagccg ccaccatgag cgtaccaacc caggtgctcg gactcctgtt    60
gttgtggctc accgatgcaa gatgcgatat acaaatgaca caaagcccaa gtagtttgtc   120
agccagcgta ggggatagag ttactataac ttgccgaacg tctgaaaata tatataataa   180
cctcgcgtgg taccagcaga agcccggcaa ggccctaaa ctcctcattt atgcagctac    240
taacctcgct gaaggagtac catcaaggtt ctcaggcagc gggtctgaa ctgactacac    300
attgactatt tcaagccttc agccagagga cttcgctaca tactactgtc aacacttctg   360
ggggactccg cttactttcg gaggcggtac caaagtggag ataaaacgga cggttgctgc   420
tccgagcgtt tttatattcc cgccctctga tgaacagctg aaatcaggca ctgcgagcgt   480
tgtttgcttg ctgaataact tttaccccg cgaggcgaaa gtacaatgga aggtagacaa    540
cgcactgcaa tctgggaata gtcaagagag tgttaccgaa caagattcaa agattccac    600
ttattccctt agttctactt tgacactgag caaagcagat tacgagaaac ataaggtcta   660
cgcctgcgag gtgacgcacc agggcctgag cagcccagtt acaaagtcct tcaatcgagg   720
tgagtgttag gcggccgcta taagggt                                      747

SEQ ID NO: 469          moltype = RNA  length = 35
FEATURE                 Location/Qualifiers
source                  1..35
                        mol_type = mRNA
                        organism = Homo sapiens
SEQUENCE: 469
ctcgctcagc tataagaaga gcctcaacca ttgaa                              35
```